US008765928B2

(12) United States Patent
Ryan

(10) Patent No.: US 8,765,928 B2
(45) **Date of Patent: *Jul. 1, 2014**

(54) IDENTIFICATION OF ISOLATED GENOMIC NUCLEOTIDE FRAGMENTS FROM THE P15 REGION OF CHROMOSOME 11 ENCODING HUMAN TUMOR SUPPRESSING SUBTRANSFERABLE CANDIDATE 4 (TSSC4) AND VARIANTS THEREOF

(71) Applicant: Ryogen LLC, Suffern, NY (US)

(72) Inventor: James Ryan, Augusta, GA (US)

(73) Assignee: Ryogen LLC, Suffein, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/846,050

(22) Filed: Mar. 18, 2013

(65) Prior Publication Data

US 2013/0189697 A1 Jul. 25, 2013

Related U.S. Application Data

(62) Division of application No. 13/244,468, filed on Sep. 24, 2011, now abandoned, which is a division of application No. 09/999,121, filed on Oct. 31, 2001, now Pat. No. 8,039,602.

(60) Provisional application No. 60/244,705, filed on Oct. 31, 2000.

(51) Int. Cl.

| | |
|---|---|
| ***C07H 21/02*** | (2006.01) |
| ***C07H 21/04*** | (2006.01) |
| ***C12Q 1/68*** | (2006.01) |
| ***C12P 19/34*** | (2006.01) |
| ***C12N 5/00*** | (2006.01) |
| ***C12N 5/02*** | (2006.01) |

(52) U.S. Cl.

USPC ..... 536/23.1; 536/24.3; 536/24.33; 536/24.5; 435/6.1; 435/91.1; 435/325; 435/375

(58) Field of Classification Search

USPC ............ 536/23.1, 24.3, 24.33; 435/91.1, 325, 435/375

See application file for complete search history.

(56) References Cited

U.S. PATENT DOCUMENTS

| | | | |
|---|---|---|---|
| 5,582,979 | A | 12/1996 | Weber |
| 5,591,623 | A | 1/1997 | Bennett |
| 6,150,092 | A | 11/2000 | Uchida |
| 6,184,212 | B1 | 2/2001 | Miraglia |
| 6,537,751 | B1 | 3/2003 | Cohen |
| 6,566,135 | B1 | 5/2003 | Wall |
| 6,812,339 | B1 | 11/2004 | Venter |
| 7,125,858 | B2 | 10/2006 | Fillion |
| 8,039,602 | B2 | 10/2011 | Ryan |
| 8,399,641 | B2 | 3/2013 | Ryan |

FOREIGN PATENT DOCUMENTS

| | | |
|---|---|---|
| WO | 9520678 | 8/1995 |
| WO | 9844152 | 10/1998 |
| WO | 9918198 | 4/1999 |
| WO | 0015795 | 3/2000 |
| WO | 0162778 | 8/2001 |

OTHER PUBLICATIONS

Mir et al. (Annu. Rev. Genomics Hum. Genet., 2000 vol. 1:329-360).*
Altschul et al., "Gapped BLAST and PSI-BLAST: a new generation of protein database search programs", Nucleic Acids Res. 25: 3389-3402. 1997.
Alders et al., "The human Achaete-Scute homologue 2 (ASCL2, HASH2) maps to chromosome 11p15.5, close to IGF2 and is expressed in extravillus trophoblasts", Human Molecular Genetics 6: 859-867. 1997.
Andria et al., "Genomic organization and chromosomal localization of the TAPA-1 gene", J. Immunol. 147: 1030-1036. 1991.
Bowie et al., "Deciphering the message in protein sequences: Tolerance to amino acid substitutions", Science 247: 1306-1310. 1990.
Burge et al., "Prediction of complete gene structures in human genomic DNA", J. Mol. Biol. 268: 78-94. 1997.
Examiner's Interview Summary dated Oct. 6, 2005 for U.S. Appl. No. 09/999,121.
Examiner's Interview Summary dated Mar. 4, 2009 for U.S. Appl. No. 09/999,121.
Examiner's Interview Summary dated Jul. 14, 2009 for U.S. Appl. No. 09/999,121.
Examiner's Interview Summary dated May 21, 2010 for U.S. Appl. No. 09/999,121.
Examiner's Interview Summary dated Mar. 31, 2011 for U.S. Appl. No. 09/999,121.
International Search Report from counterpart international application PCT/US01/45381.
International Preliminary Examination Report from counterpart international application PCT/ US01/45381.
Itoh et al., "Proportions of cells with paternal 11p15 uniparental disomy correlates with organ enlargement in Wiedemann-Beckwith syndrome", J. Med. Gen. 92: 111-116. 2000.
Kenmochi et al., "A Map of 75 human ribosomal protein genes", Genome Research 8: 509-523. 1998.
Koi et al., "Tumor cell growth arrest caused by subchromosomal transferable DNA fragments from chromosome 11", Science 260: 361-364. 1993.
Lee et al., "Two novel genes in the center of the 11p 15 imprinted domain escape genomic imprinting", Hum. Mol. Gen. 8: 683-690. 1999.
Ngo et al., "Computational complexity, protein structure prediction, and the Levinthal Paradox", The Protein Folding Problem and Tertiary Structure Prediction, 1994.
Office Action dated Aug. 24, 2004 for U.S. Appl. No. 09/999,121.
Office Action dated Sep. 8, 2005 for U.S. Appl. No. 09/999,121.
Office Action dated Jul. 27, 2006 for U.S. Appl. No. 09/999,121.
Office Action dated Jul. 7, 2009 for U.S. Appl. No. 09/999,121.
Office Action dated Jan. 5, 2010 for U.S. Appl. No. 09/999,121.
Office Action dated Nov. 8, 2010 for U.S. Appl. No. 09/999,121.
Notice of Allowability dated Jun. 3, 2011 for U.S. Appl. No. 09/999,121.

(Continued)

*Primary Examiner* — Terra Cotta Gibbs

(74) *Attorney, Agent, or Firm* — Cheryl H. Agris; Agris & von Natzmer, LLP

(57) ABSTRACT

Provided herein are isolated genomic polynucleotide fragments from the from the p15 region of chromosome 11 encoding human and tumor suppressing subtransferable candidate 4 (TSSC4) and methods of use.

2 Claims, No Drawings

(56) References Cited

OTHER PUBLICATIONS

Office Action dated May 14, 2012 for U.S. Appl. No. 13/235,404.
Office Action dated May 10, 2012 for U.S. Appl. No. 13/239,243.
Office Action dated May 11, 2012 for U.S. Appl. No. 13/239,327.
Office Action dated May 11, 2012 for U.S. Appl. No. 13/244,463.
Office Action dated May 11, 2012 for U.S. Appl. No. 13/244,465.
Notice of Allowance dated Nov. 13, 2012 for U.S. Appl. No. 13/235,404.
Notice of Allowance dated Nov. 13, 2012 for U.S. Appl. No. 13/239,243.
Notice of Allowance dated Nov. 13, 2012 for U.S. Appl. No. 13/239,327.
Notice of Allowance dated Nov. 13, 2012 for U.S. Appl. No. 13/244,463.
Notice of Allowance dated Nov. 13, 2012 for U.S. Appl. No. 13/244,465.
Notice of Allowance dated Oct. 12, 2012 for U.S. Appl. No. 13/244,468.
Oren et al., "TAPA-1, the target of an antiproliferative antibody, defines a new family of transmembrane proteins", Mol. Cell. Biol. 10: 4007-4015. 1990.
Pileri et al., "Binding of Hepatitis C Virus to CD81", Science 282: 938-941. 1998.
Reik et al., "Imprinting in clusters: lessons from Beckwith-Wiedemann syndrome", Trends in Genetics 13: 330-334. 1997.
Segade et al., "Differential Regulation of the Murine Ribosomal Protein L26 Gene in Macrophage Activation", Life Sciences 58: 277-285. 1996.
Sequence: EMBL Database 'Online' 1997 "Human chromosome II pac pdJI075f20" see nucleotides 17080-34380.
Sequence: GenBank Accession No. 003693 (version 003693.1) Human Chromosome 11 p15.5 PAC clone pDJ915f1 containing KvLQT1 gene, complete sequence, PRI Sep. 30, 1995.
Sequence: GenBank Accession No. AC026645 submitted by Waterston, R. H. et al. Mar. 22, 2000 bases 2312-4001.
Sequence: GenBank Accession No. BE295955 (version BE295955. 1) 60117424SF1 NIH_MGC_17 *Homo sapiens* cDNA clone Image: 3529954 5-, mRNA sequence, Entry Created: Jul. 5, 2000 (Entry Updated: Jul. 20, 2000).
Sequence: GenBank Accession No. BE560890 (version BE560890. 1) 601346329F1 NIH_MGC_5 *Homo sapiens* cDNA clone Image: 3679567 5-, mRNA sequence, Entry Created: Aug. 10, 2000 (Entry Updated: Aug. 15, 2000).
Sequence: GenBank Accession No. AC002536.1 submitted by Evans et al., Dec. 10, 1997.
Sequence Alignments from Office Action dated Sep. 8, 2005 for U.S. Appl. No. 09/999,121.
Sequence Alignments from Office Action dated Jul. 27, 2007 for U.S. Appl. No. 09/999,121.
Sequence Alignments from Office Action dated Jul. 7, 2009 for U.S. Appl. No. 09/999,121.
Sequence Alignments from Office Action dated Jan. 5, 2010 for U.S. Appl. No. 09/999,121.
Sequence Alignments from Office Action dated May 11, 2012 for U.S. Appl. No. 13/239,327.
Sequence Alignments from Office Action dated May 11, 2012 for U.S. Appl. No. 13/244,463.
Sequence Alignments from Office Action dated May 11, 2012 for U.S. Appl. No. 13/244,465.
Siebert et al., "An improved PCR method for walking in uncloned genomic DNA", Nucleic Acids Res. 23: 1087-1088. 1995.
Virtaneva et al., "Chromosomal localization of three human genes coding for A15, L6, and S5.7 (TAPA1): all members of the transmembrane 4 superfamily of proteins", Immunogenetics 39: 329-334. 1994.
Wade-Martins et al., "Long term stability of large insert genomic DNA episomal shuttle vectors in human cells", Nucleic Acids Res. 27:1674-1682. 1999.
Westerman et al., "The human Achaete-Scute Homolog 2 gene contains two promoters, generating overlapping transcripts and encoding two proteins with different nuclear localization", Placenta 22: 511-518. 2001.
Witherden et al., "CD81 and CD28 costimulate T cells through distinct pathways", J Immunol. 165: 1902-1909. 2000.
Office Action dated Jul. 16, 2013 for U.S. Appl. No. 13/845,430.
Office Action dated Jul. 5, 2013 for U.S. Appl. No. 13/845,480.
Office Action dated Jul. 5, 2013 for U.S. Appl. No. 13/845,640.
Office Action dated Jul. 5, 2013 for U.S. Appl. No. 13/845,752.
Office Action dated Jul. 5, 2013 for U.S. Appl. No. 13/845,838.
Notice of Allowance dated Dec. 16, 2013 for U.S. Appl. No. 13/244,468.

* cited by examiner

IDENTIFICATION OF ISOLATED GENOMIC NUCLEOTIDE FRAGMENTS FROM THE P15 REGION OF CHROMOSOME 11 ENCODING HUMAN TUMOR SUPPRESSING SUBTRANSFERABLE CANDIDATE 4 (TSSC4) AND VARIANTS THEREOF

PRIORITY CLAIM

This application is a divisional of application Ser. No. 13/244,468, filed Sep. 24, 2011, the contents of which are incorporated herein by reference. Application Ser. No. 13/244,468 is a divisional of application Ser. No. 09/999,121 filed Oct. 31, 2001, the contents of which are also incorporated herein by reference. Application Ser. No. 09/999,121 claims priority under 35 U.S.C. 119(e) from provisional application serial. No. 60/244,705, filed Oct. 31, 2000, the contents of which are incorporated herein by reference.

FIELD OF THE INVENTION

The invention is directed to isolated genomic polynucleotide fragments located in the p15 region of chromosome 11.

BACKGROUND OF THE INVENTION

Chromosome 11 contains genes encoding, for example, KCNQ1, a voltage-gated potassium channel; IPL, a homolog of a mouse apoptosis-inducing entity; human achaete-scute homolog 2 (HASH2), human SMS3, human tumor suppressing subtransferable candidate 6 (TSSC6), human ribosomal protein L26 (RIBO26), cluster of differentiation antigen 81 (CD81) and tumor suppressing subtransferable candidate 4 (TSSC4). Human achaete-scute homolog 2 (HASH2), human SMS3, human tumor suppressing subtransferable candidate 6 (TSSC6), human ribosomal protein L26 (RIBO26), cluster of differentiation antigen 81 (CD81) and tumor suppressing subtransferable candidate 4 (TSSC4) are discussed in further detail below. Genes for the latter six proteins are located in the p15 region of chromosome 11, a region known to be associated with the Beckwith-Wiedemann Syndrome (Itoh et al. Am. J. Genet. 92, 111-6, 2000) and some childhood tumors.

Beckwith-Wiedemann Syndrome is characterized by pre and postnatal overgrowth up to 160% of normal birthweight, macroglossia, hypoglycemia, hemi-hypertrophy and childhood tumors, such as Wilm's tumor (Reik et al., 1998, Trends Genet. 13:330-334). This syndrome appears to be associated with deregulation of imprinting. Imprinted genes are genes that are predominantly expressed from one of the parental chromosomes. There appears to be two imprinted subdomains, since the imprinted gene domain of 11p15 contains at least two imprinted subdomains (Lee et al., 1999, Hum. Mol. Genet. 8:683-690). Mosaicism may also play some role in the Beckwith-Wiedemann Syndrome phenotype and may explain the variable phenotypes in Beckwith-Wiedemann Syndrome patients (Itoh et al., 2000, Am. J. Med. Genet. 92:111-116).

Human Achaete-scute Homolog 2 (HASH2)

HASH2 is a basic helix-loop-helix protein that serves as a critical transcription factor for the development of the trophectoderm. Mice deficient in the HASH2 homolog, MASH2, die 10 days postcoitum due to placental failure (Guillemot et al., Nature 371, 333-6, 1994).

Human Tumor Suppressing Subtransferable Candidates 4 and 6 (TSSC4 and TSSC6)

Both TSSC 4 and TSSC6 are believed to function as tumor-suppressing proteins in that the genes are among the genes of a subchromosomal fragment that suppresses in vitro growth of the rhabdomyosarcoma cell line RD (Koi et al., Science 260, 361-4, 1993).

Human Ribosomal Protein L26 (RIBO26)

RIBO26 is one of the approximately 80 proteins that compose the human ribosome (Kenmochi, N. et al., Genome Res. 8, 509-23, 1998). It has been found in mice to be induced by LPS and IFN gamma but is down regulated by TNF-alpha (Segade et al., 1996, Life Sci. 58:277-285).

Human Cluster of Differentiation Antigen 81 (CD81)

CD81 (also called TAPA1) binds the E2 envelope protein of the human hepatitis C virus and is believed to play a role in hepatitis C infection (Pileri et al., Science 282, 938-41, 1998). CD81 also appears to play a role in T cell activation (Witherden et al., 2000, J. Immunol. 165:1902-1909).

OBJECTS OF THE INVENTION

Although cDNAs encoding the above-disclosed proteins have been isolated, their precise locations and exon/intron/regulatory element organizations on chromosome 11 have not been determined. Furthermore, genomic DNA encoding these polypeptides have not been isolated. Noncoding sequences play a significant role in regulating the expression of polypeptides as well as the processing of RNA encoding these polypeptides.

There is clearly a need for obtaining genomic polynucleotide sequences encoding these polypeptides. Therefore, it is an object of the invention to isolate such genomic polynucleotide sequences.

There is also a need to develop means for identifying mutations, duplications, translocations, polysomies and mosaicism associated with Beckwith-Wiedemann syndrome.

SUMMARY OF THE INVENTION

The invention is directed to an isolated genomic polynucleotide, said polynucleotide obtainable from human chromosome 11 having a nucleotide sequence at least 95% identical to a sequence selected from the group consisting of:

(a) a polynucleotide encoding a polypeptide selected from the group consisting of human achaete-scute homolog 2 (HASH2) depicted in SEQ ID NO:1, human SMS3 depicted in SEQ ID NO:2, human tumor suppressing subtransferable candidate 6 (TSSC6) depicted in SEQ ID NO:3, ribosomal protein L26 (RIBO26) depicted in SEQ ID NO:4, cluster of differentiation antigen 81 (CD81) depicted in SEQ ID NO:5, and tumor suppressing subtransferable candidate 4 (TSSC4) depicted in SEQ ID NO:6;

(b) a polynucleotide selected from the group consisting of SEQ ID NO:7 which encodes human HASH2 depicted in SEQ ID NO:1, SEQ ID NO:8 which encodes human SMS3 depicted in SEQ ID NO:2, SEQ ID NO:9 which encodes human TSSC6 1 depicted in SEQ ID NO:3, SEQ ID NO:10 which encodes ribosomal protein L26 (RIBO26) depicted in SEQ ID NO:4, SEQ ID NO:11 which encodes human CD81 depicted in SEQ ID NO:5 and SEQ ID NO:12 which encodes human TSSC4 depicted in SEQ ID NO:6;

(c) a polynucleotide which is a variant of SEQ ID NOS:7, 8, 9, 10, 11 or 12, (d) a polynucleotide which is an allelic variant of SEQ ID NOS:7, 8, 9, 10, 11 or 12:

(e) a polynucleotide which encodes a variant of SEQ ID NOS:1, 2, 3, 4, 5, or 6;

(f) a polynucleotide which hybridizes to any one of the polynucleotides specified in (a)-(e);

(g) a polynucleotide that is a reverse complement to the polynucleotides specified in (a) to (f) and (h) containing at least 10 transcription factor binding sites selected from the group consisting of AP1FJ_Q2, AP1_C, AP1_Q2, AP1_Q4, AP4_Q5, AP4_Q6, ARNT__01, BRN__01, CDPCR3HD__01, CEBPB__01, CETS1P54__01, CMYB__01, CP2__01, CREB__02, CREB_Q4, CREL__01, DELTAEF1__01, E47__01, FREAC7__01, GATA1__02, GATA1__03, GATA1__04, GATA1__06, GATA2__02, GATA2__03, GATA3__02, GATA3__03, GATA_C, GC__01, GF11__01, HFH2__01, HFH3__01, HFH8__01, IK1__01, IK2__01, LMO2COM__01, LMO2COM__02, LYF1__01, MAX__01, MYCMAX__02, MYOD__01, MYOD_Q6, MZF1__01, NF1_Q6, NFAT_Q6, NKX25__01, NKX25__02, NMYC__01, OCT1__02, PADS_C, RORA1__01, S8__01, SOX5__01, SP1_Q6, STSSC6__01, SRV__02, STAT__01, TATA__01, TCF11__01, USF__01, USF_C, USF_Q6 and VMYB__02, as well as nucleic acid constructs, expression vectors and host cells containing these polynucleotide sequences.

The polynucleotides of the present invention may be used for the manufacture of a gene therapy for the prevention, treatment or amelioration of a medical condition by adding an amount of a composition comprising said polynucleotide effective to prevent, treat or ameliorate said medical condition.

The invention is further directed to obtaining these polypeptides by (a) culturing host cells comprising these sequences under conditions that provide for the expression of said polypeptide and (b) recovering said expressed polypeptide.

The polypeptides obtained may be used to produce antibodies by (a) optionally conjugating said polypeptide to a carrier protein;

(b) immunizing a host animal with said polypeptide or peptide-carrier protein conjugate of step (b) with an adjuvant and (c) obtaining antibody from said immunized host animal.

The invention is further directed to polynucleotides that hybridize to noncoding regions of said polynucleotide sequences as well as antisense oligonucleotides to these polynucleotides as well as antisense mimetics. The antisense oligonucleotides or mimetics may be used for the manufacture of a medicament for prevention, treatment or amelioration of a medical condition. The invention is further directed to kits comprising these polynucleotides and kits comprising these antisense oligonucleotides or mimetics.

In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to diagnose a pathological condition in a subject comprising (a) determining the presence or absence of a mutation in the polynucleotides of the present invention and (b) diagnosing a pathological condition or a susceptibility to a pathological condition based on the presence or absence of said mutation.

The invention is also directed to an isolated polynucleotide from the p15 region of human chromosome 11 selected from the group consisting of SEQ ID NOS: 13 and 14. SEQ ID NO:13 consists of nucleotide sequence immediately preceding the HASH2 gene; SEQ ID NO:14 consists of the gap between the RIBO26 and CD81 gene. Both of these polynucleotides are located in the imprinted subdomains of 11p15. Oligonucleotides derived from these sequences may be used to identify mutations, duplications, translocations, polysomies and mosaicism associated with Beckwith-Wiedemann syndrome. Furthermore, oligonucleotides derived from SEQ ID NO:13 may also be used as a marker for the HASH2 gene and SEQ ID NO:14 may be used as a marker for the RIBO26 and/or CD81 gene.

DETAILED DESCRIPTION OF THE INVENTION

The invention is directed to isolated genomic polynucleotide fragments that encode HASH2, human SMS3, human TSSC6, human RIBO26, human CD81 and human TSSC4, which in a specific embodiment are the HASH2, SMS3, TSSC6, RIBO26, CD81 and TSSC4 genes, as well as vectors and hosts containing these fragments and polynucleotide fragments hybridizing to noncoding regions, as well as antisense oligonucleotides to these fragments.

As defined herein, a "gene" is the segment of DNA involved in producing a polypeptide chain; it includes regions preceding and following the coding region, as well as intervening sequences (introns) between individual coding segments (exons).

As defined herein "isolated" refers to material removed from its original environment and is thus altered "by the hand of man" from its natural state. An isolated polynucleotide can be part of a vector, a composition of matter or can be contained within a cell as long as the cell is not the original environment of the polynucleotide.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand.

The HASH2 gene is 17290 base pairs in length and contains a single exon (see Table 1 below). The HASH2 gene is situated in genomic clone AC002536 at nucleotides 17081-34370. The SMS3 gene is 25970 base pairs in length and contains 3 exons (Table 2). The SMS3 gene is situated in genomic clone AC002536 at nucleotides 34371-60340. The TSSC6 gene is 30196 base pairs in length and contains 9 exons (Table 3). The TSSC6 gene is situated in genomic clone AC002536 at nucleotides 51731-81926. The RIBO26 gene is 21630 base pairs in length and contains a single exon (see Table 4 below for location of the exon). As will be discussed in further detail below, the RIBO26 gene is situated in genomic clone AC002536 at nucleotides 77701-99330. The CD81 gene is 21573 base pairs in length and contains 8 exons (Table 5). The CD81 gene begins at nucleotide 120961 in genomic clone AC002536 and extends to nucleotide 3640 in the downstream genomic clone AC003693. Clones AC002536 (140977 base pairs) and AC003693 (155074 base pairs) have a 2084 base pair overlap. The TSSC4 gene is 15540 base pairs in length and contains a single exon (Table 6). The TSSC4 gene is situated in genomic clone AC003693 at nucleotides 3641-19,180.

The polynucleotides of the invention have at least a 95% identity and may have a 96%, 97%, 98% or 99% identity to the polynucleotides depicted in SEQ ID NOS:7, 8, 9, 10, 11 or 12, as well as the polynucleotides in reverse sense orientation, or the polynucleotide sequences encoding the HASH2, SMS3, TSSC6, RIBO26, CD81 or TSSC4 polypeptides depicted in SEQ ID NOS:1, 2, 3, 4, 5 or 6 respectively.

A polynucleotide having 95% "identity" to a reference nucleotide sequence of the present invention, is identical to the reference sequence except that the polynucleotide sequence may include, on average, up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identify, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total numbers of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time, the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for purposes of the present invention.

A polypeptide that has an amino acid sequence at least, for example, 95% "identical" to a query amino acid sequence is identical to the query sequence except that the subject polypeptide sequence may include, on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted (indels), deleted, or substituted with another amino acid. These alterations of the reference sequence may occur at the amino or carboxy terminal positions of the reference amino acid sequence or anywhere between those terminal positions, interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutlag et al. (Com. App. Biosci. (1990) 6:237-245). In a sequence alignment, the query and subject sequence are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

The invention also encompasses polynucleotides that hybridize to the polynucleotides depicted in SEQ ID NOS: 7, 8, 9, 10, 11 or 12. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5×SSC, 0.1% SDS, 0.25% milk, and no formamide; or 40% formamide, 5×SSC, 0.5% SDS). Moderate stringency hybridization conditions correspond to a higher temperature of 55° C., e.g., 40% formamide, with 5× or 6×SCC. High stringency hybridization conditions correspond to the highest temperature of 65° C., e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the variant polypeptides may differ from the amino acid sequences depicted in SEQ ID NOS:1, 2, 3, 4, 5 or 6 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the HASH2, SMS3, TSSC6, RIBO26, CD81 and TSSC4 genes. These include but are not limited to an intron, a 5'-non-coding region, a 3'-non-coding region and splice junctions (see Tables 1-6), as well as transcription factor binding sites (see Table 7). The polynucleotide fragments may be a short polynucleotide fragment which is between about 8 nucleotides to about 40 nucleotides in length. Such shorter fragments may be useful for diagnostic purposes. Such short polynucleotide fragments are also preferred with respect to polynucleotides containing or hybridizing to polynucleotides containing splice junctions. Alternatively larger fragments, e.g., of about 50, 150, 500, 600 or about 2000 nucleotides in length may be used.

TABLE 1

Exon/Intron Regions of the human achaete-scute homolog 2 (HASH2) gene, 17290 bp, reference cDNA accession number U77629; reverse strand coding.

| Exon | Location (nucleotide no./amino acid no.) |
|---|---|
| 1 | 7031-7609 |
| | 193-1 |
| | stop codon 7028-7030 |

TABLE 2

Exon/Intron Regions of the human SMS3 gene, 25970 bp, reference cDNA accession number AB029488; reverse strand coding.

| Exon | Location (nucleotide no./amino acid no.) |
|---|---|
| 3 | 18962-19210 |
| | 132-50 |
| 2 | 20023-20118 |
| | 49-18 |
| 1 | 21261-21311 |
| | 1-17 |
| | stop codon 18959-18961 |

TABLE 3

Exon/Intron Regions of the human tumor suppressing subtransferable candidate 6 (TSSC6) gene, 30196 bp, reference cDNA accession number NM_005705; plus strand coding.

| Exon | Location (nucleotide no./amino acid no.) |
|---|---|
| 1 | 5011-5100 |
| | 1-30 |
| 2 | 6249-6347 |
| | 31-63 |
| 3 | 10879-10953 |
| | 64-88 |

TABLE 3-continued

Exon/Intron Regions of the human tumor suppressing subtransferable candidate 6 (TSSC6) gene, 30196 bp, reference cDNA accession number NM_005705; plus strand coding.

| Exon | Location (nucleotide no./amino acid no.) |
|---|---|
| 4 | 15797-15898 |
| | 89-122 |
| 5 | 16628-16714 |
| | 123-151 |
| 6 | 18372-18455 |
| | 152-179 |
| 7 | 18719-18811 |
| | 180-210 |
| 8 | 19488-19664 |
| | 211-270 |
| 9 | 20005-20064 |
| | 271-290 |
| | stop codon 20065-20067 |

TABLE 4

Exon/Intron Regions of the human ribosomal protein L26 gene, 21630 bp, reference cDNA accession number AF083248; reverse strand coding.

| Exon | Location (nucleotide no./amino acid no.) |
|---|---|
| 1 | 11490-11924 |
| | 145-1 |
| | stop codon 11487-11489 |

TABLE 5

Exon/Intron Region of the human CD81 gene, 37113 bp, reference accession number NM_004356; plus strand coding.

| Exon | Location (nucleotide no./amino acid no.) |
|---|---|
| 1 | 10471-10536 |
| | 1-22 |
| 2 | 23333-23446 |
| | 23-60 |
| 3 | 27015-27113 |
| | 61-93 |
| 4 | 27893-27964 |
| | 94-117 |
| 5 | 28334-28441 |
| | 118-153 |
| 6 | 28790-28891 |
| | 154-187 |
| 7 | 29549-29635 |
| | 188-216 |
| 8 | 29725-29784 |
| | 217-236 |
| | stop codon 29785-29787 |

TABLE 6

Exon/Intro Region of the human tumor suppressing subtransferable candidate 4 (TSSC4) gene, 15540 bp, reference cDNA accession number NM_005706; plus strand coding.

| Exon | Location (nucleotide no./amino acid no.) |
|---|---|
| 1 | 13982-14968 |
| | 1-329 |
| | stop codon 14969-14971 |

TABLE 7

TRANSCRIPTION FACTOR BINDING SITES

| BINDING SITES | HASH2 | SMS3 | TSSC6 | RIBO26 | CD81 | TSSC4 |
|---|---|---|---|---|---|---|
| AP1FJ_Q2 | | 14 | 8 | 10 | 16 | |
| AP1_C | 4 | 6 | 8 | 10 | 8 | |
| AP1_Q2 | 4 | 7 | 5 | 10 | 6 | |
| AP1_Q4 | | 4 | | 5 | 5 | |
| AP4_Q5 | 30 | 44 | 55 | 12 | 71 | |
| AP4_Q6 | 14 | 22 | 26 | 4 | 34 | |
| ARNT_01 | 7 | 4 | | | 6 | |
| BRN2_01 | 5 | | | 4 | | |
| CDPCR3HD_01 | | | | 5 | 8 | |
| CEBPB_01 | | 9 | 5 | 13 | 4 | |
| CETS1P54_01 | | | | | | 5 |
| CMYB_01 | 4 | | | | | |
| CP2_01 | | 4 | 5 | | | |
| CREB_02 | | | | | 4 | |
| CREB_Q4 | | | | | 4 | |
| CREL_01 | 5 | 11 | 11 | | 7 | |
| DELTAEF1_01 | 42 | 49 | 67 | 57 | 84 | |
| E47_01 | | | 6 | | 17 | |
| FREAC7_01 | | 4 | 6 | | | |
| GATA1_02 | 6 | 7 | 6 | 9 | 11 | |
| GATA1_03 | 8 | 7 | 4 | 15 | 5 | |
| GATA1_04 | 9 | 16 | 10 | 11 | 10 | |
| GATA1_05 | | 5 | 7 | 5 | | |
| GATA1_06 | 4 | 7 | | | | |
| GATA2_02 | 7 | 12 | 6 | 8 | 4 | |
| GATA2_03 | | 6 | | | | |
| GATA3_02 | 4 | 6 | | | | |
| GATA3_03 | | 4 | | | | |
| GATA_C | 6 | 13 | 5 | 7 | 7 | |
| GC_01 | | | | | | 7 |
| GFI1_01 | | 6 | | | | |
| HFH2_01 | | | 4 | 4 | | |
| HFH3_01 | 5 | | 9 | 7 | 4 | |
| HFH8_01 | | | | 4 | 5 | |
| IK1_01 | | | 4 | | | |
| IK2_01 | 22 | 24 | 34 | 33 | 56 | |
| LMO2COM_01 | 21 | 33 | 41 | 18 | 57 | 7 |
| LMO2COM_02 | 13 | 15 | 10 | 11 | 14 | |
| LYF1_01 | 5 | 7 | | 4 | 6 | |
| MAX_01 | 4 | | | | | |
| MYCMAX_02 | 4 | | | | | |
| MYOD_01 | | | | | 4 | |
| MYOD_Q6 | 13 | 13 | 22 | 5 | 34 | 11 |
| MZF1_01 | 73 | 106 | 136 | 63 | 211 | 21 |
| NF1_Q6 | | 5 | 6 | | 6 | |
| NFAT_Q6 | 23 | 33 | 20 | 39 | 16 | |
| NKX25_01 | 6 | 4 | 4 | 7 | 4 | |
| NKX25_02 | | | | 4 | | |
| NMYC_01 | 14 | 15 | 4 | 10 | | |
| OCT1_02 | | | | 6 | | |
| PADS_C | | | 6 | | 4 | |
| RORA1_01 | | 4 | | | | |
| S8_01 | 5 | 25 | 15 | 23 | 7 | |
| SOX5_01 | 5 | 9 | 5 | 8 | 11 | |
| SP1_Q6 | 6 | | | | 11 | |
| SRY_02 | | 4 | | 6 | 9 | |
| STAT_01 | 5 | | | | 5 | |
| TATA_01 | | | | 6 | | |
| TCF11_01 | 24 | 27 | 27 | 43 | 43 | 9 |
| USF_01 | 14 | 16 | 4 | 10 | 12 | 4 |
| USF_C | 14 | 16 | 4 | 10 | 12 | 6 |
| USF_Q6 | | 10 | | | 6 | |
| VMYB_02 | 9 | 5 | | 4 | 11 | |

Abbreviations:
HASH2, human achaete-scute homolog 2;
TSSC6, tumor suppressing subtransferable candidate 6;
RIBO26, ribosomal protein L26;
CD81, cluster of differentiation antigen 81; and
TSSC4, tumor suppressing subtransferable candidate 4.

In a specific embodiment, such noncoding sequences are expression control sequences. These include but are not limited to DNA regulatory sequences, such as promoters, enhancers, repressors, terminators, and the like, that provide for the regulation of expression of a coding sequence in a host cell. In eukaryotic cells, polyadenylation signals are also control sequences.

In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. A transcriptional control sequence is "operatively linked" to a polynucleotide encoding a heterologous polypeptide sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the DNA sequence under the control of the expression control sequence and production of the desired product encoded by the polynucleotide sequence. If a gene that one desires to insert into a recombinant DNA molecule does not contain an appropriate start signal, such a start signal can be inserted upstream (5') of and in reading frame with the gene.

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

Expression of Polypeptides

Isolated Polynucleotide Sequences

The human chromosome 11 genomic clone of accession number AC002536 has been discovered to contain the HASH2 gene, the SMS3 gene, the TSSC6 gene, the RIBO26, part of the CD81 gene by Genscan analysis (Burge et al., 1997, J. Mol. Biol. 268:78-94), BLAST2 and TBLASTN analysis (Altschul et al., 1997, Nucl. Acids Res. 25:3389-3402), in which the sequence of AC002536 was compared to the HASH2 cDNA sequence, accession number U77629, the human SMS3 cDNA sequence accession number AB029488, TSSC6 cDNA sequence accession number NM_005705, and the RIBO26 cDNA sequence, accession number AF083248. The remainder of the CD81 gene and the TSSC4 gene were found by similar means in the downstream clone AC003693. The accession numbers for the CD81 and TSSC4 cDNAs are, respectively, NM_004356 and NM_005706.

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligated activated transcription (LAT) and nucleic acid sequence-based amplification (NASBA) or long range PCR may be used. In a specific embodiment, 5'- or 3'-non-coding portions of each gene may be identified by methods including but are not limited to, filter probing, clone enrichment using specific probes and protocols similar or identical to 5'- and 3'-"RACE" protocols which are well known in the art. For instance, a method similar to 5'-RACE is available for generating the missing 5'-end of a desired full-length transcript. (Fromont-Racine et al., 1993, Nucl. Acids Res. 21:1683-1684).

Once the DNA fragments are generated, identification of the specific DNA fragment containing the desired HASH2 gene, the SMS3 gene, the TSSC6 gene, the RIBO26 gene, the CD81 gene, the TSSC4 gene, SEQ ID NO:13 or SEQ ID NO:14 may be accomplished in a number of ways. For example, if an amount of a portion of the HASH2 gene, the SMS3 gene, the TSSC6 gene, the RIBO26 gene, the CD81 gene or the TSSC4 gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in SEQ ID NOS:7, 8, 9, 10, 11, 12, 13 or 14. Preferably, a fragment is selected that is highly unique to the polypeptides of the invention. Those DNA fragments with substantial homology to the probe will hybridize. As noted above, the greater the degree of homology, the more stringent hybridization conditions can be used. In one embodiment, low stringency hybridization conditions are used to identify a homologous HASH2, SMS3, TSSC6, or RIBO26 polynucleotide. However, in a preferred aspect, and as demonstrated experimentally herein, a nucleic acid encoding a polypeptide of the invention will hybridize to a nucleic acid derived from the polynucleotide sequence depicted in SEQ ID NOS:7, 8, 9, 10, 11 or 12 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the HASH2, SMS3, the TSSC6, RIBO26, CD81 or TSSC4 polypeptide.

A gene encoding HASH2, SMS3, TSSC6, RIBO26, CD81 or TSSC4 polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the HASH2 gene (nucleotides 7028-7609 of SEQ ID NO:7), SMS3 gene (nucleotides 18959-21311 of SEQ ID NO:8), TSSC6 gene (nucleotides 5011-20067 of SEQ ID NO:9), RIBO26 gene (nucleotides 11487-11924 of SEQ ID NO:10), CD81 gene (nucleotides 10471-29787 of SEQ ID NO:11) or TSSC4 gene (nucleotides 13982-14971 of SEQ ID NO:12) operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The invention is further directed to a nucleic acid construct comprising expression control sequences derived from SEQ ID NOS: 7, 8, 9, 10, 11 or 12 and a heterologous polynucleotide sequence.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences which regulate the expression of the polynucleotide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the prokaryotic beta-lactamase gene (VIIIa-Komaroff et al., 1978, *Proc. Natl. Acad. Sci. USA* 75: 3727-3731), as well as the tac promoter (DeBoer et al., 1983, *Proc. Natl. Acad. of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans acetamidase, Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8: 423-488.

Eukaryotic promoters may be obtained from the genomes of viruses such as polyoma virus, fowlpox virus, adenovirus, bovine papilloma virus, avian sarcoma virus, cytomegalovirus, a retrovirus, hepatitis-B virus and SV40. Alternatively, heterologous mammalian promoters, such as the actin promoter or immunoglobulin promoter may be used.

The constructs of the invention may also include enhancers. Enhancers are cis-acting elements of DNA, usually from about 10 to about 300 bp that act on a promoter to increase its transcription. Enhancers from globin, elastase, albumin, alpha-fetoprotein, and insulin enhancers may be used. However, an enhancer from a virus may be used; examples include SV40 on the late side of the replication origin, the cytomegalovirus early promoter enhancer, the polyoma enhancer on the late side of the replication origin and adenovirus enhancers.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region, which codes for an amino acid sequence linked to the amino terminus of the polypeptide which can direct the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or pro-polypeptide (or a zymogen in some cases). A pro-polypeptide is generally inactive and can be converted to a mature active polypeptide by catalytic or autocatalytic cleavage of the propeptide from the pro-polypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the polynucleotide of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. An example of suitable selectable markers for mammalian cells are those that enable the identification of cells competent to take of the nucleic acids of the present invention, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980).

The vectors of the present invention preferably contain an element(s) that permits stable integration of the vector into the host cell genome or autonomous replication of the vector in the cell independent of the genome of the cell.

For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional polynucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS 1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a polynucleotide sequence of the present invention may be inserted into the host cell to increase production of the gene product. An increase in the copy number of the polynucleotide sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, or a *Streptomyces* cell, e.g., *Streptomyces lividans* or *Streptomyces murinus*, or gram negative bacteria such as *E. coli* and *Pseudomonas* sp.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian cell (e.g., human cell), an insect cell, a plant cell or a fungal cell. Mammalian host cells that could be used include but are not limited to human Hela, embryonic kidney cells (293), lung cells, H9 and Jurkat cells, mouse NIH3T3 and C127 cells, Cos 1, Cos 7 and CV1, quail QC1-3 cells, mouse L cells and Chinese Hamster ovary (CHO) cells. These cells may be transfected with a vector containing a transcriptional regulatory sequence, a protein coding sequence and transcriptional termination sequences by lipid-mediated, calcium phosphate mediated or DEAE-dextran mediated transfection (reviewed in Sambrook and Russell, Molecular Cloning, A Laboratory Manual, Cold Spring Harbor Laboratory Press, Cold Spring Harbor, N.Y., 2001). Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells. The polynucleotide may be directly introduced into the eukaryotic cell via electroporation, bolistics, or polybrene (reviewed in Sambrook and Russell, supra).

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra). The fungal host cell may also be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980). The fungal host cell may also be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M I., editors, *Guide to Yeast Genetics and Molecular Biology*, Methods in Enzymology, Volume 194, pp 182-187, Academic Press, Inc., New York; Ito et al., 1983, *Journal of Bacteriology* 153: 163; and Hinnen et al., 1978, *Proc. Natl. Acad. Sci. USA* 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, the presence of the HASH2 and RIBO26 protein may be detected using standard transcription assays. The presence of TSSC4 and TSSC6 may be detected by assaying for tumor suppressor activity in rhabdomyosarcoma cells (Koi et al., 1993, Science 260:361-364). The presence of CD81 may be detected by assaying for binding to E2 hepatitis C protein (Allander et al., 2000, J. Gen. Virol. 81:2451-2459).

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Antibodies

According to the invention, the HASH2, SMS3, TSSC6, RIBO26, CD81 or TSSC4 polypeptides produced according to the method of the present invention may be used as an immunogen to generate any of these antibodies. Such antibodies include but are not limited to polyclonal, monoclonal, chimeric, single chain, Fab fragments, and an Fab expression library.

Various procedures known in the art may be used for the production of antibodies. For the production of antibody, various host animals can be immunized by injection with the polypeptide thereof, including but not limited to rabbits, mice, rats, sheep, goats, etc. In one embodiment, the polypeptide or fragment thereof can optionally be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the HASH2, SMS3, TSSC6, RIBO26, CD81 or TSSC4 polypeptide, any technique that provides for the production of antibody molecules by continuous cell lines in culture may be used. These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for the HASH2, SMS3, TSSC6, RIBO26, CD81 or TSSC4 polypeptide together with genes from a human antibody molecule of appropriate biological activity can be used; such antibodies are within the scope of this invention.

According to the invention, techniques described for the production of single chain antibodies (U.S. Pat. No. 4,946,778) can be adapted to produce polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for the HASH2, SMS3, TSSC6, RIBO26, CD81 or TSSC4 polypeptides.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$, fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a particular polypeptide, one may assay generated hybridomas for a product which binds to a particular polypeptide fragment containing such epitope. For selection of an antibody specific to a particular polypeptide from a particular species of animal, one can select on the basis of positive binding with the polypeptide expressed by or isolated from cells of that species of animal.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Uses of Polynucleotides

Diagnostics

Polynucleotides containing noncoding regions of SEQ ID NOS:7, 8, 9, 10, 11, 12, 13 or 14 may be used as probes for detecting mutations from samples from a patient. Genomic DNA may be isolated from the patient. A mutation(s) may be detected by Southern blot analysis, specifically by hybridizing restriction digested genomic DNA to various probes and subjecting to agarose electrophoresis. Alternatively, these polynucleotides may be used as PCR primers and be used to amplify the genomic DNA isolated from the patients. Additionally, primers may be obtained by routine or long range PCR that yield products containing contiguous intron/exon sequence and products containing more than one exon with intervening intron. The sequence of the amplified genomic DNA from the patient may be determined using methods known in the art. Such probes may be between 10-100 nucleotides in length and may preferably be between 20-50 nucleotides in length. Specifically, probes derived from SEQ ID NOS: 13 or 14 may be used to identify mutations duplications, translocations, polysomies and mosaicism associated with Beckwith-Wiedemann syndrome.

Thus the invention is thus directed to kits comprising these polynucleotide probes. In a specific embodiment, these probes are labeled with a detectable substance.

Antisense Oligonucleotides and Mimetics

The antisense oligonucleotides or mimetics of the present invention may be used to decrease levels of a polypeptide. For example, HASH2 is required for development of the trophoblast. Therefore, the HASH2 antisense oligonucleotides of the present invention could be used as an antifertility agent. RIBO26 is expressed in abundance in small cell tumors of the lung. RIBO26 antisense sequences could be used to inhibit small cell tumor growth. CD81 plays a role in T cell activation, and its antisense sequences may help control autoimmune disorders in which T cell activation is uncontrolled. CD81 also binds the human hepatitis C virus; thus CD81 antisense sequences may, by reducing CD81 expression, reduce the infectivity of the human hepatitis C virus. The TSSC4 and 6 proteins act as tumor suppressors. Therefore, antisense sequences may act as antiapoptosis agents.

The HASH2, SMS3, TSSC6, RIBO26, CD81 and TSSC4 genes are all situated in a region of chromosome 11 known to be associated with the Beckwith-Wiedemann Syndrome. Thus, antisense sequences of any of these six genes may provide means of managing patients with the Beckwith-Wiedemann Syndrome. Furthermore, antisense oligonucleotides of SEQ ID NOS:13 or 14 may be used for the same purpose.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ as found to be effective in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, HASH2 is necessary for development of the trophoblast, RIBO26 is a component of the ribosome, TSSC6 and TSSC4 are involved in repressing tumor growth, and CD81 is involved in T cell activation. Therefore, the HASH2 gene may be used to treat some forms of infertility. The CD81 gene may be used in patients whose ability to activate T cells is impaired. CD81 also binds the human hepatitis C virus, thus gene therapy designed to yield a secretable form of CD81 may, by binding the virus in an excretable form, reduce the spread of hepatitis C. Given the tumor suppressing actions of TSSC6 and TSSC4, their genes may be used to prevent tumor growth. RIBO26 may be used to treat disorders in which ribosome assembly is defective. The SMS3 gene is situated within the Beckwith-Wiedemann Syndrome locus and may thus be useful for treatment of patients in which the SMS3 gene is nonfunctional.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," *Science,* 247, 1465-1468, 1990; and Wolff, Jon A, "Human dystrophin expression in mdx mice after intramuscular injection of DNA constructs," *Nature,* 352, 815-818, 1991. As used herein, vectors are agents that transport the gene into the cell without degradation and include a promoter yielding expression of the gene in the cells into which it is delivered. As will be discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes:

a) Biological agents derived from viral, bacterial or other sources.

b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous poly A addition signals. Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN™ and LIPOFECTACE™, which are formed of cationic lipids such as N-[1-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, Nature 337:387 (1989)). Intravenous injection of cationic lipid-plasmid complexes into mice has been shown to result in expression of the DNA in lung (Brigham et al., Am. J. Med. Sci. 298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J-P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is $N^4$-spermine cholesteryl carbamate (GL-67) disclosed in U.S. Pat. No. 5,767,099. Additional preferred lipids include $N^4$-spermidine cholestryl carbamate (GL-53) and 1-($N^4$-spermidine)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class I molecule complexed to beta2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

What is claimed is:

1. A method of identifying variants of SEQ ID NO:12 or its complementary sequence comprising (a) isolating genomic polynucleotide from a subject and (b) determining the presence or absence of a variant in said genomic polynucleotide using an isolated polynucleotide at least 50 nucleotides in length identical to a region of SEQ ID NO:12, said region selected from the group consisting of a 5'-noncoding region, a 3'-noncoding region and a contiguous coding and non-coding nucleic acid sequence of SEQ ID NO:12 or reverse strand of said polynucleotide wherein said 5'-noncoding region consists of nucleotides 1-13981 of SEQ ID NO:12 and said 3'-noncoding region consists of nucleotides 14968-14972 of SEQ ID NO:12.

2. The method of claim 1, wherein the genomic polynucleotide is genomic DNA or RNA.

* * * * *

UNITED STATES PATENT AND TRADEMARK OFFICE

CERTIFICATE OF CORRECTION

PATENT NO. : 8,765,928 B2
APPLICATION NO. : 13/846050
DATED : July 1, 2014
INVENTOR(S) : Ryan It is certified that error appears in the above-identified patent and that said Letters Patent is hereby corrected as shown below:

ON THE TITLE PAGE:
Item (73) (Assignee): Replace “Ryogen LLC, Suffein, NY” with --Ryogen LLC, Suffern, NY--.

Signed and Sealed this
Seventh Day of October, 2014

Michelle K. Lee
*Deputy Director of the United States Patent and Trademark Office*

SEQUENCE LISTING

```
<160> NUMBER OF SEQ ID NOS: 14

<210> SEQ ID NO 1
<211> LENGTH: 193
<212> TYPE: PRT
<213> ORGANISM: Homo sapiens

<400> SEQUENCE: 1

Met Asp Gly Gly Thr Leu Pro Arg Ser Ala Pro Pro Ala Pro Pro Val
1               5                   10                  15

Pro Val Gly Cys Ala Ala Arg Arg Arg Pro Ala Ser Pro Glu Leu Leu
            20                  25                  30

Arg Cys Ser Arg Arg Arg Arg Pro Ala Thr Ala Glu Thr Gly Gly Gly
        35                  40                  45

Ala Ala Ala Val Ala Arg Arg Asn Glu Arg Glu Arg Asn Arg Val Lys
    50                  55                  60

Leu Val Asn Leu Gly Phe Gln Ala Leu Arg Gln His Val Pro His Gly
65                  70                  75                  80

Gly Ala Ser Lys Lys Leu Ser Lys Val Glu Thr Leu Arg Ser Ala Val
                85                  90                  95

Glu Tyr Ile Arg Ala Leu Gln Arg Leu Leu Ala Glu His Asp Ala Val
            100                 105                 110

Arg Asn Ala Leu Ala Gly Gly Leu Arg Pro Gln Ala Val Arg Pro Ser
        115                 120                 125

Ala Pro Arg Gly Pro Pro Gly Thr Thr Pro Val Ala Ala Ser Pro Ser
    130                 135                 140

Arg Ala Ser Ser Ser Pro Gly Arg Gly Gly Ser Ser Glu Pro Gly Ser
145                 150                 155                 160

Pro Arg Ser Ala Tyr Ser Ser Asp Asp Ser Gly Cys Glu Gly Ala Leu
                165                 170                 175

Ser Pro Ala Glu Arg Glu Leu Leu Asp Phe Ser Ser Trp Leu Gly Gly
            180                 185                 190

Tyr


<210> SEQ ID NO 2
<211> LENGTH: 132
<212> TYPE: PRT
<213> ORGANISM: Homo sapiens

<400> SEQUENCE: 2

Met Gly Arg Thr Trp Cys Gly Met Trp Arg Arg Arg Arg Pro Gly Arg
1               5                   10                  15
```

-continued

```
Arg Ser Ala Val Pro Arg Trp Pro His Leu Ser Ser Gln Ser Gly Val
            20                  25                  30

Glu Pro Pro Asp Arg Trp Thr Gly Thr Pro Gly Trp Pro Ser Arg Asp
        35                  40                  45

Gln Glu Ala Pro Gly Ser Met Met Pro Pro Ala Ala Ala Gln Pro Ser
    50                  55                  60

Ala His Gly Ala Leu Val Pro Pro Ala Thr Ala His Glu Pro Val Asp
65                  70                  75                  80

His Pro Ala Leu His Trp Leu Ala Cys Cys Cys Cys Leu Ser Leu Pro
                85                  90                  95

Gly Gln Leu Pro Leu Ala Ile Arg Leu Gly Trp Asp Leu Asp Leu Glu
            100                 105                 110

Ala Gly Pro Ser Ser Gly Lys Leu Cys Pro Arg Ala Arg Arg Trp Gln
        115                 120                 125

Pro Leu Pro Ser
    130


<210> SEQ ID NO 3
<211> LENGTH: 290
<212> TYPE: PRT
<213> ORGANISM: Homo sapiens

<400> SEQUENCE: 3

Met Val Thr Leu Thr Tyr Phe Gly Ala His Phe Ala Val Ile Arg Arg
1               5                   10                  15

Ala Ser Leu Glu Lys Asn Pro Tyr Gln Ala Val His Gln Trp Ala Phe
            20                  25                  30

Ser Ala Gly Leu Ser Leu Val Gly Leu Leu Thr Leu Gly Ala Val Leu
        35                  40                  45

Ser Ala Ala Ala Thr Val Arg Glu Ala Gln Gly Leu Met Ala Gly Gly
    50                  55                  60

Phe Leu Cys Phe Ser Leu Ala Phe Cys Ala Gln Val Gln Val Val Phe
65                  70                  75                  80

Trp Arg Leu His Ser Pro Thr Gln Val Glu Asp Ala Met Leu Asp Thr
                85                  90                  95

Tyr Asp Leu Val Tyr Glu Gln Ala Met Lys Gly Thr Ser His Val Arg
            100                 105                 110

Arg Gln Glu Leu Ala Ala Ile Gln Asp Val Phe Leu Cys Cys Gly Lys
        115                 120                 125

Lys Ser Pro Phe Ser Arg Leu Gly Ser Thr Glu Ala Asp Leu Cys Gln
    130                 135                 140

Gly Glu Glu Ala Ala Arg Glu Asp Cys Leu Gln Gly Ile Arg Ser Phe
145                 150                 155                 160

Leu Arg Thr His Gln Gln Val Ala Ser Ser Leu Thr Ser Ile Gly Leu
                165                 170                 175

Ala Leu Thr Val Ser Ala Leu Leu Phe Ser Ser Phe Leu Trp Phe Ala
            180                 185                 190

Ile Arg Cys Gly Cys Ser Leu Asp Arg Lys Gly Lys Tyr Thr Leu Thr
        195                 200                 205

Pro Arg Ala Cys Gly Arg Gln Pro Gln Glu Pro Ser Leu Leu Arg Cys
    210                 215                 220

Ser Gln Gly Gly Pro Thr His Cys Leu His Ser Glu Ala Val Ala Ile
225                 230                 235                 240

Gly Pro Arg Gly Cys Ser Gly Ser Leu Arg Trp Leu Gln Glu Ser Asp
                245                 250                 255
```

```
Ala Ala Pro Leu Pro Leu Ser Cys His Leu Ala Ala His Arg Ala Leu
            260                 265                 270

Gln Gly Arg Ser Arg Gly Gly Leu Ser Gly Cys Pro Glu Arg Gly Leu
        275                 280                 285

Ser Asp
    290


<210> SEQ ID NO 4
<211> LENGTH: 145
<212> TYPE: PRT
<213> ORGANISM: Homo sapiens

<400> SEQUENCE: 4

Met Lys Phe Asn Pro Phe Val Thr Ser Asp Arg Ser Lys Asn Arg Lys
1               5                   10                  15

Arg His Phe Asn Ala Pro Ser His Val Arg Arg Lys Ile Met Ser Ser
            20                  25                  30

Pro Leu Ser Lys Glu Leu Arg Gln Lys Tyr Asn Val Arg Ser Met Pro
        35                  40                  45

Ile Arg Lys Asp Asp Glu Val Gln Val Val Arg Gly His Tyr Lys Gly
    50                  55                  60

Gln Gln Ile Gly Lys Val Val Gln Val Tyr Arg Lys Lys Tyr Val Ile
65                  70                  75                  80

Tyr Ile Glu Arg Val Gln Arg Glu Lys Ala Asn Gly Thr Thr Val His
                85                  90                  95

Val Gly Ile His Pro Ser Lys Val Val Ile Thr Arg Leu Lys Leu Asp
            100                 105                 110

Lys Asp Arg Lys Lys Ile Leu Glu Arg Lys Ala Lys Ser Arg Gln Val
        115                 120                 125

Gly Lys Glu Lys Gly Lys Tyr Lys Glu Glu Leu Ile Glu Lys Met Gln
    130                 135                 140

Glu
145


<210> SEQ ID NO 5
<211> LENGTH: 236
<212> TYPE: PRT
<213> ORGANISM: Homo sapiens

<400> SEQUENCE: 5

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
            20                  25                  30

Leu Trp Leu Arg His Asp Pro Gln Thr Thr Asn Leu Leu Tyr Leu Glu
        35                  40                  45

Leu Gly Asp Lys Pro Ala Pro Asn Thr Phe Tyr Val Gly Ile Tyr Ile
    50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
        115                 120                 125
```

```
Gln Ala Leu Gln Gln Ala Val Val Asp Asp Asp Ala Asn Asn Ala Lys
    130                 135                 140

Ala Val Val Lys Thr Phe His Glu Thr Leu Asp Cys Cys Gly Ser Ser
145                 150                 155                 160

Thr Leu Thr Ala Leu Thr Thr Ser Val Leu Lys Asn Asn Leu Cys Pro
                165                 170                 175

Ser Gly Ser Asn Ile Ile Ser Asn Leu Phe Lys Glu Asp Cys His Gln
            180                 185                 190

Lys Ile Asp Asp Leu Phe Ser Gly Lys Leu Tyr Leu Ile Gly Ile Ala
        195                 200                 205

Ala Ile Val Val Ala Val Ile Met Ile Phe Glu Met Ile Leu Ser Met
    210                 215                 220

Val Leu Cys Cys Gly Ile Arg Asn Ser Ser Val Tyr
225                 230                 235


<210> SEQ ID NO 6
<211> LENGTH: 329
<212> TYPE: PRT
<213> ORGANISM: Homo sapiens

<400> SEQUENCE: 6

Met Ala Glu Ala Gly Thr Gly Glu Pro Ser Pro Ser Val Glu Gly Glu
1               5                   10                  15

His Gly Thr Glu Tyr Asp Thr Leu Pro Ser Asp Thr Val Ser Leu Ser
            20                  25                  30

Asp Ser Asp Ser Asp Leu Ser Leu Pro Gly Gly Ala Glu Val Glu Ala
        35                  40                  45

Leu Ser Pro Met Gly Leu Pro Gly Glu Glu Asp Ser Gly Pro Asp Glu
    50                  55                  60

Pro Pro Ser Pro Pro Ser Gly Phe Leu Pro Ala Thr Val Gln Pro Phe
65                  70                  75                  80

His Leu Arg Gly Met Ser Ser Thr Phe Ser Gln Arg Ser Arg Asp Ile
                85                  90                  95

Phe Asp Cys Leu Glu Gly Ala Ala Arg Arg Gly Pro Ser Ser Val Ala
            100                 105                 110

His Thr Ser Met Ser Asp Asn Gly Gly Phe Lys Arg Pro Leu Ala Pro
        115                 120                 125

Ser Gly Arg Ser Pro Val Glu Gly Leu Gly Arg Ala His Arg Ser Pro
    130                 135                 140

Ala Ser Pro Arg Val Pro Pro Val Pro Asp Tyr Val Ala His Pro Glu
145                 150                 155                 160

Arg Trp Thr Lys Tyr Ser Leu Glu Asp Val Thr Glu Val Ser Glu Gln
                165                 170                 175

Ser Asn Gln Ala Thr Ala Leu Ala Phe Leu Gly Ser Gln Ser Leu Ala
            180                 185                 190

Ala Pro Thr Asp Cys Val Ser Ser Phe Asn Gln Asp Pro Ser Ser Cys
        195                 200                 205

Gly Glu Gly Arg Val Ile Phe Thr Lys Pro Val Arg Gly Val Glu Ala
    210                 215                 220

Arg His Glu Arg Lys Arg Val Leu Gly Lys Val Gly Glu Pro Gly Arg
225                 230                 235                 240

Gly Gly Leu Gly Asn Pro Ala Thr Asp Arg Gly Glu Gly Pro Val Glu
                245                 250                 255
```

-continued

```
Leu Ala His Leu Ala Gly Pro Gly Ser Pro Glu Ala Glu Glu Trp Gly
            260                 265                 270

Ser Pro His Gly Gly Leu Gln Glu Val Glu Ala Leu Ser Gly Ser Val
        275                 280                 285

His Ser Gly Ser Val Pro Gly Leu Pro Pro Val Glu Thr Val Gly Phe
    290                 295                 300

His Gly Ser Arg Lys Arg Ser Arg Asp His Phe Arg Asn Lys Ser Ser
305                 310                 315                 320

Ser Pro Glu Asp Pro Gly Ala Glu Val
                325


<210> SEQ ID NO 7
<211> LENGTH: 17290
<212> TYPE: DNA
<213> ORGANISM: Homo sapiens

<400> SEQUENCE: 7

gcccctgcct ggatcacaac aggcaggacg gctgagcagg cacacatctg tctctccctc      60

tgctgatctg tggccttgga caggggctac tctgggggag ctgacaggtg acccccccag     120

gaggcccctc cctgcctctg ggctgggaat ccacctctgt ggagcccctg ggaatggcct     180

gtttcaaata cgtaagtggg agcaaggtct catcctcagc gggggacatc gctgggggca     240

aggccagtgg gtgggtggga aggtttctgt ggcactgggg cctcctgttg attgattcac     300

ccaattaatc acagccagca gctggggagg gggtaggaag gcggtgaagg gaaaaggagc     360

ccacagccgg gaggccctgg gaggttggca gaggcctgca cctgcctgca gccagccctc     420

cggcccagcc ctcttccctc ctttcggagg ggccagagca tggggtgcta agggctcagt     480

ctttaacccc tccccagctc tcagggagcc cctcccatgc tccccaggcc tctgccccac     540

ttgcacctcc ccgggcccca gggcacagga cgctttcccc accctttggg aggctgaggg     600

tgtcaggagg cctgggctga gtgctggctt ccgtctcact ggcttgcaga caagaccctc     660

catttcggtg gaaaaacagc aagaacagca ccccccctcca ggcagaccca agggaggcat     720

cggtgtgagg gcttcaagct ctgtactgtg ggtttaagcc ttgcacctct ggatacctgt     780

gggcctcggg cagatcactg agcctccctg catctggaag tcggggtgag accccctcaga    840

gggggctggg aggaggaagg gcccctcttg atgggcagcc cccaccctcc acctactgcc     900

ctgccctccc agccttcagg gtcctcccca gcttctgtgg gctcccaggt ggacctgggc     960

cacccctgag accccgaaga gctcaaggcc agctaatagc ccacaggctc aggacagcac    1020

tggacaggcc tctgggccca cctggcccca ctcccgattt ttatgggaac aaagactgaa    1080

ggtgtggccc caaaggaacc accccctcccc cagtgccccg ctgctgggaa aagggtcagc   1140

agagtttggg tctcccccca caagccctct gggctgtgcg tgctacagct gaggacatgg    1200

cgttgagggg caggccgcct ccaaccccgt ccaccttgcc ctgtctagct ctgtccaagg    1260

ctctctccgg ctggctaatc acctctgggc acagctgtgc tgctgaggtc tctgggatga    1320

ctgaaggtct ttgaaggcca ctttgggaga agcgaaggtg catggacacc agggaccctg    1380

ctcacagcga gtgtccctgc cccatccctt tctgcattga gtgggacaag cttgcttcca    1440

tttgggggat cgccatctga ctattccact tgtcttaggg tggggcagag attaggtgat    1500

gtggaggggc ttctctacat ggcccccctg ccccagctct gaggggtagc accagagtgg    1560

gtttcaccag cgtagggcac gtaggccccg ccatgaacag ggccccaacc ttggtttaat    1620

gctttgctac tgccatctta aagttctttt tttatttttt attttgcttt attttttatt    1680
```

-continued

```
agagatgggg tctcccagtg ttgcccaggc tggtcttgaa ctcctggctc aagcaatcct   1740
ccggcctcag cctcccaaag cactgggatg acacgtgtga gccaccttgc ctggcctttg   1800
gaatctgact acttttatct tctaacttgt tttgcaggtg caggccaacg gcatacagca   1860
gcactcacat aagcaaagga gagcgtgcac aaggcgccaa atgtatatcc accctcactc   1920
gtccccccac ttgagtagcg catccacgat gcccacagac accaggccac acagaaaagg   1980
tgccagggac ccacagcagt gcaaggcagc gtgtcacacc tacgcatgag caagccgggc   2040
gctgatggcc accgagcagc cacgttttcc attcaaatcc gcacttgcta aggatgcagc   2100
aggaagccag tggtgttcta acaaacgtgc aggacccggg aacctgtcat gtcctttctt   2160
acttgtgcga cttctctgtg ttagccgagg tctcttgctg atggatctac ccacagtgcc   2220
ttttgtcttt gaacttgtcc cttccctcct tcctcgccca tcagcgagca ggaggtggag   2280
ggtgctggtg gaacaagcct gcgtcaagga gtgaaatcag ctgatttcat ttttgtgcag   2340
tttccactgt tctagtagca aatgaaatag agacgcctgt gccaggacaa aacacacact   2400
gtgtcattcc agtgattccg catagaagtt aaatgctctt atgcttgcat tttaaactgg   2460
catcacataa tataaagatg gataactaca ttcacgctag tcacttaaat tcctaatctt   2520
tcttactcag aatggcatta aatagtgagt ataaaataag aagtataaaa tagtaagtca   2580
agaggttgac tatagaagaa agaaaaatgc tttatatttt agcaccttga acatgacatc   2640
acgatcacct tctccctgga atcagtttct aacttccagg tggggactag gcctggacca   2700
tgagctccta gcagagccct gctgccccca cagcagagcc caggacaggc tggcacctgg   2760
gccaggtgag gctctgtcca ggctcactga tctcaaatgc tgaactgcta aggatgtcat   2820
gtccccaaag gagccgccag gctcagcctc acttcctgga aggcgtgaac attgcaagaa   2880
tgtggaagtg aaagagtcca gggcttaaat ctcaattctc atcattttca agctgagtcc   2940
aagggagaga agacagtcat ggattcttag tttctgtttc tggttgagcc agcagggtcc   3000
cttcctcatc cctcttttct gcttatcact agagacagaa actaaaacca tgactttagg   3060
ctgctgagag cctaaaacaa aacgacagca agagaaggtg ggttggacca gcttgcctgt   3120
gacttcaggc acttcatctt tactgggcac tgggtgaatg acagtgtggg gaggggtctt   3180
cataacacgg caatcagcag cccactgtgc ccaggagact cgcctgtggt cctggttatc   3240
aaccacagcc ctttccagtc tcaaaaatgt ccccgctggg acagcaagtt acatcgtcgc   3300
tacaagtcct gtctcctggg agatgcagtc cagcagcact acatcctctg agcagcaggt   3360
gccaagtggg atgaactgga taaggactgc attcggggaa acgcccgtgt gaaaggaaat   3420
acacaggaag gaggtggcaa cgggtgggaa gccactagac cacgacgcga ttctgcccca   3480
gtgaaggcga ggggatagcc tggggcctaga tcgctgtgag gtctatggaa gtttccacaa   3540
gcttgctggg tagttctcga ggcaaactcg gaaagggagt cccttgtctc cctggaacgg   3600
atctttcttg gcatctctgt cacactcatt aggtgggcct ggtgtcaacc ccatttgcag   3660
gccaccccaa acttgatcaa aggtccgctt ctggcacccc ataccctgtc ctacaggaaa   3720
tacagggaca ggctcccaat aacaacaccc agcacggtgc catcaacacc accacgcaca   3780
cgggggctca acggaacaga catctccgct tcttcaatga agacactgga gggaaattgc   3840
ttacaaggcg cttaagagac ctattaagca aacttgatgt gtggacctgc ggcggatccc   3900
gattctataa ggccaactgc acaaaaccac gagacccccct gaggactgcg ccattggctg   3960
ggtccccgat gatatgaaag aacggtggtt catttgagcg ggtgatgttt ttgcggtttc   4020
ctttagaggc acacgtgaaa catgacgggt gaaaggattc aaagtctggg atttgcttca   4080
```

-continued

```
aagcaacgca gggatggcgt gggggatgga tggggcagga agggccttga aactggtgct   4140
ggaggcttcc cagggctgcc ctggagccca gtgcgtcctc caccggccag actgtacaac   4200
ggttggatcc tgtgtccact gctaggaccc aggctccacg agcacgggct tgtgtggcac   4260
acggatgcac cctaagtcct ggcacagaga ctgctcaaca aaggcctcgg tgcttttgtg   4320
tatgtttgaa attttccata ataaaatgaa aaatgggaaa atgggaaaac aaaaatggca   4380
gcactactta ccctctgcag agttttgtcc gcttcacgcc agtgggtggc agtcgtttcc   4440
tctgccctgg ccttccatcg tttcccccct accctcttca cccacccaac agccccctgt   4500
ggtcctggca gctgtgggcc tttccttgag gtcaaggtgt ggagtcctgg ggagggctca   4560
gggaggccac cgacccgggt gtggattctg ggagaagcct gtgggatgtc cctccctggg   4620
tgaccacggc aatgtgcccc ctcctgtccc ttggccaagg ccagttccct gagccctgca   4680
gccccaagcc acagctggtc cactgacccc agttgagcct ggtcctcatc agaccagctg   4740
acccctttga cccccgctac agactcggct ttgaccttgg ctgctgagga gcccccacct   4800
ggactgaggc tgcagctggc gagagaggag ccctgagctc ctctgataag aagggacctg   4860
gccagcctga cgtttgagac ccaggcatcc cggtagcctg ggtgtcctgt tgccgtggtt   4920
attcaggagc cacccactct gggacaacac cagctgctcc cacctcgcag ggctcccacg   4980
gctctgtccc aaccactcct ttctgaagga aggggtgcct ctgcgcccta aagaaaccgg   5040
gggagcccca caacccctcc cccaccagga cactaaaagg cagctttcgg tacagtgaga   5100
catcaaagcc tcctaggccc tgagtcaaag gtatagccgt gtaatatccc agtgccagct   5160
ctccggctgc ggggagcctg gcgcaaagct tccaagcctt ccttgttcct ttcaagagcc   5220
gctcttagaa ttcaggtgag cggagacctg cagggcctcc ccagtgcggg caaaacccaa   5280
agctagcgag agggcagcct ccaggcacct ctcactaact cctcccagag gccgttgagg   5340
tgggtctggt caaacccatt tgcaagttaa cccacttgcc ctgggctgcc cagctgccac   5400
gttagtggag atctgagcgt ggtggcctgc gcaggagccc atgccctcag ccccacagcc   5460
ggtgctctct ggtcagacca cctcagccta gccccacacc cagcacttac cccagccctc   5520
gggatgggtc agcagcctcc agcctgcagc ttccaagcca gcgagtagcc ctgtctggac   5580
aacccaccag cccaccacct cctggaggat gcccccagcc tcacaaggtg tcccaatggc   5640
tccgctatca acggcctggc tgcactccag atctcaccca gacccaccct acggaggagg   5700
cagcagggtt tgaggagtag tgaccacgga agtctggccg tcacctggga agtgtaggtg   5760
ataggagcca ctggtaaaca gaactgattt atttataaag ttcacgctcc cttgaagagg   5820
tgtgccccac acaggcttct ccctagcaga gcagcagtgc ccacaaaccc accccagggt   5880
gggctgtcac gggggcctca cgccagggac cccgcccctc agggactgct cgtgtccaga   5940
tcttggccag catggaaaac tccagatagt gggggcaggg gtccaggtca tctttattac   6000
gccccaggtc aagggttctt tgtacaaaaa taggtctccg tttgccagca gtgtccctcc   6060
agcagctcaa gttaatgtgt agaaaatgga ttctctgtgc ccttagaaaa tcctctcccc   6120
tccggaaaaa tctccaagtg ttggtgcccc ccgccccact gcagtcgaga agctgtgggg   6180
aggggcggcg tcggaggaag ccgccagccc ttatggggcc agctccaagc ccgtttccac   6240
cgcggcattg gtcaggctgg gccggacgaa cgaggcggcg tcggcggtgc ggggggtggt   6300
gggtgggtcc ccggctcgct gggggcggag cgcgggccgg tccacctggc gggctccccg   6360
gcgatgagcg cgccggccgc tcgctcggct tccggggctg aggctgcggg gggaaggtgg   6420
```

-continued

```
ggaaccaaac gcgcgtcaac gcgggcgcgg gcccggggca gaccccgccc gggccggccc   6480
tgcccgcacc tcccccaagc gaactcggca gtttcgtttg ctcggttggt tttggagtct   6540
tgagtccgtg ggtgccgcga ctcggtctga gacacggcgg gggcggggcg ggcgctcgga   6600
gccgcggtga gtcagggctc cgcgcccgcc gactcatttc tgccgccccg gcccgggagc   6660
gcgatttgca atgcaaagtc accccgcctc cagcacccca atctgcccca ggatccgcca   6720
gcactagaga cctcaacggc ccgacggccg ctcccctccc ctcgtctacc cctccctcgt   6780
cggcggctga gccgcgaggg gaagttttgc aatcccggac aaacaaacgc cggtcttgca   6840
cgggcttgaa aaactttggg ggaaatgaag agtgagcgaa atcgaagcca tcgctcgggc   6900
ctggcgctcg gctccgcggg ctcctggggg cgcgacccgc cgggcctgcc caccccgtcc   6960
ctccaccccg gcccccggcc ctccctcctc cctgcctccc ggctgttacc tcataggtcg   7020
agggcgctca gtagcccccct aaccagctgg agaagtcgag tagctcgcgc tccgcaggac   7080
tcagcgcgcc ttcgcagccg ctgtcgtccg acgagtaggc ggaacgcggg gagccgggct   7140
ccgagctgcc cccgcggccc ggggacgaag aagcgcggga gggcgaggcg gcgaccgggg   7200
tggtccctgg cggcccgcgg ggcgcagacg gccgcacggc ctgcggcctc agccctcccg   7260
ccagcgcgtt gcgcacggcg tcgtgctcgg ccagcaggcg ctgcagcgcg cggatgtact   7320
ccacggctga gcgcagcgtc tccaccttgc tcagcttctt gctggcgccg ccgtgcggca   7380
cgtgctgccg cagcgcctgg aagcccaagt tcaccagctt cacgcggttg cgctcgcgct   7440
cattgcgccg cgctacggcc gctgcgccgc ctccggtctc tgcggtggcc ggtcgccgcc   7500
gccggctgca gcgcaacagt tccggggacg cgggtctccg ccgggcagcg cagccgacag   7560
ggacgggggg cgcagggggc gcggacctgg gcagtgtgcc gccgtccatc gcgcctgcat   7620
ccacccgccc gctccaggtc ccggcgcgcc gcaggaaggt gcaggcagag gaaccggagg   7680
cgacggggaa aactgtggcg ccccaagggg gcttctggca cggcgccgcc aggcaactcc   7740
ccagggcacg cgtcctaggt cgtctggagc ccggggatag gaggcctagt ggtggcaggc   7800
cgtacgcgcc agggagcgtg ggacgctcgt gtcccgcgcg tgcggccgga ctctcccagg   7860
tctccgcagg cgcggcgcag gcggctggtt tttaaatgta tagataaccc tcctccgcgc   7920
cgccgccgtc gcctttctca cgccctcctt ccttcgcctc gccctcccgc cacgcttcgc   7980
cctccccctc gcgcgatcac attctgtaag gcccaaagcg tgcgcatgtc cccctagccc   8040
atcccccgga cgcagtccac agatccccag tgcgcccaac tggcgaaatc tgcgagttcc   8100
cggtgcgccc cctgctcccg gcaggtgctt agtgcgcccc caaagcaagg tacgcaggtc   8160
ctgggttgag ccttcccgta cccccaccct aaccccgcgc gcagccccgc cagtcccaag   8220
agccgccaga ccttcgcacg cgcagcgcgc gctgtgggag ggaaggcgcg gccctggcga   8280
caacacggct gttcgggagg cgcgcaagat ccccgggggc agcacgcgcc gcgcagccca   8340
cacccacgcc ccaccctcct ggggccgagg aggcgggggc cagggtctca gccaatcgtg   8400
ggccacccgt ttggccaatc gcgcagggcg cggctccacg cccggcccca ttgaggaagc   8460
gcgtacgcgt ggcgcgtggc tcacggggag catcgctaac aaagctgggt tcctgctggg   8520
ccccgccctg ctcctcgccc ccgcgactgg gctgggcgcg ctgtccccta gcgcagctat   8580
gtcccgagcg cgcccccacc tgtgcgttaa tctactggga atgggggtgg actgcgcctt   8640
acctggggcg gggtggggct taaggagtgg tcgagactga ggcggggtgg gaggttcagg   8700
ttcccggggc gccttcccca acccgccccg ctttccccgt ccctccacgc gcaccctgcc   8760
tgtggtttcc gtgcgccccc ggcctgaggg ctctgggcgg caccttaacc cggagggcct   8820
```

```
ggaggtctgc acccgaccgc cttgtgccag gacggtcagg tccacgccct cccccaccgt   8880
ggctccctcc atctgcagta tcccccacct ccagcccgtc ctgccctcct gttctccgtc   8940
tcgcttcccg tcggtgcctc cgggatctca cagccctcgc acctcttttg tgacccaggc   9000
tgtttttctg caccccccctc tcccctgagg gcactgagat tgggccattg gcctgaaggt   9060
ctctgggagc agcacccttc caggggaggt gggacgtcga gaacttctcc ctaagagatg   9120
cggggaaatg gtggggcctg agagtgcaaa cactgcagaa atgcgaaaaa tgtagtgtta   9180
acggaagagt ttaggtcctg cctcactgtc cgggaaacgc gtgccctcgg gggagccttt   9240
gccaagccgg tttttcccga aggtgaccag atgctcctgg gccactgcct ctgagacctc   9300
agggaacgga gatttttgtg gacccagctg cctggagctg ctttcctgtt ccggccggag   9360
gaggtgaggc ccaagacccc tcctgggagc ctgggggcag atagccagtg tttactgcca   9420
gcctcggggt gcccacctgc tcccattacc ctgcaggatg ctgctggctg gcccacctgg   9480
gcccccagca cacctgtgtc tcgagtacgc ctggccctcc tgccttggga ggggccggaa   9540
gagtagcacc tgcctgggag ctggtggtct gcggtctcta tttggcagat gaggaagccg   9600
acttggagag aaccctggat gtgtccacag tcactcctcc gcccagtgga gcgatccagg   9660
cagaaatcgg ggccctgagt ctgaatccgg gttctgcaac cagggcagat gcgggcttgc   9720
ctctgctccc tgtccctggt ctgagagccc attcttccca gatggtcact tggcaaatca   9780
cagcctggca tggattgttc tgccctcctt ctgctgcctc cctccttccc cttgtcaagg   9840
ctgcaagacc aggatctagg aacgatcctg gagccctgca aactaggcct tggaaatccc   9900
tgctggattt ccacctcccg ggctgggagc ccctcggtca tctgttgctg tgtaaggagc   9960
caccaggatt ttagcggtct gaacaacgat gtattatttc tcaggattct gtgacttgat  10020
gggtgggccc tctgctgctc tgggtgtggc tgcatacacc ccgggggtca acagggacga  10080
gcggtacagc ggctgggttg ctctctaccc ggtcttcgtc caagcccctc cacagctggt  10140
aagatctccg gagcaggacc tgcaagccct cttcagatca ccccagaact tcctgtctaa  10200
aaactgaagc ctctcactgc ccaggcatgg cttcttgcta ccctgccctc aggcacagtc  10260
ctgcacccac ctgcgtctgc tgtgccatgt ccaggccagt cccccccac caccaacacc  10320
tctctctatc ttcatcctct tcccaatctg gtcctcccac cgctgtggaa accccgtctg  10380
cccccaaagc ctagcttaaa aataattccc tagggacctg tgtctctccc tgcctcggcc  10440
cctccttcat tcctgggtgc ctccggctgt gcagcatttg acactgcagc accccccctta  10500
attcggaagc atgctgtctc ctggactggt gagtctccac actatctgag ccgtcttctc  10560
tggaactctt ggcctctcag tccgttctga gaatacagcc ttggtaagca cggtgcccac  10620
atgaatgttt ccagcagcag gattcaaaat agccacatgt ccatcaacag atgagtggat  10680
aaacaaaaca tggtccagaa taatggaaga ttactcagcc ctaaaaagag acgaagctgg  10740
tgaacctcga gaacacgagg ccgcgtgaac gaagccagac accgaggacc acgtagcgtg  10800
agactctcag tctatgaaat gtgcggagtc gataaattca cagagacaga aaggagattc  10860
acggttgcca ggggctgggg agtgacaaca gagggatggg ggtgactgtg aaagggtacg  10920
tggtttcttt cccagaggat aagaacgttc taacatggcc tgtcctgttg gcttcacagc  10980
tctgtacaac acacaaaaaa accattgaaa tgtacacttt gtggaatgtg aactgtatct  11040
tgataaagca gttagaagac cttcgaacat aagcatgcgg cctcatgggg cctttgcctg  11100
ggcaccctgg cacctctccc aggctctacc tatctccgac ttcattcctg agctcttgaa  11160
```

-continued cagggggtaag gcaaactttt tctgcaaagg aacacgtggt aagtattttc ggccttgacg 11220
gtcacatgtc tctgccacga gtcgtctgcc ttggggcgca aatgcaggct tgggcaggga 11280
agaaataaca aaacttgctt cctggtcact gaaacatgaa gtccaggtca cactcactgt 11340
tacaaaatac tccgaatttt cagactgtgg ttcaatacac atgacataaa atggaccttc 11400
ttaaccattt gtaagtgcac ggttccgtgg aattcagtat attcatgtgg ctgtgcaatc 11460
atcaccacca tccatctcca aaagtttctc attttcccaa accgaaagtc tgtccccatt 11520
aaacagcagc ttcccatgac ccttccccca gcccctggca cccaccatcc actctgtgtc 11580
tgtagatttg actgctctgg agacctcctg taagtggaat cctacagcat ctgtcttttt 11640
gtggaccggc ttcttacact gatgctgatg ccctcgagct tcatccatgt cgtagcctgc 11700
ataaggattt cctctctttt tatgggtgaa taatattcca ctgtatgggt agaccacggt 11760
gttgatccgt tcctccgtca gtggatgctg gggtggtttc caccccttggg ctaccgtcag 11820
tgacgctact gtggacatgg gggtacaaat atctctttga gatcctgctt tcagttcttt 11880
tggggataga cggagaagcg gagttgccag gtcatacggc aaacctctgt ttaacctttt 11940
gagggaccac catgttgttt tccgcagtgg ctgcccacag tacattcctg ctgcgcacga 12000
ggttctgatg tctccacatc cccgcccaca cttggtgctt tctgggtttg tttcgtttcg 12060
ttttgttttt gtttgttttt gagacggagt ctcgctctgt ctcccaggct ggagtgcagt 12120
ggcgcaatct tggctcactg cgacttctgc ctcccgagtt ccagccattc tctagtttca 12180
gcctcccgag tagctgagac tacagatacg tgccaccatg cccggccaaa tttttatttt 12240
ttgtagagat agagtctgac tatgttgccc agcctggctg aggtgataat agttttttga 12300
tgatagctaa tgggtatgga ttttaatttt ttaaccactt aagaatttaa agaaaattcc 12360
tagcttttgg gcaatacaaa agcaggccag gggctggatc tggcccatgg gcctcggtct 12420
gctgacagct gctccagagg actggtatgt ccacgtgaca cctggcccga cccccatcct 12480
cctgcagctc ctcaaactca acttgttgca ggttgaactc ggcctccttt cctctaagga 12540
aagatcccct ccgcagcaga gaacaccagg tcggcagtgt gggcactgcc cttcctctcc 12600
cctgccctct gctgtacgtc agcccagccg cttctccagc caggtcccca tcttgccttg 12660
gacactgccc ctgcctctgc cctggtctcc tgggttctca gtttgctgct tctgtctgtg 12720
caccgcctgg aagtgggggg gccttaccca gcatccagcc cagctagatc atgtccgggc 12780
cctcggggtt caggcccagc accctcacgt gccatcactc actgcctcct ctccagctcg 12840
gacgttgtat ctcctggaag ccttccctga tcccagtggc ctcctgaagc ctcctcgccc 12900
ctgtgctcca cagggagctg tgctgcccgg gcctgctctg tccaataggc taacctgacc 12960
tgctccttcg acatctaagg tgctgctcat gtgtattcat gacctgggtg gatgttgggg 13020
agcccaggcc cagcaaagag gggcaggagc aggcagttcc ggggttggcg atggcccagg 13080
ggaagctttc ggcctggttg gtcagagctc ctggtgacca agggtgactt caaagtcaac 13140
gtgagcctca ctcacatgag atgagcctag agcgtccaag aacagctctg tagctggcca 13200
gccgggagct gcagccctcg gtcctgctgt ccccccgggg agccggctcc tgctccaggg 13260
atgagcaagg ctcaaattga ctttgaagtc tcccacaggc cgtttggaac tggggtgcag 13320
gagctggaag tgtggggcac cctggggagt cacgaagcct gactgattgt caggcagatg 13380
tgtggcggga gttggggaga tgcggtagga cacagggggg atctgggggg tgccagtgtg 13440
ggccgcgggc tgggaggtat catcagtaac ttcagatcgt ttcgtagcga cacttaaaaa 13500
atacctgaag agggacgggt ggaatgaact tcaacatcat acccaaaata ttagcatttc 13560

-continued

```
aacatgtaat cagtataaaa attacttgag agctgtttca cattttcttt tcataccaag  13620
gtttttgaaa tccggcgtgc gtctttttac actcacagta cctctcactg tggaccggcc  13680
acgtctcaat gctcagtggc acccagggct ggtggctccc gtcttagaca acacacatct  13740
ggaccgggag agcctcaggt cccctgtgat accagttttc tagtctctgt atctgacagt  13800
gtgacatctt ggggacttgc tgactatgaa gggccacccc tcccaggata aactaattcc  13860
tagagacagt gaaggagacc cttttcatgg gcaaacccac caacgcagag cccaacccct  13920
tcctctatca gggtcttacc tttgagggca ctacacctgc ccttgttacc ccaagggaag  13980
gtcccagaca accagcagcc cctaggccct agagttctga acttatgtca gcctggccaa  14040
tcctaaaccc atataccctg ccttgcccat tccttctaca gaaaccacaa gaaaggttct  14100
tgcccaggtc tccctgtggc tcccccacct tctgaccgac cctgtgcctg tgcccgcccc  14160
gctgcctgtg gcatgccacc cgctttgaga actgtgagct aacaattatc tcttctatgg  14220
caattgactc tcgatctgtt ggcctcacca tacctgaata ataacggaac tacattttag  14280
aaagccagta gaaagccatt gcctcgcatg acagaccagg aagctggggc ccagagaaaa  14340
gccacgtgct caaggctggc cagtgagtga gaggcagaga ctcaggagtg gatcatgggc  14400
ttcccttggt tcagcctcct ttacatccgt ccccttaccc caccgtggag gcttggggct  14460
gagagggaga ttctgtggct gcactccaag gactggccag ttccaggcag gaggcggcac  14520
tcccagctgg ctggaaaaga agaggctgct tctctgtcaa gctcatgtca ttcccccatg  14580
aaactgaaag ctgcccgggt atgagaccat ggagaagaca ggtctcattc tctgggccac  14640
gtttcctaac cacagtacaa taaggctaga aagaaaaccc caaagtccca gctctaacat  14700
ggcaaatgca tgaagaaaag aacagtcttc taaacaactc ttaggtttaa gaagaatgaa  14760
aacagtgatc atgggccttt cgaaaatcaa cagccaaaaa actttataac ctcaaacaaa  14820
ttcctccgaa acaagaaact ctgaacaaaa gtgaacaaag cattcaactc taggagatca  14880
ggaaaacaaa acccgaaata tgtgtgaaag aagtaataag ggctaattaa tgatgaggag  14940
gagagaaatt aacaaggcag aaaagtgaac tgttaactaa gttgatataa tgaaaaactg  15000
ctgtttttta aaagaccaac aaaataggcg catttaaata agaaagaaga cacattttta  15060
aaataccaga aagggtgaaa ggtgacttaa gtacaaatat gtaaaagatt aaaaacagga  15120
tgttcattta tgaccacgat ggagtaacag ggactgaatt tactgctctc ctcccgcccc  15180
ctccaaaaca acaataacaa caaaaaggat caaattcagg aaacaacagt tttcaataca  15240
ctgcacatac gacaacaaag gacagtagtc ctcaagagat ggcaaacagg tgaacggggc  15300
cctacagctt cccagctgct cccctgagtt tcccaaccat ggcccagaag gaggtacctg  15360
ggcagagccc agtggagtac ttggaggagg agacagagct cagagccaag gaggcccagg  15420
cagctgggtt ctcaggacag aggagtggat tggagagagc tgcatagagg gagagcccta  15480
gagagctgca gaaagttcct ccaaggactc agcagagaac tgatcaggga tgtgtgtgaa  15540
gagccagagg ctagggaaga aattgtccgg aaggatcaga gagaagtgcc cagttctcac  15600
tcaggactgg aggagggctg tcctaaccag cccacatggg aaactcatag ttcatgaggc  15660
cgtggacaga gtatacagca ggctcttgcc tcactggcgg ggatcatttg ccctagactg  15720
gacaccgttc caatcccacc tcaccccaaa aaatcaagtg tttctaagta actcaactat  15780
gccccaggca aaactaaaaa ataggaatac aaaaatatct ggcatctaaa aagataaaga  15840
ttacaatgta tgatatttaa taaaaaatgc caagcatgca taaagcagaa aaatatgcca  15900
```

-continued tctaataagg atatagataa aaagtaaata aatatccaga gctgacaaag gcattaacaa 15960
ggaaagaaca tcaaaacagg tgttatgact gtatttccta tgttgaaagc caagtggaga 16020
catggaagag atgtatatat attacatatg tctcttctat gtctctagtt agggggattc 16080
tatggctgca ctccaaagac tggccaatca ctggccagag gcagcacccc cagcctgctg 16140
gaagaggaga ggctgcccct ctgtcaacct catgtcattc tcccatgcaa ccagaagctg 16200
tccggatatg agatcatgca gaaagtgacc atatactcag gacaggacag gttcatttgg 16260
gactatttat ttatttattt agagatgata gctacaatgt ctgagacaaa gaatacactg 16320
agctggaaaa acagtaagga tattatgaaa gaaaaggtta atgaacttga agacattgca 16380
atagataata ttcaaaatta agcatagaga gaaaacagaa ttgtttaaaa gtgaagagag 16440
cagcagtgag ctatggaaaa attcaagtgg tctaatatac atgtaatcaa agtccctgaa 16500
tgaaaggaca gaagagacag aaaaagtatt tggagaaaat aaatgacaga aaattttcca 16560
aagttgatga aaattataac acacagatct gcaaagctca acaaattctg ataaggagga 16620
acttgaagaa aatgacagca tcaagacaca tcttctttgt atatcttcat cttttctgag 16680
atagggtttc actcttgtcg cccaggctgg agtgcaatgg tgcgatctcg gctcaccgca 16740
acctctgcct cctaggttcc agcgattctc ctgccttagc ctcccgagta actgggatta 16800
caggcatgca tcaccatgcc cagctaattt tgtattttta gtagagatgg ggtttctcca 16860
tgttggtcag gctggtctca aattcccgac cttgggtgat cctcccacct tggcctccca 16920
aagtgctggg attacaggaa gacatatctt aatcaaattg cttgaaacca gtagtaaagc 16980
aaaataaaat aaaatgaaat aaaaccttaa aagcaaccag aggaaaaaag atacatttac 17040
atatgtacaa aagaatgact tatatacaga ggaatagaaa taaggatgaa acaatatttg 17100
tacacctgtg ctcatagcag cactatttac aatagccaaa aagtgaaagc aaccgactat 17160
ccattgatga tgaatgaata aacaaaatgt ggtccatcca tgcagtggaa tattatccag 17220
ccttaaaaag caagggaatt ctgatacatg tcacaacata gatgaacctg gaggacatta 17280
tgctgagtag 17290

<210> SEQ ID NO 8
<211> LENGTH: 25970
<212> TYPE: DNA
<213> ORGANISM: Homo sapiens

<400> SEQUENCE: 8
aataagccag acacaaatat tgtatggttc cgcttacatg aggtagcatc attaaatcca 60
taaaggcaga cagtaaaatg gtggttgcca aggcctagga gttagtgatt aatgggatcg 120
agatacagtt tggaaagatg aaaaagttct ggagatggat ggtgataatg gctgcacaac 180
aatatgaatg tacttaatac cattgagtta tatacctaaa aatgattaag gtagtaaatt 240
tgtatgtcat gtatatttta ccacaattaa aaaattagac aaaatacaaa aataaaaaag 300
gatgatacaa atttctcact ggaaacaatg caaggagaag acaatggagc aacatcttta 360
aagaactaaa aaaatactgt caacctagaa ttctataccc agtgaaaata tctttcaaaa 420
gtacagatga aatcgtttgt tcagacattc aaaagctgaa agaattcatc accagcagac 480
ctgcactaca aaaatattaa aggaagtctt tcaggaagaa ggaaaattat atgagataga 540
attatagaat tagcaaacgg atgaagagca ccagaaatgg taactatatg gataaataca 600
tataaatttt tgttgctatt taaatatttt taaaaaatag gtgactactt aaacaaaaac 660
agtaactgat agggagttga taccatatgt aaaaatagat catatggcaa taccacaaag 720

-continued

```
gcaaggaggg gagaaatgga ggtatactat cataaaattc tcatactgta tgtgaagttg    780
tatcatttca ctttaaggtt gactgtgata agttgaagat gtaagctata taccctacag    840
gaagcactaa atttaaaaaa aagaattaca gtaaataaat taattaaaaa ttaatggaat    900
cattaacaaa ttattcaatt aattcttacc accaaaaaaa aaaaaaaaag aaacagaaaa    960
agagacgaaa tgggacaaag acagatagaa cgaatagaaa tgacaggttt atatactcag   1020
gcctaaccat aacaataaac acattaaatg tcaatggtct aaatacccag ttaaaacctc   1080
atagtcaggt tggataacaa agtaatacct aactgtctgc tgccttcaag aaacatgctt   1140
caaatataaa tatataaata tgtttaatgt aagatggtgc tatggtaagt ggcttttaag   1200
gaggcccgaa gcatcttagt attcacatcc atggctggga ctagggggag gcaagtaagc   1260
cacttgcctc ggtcatgaaa ttcaaagaag gaccacaaaa ttcagtaatc aagacaaata   1320
atatttcaat gcaatatttt taaaaataca aattaatgca aaaatatatg aagaccaaat   1380
tttcagaatt ttaaataaag acaggatgag taacagtacc atactatgct gagcctctgt   1440
tggagcctga agcaaaaggg aaaattcagc cttctgagaa gccctgattc ggaggcacca   1500
agataaactg tgcttagttt cctggcccac aggaatctgt gagataagta tctgttgttt   1560
taagctacta agttttgggg tatttgttag acagcagtag atagtatgaa gttcaggatt   1620
ctatgtcaaa accaatcaaa agaaagcaga agtggccatt ttaatagatt tcaggataaa   1680
gaatattacc aggcattaag aaggtcactt cagaacaatt aaggggccat tcatgagggc   1740
atgacaatcc caaatgttaa cgaataaagc aaaagcatca tgatagacct acaaggagaa   1800
atagattaac ccacaattac agtcagagtc ttcaacactc ctttctagat acttgataga   1860
ataaatagac agaacatcat aaaaaatata gaaaaggtaa acaacactat caacttgctt   1920
gacctaattg acattaatgg aaaatcccac ctgttaacag caaaatacac attcttttaa   1980
agtgcacgtg aagtatttac caaggtaaat tgtcttatgg gcaatagaac aagtcttgga   2040
aaatgtaaaa gaggattcaa gtcatacaaa gtatattctc tgaccataat gaagttaaat   2100
tctgctaata acagagatat atgaaaaatg cccaaatatt tggaaataaa taaaatagat   2160
ctaaataacc catggtttaa caaataaatc aaaagagaaa ttagaaacta ttttaaacca   2220
agtaaaaatg aaaacacagc atttcaaaat ttatgcaatg cagtacttgg agggggattt   2280
agacagctaa acacatatat tagaatagaa taaaagcctg aaatcaatga caccagctcc   2340
ttagaaacta ggaacacaaa cccaatgtaa gtgcaaggag tacaaaataa gaatcagagt   2400
agaatcagtg aaacagaaaa aaatagagct atcagtgaaa cacaaagctg gttcattgag   2460
aaggtcagta atatcaataa aagccagaat ggtcaggagg aaaaggaaaa agatgctatt   2520
tgccaatatc atgaatgagt gagaggtcat cattacagat cctacaggta ttaaaagtat   2580
aataaaagaa tattaggaac aactttatac caataaattc accgacttag atgaaataga   2640
caaaatcttt gtgagacaca aactaatagc acttacttaa gaagaattga ataaccagaa   2700
tagcaccata tttattcagt aaattaaatg tgtaggtaaa atccttcctt caaagaaaac   2760
cccaggccta tgtgatatca ctagtgaatt ctatcaaata tttaaggaag agataaaacc   2820
aattctacat aaataaatcc agaagaattg aaaaagatgg aatactttta aattcattct   2880
ataagaacag cattaccctg ataccaaagc cagacaatca caacacaagg gaagaactac   2940
aggctgatat tcctcatgaa cgtagatgca agaattctaa aaaaaagttt agcaaattga   3000
acccaaccat atacaagtgg ggcctattca aggaatcaag gtgcgtttaa cattcaaaag   3060
```

-continued

```
atcaactcaa cgaattgacc atattaaatt taaaaagaag gaccatataa taatgtcaat   3120
agcacagaaa aagcatttga caaaatccag tggccattca tgatttttaa aatctcagcg   3180
aactaggaat agaaagaagg acaatttctc agcctgtaaa gggtatcaaa cttaatggta   3240
caagactggt tactttcctg ctaaaacaca tagacaagac aaaggtgtcc tcataatttc   3300
tatttagcaa tgtcctagag gttttagtca gtggaacaaa gcaagaaaaa ggaacaaaag   3360
ccttccagtt tggaaggagt aaaactatcc tcattcacag aaaatgatca gctgtgaaga   3420
aaatctgacc aaatctgcaa aaacactaca ttaattaaag tgagtttagc aaggttgcag   3480
gatacaagat caatctagat aatcaattgt atttccatat agtagcaaag aacaattgga   3540
aattgaagta aaaaatgcca tttgcaaaaa catcaaatat taaatactca gctataaata   3600
tggcaaaaga tttgcaaacc tgtacactga aaactgaaaa acattgatga gggacattaa   3660
agaagactta tctaagtgga gagatatgct gtgttaatgg attggaaaat tcagtattaa   3720
gatgtcaatt ttcctcacgt taatctatga attcaacaca attcaaataa aaaaaatatc   3780
agaaggcttc tttgtagaaa ctggcaaaat ggttttaaaa tctgtaaatt cttaatttcc   3840
catacgaatg tattttcgtt cttcaactga cattttatct gtaaaaatct gagaagtgtc   3900
aggttggcat ggagcatatc ataatttttc acattaaaaa tattggaaat atttttgttt   3960
aattgctttt tctttcacag aagggcagtt atgaatgaat gtatatctct atataataca   4020
tatacatata tataatacat atatagtata cataaatatat atataatatg tattgcatgc   4080
atatattcag agacagaatc tcactgtgtt gcccaggctg gagtgcagtg gtgcgatcat   4140
agctcactgc ggcctcaaac tcctgacttc aagatatttt cttgcctcgg cctcccaaag   4200
cactgtgatc acaggcatgt gagccactgc acccagccta aatggatgtt tgtaagtgtg   4260
gaatatgtgc atacaggagt ctgcctccaa actctctacc cctctgtctt tggtctaact   4320
ttcctcttat gccaatccca tgggatttc ctattaggct tcactgtatg tcttcatatc   4380
agacagagca aattcctctc tttttgttct tttcaatcaa agttgacatg taacaggcat   4440
atgccagaca tcactgtgga aacgctatac tcaactgagg actttggtag atttacggag   4500
agtacgcaga cagacatttc gtgtgggaat gccttaatat tacaaagctg tcaaaccccc   4560
ctacatgaac gtaaggatcc agtgcaatcc cagtccacat ctcagctggg gtgtggcaaa   4620
cgctccacga ccttactcca acactaagat cgaagtgtag aagtccgtga gtagctcagt   4680
cagctttgag tgtttgcaaa gtgagtgttt cagtggcaaa tattcctaat attctctgag   4740
gcttggtgtg cctaagggta ttttcatctc gctgctgcat ttaaacaata atcatacccg   4800
taaaatcctg tgttcaaagt taccttccac gcctttgaaa tattattctt ttgtcttctc   4860
acatccggta tcgctcttga gaagaatgat gcgattcttt cttgctcttt ttaggcaatt   4920
ctgccgattc tctatgggcc aattcaggac tttgatattt taaaacttca ccgtaacgca   4980
tctatgttct ttcttatctg tcctcgccgg cctgtcaaga gcccttgcgt gtgtttctgt   5040
aattctgggg tatttatttt cattatttct ttaaatacct cctctcttcc tctgctttct   5100
gagactcttc ctagccaatc cactactttc tccttttctc ctcaaacgtc tctgcttccc   5160
ttttaagttt ttttctcatt attgctcctg aaccttctag aacaattcca ccacacttga   5220
tattttatct cacttgtttc ctagcagcac ccatgctgtg atgtacccca ttcactgttg   5280
aactggcatc ttcctcacac tcagtatttt cccccagctc cttgtatatg cctcttcatc   5340
ccatttcaca ctgtgccagc accatccctt atgtttttga gggttttttt ctttcaagtc   5400
tggagtgcag tggcacaatc ttggatcact cagcctcaat ctcctgggct caagcaatcc   5460
```

-continued

```
tcctgcctca gcctcccaag tagctgggac aacaggcacg aaccgccatg gttggttaat   5520
gtttgtatgt tttgtagaga tgggatcttg ctacgttacc caggctggtc ttgaactcct   5580
cagcccaagc gatgcgctca cctctgcttc ccaaaatgct gggattatgg catgaatcac   5640
tgcacccagc catgtttttg agtttctacc aggattgctt tagcctcaca gttcatgttt   5700
ttcagcagtt cttgtctgta tgcaatgtga tgatcagatt gctgcctttc cattctcgca   5760
ggtatgccca tgagttcagg ctccacctga agtgacggtg actgcgtcgg gcagtgtgtt   5820
gggggaggaa ccagggcctg gccctggctg ggccatccca ggccgtggaa tgtagggacc   5880
agccccacag ggtcggtggg tctctccccg tgtgcggcga cgagagagtg taaaaataaa   5940
gacacaggac aaagagataa aagaaaagac agctgggccc gggggaccac taccaccaat   6000
gcgcggagac cagtagtggc cccgaatgtc tggctgtgct gatatttatt ggatacaaag   6060
caaaaggggc agggtaaaga gtgtgagtca tctccgatga tagataaggt cacgtgggtc   6120
acatgtccac tggacagggg gcccttccct gcctggcagc cgaggcagag agagagggga   6180
gacagagaga gaaacaactt acaccattat ttctgcatat cagagacttt tagtactttc   6240
actaatttgc tactgctatc tagaaggcag agccaggtgt acaggatgga acatgaagga   6300
ggactaggag cgtgaccgct gaagcacagc atcacaggga gacggttagg cctccggata   6360
actgcgggtg agcctgactc atgtcaggcc ctccacaaga ggtggaggag cagagtcttc   6420
tccaaactcc accagggcaa gggagactcc ctttcccggt ctgctaagta gcggatgttg   6480
ttccttgact ctttttgcta ccgctagacc acggtccgcc tggcaacggg cgtcttccca   6540
gacgctggcg tcaccgctag accaaggagc ccttctggtg gccctgtctg ggcataacag   6600
aaggcttgca tgcttgtctt ctggtcactc ctcactatgt cccctcagct cctatctctg   6660
tatggcctgg tttttcctag gttatgatta tacagtgagg attattataa tattggaata   6720
aagagtaatt gctacaaact aatgattaat gatattcata tataatcatg tctatgctcg   6780
agatctagta taactcttgt tgttttatat attttattat actggaacag ctcgtgccct   6840
cggtctcttg cctcggcacc tggatggctt gccgcccacc gtggaagaag aggaaagcgt   6900
tcctcttccc ttcccttccc ctttccttta acacttaaaa catatttatc cctcccctcc   6960
catctcccct cccaactcat aaatatagta ggattccaac taataaacat agaaggcatt   7020
tggcaaccag cacagcaatt atttaggcac aaatcctcaa ctgatgctaa aacgagtgag   7080
taaaagtcta agaagcaaca ggaagttaca cggcatcacg tttctcccca caaactggaa   7140
attacaaagc acagaacatc aacgtgacat tggagaaacc tgccagctac aattttaacc   7200
gtgttccaag ttaacactgc cgggtccttc ttcctctttg ggccgtgata gagcagttag   7260
gaccacacgt ggccttcact gcacacaacc agcaaccagg atgcagtcac acagtttgtg   7320
aggcaagttc tcaaacgctg gacagcgcgc cgtgggtggt ctgtgaagga cgtgaaacca   7380
gccgggggag cctggtgatc ttccagccga ccgagagtct ctgggctggg ccctgggtct   7440
cactgaggtg aggagacaga ggtcagagct cagcgaggat gaggcaacta gaattttcag   7500
ggtagatctt tgaagaggag gtgggggaaa gagagaaaga cagaggagag agacagaggc   7560
agagatacgc agagagggag agagagagag cgggagaggg agagaggggg aagagaggga   7620
ggaagagatg aagaaagggg gagaaacagg gatacagaca gggagagaga taactaggca   7680
gagagagtta gaaaggggag aagagagaga tagagaaaga cagagagaga gagagaaaga   7740
gatacagaga gagagagaga gaaaaaaaaa aactccaggg atctgcagag accctcaggt   7800
```

-continued

```
ccttggctga atatggatcc acacatgcat gaagataaac cacctgaggc cagagaaaaa   7860
acccccgtag ctcaggtcac acggtctgga gacagtttgt gttcccacaa aactatataa   7920
tacacaggat gtcgggaagg gtcctcataa gagcctctct tgagtgctga ttctaaacca   7980
accctagact aaaggcagcc ctggattcac cctacaaagc atagaagcaa agctccaaag   8040
atccgatggg tatcaggaac tcatggatgc cagaacaaaa tccgacagca attaaaggaa   8100
tacaacaaaa tctagcaacg gactgtgcaa tatttgcaaa aaaaaaaaaa aaggccaggc   8160
atgcagagga acagggaaac gtgacccaga accaggagaa aagccagtca gtggaggcag   8220
gtgcagaaag gccagaggtg ctactgtgac cagacaagga ttgaaacagc tgttttagag   8280
gggccctacg tgtaagaagg tccagtaata gaaagagggt gataaagcaa tggtggtagg   8340
gtgctcacag ttggagaata ggcggaggta caggaatcct ttgtactatt aatgaagctt   8400
ttctgcacat tggaaatgat acaaaacaaa aagttaaaaa atgaaagaga ggtggggtga   8460
gcctagagca tggagcccca ggacccatag aattttgttg attcctctta gtgttcctgc   8520
tagccaggca ccttgtgtga aatttgccat taactctctg gaaaaaatcc gctttgggag   8580
gaggccactg cccgtgtggc cacctccagc cttgagacca gagcagaagg atacaggagc   8640
aactgcttgg agacggctgg cagatctgca cgtgtttcta tccatcccac ttcccctctg   8700
taaggttcta actctgccct gctgttctcc ctgctgtcca ggccattgct gctgatttct   8760
gcagtgacgg ggccagcaac aactgtctca aggcagcttg ggaaaagaca agcctgcctc   8820
caactgttgc tcttgtcact gcttctagct gtctcctccc caggttgcag ttcccaacac   8880
cacacacacg tgtgcacaca catgcatgca tgcacacaca tgcacatata gcacagcatt   8940
catgcataca catgtaccca cacacgcaca cacttgcaca cacatgcaca atgcatacac   9000
atgcacatac atgtgcacat gcacaccagc tcaccacagc ctgtagtctt tttttttga    9060
gacggagtct cactctctcg cccaggctgg agtgcagtgg tgcaatcttg gctcactgca   9120
agctccgcct cccaggtttc caccattctc ctgcctcagc ctcccgagta gctgggacta   9180
caggcacgcg ccaccacgcc cggctaattt tttgtatttt tagtagagac ggggtttcac   9240
cgtgttaacc aggatggtct cgatctcctg acctaatgat ctgcccacct tggcctccca   9300
aagtgctggg actacaggcg tgagccaccg cgccctgccg cctctagtat tcttagagat   9360
gtgccacatt gttgattttt cctcaaggct gtttctccct ctagatgctg gagcttctcc   9420
agcattgatt ttggggacgg aagcctgggc gaggtacaca ttccggcagc cagtgccagc   9480
tcttagaagg tcacactgcc tattgtgtgg acagattaga tggggtgggg gtgggacttg   9540
tgagtccagc aagggggcta ttgtaggcag agctgcaaga ggcaccagca ggctgcatgg   9600
gctccaggag agaggtgcga cctgagagcc attctggaca ctgggctcag tgaaagaagc   9660
cggtcagaaa aggacaaatc ctgtgtgatt ccctgggtag aaggtcccta gggtggtcaa   9720
atccatagag acagaaagtg gatggtgggt gccagggcct aggagagggg atggggaacg   9780
agtgtttaat ggggatagag tttcagtttg ggaagatgag aaagttctgg agatgaaggg   9840
tggtgacagc tgcacaacag cacgaatgtg tctaatgacg ctgaagtgta gtttaaaatg   9900
gttaagatgg tcagttttgt attatgtcga ttttaccaca ctgtttttaa aaagaagcat   9960
cctggagaaa gcgtcagtac tgctcatggg ggtggggtga ggagtcagct ccagtggctg  10020
ctgggctctc gtccgagagg agaagggagg ctggccctcg ggggaagggc tgcagggatc  10080
cagggttcct gggtggatgt gcggagtctg ggtacctgg  gaactatccc cacagaaatg  10140
ggaggccacc actgaaattc caatgagggg ctcgaagtta aaacttaaca catgaaagat  10200
```

-continued

```
aagtggggtg acagcgtgga gccccaggac ctgttgattc ctcttaccgt tgctgagggg  10260
ctaatggaag gggctgggct ggagggtccc ctgcagtcag tggcaactca gcccctgggc  10320
actgagggac catgcaagaa gcgggagaga gaacagaaaa ggcaggaaga gccctttcc  10380
tccactgagg gagtaggcag agtcagggag tggctgagaa agggcaacac agtcagcaac  10440
gggaaatgca aggaagacat gaggacccgg tccccccatg cctggagggc tggagtgagg  10500
acagaggggg cctgctggac ccaggagcgt ggagctcact ggtgactcct gagagtcagg  10560
ggactcccag gaatggcgtg gaatccagga tgccacttcc tcctgcctgg cagcagggca  10620
ggcagctggc tggggcccag actcccagga ggatgccact gctgcccaga cctactgcag  10680
tgcacagcag agcggcaagg gcccctggtg cgttgagcaa acttccaggc ttaaaaagag  10740
cgtggctgcc tcatccctcc accacccaga gctggctcag gccacgtgtg acccacccta  10800
cccttaacaa ggcagctccg ggagtcctgg aagatgaaca tcccgctcag ctagggcgac  10860
actgtgccaa tccctcccat gggcttccac ctgtacctct tgttttctac acagctttat  10920
tgaaatataa ttcacatact ataaaattca ctgttttaac tgtaccattc aggggctttt  10980
agtatattca cagaagcatg cctccctcag cacccccaaa aacaactccc cgctttagta  11040
tattcgcaga ggcgtgccac ccgcagcacc cccaaaaaca actccccact ttattcgcag  11100
aggcgtgcct cccgcagcac ccccaaaaac aactccccgc tttagtatat tcgcagaggt  11160
gtgcctcccg cagcaccccc aaaaacaact ccccgcttta gtatattcgc agaggtgtgc  11220
ctcccgcagc acccccaaaa acaattcccc gctttattca cagaggcatg ccacccgcag  11280
cacccccaaa aacaactccc cgctttagta tattcagagg cgtgccaccc gcagcacccc  11340
caaaaacaac tccctgcttc agtatattca cagaggcgtg cctcccgcag cacccccaaa  11400
aacaactccc tgctttagta tattcagagg cgtgcctccc tcagcacccc caaaaacaac  11460
tccccgcttt agtatattca cagaggcgtg ccacccgcag cacccccaaa aacaactccc  11520
cgcttcagta tattcacaga ggcgtgccac ccgcagcacc cccaaaaaca actccccgct  11580
ttattcacag aggcgtgcca cccgcagcac ccccaaaaac aactccccac tttattcgca  11640
gaggtgtgcc tcccgcagca cccccaaaaa caactccccg ctttagtata ttcacagagg  11700
cgtgccaccc gcagcacccc caaaaacaac tccccgcttt agtatattca gaggcgtgcc  11760
acccgcagca cccccaaaaa caactccccg ctttagtata ttcagaggcg tgccacccgc  11820
agcaccccca aaaacaactc cccgctttag tatattcaca gaggcgtgcc acccgcagca  11880
cccccaaaaa caactccccg ctttagtata ttcagaggcg tgcctccctc agcaccccca  11940
aaaacaactc cccgcttcag tatattcaca gaggcgtgcc acccgcagca cccccaaaaa  12000
caactcccta cttcagtata ttcacagagg cgtgccaccc gcagcacccc caaaaacaac  12060
tccccgcttt agtatattca cagaggcgtg cctccctcag cacccccaaa aacaactccc  12120
cgctttagta ttttcacaga ggcgtgccac ccgcagcacc cccaaaaaca actccccact  12180
cactagcagc cgctcccctt gccccagcct ctgccaaaca ctgacccact tcccacctcc  12240
atggagttgc acgttctgga catttcatac aaatggggtc ctctgattcc ccacccacaa  12300
tttttaatca tacttaactt ccaaataaag acaaagtcaa atccctcttc cacccaacaa  12360
gatgtggcca agcgtataca agagaacagc atgtcccccct ctcccccaga gaagaggaga  12420
gcccctgatc ctgattcatc tctgggtgtt cttcccctta aaaaaaaaaa aaaaaaatca  12480
aagggggaat aggattcagc tggaatggga ttcagctgat tctcattctc cctttgatat  12540
```

-continued

```
cctaattttt tttttttttt tttttttttt tttttgagac agactctgtc agccaggctg  12600
gagtgcagta gtgcaatctc ggctcactgc aacctccacc tcctgggttc aagcaattct  12660
cctgcctcag cctctcacat agctgggata acaggcacgg gccatcacgc ccggctaatt  12720
tttgtatttt tagtagagac ggggtttcac cacattggcc aggctggtct caaactcctg  12780
acctcaggtg attcgcctgc ctcagcctcc caaagtgcta agattacatg cctgagccac  12840
cgtgcccagc ctgatagcct aaaatttaaa cactgagatg tttgaaataa ttaaatatca  12900
actactatca aacgtacact tcatacacta gtaccgtatg aagtggtagg gaatggaaga  12960
ggagaagaaa cagtggctaa tgtggtccta cccaatacac tcggatcaaa ataagaaaca  13020
cgcacacctg tgataggctt cgtttctgca gcagccgagc agcgggaact agcgtttcag  13080
cctccgtctc ccgcatagcc ttcgcctccg caagcactca gctgatgtgg ctctttgcct  13140
ggtgggatgc cctaagcctt cattcctgga gagcctgggt cctgaatgac cctgcttgga  13200
tcaggggtga tggttttcca tgattttaat cacaggacat gggaacctta agaggcgctg  13260
caggggaccc tccgcattcc agacgtgctc ctcctcatcc tccttgtgca acccggccga  13320
ttccgcccga taaaatcagt cccgtggccc gggcagtaac tgcctttttt acctattgat  13380
tctctgcagt gaggatccca aaatggcctg gtgcaatctc accttccagt ctggtggagc  13440
cgttggtgtc tctgcgggaa actctcctcc ctcgagaact cagacttcta caccaagagg  13500
acctagagtt gtggggacag ggagcaaaca catcaccagc agaatgtcat gagggtgaag  13560
agaagccatt gccacttccc cttctggact cccagaaccg tgaggtctgg gcggcaggag  13620
aaaccgctcc atagactgac tctaattcag agcctggacc gcctcctgga ggacacggcc  13680
ctctctgcaa agcgtcccca ctcagcaggc gccgtgtgag tctcccgaag gccattccac  13740
ggtcctgttc gtgagctgct tcggggagag gaggaccacg gaagacctcc aaggtcacaa  13800
gcattgggcc tttgccctac tccattaact gtggtgaatt ccttgagcag cagtgtgaga  13860
atgccgaatg aggcgctcca gagtccacag gtggtttcgg caaaagcacc gtgggcaagg  13920
agggccagtc cacctgcaga gcaagcctct atcctggtga aagcgcagcg gtgccagttc  13980
catgccggca gctgtctcat atcatccact ccacctggag gctggcagat cccctgcaac  14040
actggggcag gcgggcactt agtggatggg ccttggtgag tggagcccct gtgccgatcc  14100
catgtgtgac ctccatccct gctaccacag tctctatctt caccagcctg ctgacaatga  14160
cagggtggct ggggaaggag cctgactgat gcccaaagaa agggccatct tgtctacctg  14220
gtcactgagc ttctcctcgg ctgaggcggt tgccctttgg caaatgtcac atgggctgcg  14280
aggatcttca cgctctgccc tttcagagac ctctaaccac acaacacttc cccacacctc  14340
ctgctaccgt tttcccaaat gtgttccttt caagtccctg accatccatc tggccaagcc  14400
aggagcaact gaccatgagt gggtggcacc tgtagctccg aactctcctt ccaggaaaaa  14460
tgaaaacacc taggggccct gcccagagta tggaccacgg gtgttggaac cactttttca  14520
tgtaacttgc ttgtgacttc agggcctgcc tgagccccgg gttgtatatt gctgcttcca  14580
cttgaagaca gaacacagct gtgcatgccc aactctgtgg ctcgctgggt ccagcaacat  14640
cccactcatg acgtacagtt cagatcacgt ggcgacttag tggcctgtcc agtctctatg  14700
gaggcctgga cgcaatccac agagttatcc agagaggatg gcagagcttg actccaaaat  14760
cctaagggcc ctgggctgtg attcacctgc aggagcctat catggccccc acgcagcatc  14820
cttacctgcc acagacacct caaatgccat gggatctgtt ggtcccgtgg ctcaagtggc  14880
tcagcagctt tcatgaccac atgcacttgc tgcagagcct tctcttgttc tgggactccc  14940
```

-continued

```
agaaagcaga cagcatttta ggtcattcct acatgggttt tcctacccat gtcttcctac  15000
ctacccgtgg gtcatatggc ccatgttgca aaacattttg gaaaaggcaa aactatgcag  15060
acaatgaaat gatcagtggt ttccaggagt cagtggggag ggagggaaga ataaatggag  15120
cacagacgga ttttagggca gtaaaataat tctgtgtgac actgtaatag tggagatatg  15180
ccattacaca tttgcccgaa ctcacagcat gtacaacaag aagagtgaac cctcatgtaa  15240
cctgatcaat gactaggtca atattggttc atcaattgca aagatgtatc acagtaattc  15300
aagatatgaa taataaggga aactgtgtgt agggagagat gctatatgag gactctcaaa  15360
tatgctcaat ttctctgtaa acatgaaact gctctgaaaa ataaaatcta tattaaaaat  15420
taaagctttc accagatcaa tggctgtaga ccaggtgtcc ggggatgctt tgatttgccc  15480
cagtgatcag tagtcatatc tggaacagca gttgcaattg gagtcctggt taagtttacc  15540
aggattcact gtccttcttt ctccgggacc cccctgtctt ccacacaagc caattagacg  15600
agtggaacga ggctgcagtg ggggtcacca ccctgcatct tccaagtcct cgatggcggc  15660
actgaccttt gcagtccctc cagggctgca ggttgctttt gactgacaat tttcctaggc  15720
agagttcacc ccaatggctt ccacctggcc tttcccagca tagtagcccc caccctcagg  15780
tcagggaaca aatgtggggg ctctgctggc tgccacatac gtctgtttac tcacccatct  15840
gaggctaggg aagtgacctc tgcacccacc gagggttgga cctgagctag aactccgtga  15900
gcccactgac ctccatacgc ccctcctctg actattagat ccgatgggtg tttgtgtccc  15960
caggagtggg tgtcaggtta gagttagagt ccagtaatcc ccctgagtct gatgatcccc  16020
ctttccacta gccaccccag caaatggctg caggtccctg aggggagact ggggaaagaa  16080
gaataatgta aatttgtagg agtatggcaa ggtccttcct caggggcacc cagtcctcct  16140
tcactcaggc accaggcaag ggaggccacc cattgctcca gctcccgtgg caccgtgagc  16200
caccggccaa ggccacaggg ctccatgggc tggactgttc caatcactgc cggtgccagt  16260
tgccatctca gccacaggcc cggggcctcg tggccacccc cactgggctg tgccctgcct  16320
ccttaaagac tgtgagcgag ctcccaactg ggacacccct gaccagctca ctcttatttt  16380
gtctgccctg gccctgatgc tggtgtttga gatatcagaa ctcacctcaa accaccctaa  16440
gcagagatca ctccggctga cgcaggggtg cggcccacat gtgagggacc ctcaggctgg  16500
gcagcattgg ctgagccccc accgcacctt ccctcccacc ctggggtcct cagcctccgc  16560
ccaaggcagg ggggacactg ctggcaactg gtcacccaga gagcatgggc tgcagggatg  16620
gccctgagta ggacacacag ctcccgagac ccctcactgg ggacacaggg gggccctgca  16680
gccagggtgt cagtgtgggg acagcccagc agaccccaag ccacccactg aggttgcttc  16740
tcaggggagc accactggtg ggctgtcagc tcctgcctgg gccccggcct cttgcccctg  16800
tcccacctcc cacctgcacg gcctccagca ttgcccaaat tcactgcctt cactcccaag  16860
tccacagagg tgtctcatcc aggcgggtga acactcgtgt gttgggaggc tggtgaagcc  16920
tggcattggg gggcaccacc catctccctt ctttgtctca ctgccttgaa acaccccaca  16980
tctatcacct ctgcccccga ggctccccag gttcacccca tgccagcctc agcccaacaa  17040
ggcctgtgct tctgaccagc accgctgggg ttctcagggc atctaccctt tccgctgtag  17100
cccactgtct ctaaacatat ttcacacgtt gctgggggca gtgtgtgtga ctcactgctt  17160
cccagagcca gcccagagct gtttagtaga catgaggtga gtgaatgaat gaatgaatga  17220
atgagtgctg ggagctgtct cagttagctc caatctgcca taaggaagca ctgcaggctg  17280
```

ggcatgtaaa cagcaggtgc ttatttcttg cagttctgga ggctggaagt ccaatatcaa 17340
ggtgctgctg attccagtct tggtgagggc tctcttcctg gcttacagat ggctgccttc 17400
tctctgtgtc ttcatacagc tgtccttcag tgcatgtaag gagagagaga gagaagaggg 17460
agctcctaaa tgtctcttgg tataagggca ctaatcctat gggaccaggg accttcatgt 17520
cctcatctgt ccctaattac ctcccagaga tccacttcct aacactatct cattgcgggg 17580
cagggcttca acctatgaat tttgcaggaa cacgattctg tccatagcga acactgacac 17640
tgaacccgcc tcctaaagcc ttctctcacc atattcctca tgctgctcaa agatcctctg 17700
caaccttgtg cccctcccaa gggtccctgc acctgtccca gagagagggc agcctggcaa 17760
tgggcctggg ccctgacgct tgagcatcgg ggtctggcct gaaaggggat gggcgttcac 17820
ttctaggttc ctgagagagg caacactgca cctttaaagg tgtcaggagc tcactgcccc 17880
agctggtcat gaaacagtct cttcatcaag ggctaaataa agcacgctga ccaccaggaa 17940
tggggcagga agcttctgcc ctgcagcctg ccttgtctgc acagggagtg tggggaccat 18000
tagggggagg gtccgatgtg catttttctg ccagcgggac cttcccctgc ccccagtcct 18060
gcccaggccc ggggggtcac tctgaaggca tctggctctt accccaggca tctcctgcct 18120
ctgccccact cctccacccc cacggggtgc cgagtctcag cccaggctgg ggtggcccag 18180
gcaggacagc aggcttggtg gtgcccggcc ccacatacta gtgggtggca cagcgtggat 18240
gtggatagag acgcctcccc tacagtctgt ccctggtatc tgtgacgcag gtgtggggtc 18300
cctttagact cccctgggag acagctgtgt ctatgaaggg gcagccatcc ctgggtcccc 18360
tctgccctca ctgagggcag agcctaggct ccttgggggg ggaagcaggg tgcccctcag 18420
tgcccactgg agttggccag cggaggcagc agcccacggc actgagaggg aaggcccggg 18480
cagccatgcc ccagaaactc ccttggttgg gagcagagca gtgcccagag cccagaaccc 18540
agtttgagta tggtcttggc tctcaaggga caggccaggg tgcctccagg ggaagggggc 18600
tgcccaggca gtaggggttc aaaggtcccc tggggcccac ccagctgacc caggcctagg 18660
gtaatccaga aggggagctg ccctcctcct ccctgggctc aggagaggct gcaaaggcag 18720
ctcctgggac gtggatttca gaatcagggc aaaggacaga catgagccag attcaggtgc 18780
ccgcgtggcc cccacaggtc tcttcaagct ccaggcccca ctcgctgtga cgcaggtggg 18840
aagctcttga gtgcctcccc ggtgggaggg gccgcgctca cagacagcac aggggccccc 18900
aggctccagc ctcagagccc ggctgctcac ctctgatgga cagaaaaggg tccctgtctc 18960
aggaaggtag aggctgccac ctcctggccc gaggacacag ctttccagag gaggggcctg 19020
cttctaagtc caagtcccat cccagccgga tagccagggg caactgccca ggtaaactga 19080
gacagcagca gcaggcaagc cagtgcagag ctgggtgatc cacaggttca tgagcggtgg 19140
caggtggaac aagggcacca tgggcggagg gttgggcagc tgcaggtggc atcattgagc 19200
caggggcctc ctggtgggta aggacattgt agagtgagcg ggcgcacctg ggacccagga 19260
attcacagga aggagagagg aaaaaggaag tccctggcgg gtaaacacat atgcatgcac 19320
acacatccac gtctgcacac gcatccacgc ctgcacacgc atccatgcct gcacatgcat 19380
ccacgcccaa tctcttccct ggaaataaag ccaggggccc ttaggccagc ttgcagtggg 19440
gcccagccct taggacaggc tccttggtgg ggtaggggtg ggggcagctg tcctcctggg 19500
ccagctcctt ggggctgaac ccgctgctcg aggggtcttc caggctccca gcggccggca 19560
ccacctctag agcaggtggg caggggtgtg tggggtgggc aggggtttgt gagggtgggc 19620
aggggtgtgt ggggtgggca ggggtgtgtg gggtgggcag gggcatgtgg ggtgggcagg 19680

```
ggtgtgtgag gttgggcagg ggcgtgtggg gtgggcaggg gtgtgtgagg gtgggcaggg  19740
gtgtgtgggg tgggcagggg tgtgtaaggt tgggtagggg tgtgtggggt gggcagggat  19800
gtgtggggtg ggcagcggtg tgcggggtgg gcaggggtgt gcggggtggg caggagggtg  19860
tggggtgggc agcagcctgc acagtggctt cccctcaaca agccacttcc tcttgcagag  19920
ggaatgttgg ggtgggaggg tgtggctcag caaagggcgt gggggttcca ccggctccct  19980
gcccccgctg gtggggcaca gtgagggggg ctgtggtcag acctggtctc tggagggcca  20040
gccgggggtt cccgtccacc tgtcaggggg ttcgacgcca ctttgagatg acaagtgagg  20100
ccacctgggc acagcgctgg tgtgagaagg aggccatcag gacaggtcaa gaacccaggc  20160
ccgccctgct ccgaaattct tcagacctga tgaagaggtg tcccagaagc gggtggtgct  20220
ccaggcccgc ctcaccagct ccagggaggt caaggttgga gagagacaat tctaggggcg  20280
aaccagacat agccaagagc agctcatctt ccctggagag gacgggctgc ccacttgcac  20340
agcccggggg cctcctgccc ctagacctgg taccttcact cttgttgcca cccctacatt  20400
catacctgcg ccccagtctg agccacacct aggcccccag ctgaagtgac actgtgggtg  20460
ccaggcatct gaggtctcca caagccccca cagactcagg gtgggaattc ctgggggcca  20520
gagctgcaga gggtgctgcc tgggggtgct gggctggacg gggtcctggt ttgtccctcc  20580
tggttctcct ggttctccct ccgcagaggg agggaggcgg tggcctcagc agttcctcca  20640
gcagcgttcc tgagcgggcg gcagctgggc cctcttccca cagccacgct ggggttgcca  20700
tgcctgcagg tcttggggcc ccctccccct tgatgaggtc ctgaccaaat gcaggaggag  20760
caattccagc accgaggggc gagcagagcc gcctgttagc actcctggga gggcccggag  20820
tggtccctga atgatggatt cacctggaac attttcaccc tcttcaggcc caccctgccc  20880
cagaggccca cggaaaccct gcctgtactg gggccgcagc gctgccccca cccatacgta  20940
attacacggc tcggtgtaat tgcaaattcg aggtttacaa agcctccccc tggaggcccc  21000
acgtgagtgt gagcgaggcc ccagcccacc cctgtggccc caagaaggct ctgcgacaaa  21060
atatccatga gtgccgccca cgaaggcatt aaaaccaacg accttctcaa aacttaagct  21120
gtcacaggac atttcaaagg gtgtttccta agaacacctc aataatgatg ttccaaggag  21180
accccatcca aattcctcca aggattacgc ccccaaggcc cagtccacac ttgctcactc  21240
ccaggacggg gagctcacct cctcctcccc gggcgccgtc tcctccacat cccacaccag  21300
gtcctgccca tgactttccc cctctcagcg ccgtcctcag tggccacacc aagaacgagg  21360
ccatgtcttc ctgggaaggg cctcagatgt cagcaaatgc cctggtgtct tgggctgggc  21420
tgggggcacc agggtgaggt ggtgggggga gccaacctca ctgcccctcc ccttcctgcc  21480
tgcccttctt ccggggcacc cagcagctcg gtcctagggc gatgttgaca gacagacaga  21540
ggggcggatg cagcctacct cctgggcagt gagctgcggt ctgaggcccc tgcccagctg  21600
gaaaccacag ggaggggaag ggaggggagg agaggagagg agaggaaccg tcatggggcc  21660
ttggagtcga gtcagggttg ccaaatgcca gatgctggtc acctgcttct ttatcttggt  21720
aacaggcagg tcgggcagga gtgggtggtg ggtgggggtg agcaggggtg aggggtggca  21780
gggcctcagc acagggatta tccctcccct gacacacaca ccagccctac tgtccctgtc  21840
ctgcccttgc agacatgtgt cctgcccttg cagacagccg caggcaggca gggaccacca  21900
tgagcaaccc cgtctctcct cctgaggggc agcacagagc ctggaggagg cctgagtggg  21960
gctgaggcct ggggcgagct ggggtggagg ggcactggct gccgggctcc agggatcttc  22020
```

-continued

```
tccccttcct gccccggagg gtgctggcac aggggtgggg ctcactccca ctccgtagac  22080
acaatgatca gaggtcctgg gtgtctgggg aagctgggct gtgcgtgtat gcgtctacca  22140
tgtgggggtg cctgtgagtg tgctggggcg tctgcagtga aggcctcctg agaccactcc  22200
acggaaacac cgggaatccc tgcagctgag cctgtctctc acgggaccgg gaagctggag  22260
agagccccaa ccctgcccgc tggggccgag ctccctgctc ctgcagcagt cccatgcccc  22320
acactctgag tctgccctat ccacagctgc tgggcctctc tgtggccacc atggtgactc  22380
ttacctactt cggggcccac tttgctgtca tccgccgagc gtccctggag aagaacccgt  22440
accaggctgt gcaccaatgg ggtaagtgag gtccaggcct ggctgcatcg ggaggggcct  22500
cgggtgcaag ggtggctggc acgagcccag ctggacgcct cacagccaga atggtgccag  22560
gccctaggca ggagccagag gtggtcaggg gcagggaggg gctgccctgg agtcctagct  22620
cccctgggca gggcctcggg tctgggtgac agccagtgtt cctgcctggt tctcgtgccc  22680
cacaggagcg tgggcacagt gtgggtatat gtcgggcagg gtcaggaagt ggctctgtgc  22740
ggtcaggacc tggctctgtg cagtcagggc tcagtcccag gcaggcctgg gactggcctg  22800
gggctgggca cagcaggtcc atgagggctc cacatggctg atgttccact caggacctgg  22860
gatgtgggtg gggagggggt gggggctgct ctagccagac gcctccctgc agggactcag  22920
cagcgactta tccaacatcc agagagcggg agcgagggcc agagcctgct ggggccactc  22980
aggggtaagg ctgaggaagg cccctttaat gaggggatgt cagagccaga tctgcagggg  23040
actctcaggc aggagctcag gggcccagg aaggctgcag cccggtgggc agatgtaggg  23100
aaactgaggc ccaggaggtc agggatactg ccttagaacc caatgctttt ccccaagtcc  23160
taggaccagg gcctccctgg aggaggacgc ctggggccca ggtccaggtc cggactgata  23220
agattacagc tccagtccgg ccacttgtca ctaggacatg gcaggaggat gcctggggcc  23280
caggtccagg tccagactga taagattaca gctccagtcc ggccacttgt cactagggca  23340
tggcagggag catgtggctt ccaagatagc cccacaggca tggagggcag ggaggaaaag  23400
agggaaggag gggcagtccc ccaggctgaa cgagtcccac ctccctcctc cttccctcag  23460
ggccgtctga tggagagaca ggcccattca gagcccccca ggagtccctc acggcccctg  23520
actcccaagt tagatttcac acccaggctg tgtgcactca ggacctgtcc tgggcacccc  23580
taaccctcct cctctctcct cccaaccagc cttctctgcg gggttgagcc tggtgggcct  23640
cctgactctg ggagccgtgc tgagcgctgc agccaccgtg agggaggccc agggcctcat  23700
ggcaggggtg agttcattgt gttcccagat gcccaggccc ccagaaaaga attagaaagg  23760
agtgaagagc tggcagggct gtgtgccacc cccacacctg agtgaccagg cagaaccaga  23820
ggccccaggg atgctggcca gccgagaccc ccacgtcaac cccacacctg agtatctagg  23880
cagaaacaga ggccccaggg atgctagcca gccgagaccc cctacctggg tagccaaggc  23940
ccctccacca ggccctacct caccctgtca tctacacgcc caacaagggt tcctatagga  24000
gctctgaaag agagagacgg ccctcctgac cctgggagct gtttccaaag tccctgggag  24060
ggtctggttc tattgcccag caagctctgg gagggcactg ggagcatccc atttcctgtt  24120
cggaggaggc cgggccaggc tcaggaaacg ccccttgagc tctccagcct gggctctccg  24180
gagctgcaca ctctccttcc cagctgccgg aggtgtctcc ccagccccga ggtcccatag  24240
gcccctccac cccaccccat agcagtggcc tcttgtcacc ctcattccta ctcctcccca  24300
tgggcttctg tcttggtccc tgccactcga tggtcatcgc agaccccacc tggcggcagc  24360
ctccccacgc ctgtcctgcc cctgctaggc ccacagccct cttctctcac cccagctggg  24420
```

-continued gcagctcctc cctggcgccc cgggctccca cctgtccctc tagcctcccg tctccccttt 24480
ccagccatga ggagcttgtg ctgggggctt tgcttccctg tttagcctgt gaagctggac 24540
cactctgggg gtccctgagg gcagagcctc ctgggtcccc agggctggca gggttttcag 24600
ctcagccttc aagttcagca aatgcttgtt taatgaccct ggtttataaa tgtctccaag 24660
aataggaata gagtcacctc ctggagctgc tgccgggcca accagccctg ggtgggccca 24720
tggtgggcag aggaggaccc agcagctcca gcactagcca ggattcctgc tccggggcac 24780
acgagcatgg gcagggacaa ccccggcctg tgctatctgg cttcagggcc aggtgggagg 24840
ccccagtggg gagatgacaa ggcaggtagt ctgccccccc ccccagaggg tgtgtggcct 24900
gcaaagggac acctggatgg aagaaaaggt tggcaacagg gccaggccaa ggggtccagg 24960
tcagagctgg aggcccagaa agaaccagcg ctggggctgc agtaccgtcc accagggggt 25020
gccatggtgc tgggcttgag gccacatatg cagaagccag ccgctgggcc acggggctcc 25080
tgtcccagtc accagccttt cccaccccac cttgccccccg tgcacaaacc agtctagcac 25140
cctcatctgt ggccaaggcg gtcagggagc acctgggctc aggttctgtg tccccagcca 25200
gccccaaggc cagggtgact tgacatgtgg gtcaggcctg tagagcagcc ttggaggccc 25260
ccaactggat gcctgcactg ggctggggtc ctgaggacac tccagtccca gctgggtggg 25320
ctccagcaca gctcccaagc cccaatgcac ttagacccag cctggatggt gagctcagca 25380
tggccacagc agggagctgg gagaccccag tcaagagacc tgctccattg agctgcatgc 25440
atgtgtgtgc atgagggtga gcctatgtgt atgcgtgtgc aaatatacat gtgtgtgtgc 25500
atgtgcatga gtgtgtgtgt gcatgtgtgt gtgcgtgtgc aggtgcctct gtgtgtgtgt 25560
gtgtgtgtgt gtgtaagtat ctgtcaccgg tcttcacctg cccctgttgc catacgggtg 25620
tggtgtctgc gtgttgcatc tggcacatct gtatgtgtgt ctgcacgcat gagcacaagt 25680
gaaggggcta gggaagggga gcagggagtg gaaagatttt ttccaatggg ctgggcgcct 25740
ggatgctccc cacaaagccc cttcctgcct gccccccaccc ctccggcctc tcccctagct 25800
ggcctctcgc acaggaaatg aaagagcttg ctgggctgag agagcagagc tggcagcgcc 25860
gcccaaggaa gcacattcaa ttcgcttatg tatctattta tttatttcca tttagaatga 25920
ggagaaagaa aatggccagg gcagacctga ccacccagca gcctctgatg 25970

<210> SEQ ID NO 9
<211> LENGTH: 30196
<212> TYPE: DNA
<213> ORGANISM: Homo sapiens

<400> SEQUENCE: 9
tggtgagggc tctcttcctg gcttacagat ggctgccttc tctctgtgtc ttcatacagc 60
tgtccttcag tgcatgtaag gagagagaga gagaagaggg agctcctaaa tgtctcttgg 120
tataagggca ctaatcctat gggaccaggg accttcatgt cctcatctgt ccctaattac 180
ctcccagaga tccacttcct aacactatct cattgcgggg cagggcttca acctatgaat 240
tttgcaggaa cacgattctg tccatagcga acactgacac tgaacccgcc tcctaaagcc 300
ttctctcacc atattcctca tgctgctcaa agatcctctg caaccttgtg cccctcccaa 360
gggtccctgc acctgtccca gagagagggc agcctggcaa tgggcctggg ccctgacgct 420
tgagcatcgg ggtctggcct gaaaggggat gggcgttcac ttctaggttc ctgagagagg 480
caacactgca cctttaaagg tgtcaggagc tcactgcccc agctggtcat gaaacagtct 540

-continued

```
cttcatcaag ggctaaataa agcacgctga ccaccaggaa tggggcagga agcttctgcc    600
ctgcagcctg ccttgtctgc acagggagtg tggggaccat tagggggagg gtccgatgtg    660
catttttctg ccagcgggac cttcccctgc cccagtcct gcccaggccc ggggggtcac    720
tctgaaggca tctggctctt accccaggca tctcctgcct ctgccccact cctccacccc    780
cacggggtgc cgagtctcag cccaggctgg ggtggcccag gcaggacagc aggcttggtg    840
gtgcccggcc ccacatacta gtgggtggca cagcgtggat gtggatagag acgcctcccc    900
tacagtctgt ccctggtatc tgtgacgcag gtgtggggtc cctttagact cccctgggag    960
acagctgtgt ctatgaaggg gcagccatcc ctgggtcccc tctgccctca ctgagggcag   1020
agcctaggct ccttgggggg ggaagcaggg tgcccctcag tgcccactgg agttggccag   1080
cggaggcagc agcccacggc actgagaggg aaggcccggg cagccatgcc ccagaaactc   1140
ccttggttgg gagcagagca gtgcccagag cccagaaccc agtttgagta tggtcttggc   1200
tctcaaggga caggccaggg tgcctccagg ggaagggggc tgcccaggca gtaggggttc   1260
aaaggtcccc tggggcccac ccagctgacc caggcctagg gtaatccaga aggggagctg   1320
ccctcctcct ccctgggctc aggagaggct gcaaaggcag ctcctgggac gtggatttca   1380
gaatcagggc aaaggacaga catgagccag attcaggtgc ccgcgtggcc cccacaggtc   1440
tcttcaagct ccaggcccca ctcgctgtga cgcaggtggg aagctcttga gtgcctcccc   1500
ggtgggaggg gccgcgctca cagacagcac aggggccccc aggctccagc ctcagagccc   1560
ggctgctcac ctctgatgga cagaaaaggg tccctgtctc aggaaggtag aggctgccac   1620
ctcctggccc gaggacacag ctttccagag gaggggcctg cttctaagtc caagtcccat   1680
cccagccgga tagccagggg caactgccca ggtaaactga gacagcagca gcaggcaagc   1740
cagtgcagag ctgggtgatc cacaggttca tgagcggtgg caggtggaac aagggcacca   1800
tgggcggagg gttgggcagc tgcaggtggc atcattgagc caggggcctc ctggtgggta   1860
aggacattgt agagtgagcg ggcgcacctg ggacccagga attcacagga aggagagagg   1920
aaaaaggaag tccctggcgg gtaaacacat atgcatgcac acacatccac gtctgcacac   1980
gcatccacgc ctgcacacgc atccatgcct gcacatgcat ccacgcccaa tctcttccct   2040
ggaaataaag ccaggggccc ttaggccagc ttgcagtggg gcccagccct taggacaggc   2100
tccttggtgg ggtaggggtg ggggcagctg tcctcctggg ccagctcctt ggggctgaac   2160
ccgctgctcg aggggtcttc caggctccca gcggccggca ccacctctag agcaggtggg   2220
caggggtgtg tggggtgggc aggggtttgt gagggtgggc aggggtgtgt ggggtgggca   2280
ggggtgtgtg gggtgggcag gggcatgtgg ggtgggcagg ggtgtgtgag gttgggcagg   2340
ggcgtgtggg gtgggcaggg gtgtgtgagg gtgggcaggg gtgtgtgggg tgggcagggg   2400
tgtgtaaggt tgggtagggg tgtgtggggt gggcagggat gtgtggggtg ggcagcggtg   2460
tgcggggtgg gcaggggtgt gcggggtggg caggagggtg tggggtgggc agcagcctgc   2520
acagtggctt cccctcaaca agccacttcc tcttgcagag ggaatgttgg ggtgggaggg   2580
tgtggctcag caaagggcgt gggggttcca ccggctccct gcccccgctg gtggggcaca   2640
gtgagggggg ctgtggtcag acctggtctc tggagggcca gccgggggtt cccgtccacc   2700
tgtcaggggg ttcgacgcca ctttgagatg acaagtgagg ccacctgggc acagcgctgg   2760
tgtgagaagg aggccatcag gacaggtcaa gaacccaggc ccgccctgct ccgaaattct   2820
tcagacctga tgaagaggtg tcccagaagc gggtggtgct ccaggcccgc ctcaccagct   2880
ccagggaggt caaggttgga gagagacaat tctaggggcg aaccagacat agccaagagc   2940
```

-continued agctcatctt ccctggagag gacgggctgc ccacttgcac agcccggggg cctcctgccc 3000
ctagacctgg taccttcact cttgttgcca cccctacatt catacctgcg ccccagtctg 3060
agccacacct aggcccccag ctgaagtgac actgtgggtg ccaggcatct gaggtctcca 3120
caagccccca cagactcagg gtgggaattc ctgggggcca gagctgcaga gggtgctgcc 3180
tgggggtgct gggctggacg ggggtcctgg ttgtccctcc tggttctcct ggttctccct 3240
ccgcagaggg agggaggcgg tggcctcagc agttcctcca gcagcgttcc tgagcgggcg 3300
gcagctgggc cctcttccca cagccacgct ggggttgcca tgcctgcagg tcttggggcc 3360
ccctccccct tgatgaggtc ctgaccaaat gcaggaggag caattccagc accgaggggc 3420
gagcagagcc gcctgttagc actcctggga gggcccggag tggtccctga atgatggatt 3480
cacctggaac attttcaccc tcttcaggcc caccctgccc cagaggccca cggaaaccct 3540
gcctgtactg ggccgcagc gctgccccca cccatacgta attacacggc tcggtgtaat 3600
tgcaaattcg aggtttacaa agcctccccc tggaggcccc acgtgagtgt gagcgaggcc 3660
ccagcccacc cctgtggccc caagaaggct ctgcgacaaa atatccatga gtgccgccca 3720
cgaaggcatt aaaaccaacg accttctcaa aacttaagct gtcacaggac atttcaaagg 3780
gtgtttccta agaacacctc aataatgatg ttccaaggag accccatcca aattcctcca 3840
aggattacgc ccccaaggcc cagtccacac ttgctcactc ccaggacggg gagctcacct 3900
cctcctcccc gggcgccgtc tcctccacat cccacaccag gtcctgccca tgactttccc 3960
cctctcagcg ccgtcctcag tggccacacc aagaacgagg ccatgtcttc ctgggaaggg 4020
cctcagatgt cagcaaatgc cctggtgtct tgggctgggc tgggggcacc agggtgaggt 4080
ggtgggggga gccaacctca ctgcccctcc ccttcctgcc tgcccttctt ccggggcacc 4140
cagcagctcg gtcctagggc gatgttgaca gacagacaga ggggcggatg cagcctacct 4200
cctgggcagt gagctgcggt ctgaggcccc tgcccagctg gaaaccacag ggaggggaag 4260
ggaggggagg agaggagagg agaggaaccg tcatggggcc ttggagtcga gtcagggttg 4320
ccaaatgcca gatgctggtc acctgcttct ttatcttggt aacaggcagg tcgggcagga 4380
gtgggtggtg ggtgggggtg agcaggggtg aggggtggca gggcctcagc acagggatta 4440
tccctcccct gacacacaca ccagccctac tgtccctgtc ctgcccttgc agacatgtgt 4500
cctgcccttg cagacagccg caggcaggca gggaccacca tgagcaaccc cgtctctcct 4560
cctgaggggc agcacagagc ctggaggagg cctgagtggg gctgaggcct ggggcgagct 4620
ggggtggagg ggcactggct gccgggctcc agggatcttc tccccttcct gccccggagg 4680
gtgctggcac aggggtgggg ctcactccca ctccgtagac acaatgatca gaggtcctgg 4740
gtgtctgggg aagctgggct gtgcgtgtat gcgtctacca tgtgggggtg cctgtgagtg 4800
tgctggggcg tctgcagtga aggcctcctg agaccactcc acggaaacac cgggaatccc 4860
tgcagctgag cctgtctctc acgggaccgg gaagctggag agagccccaa ccctgcccgc 4920
tggggccgag ctccctgctc ctgcagcagt cccatgcccc acactctgag tctgccctat 4980
ccacagctgc tgggcctctc tgtggccacc atggtgactc ttacctactt cggggcccac 5040
tttgctgtca tccgccgagc gtccctggag aagaacccgt accaggctgt gcaccaatgg 5100
ggtaagtgag gtccaggcct ggctgcatcg ggaggggcct cgggtgcaag ggtggctggc 5160
acgagcccag ctggacgcct cacagccaga atggtgccag gccctaggca ggagccagag 5220
gtggtcaggg gcagggaggg gctgccctgg agtcctagct cccctgggca gggcctcggg 5280

-continued

```
tctgggtgac agccagtgtt cctgcctggt tctcgtgccc cacaggagcg tgggcacagt   5340
gtgggtatat gtcgggcagg gtcaggaagt ggctctgtgc ggtcaggacc tggctctgtg   5400
cagtcagggc tcagtcccag gcaggcctgg gactggcctg gggctgggca cagcaggtcc   5460
atgagggctc cacatggctg atgttccact caggacctgg gatgtgggtg gggagggggt   5520
gggggctgct ctagccagac gcctccctgc agggactcag cagcgactta tccaacatcc   5580
agagagcggg agcgagggcc agagcctgct ggggccactc aggggtaagg ctgaggaagg   5640
cccctttaat gaggggatgt cagagccaga tctgcagggg actctcaggc aggagctcag   5700
ggggcccagg aaggctgcag cccggtgggc agatgtaggg aaactgaggc ccaggaggtc   5760
agggatactg ccttagaacc caatgctttt ccccaagtcc taggaccagg gcctccctgg   5820
aggaggacgc ctggggccca ggtccaggtc cggactgata agattacagc tccagtccgg   5880
ccacttgtca ctaggacatg gcaggaggat gcctggggcc caggtccagg tccagactga   5940
taagattaca gctccagtcc ggccacttgt cactagggca tggcagggag catgtggctt   6000
ccaagatagc cccacaggca tggagggcag ggaggaaaag agggaaggag gggcagtccc   6060
ccaggctgaa cgagtcccac ctccctcctc cttccctcag ggccgtctga tggagagaca   6120
ggcccattca gagcccccca ggagtccctc acggcccctg actcccaagt tagatttcac   6180
acccaggctg tgtgcactca ggacctgtcc tgggcacccc taaccctcct cctctctcct   6240
cccaaccagc cttctctgcg gggttgagcc tggtgggcct cctgactctg ggagccgtgc   6300
tgagcgctgc agccaccgtg agggaggccc agggcctcat ggcaggggtg agttcattgt   6360
gttcccagat gcccaggccc ccagaaaaga attagaaagg agtgaagagc tggcagggct   6420
gtgtgccacc cccacacctg agtgaccagg cagaaccaga ggccccaggg atgctggcca   6480
gccgagaccc ccacgtcaac cccacacctg agtatctagg cagaaacaga ggccccaggg   6540
atgctagcca gccgagaccc cctacctggg tagccaaggc cccctccacca ggccctacct   6600
caccctgtca tctacacgcc caacaagggt tcctatagga gctctgaaag agagagacgg   6660
ccctcctgac cctgggagct gtttccaaag tccctgggag ggtctggttc tattgcccag   6720
caagctctgg gagggcactg ggagcatccc atttcctgtt cggaggaggc cgggccaggc   6780
tcaggaaacg ccccttgagc tctccagcct gggctctccg gagctgcaca ctctccttcc   6840
cagctgccgg aggtgtctcc ccagccccga ggtcccatag gcccctccac cccaccccat   6900
agcagtggcc tcttgtcacc ctcattccta ctcctcccca tgggcttctg tcttggtccc   6960
tgccactcga tggtcatcgc agaccccacc tggcggcagc ctccccacgc ctgtcctgcc   7020
cctgctaggc ccacagccct cttctctcac cccagctggg gcagctcctc cctggcgccc   7080
cgggctccca cctgtccctc tagcctcccg tctccccttt ccagccatga ggagcttgtg   7140
ctgggggctt tgcttccctg tttagcctgt gaagctggac cactctgggg gtccctgagg   7200
gcagagcctc ctgggtcccc agggctggca gggttttcag ctcagccttc aagttcagca   7260
aatgcttgtt taatgaccct ggtttataaa tgtctccaag aataggaata gagtcacctc   7320
ctggagctgc tgccgggcca accagccctg ggtgggccca tggtgggcag aggaggaccc   7380
agcagctcca gcactagcca ggattcctgc tccggggcac acgagcatgg gcagggacaa   7440
ccccggcctg tgctatctgg cttcagggcc aggtgggagg ccccagtggg gagatgacaa   7500
ggcaggtagt ctgccccccc ccccagaggg tgtgtggcct gcaaagggac acctggatgg   7560
aagaaaaggt tggcaacagg gccaggccaa ggggtccagg tcagagctgg aggcccagaa   7620
agaaccagcg ctggggctgc agtaccgtcc accagggggt gccatggtgc tgggcttgag   7680
```

-continued

```
gccacatatg cagaagccag ccgctgggcc acggggctcc tgtcccagtc accagccttt   7740
cccaccccac cttgcccccg tgcacaaacc agtctagcac cctcatctgt ggccaaggcg   7800
gtcagggagc acctgggctc aggttctgtg tccccagcca gccccaaggc cagggtgact   7860
tgacatgtgg gtcaggcctg tagagcagcc ttggaggccc ccaactggat gcctgcactg   7920
ggctggggtc ctgaggacac tccagtccca gctgggtggg ctccagcaca gctcccaagc   7980
cccaatgcac ttagacccag cctggatggt gagctcagca tggccacagc agggagctgg   8040
gagaccccag tcaagagacc tgctccattg agctgcatgc atgtgtgtgc atgagggtga   8100
gcctatgtgt atgcgtgtgc aaatatacat gtgtgtgtgc atgtgcatga gtgtgtgtgt   8160
gcatgtgtgt gtgcgtgtgc aggtgcctct gtgtgtgtgt gtgtgtgtgt gtgtaagtat   8220
ctgtcaccgg tcttcacctg cccctgttgc catacgggtg tggtgtctgc gtgttgcatc   8280
tggcacatct gtatgtgtgt ctgcacgcat gagcacaagt gaaggggcta gggaagggga   8340
gcagggagtg gaaagatttt ttccaatggg ctgggcgcct ggatgctccc cacaaagccc   8400
cttcctgcct gcccccaccc ctccggcctc tcccctagct ggcctctcgc acaggaaatg   8460
aaagagcttg ctgggctgag agagcagagc tggcagcgcc gcccaaggaa gcacattcaa   8520
ttcgcttatg tatctattta tttatttcca tttagaatga ggagaaagaa aatggccagg   8580
gcagacctga ccacccagca gcctctgatg gtgaaggccc tggggaggtc tgggtgggcc   8640
catccaccac ccaagatcct ctctgcgcgg gaggttggtg gtggggggag agagagaaag   8700
agagaaagag agaaagagag agagaggccg tggatgctct ttctcctgag gaatgaaatg   8760
gtttctggaa aatgctggtc tcctgagctg gctcagggcc tcaagcctgg gaggcagcat   8820
tgagtgatag cttccagatg gggatggtgg ccctcagcca gcaaggagga ggaggaggag   8880
gacgaagaag gaggagggca gaggagaagg agggagaaag agggagaggg aagaggagga   8940
aaaggaggga aaagggggga gaagggagag ggagaggggg agggagaggg agggggaggg   9000
gggagaagaa ggagggaggg ggagaaggga agaggaggga gaaggaggga ggacaaggga   9060
ggaggagatg gaggaggggg aaggaggaga aggaggaggg agaaggagga ggaaagagaa   9120
aagaggaaag aaggtgagga gaagaaagaa ggggagggtg gaaggaggag gaggaagagg   9180
aggaaggagg aggagagaga agagaggagg aggaggcagc tcccaggcca tcccccatca   9240
ggccttgcag cctccagggc aggcaggagg gccatgagga gccgccagcg ccctgtccct   9300
gcagggctgg aggccccatg ctcacgcctg tgcttggggg ccagcagggc tccccagctc   9360
tttccacgcc cctctggccc agcttcccct ggcatgccag cgttgtcgct gcccacctgc   9420
cagcatgtgt gggtctccgt ctatcccacg ggcacccatg ctcctggcat caccctgaat   9480
ggggccccag ggtttgaagg gcccagaccc aacctgctcc agcctgtgga ccacccaggc   9540
gggcacagtg ctgcctgagg gggctggcgt ttcaccgggg cctcaggact cctgggggag   9600
ctgcccggtc ggtggctaga ctcaccgtca ggtactccag gtcctcaggg caccagcatg   9660
aaggcaaagg cggctgccca gaccctgagt gggaggacat ccccagggtt cttagcctgg   9720
gtgacctctg ccaccatcca taaaactgta tcgggggcat ctgtatgctc tcagaggagg   9780
ggtctctcgt gttccttagc ttccgcaagg gggctctcaa aagcctggaa gccttgaccg   9840
agagaacaac gggcaagtgc cgggggcggg tgcgcagacg tttccaccag agaacgcccc   9900
actccacgac taggggcacg ggcatcagtg agagagaggg gacagtggtt ggccgggcca   9960
tggagaccca ggcagagtat ggagagaaag tgaggtgagg gaggtgggct caactgcaaa  10020
```

-continued

```
gagagaggcc acagcatcct gagcaggcac cacacctgtc ccaagcctca ccagcactgg  10080
gctagctggt gccttgtttc agaaaagaag gcaaaacaga agatcctaca gccccggccc  10140
tggagaggct caggctcagg ggagactctg cccggccctg tccaggtcca tgcccctcag  10200
gaagcagccc cagtgggcag aggtctccat cttctcaggg gtgccctgcc cctgctgggc  10260
aggggtgcag tgttgccatc aacaggcccc tgggggccaa aatgggagaa caagggatga  10320
attcccaaaa agcgcagggg aaggggatgg gaaggtgcta tggaacccac gcacccagcg  10380
cccacgctct ccccaggcca agtctccctc tcaggcagtg gggagcggga ctcagaccca  10440
cacctcgacc aagcatcctg ctgggggcgc agcctgaggg cactgccctg cccaggcctg  10500
ccaggcccca ccaggccccg cagtgactgc cccccacccc gcagtgacca cccccccaca  10560
gtgaccggcc ccccgcagtg accagccccc cgcaatgacc agcccccaac agtgaccagc  10620
cccccatagt gaccggcccc ccacagtgac cagccccccg caatgaccag cccccaacag  10680
tgaccagccc cccatagtga ccggcccccc gcagtgacca gcccccgca atgaccagcc  10740
cccaacagtg accagccccc catagtgacc ggccccccac agtgactggc ccgcccacag  10800
tgaccggccc cccccagcag cgaccagccc cccgcagtga ccagccctca acagtgacca  10860
gccccgctct gcccccaggg cttcctgtgc ttctccctgg cgttctgcgc acaggtgcag  10920
gtggtgttct ggagactcca cagccccacc caggtgagca ccagctgccc ctaccctgca  10980
gtggagggtc ccccagtaag ccagtgggca cctggggact ggggagcagt cctgggagga  11040
gcagccccag cttccaggct tgtgctgacc gggtggggtg ggggagaccg cagcctgggt  11100
tccctctgcc tgaggcttca gggaggccaa gcgctggagg tgggtgaggg ccagcagctc  11160
cctggtgggg agggacctat gctgtacccc tgccttcgcc ccagtctcat tttcttaaag  11220
cccctcagcc cacccccctcc tgagctgatg cccctcgggt ttgagggagg gaatgaggag  11280
gaagaagaag gaaagccact ggcttggcct taggggttga ctagaaggag cagagtgttc  11340
cagaaaatga gacctgaggg ccagcgctcc tgatggcctg gtggggcaga cggtaccagt  11400
ggggaaggga cctggagacc cgcggactgg ggtgtcgcag cctccacccc ctccacggaa  11460
cagcacccat ccttccgtcc tggatgctga cctgcctgga ggagggtccg gcctagctga  11520
ccgtgggcag gggccaaggg cgtccccgtg gaaaggccag cagcttggag aggaaggagg  11580
cctccctggc ccagcagaga atgagagctc ggtagcagag ccagccccac cttccccttg  11640
agagccagac ctggtgagag cccccagggc agccgggcgg caccagggac agccacgggc  11700
agggtcatgg agtggggcag gagagcctgg caggtcacaa gaggtgattt cttggagccc  11760
tagctggagt cctagtggcc tcgtgtattc aagtgcctgg ttgcccaggg ccctcaaaca  11820
caggcttggc catgagagat accgaggctg gtagcaggca ggtcctctgg ctgagctctg  11880
caggggggcct gctgtgcagt ttcttgagct gtgctggcag cctgagtgtg gtggtcccca  11940
ccgtggtttg caaatggggg gactcaggcc ctctgggggt ggggggagct caaggttacc  12000
ctggcagtgc cggggctgga tgggggctcc aggcttacga caaaggctct tggccccaaa  12060
gtgcccaccc acccctggca tcatttggga ggaaccgcct gaaccaggtg ggagaaacac  12120
cattttatca ggcccagaag gatcccagag gggctgagcc cccagaagag ggctgtggct  12180
ttgaggactg gcacaggagt cttaccaggg tggtgagctg ggccaggtcc gtgtttcggc  12240
ctcacgtttc ctgtccactg aggggtggtc tggctcattt gaggtctggg tcacagtgtg  12300
ggtggccgag gtcaagacag ctgccagggt tccccgggct cgtctggggc agctgcggcc  12360
catgccccat gcttctgtgt gtttatggct ctgatcgtgg agccacaatt ctggagggga  12420
```

-continued

```
gggggccata caggggccac aggacagaac gcagctgggg cctgctctcc aggaagggaa  12480
gggggtgcaa gaagatagat gccccagccg ggctcaccta tggcctgtcc cagccccagg  12540
cagcatcccc cacacacatg gtccttgtct ggcccgtgcg cccagctgcc cttcaggggt  12600
cagttctcag ggccttgcct gaccccaggc aggggactgg ggcttcctcc tgggcctctg  12660
gtccccatct gcccctccca gtgggtcttg acttctggca tcatctgtgt caggcctggt  12720
ggccatggag gtggcctggg tgaaggagct ctgaatatga agtcagtgtc cttgggccgc  12780
ccttgggcaa gccactttaa cttcctgggc ctcagtttcc ttttctgtga agggagcacc  12840
aagatccagg ggctgcatgg gtgggaatgg ccaggtgtgt gcaaagactc ttcctcctca  12900
cctgcgtgcc tcctgccgtg ccccgttgcc caggctggtc ctccaggacg tgggacttgc  12960
tcgaagctgt cctgggtgtg gatggagtgg ctttggtgcc agggcccggg ccctgagcag  13020
gaggggcggc tgcacatccc gtctcctgcc ctccaccctc agggcccacc agagccgaat  13080
gggcttcaac cttgggctcc ctgtccaaca aagtcctgct ggcagcctag acagtggcaa  13140
aggccaaagg ccccaagctg ttggcaccgg aaacgtcgag gtgagagccg ggggcccaga  13200
gcccagcccg gcccattcac ccattccccc tgtccctccc cacagggcca ctgaggtgtc  13260
ctgaacacag ggtcagggtg actcatgtgg tgcccctgcg gatgggaagg cagaggacag  13320
aggagggaag ggaccagcca catgcccttg gtggtgccct gtggccacag acccgggccc  13380
agagctgaaa gtggggtgcc cctccacctc cccaactctt gccccaggga gtcctggctg  13440
ccacttccct gggatgctca tgcgggcagg aggcgtggac cgggcttcag ggatgaatgt  13500
ggagcttgag ggctattaat tacgttctcc tcgagggctg agagccactt tgccttaacc  13560
ctccccctgt gccctgacga gtctgcttcg ggaataattc atgctcaaat taagtacagc  13620
agtgtggggt gcagcctcgt cctcacagtc tgccccaccc tggagccact accctccctg  13680
gatcctccag ccgccgagtg ggctcaggcc agagccagct ctgtacctgt ggggctggtc  13740
cacaggcctc ctgcagctcc tggtccccac ctgccgttca ggacctgtct gtaccttcct  13800
gagcactttc agcagacaca ggatggggtc gccaagccca ggcagacacc agggaagatc  13860
tggtcatggg gaaaagcccc cgggcaccgg aagacggagc ttagtgcgtt gatacctgtc  13920
aggcagcacc ttcccccagg tgtcctgaga aacacaggcc ccaggctcct tcagagcccc  13980
cagagcctgg aatggagaca gacggtgaag catcacctag gagcccaggc cccgtggaga  14040
gcagccggcc cggcctccag ggccctccag ggccagacaa ccggctttgg ggtaggaggc  14100
ctacctcgct gagctctgct tccccagtcg tggggagagc tgcttggcag agccaggcag  14160
ggcaggaaga gccaggcagg gcaggcaggg caggcagggc aggcagagcc aggcagggca  14220
ggcagagcag gcccctcagc cactagcagg agttgtcact ctcgcccatg ctgtggtaat  14280
aatgacacct tgctcacagc ctcagaggca cctttgtcct ccttgggcca tggcaggcgc  14340
ctgacaatgg gaacagtcat tggagttggg agggaagcag gaggggaggt ccgagccaac  14400
ccccgggccc actccgctgg gcctccagtc ctcaccagga cctccaccca cgaggacaca  14460
atggccaggc cagactccac ccccatttca cactcacaga cgctgaggct gaacaaggcc  14520
cccgccctgg ccgacagtgg tgtggccagc ttggtgcctg cccgcccctg ggcactgcgg  14580
ggaggacaag gctggctgag tcggggatga ctcacggaga gtggtctgac ttttattagc  14640
atcaatggga gggatgcatt agggtcagga gccaagtttg gcctggaaag tccatctgac  14700
tcctgttggg gcctccaggc ttgggcaggg ctgaccgaga gcctccactg cccactgccc  14760
```

-continued

```
gcccagttgg ccgctgtcag ggcctgccac gggggctggg ccccagtgca atgaggaccg  14820
ccgtaagcca cccttccttt ctggagggca ggtgtgagtg gctagagcgg gcctggggct  14880
tccatcctcc cccagccctt tggggcagct gctgagcacc ccccttcatgt gtcttgactg  14940
tcagcatggc atttgggga gaactgaggg cctctgaggc aggaaggaga catcagaggg  15000
cagggacctc aaagagggcc tcgccctgtg ccaggagacc agcgactcct ggagcagtca  15060
cagaagcctt cctgtaggag gcgagattcc agtttgtctt tgaaggagta acttggcagg  15120
ggagagcatc ttgcttagga gggtggagac atgaggtcca ggtgttggtg aggtgtggag  15180
cgcaggcagc acatccagcc aggccccgtc accttccacc ttcttcaccc cctgccccac  15240
agtggcctcg tccacccaga tctggcctca ggtgcccaag gcttctctgg tcaaaagcct  15300
tacccggagc ccagctgccc gggcttccag aaggcagccg ggtgattctt gggaaagatc  15360
tagaatcccc aagctttctg ggagctgagg tcctggcaca gggtctctca agccttttcc  15420
accaggccca gccccatccc ccatttccgg gtcaacagta gcgtgctgga aacttctgtg  15480
ggccaacctt gtaagaccac agcggaggcg gacgcagagc ttggcctctg ctttatcctg  15540
cgggaccctc tgggggcagg agggccactc tgacggccat tgtgtgaagg ccccatcgtt  15600
gatgttggga agcactgtga ctggctgccc agggacccag gttccgcttt ggggagatcc  15660
acctgctaca aggagggcag tgctgggacg tcactcagca ctaagggccc actagcgttt  15720
gggatgtcgt ggggaggggg ctgtgtcccc ggatctccca ccagggccag gacctccctg  15780
tggtctctcg gtgcaggtgg aggacgccat gctggacacc tacgacctgg tatatgagca  15840
ggcgatgaaa ggtacgtccc acgtccggcg gcaggagctg gcggccatcc aggacgtggt  15900
gagcgtgggg acggctgggt ggcagggcgg tcagcttctg cttggactgc agttcagaga  15960
acaggcgcag ggtggccagt gagaggtctg gccaggcacc gagggggttc caggacacag  16020
gccagagttg cccctcaggg ctgggggcaa aaagctccca ccctctgtct gcccaggaca  16080
aggccgccta ccagattctc gaggcccagt gcaaaacgag agggcagggc cctgtattca  16140
gaaacactga aggatttcaa gagcattaaa gcaaatacgg ggccgaacat agtggctcac  16200
acctgtaatc ccagcacttt gggaggaggt tgaggcaggt gaattgcttg agcccaggag  16260
ttcgagacca gcctgagcaa catagggaga ccttgtctct actttaaaaa aaaaaaaaaa  16320
agaaaagaaa aaataaaagc acatacagcg cacaggccct gtgaacaggg cggggaagct  16380
gcctggctcc agcaggtgtt ctgtcaccag caggcaggca gcgcagcttg agagagctcc  16440
ccttaccagg gcccggctgt gcaatggctg gagccccagc agaagcagct gcaataccag  16500
tagccccagc cctggcctgc agggaacccc acctggatac ttgtggtgcc tcagtttccc  16560
catatgtgct gcccgcctcc tggggtctcg ggagcacatc accactccct cccttctgtt  16620
cctgtagttt ctgtgctgtg ggaagaagtc tcctttcagc cgtctgggga gcacagaggc  16680
tgacctgtgt cagggagagg aggcggcgag agaggtgagg gggggacctg gatgctggcc  16740
aggcaagacc ctcgggggct ggacaccctg gggcccaacc ccaagaccca gggccatcct  16800
cccaccccac cccttggcct ccccagaccc ttgggaactg ccgctgaagg gctcagggaa  16860
ggttctgatg tgatcggagg ctagttaggg ttcatggtac gccaagccca ttgggtggcc  16920
aggctgggct caagacataa acacaggccc ctttgcccag ctggacgcag gccccatgcg  16980
ccattcactc cttcaagcca gttccagcct ggggacttcc caaggccagc taagtccaca  17040
gaagcctctt ggagtgcacc catgagggct ctgtgccaag ggctgcaggg ctggtgtggt  17100
gggctctgtc tagggggaag ggtgcaggcg tcctgggggg catcagaagg agttgaaggg  17160
```

```
cactcagagg agaagaagta ggccagggtg tggccagggc ttcagcaaca acagagcggg  17220
gcccgaggcc aggaagcctt tcctccccag ggccctggga gagactgggc cctcctctct  17280
ttctcctggt gcccggcagc cctcccccag cccaccctgc cccctccctg ctcccctccc  17340
cgctcccctc ccctactgtc ctggaaacaa acccacccta tctcacagtg ggaggcacct  17400
ggcgaccctc caagaaacag aggggaggag agcaaatggc tggaggcctg gtgaggggtg  17460
gagccacagc caaggctctg agggcagaag ggctggcgct gaggatggtg ctggggaggg  17520
accagcggca ttgggggcag ggctaacagt caggacccct gtgccaccca aggagagact  17580
gaaaaggccc ccgactgaaa agcaggagcg agggcctgcc tcgagcaccc ttgggatggc  17640
agggccatgg gcccgactgc aaagcctcct ggggagccgg aagagccagc acaggcggca  17700
ggcacggagc cacccagatg ggctggcatg ggcgggaggg aggcagacct gcctgcgggg  17760
gacaggaggg tgagccctga gaccctgcgg aggcctccac aggccgcccc agttgccatc  17820
atctccaggg ttcagagaca ggcctgccac ctcccttttc tgaaaagatg cctctgggtg  17880
ccatgccctg gggtggcact ggaagcctgg gatggaacca ggaagctggg actgtgcggg  17940
gacccccctc acacccctcc accagctggc ttcctgccct ccctgttagc catcaccctc  18000
tggtcaccaa ggtgctgtgc ccggccctgg gctggatgct gggaacccag agtgaattcg  18060
aagtggcccg gcccagggga gccaacgtgt ggcccaacat ggacgctcag gacagctggg  18120
agacggcacc ggccgggccc agggcagtgc cagagtgccc acagaggcca gccctgtccc  18180
actgggcttc acctgctcgt gctgcctttc cctagagccc tgggggcttc ctaggaatgt  18240
gccgcacccg ccgccctgct gccctggcat tggcctaggt gggcgctgca gctccatggc  18300
cccacagagg ccgcttgtcc aggcagggag ggccgctcag ggcgggtacc atgcctgctg  18360
ccctctcaca ggactgcctt cagggcatcc ggagcttcct gaggacacac cagcaggtcg  18420
cctccagcct gaccagcatc ggcctggccc tcacggtacc ctctcgcctc cctcactgcc  18480
ccttcccacc tcctgcccct cagcctgccc agcccccgac tcagatggaa gggtgacccg  18540
ggacaggatc tctggtcttg agcctcactg gctgccaacc tcagggagct gctctggtgt  18600
gacagggcct gcctcctaca gctgggccgc cccccttacac tgcagagtcc tgatgcttcc  18660
tggggagggg cgcccgcacc ctggggcagt ggggcagccg cgggtgtctc cctcccaggt  18720
gtccgccttg ctcttcagct ccttcctgtg gtttgccatc cgctgtggct gcagcttgga  18780
ccgcaagggc aaatacaccc tgaccccacg gtagggcccc ctgcctgccc ccacaccctc  18840
tggaagggtc ctccagctct gctcgagagg catctgctct gccagctgct aggagggagc  18900
cccgggacca agccccaggc tgacactgta gaggaaacgc tttgggggtg gctgagcacc  18960
agggtggggt gggagacctg gagagtttcc agacccaatg caccgcaccc catggcccac  19020
atggggaccc ccctttgctt acccccaggc cttaccaaga cctggagatg gatgcttctg  19080
ggcctccagg ttatagcccc aggccaggat ctctgtgctt gaatacccca gagctcctca  19140
tgcttagggg gcagggaggg tccaacccac agccaggcag ctcttcctgc ccccacggag  19200
cctggcccgt ctctgcctgc catgcccatt aacccaccca cttgctcttc ctggccatcc  19260
aagccctcat ccctgggtcc tctgcattct acaatagcct cacagtcccg tctagaacat  19320
tctgcaacag cctcacagtc cccctagaac attccacagc agctccataa tcccctccag  19380
aacattctgc aacagcccca tgatcccctc tagaacattc cacaatagcc tcacaggtcc  19440
cctgtagaac attccaccac agccccatga tccccttgct cctcagagca tgtggccgcc  19500
```

-continued

```
agccccagga gcccagcctc ttgagatgct cccagggtgg acccacacat tgtctccact  19560
ccgaagcagt tgctattggt ccaagaggat gctcgggtag tcttcggtgg ctgcaggaga  19620
gcgatgctgc gcctctgccc ctctcctgcc acctggctgc ccacagaggt gaagacgccc  19680
ctgctgtcag ccctcatggg atccctgagg ggagggtccg agctgtgagg agggaaggga  19740
gtgaaggccc agccagagag ccaggctcca ttgggaacag atgcaagggt aaggggtagc  19800
tcaccaaatc cctccatggg aacgggctgg gagcaagcac aaaggaaacc acactggagg  19860
cagcagccca gggcagactg caagacactg gtgggccacg gcctggaggg ctccacccag  19920
acacaagctg cactggtttt ctatgctgcg taagaagcag catggatgta aggactgcaa  19980
gcagtgccca tttatgatct cgcagctctc cagggcagaa gtcgcggtgg gctcagtggg  20040
tgccctgagc ggggtctctc agactgacgt caggccttgg tgggctgcac tctcacctgg  20100
aggctccggg gaagcatctg cctccaggac cattcaggct gttgacaagt caactcctca  20160
tggctgtagg actgaggatc ccaagtcctt gtccctggtc ctgtggtccc tccaccttca  20220
aaccagcaat ggtgcattga gcaaattgtg gtcaaatata catcacatca aatttaccat  20280
cttaaccatt gttaagtgta tggtttgtgg cattaaatac attcacattg ttgtgcaacc  20340
atcaccacca tctatctcca gaactttcca tcttctcaag ctgaacctct gtccccagta  20400
aacaccaact cccattctct gccccggtcc ctggcaccca ccatccactt ttcgtctcta  20460
tggattcagc tgctccagga acctcatatg tgtggggtca cacaggattc atccttttgt  20520
gtctggttta tgtcacttac tgttatgtcc ataaggtcca tccgtgttgt agcctgtgtc  20580
agaattcttg aaagagaaat cttatcagct ttcccatcat ctcacagcca catggtccgt  20640
gattaaggca ggacatttag tgggaagcgt ggagcatttt agatattctg cctgccacac  20700
ccactcttac tggacgttca gaccacgttg atgacgaatt agctctaatg gtccctaaat  20760
gtttgcacaa tttgctcaaa attctaagtc ctgggtggaa cgccaagttg gcccagccta  20820
ggccaaggtc ctaatgaagc cgacaaaaga gaaggaatgt caaggccctt ctaacttcca  20880
tagagggtgt gtggccccat ctcccaccaa caatcctgta atcccaacac tttgggaggc  20940
cgaggcagga gactgcttga agccaggagt ttgagaccag cctgggcaac atggcaagat  21000
cttgtttcta caacaacaac aaaaagaaaa cattagccag gcatggtggc acacacctgt  21060
ggtcccagcc actcaggggg ctgaggtggg aggatctctt gagcccagga tgtcgaggct  21120
gcagtgagcc atgatcacgg taccgcactc cagcctgggt gacagagtga gaccctgtct  21180
caaaatataa acaaataggc ggggggcagt ggctcacgcc tgtaatccta gcactctggg  21240
aggccgaggc aggcagatct cttgaggtca ggagttcaaa gccagcctgg ccaacatagt  21300
gaaaccccat ctctactaaa aatacaaaaa aaattagcca ggtgtggtgg cgggcgtctg  21360
taatcccagc tactgagcag gctgaggcgg gagaatcgct tgaacttagg aggcagaggt  21420
tgcagtgagc cgagatcgca ccattgcacc ccagcctggg tgacaagagc aaaactccat  21480
ctcaaataaa taaataaata ataaaaataa ataaagtaca aaaaaattag ctgggcatgg  21540
tggtgggtgc ctgtaattcc agctactcag gaggctgagg cagaagaatc acttgaagtc  21600
aggaggtgga gggtgcagtg agccaagatt gcgccactgc actccggcct gggtgacaga  21660
gcaagacacc atctcaaaaa aaaaaaaaaa tttaatatat atatatatat gtgtgtgtgt  21720
gtgtgtgtgt gtgtgtgtgt gtgtatacat atatacacat atatgactaa ctaaataaat  21780
aaatgctaat aaataaaata aataaattaa aataaatctc caaactagaa gagtaaggac  21840
taacagggcc aagaggtaaa cttttgtgaa tgttccaacc ataagtgctg ccctcactct  21900
```

-continued cacccgtagg cccccggcct gtggattctg gtttagggga acggcaccat tcaccagggt 21960
ccagggtcat atgctgtagg actctctgca gtcttgtggt ggcatcttcc agctgagctc 22020
ctaaataatc ctgagtggtc ctgagaagcc agatcaccat cccacagggg tgggtcctgt 22080
ggagggacag ggtacatgga accctagtga atcccatggg gtctccccac tgccctgtcc 22140
tttggctgta aaggcgatgc cttggctgga aacagcagta cgtgcaggag caggcagtag 22200
gctgggaagg aaagtgccgg tgccggagga agcagtgcta gtggagggga gtgggtccag 22260
atcaagaagg gttaagtgca gtcatctttc ccatcatctc atagttgcac ggtccaggga 22320
tgaagacagg acagttagca aggagagggg aaccggatca tttaagacca cagctggaag 22380
atgtccctga atgtttgcac aatttgttga aggttctaag tcccgggtcg aacaccaagt 22440
tggcccagcc taggctgagg ccctaatgta gcttggctaa caagagagaa ggaatgttgg 22500
ggcccttcta acctccatag gggggtgtgg ccccccatga agtggaaata gtgccagtgg 22560
gggagcatca aggagcaggg ccatatccta taggacttca ctgcagtctt gcggtggcat 22620
ctcccagctg tgctcctaaa tgattctgtc ccctccgcac taaatgtcct cccttcgtcc 22680
ctgggaaaag ctagaccctc tccatgaagg aaggcgtcca aagccagtca gcccttggcc 22740
aggtgaccaa tcggtctccc atgagatgtg gtgcgcttct gcggggcggg acggcacact 22800
gctgaccttg atcgggcatc ggctgcagtg caggggtgtc tggaagagct tggtaagctg 22860
agtccctgtg gctgggccac ggcggctccc ctcccctcca tgtctgcctc agggcagcaa 22920
cagctccctt ggggcagagg ctgcctgtct gccacgggtt ccaagaacct tattagagta 22980
cagtacccca tgcgcttgac agtatgccca gcctgtccag ctacaggact cagcagacaa 23040
acaacaccca ggtcagacta cacctgatgc ccatagacag ggctcagtct ccacccaggc 23100
ccaggggaaa ccgagcgctg tatatccaag cgagaagagg tcctggacac agagggcaaa 23160
ctctgctctc ctcgacgggc actgtggcct ccaccatggc ttggctcagg ctccgagggc 23220
gccttggtca gccaagaccc caagaggacc cttaggtccc tgggtcacaa ctgagtggct 23280
cagtccacac aggaacaaga ccacatgggc atcgtcactg gctgtgcctc ctgcagaaag 23340
caggccaccc ctggcgtgcc tggacacagg ggaagcacac acccaaatgc aggctgtgtt 23400
tcctccaaag agtgctgcgc acggatgact cagggtgcag gactggtcct tcaccaccac 23460
ggagtaggca tgcccggctt cgttggaccc cagagagagc ttcaggagaa agcaggagtc 23520
tctgttttta cagggtttcc ttctcaccct gccactcatg gtttttgtta aagcaaccta 23580
caacttcctc acctccaggt catatcagcc caatgtcctg tgggctgggg agacggtcaa 23640
ggtccacatg ggctaaattg tggctgagag ctaggttatt catgtaatcc caaggcaggt 23700
ccacgctgct gtccctccca ggtgagagca aaccaccttt atggttttct atatgttggg 23760
atagactgaa aaacaacaac aaaacaggtg tttgctggcg aaatagctgc ttgccagtac 23820
aaatgcctgt gctgatttgt tccaattaag aagaaaactg gtgcttgctt cagccacaca 23880
tacactaaaa ttggaaccat acagagaaga ttagcatggt cctccctgcg caaggatggc 23940
acgcaaattc ttgatgcatt ccatattttt ggaacatacc tcaaaataat aagagccata 24000
tatgacaaac ccacaaccaa tatcgtactg aatgggcaaa agctggaagc gttccccttg 24060
aaaaccagcg caagacaagg atgtcctctc tcaccactcc tatttaacat agtagtggga 24120
agttctggcc agggcaatca gacaagggaa agaaataaaa agtattcaaa taggaagaga 24180
ggaagtcaaa ctatctttat ttgcagataa catgatccta tatctagaaa accccatcat 24240

-continued

```
ctcagcccaa aagcttctta agctgataag caacatcagc aaagtctcag gatacaaaat  24300
caatgtgcaa aaatcgctag cattcctgta caccaacaac aggcaagcca aatgaactct  24360
cattcacaat tgccagaaaa agaataaaat acttaggaat acagctaaga agggatgtga  24420
aggacctcct caaggagaac tacaaatcac tgctcaaaga aatcagagat aacacaaaca  24480
aatggagaaa cattccatgc tcatggatag gaagaatcaa tatcatgaaa atggcctcac  24540
cgcccaaagc aatttatgga ttcaatgcta ttcccattaa actaccattg acattcttca  24600
cagaattaaa aaaactattt taaaattcat atggaatcaa aaaagagcct gaatagccaa  24660
ggcaatccta agcaaaaaga acaatgctaa aggcatcatg ctacccaact tcaaactata  24720
ctacaggaat acaataacca aaacagcatg gcactggtac aagaacagat acgtagactg  24780
atggaacaga ataaagaaca cagaaataaa actgcacacc tgcaaccatc tgatctttga  24840
caaacctgac aaaaataagc aatggggaaa ggattcccta tttaataaat ggagctgtga  24900
gaactggcta gccatatgca gaaaattgaa actggacccc ttccttacac catatataaa  24960
aatcaactca aggtggatta aaaacgtaaa tgtaaaaccc aaaactttaa aaaccctaga  25020
caaaaaccta ggcaatacca ttcaagacac aggcatgggc aaagatttca taacaaagac  25080
accaaaagca attgcaacat aagcaaaaat tgacaaatgg gatctaatta aactaaagag  25140
cttctgcaca gcaaaagaaa ctataaacag agtaaacaca cagcctaagg aatgggagaa  25200
aatttttgca acctatgcat ctgacaaagg tctaatatcc agtgtctata aggaacataa  25260
acaaatgtac aagaaaacaa acaaacaaac aaacaaaccc attaaaaaag tgggcaaagg  25320
acttgagcaa atacttctca caagatgaca tacacgcggc caacatttga aaaaaagctc  25380
aacatcactg accattagca aaatgcaaat gaaaaccaca atgaaatact atcccacacc  25440
agtcagaatg gccattatta aaaagtcaaa aaataacaga tgctggtgag gttgtggaga  25500
aaaaggaatg cttttacact actggcagga gtgtaaatta gttcaaccat tgtggaagac  25560
agtgtgataa ttcctcaaaa acctagaggc agaaatatca ttctacccag caatcccatt  25620
gctaggtata tacccaaagg aatataaatt gttctgccat aaagacacat gcacgtgtat  25680
gttcacttca gcacaattca caatagccaa gacatggaat caagccaact gctcatcaat  25740
gatagactgg ataaagaaaa tgtggtacat atacaccatg tagtactatg cagccataaa  25800
aagaaacgag ttcatgtcct ttgcagggac atggatggag ctggaggcca ttatcttcag  25860
caaactgaca caggaacaga aaaccaaata ccgcacgttc tcacttataa gtgggagcta  25920
gatgatgaga acacaaggac acatgggggg aaacaacaca cagtgggacc tgttgttggg  25980
ttgggggtgg gaggagggag agcatcagga agaatagcta atggatgctg ggctgaatac  26040
ctgggcgatg gaatgatctg tgcagcaaac cgccatggca catgtttacc tatgtaacaa  26100
acctgcacat cctgcacatg taccccctgaa cttgaaagct ggaatttttt tttttttttt  26160
ttttactttt taagctcttt tgttaaaaac taagacacaa acacacatag cctcggcctg  26220
cacagggtca gaatcatcag tttcactgtc tttcactgtc acatcttgac cagttttgtg  26280
accggaaggt cttatgggca gtgacatgca tgcaactgtc atcttacgtt atagcaatgc  26340
cttcttctgg atacctcctg aagaaactgc ctgaggttgt tttacattta acttgtttta  26400
tatataagta gaaggagtac actctaaata aaaagtatag taaatacata aacgagtaac  26460
gtagttgttt gttatcattg tcaagtactg tgtgctgtgc ataaatatat gtgccagatt  26520
tttatatgac tggtagcacg gcaggtttac ttacaccagc attgcacaaa acacaggagt  26580
aattgatacg gtttggctgt ttccccaccg acatctcatc ttgaatcgta attcccataa  26640
```

-continued tccccatgtg ttctgaaagg gacccggtgg gaggtaattg aatcatggag gtggttaccc 26700
ccatgctgtt ctcgtgatag tgagtgagtt ctcacaagat ctgatggttt tataaggagt 26760
ttttcccccct ttcatttggc acttctcctt gctgctgcca tgcgaagaaa gacctgtttg 26820
ctccccccttc caccatgatt gtaagtttcc tgaggcctcc ccagccatgc ttaactgtga 26880
gtcaattaaa cctctttcct ttataaatta cccaagttcg ggtatgtctt tattagcaat 26940
gtgaggatgg actaatacaa aatgcattgt gctacaacat cattaggtga taggaatttt 27000
tcagctccac tataatctta tgggaccact atcacacatg tacccgttct tgaccaaagc 27060
atcctcatgc tgtgcacaac tgtactcagc caccggctga gtccccacat tggtttcctg 27120
acgtgtgggg tgagggccac tattgtgggc caactggaag ccattagagg tgcctctacc 27180
tagaaaaata gtcaaaagcg atacaataat agtcagtcaa aagctgcatt tccagaggaa 27240
tttcagaggt tagtgccacc atcaaatacc tgaaagatgc aggggcagtg atccccacca 27300
cagccccatt ccactcacct atttggccag tatggaagac aggcgggtcc tggagaatga 27360
caagggattg tcctaagctt gactccaact gcagctgctg ggccagattt ggttccattg 27420
cttgagcaaa ttagctcatc tcttgctacc tggtgtgcag ttattgatct ggcgaatgtg 27480
tccttctcca cccctgtcca caaggcccag cagaagccag gccagcaatg caccctcact 27540
gtcccacctc aggggcctct cgcctctcca gcctgtgtca gaggtaatcc tcaggggtct 27600
ggatcaccct tcccttcccc ggcatgtcac actggcccat tacactgatg acattatgct 27660
aactggacat aaggcacaag aagcagcaat tattctatac ttgttggtgt cagagggtgg 27720
gaaataaatc caactaaaat tcagaacctt ctacctcggt gaaattttta ggagtctagt 27780
gctgtggggc ctgctctaag gtgatacata gattgttgca actgaaccct cccacgatca 27840
aaagagaacg acaccaggtg agcccgtttg atgtgaggaa gacaggttct tcctcattta 27900
ggtgtctgac tctggcccat ttactgagtg atttgaaaag ctgctagttt tgaatgtggc 27960
ccagcagcag gtccaggctc tgtgcaagct gttctgccac ctgggccaat gacccagcag 28020
atccagtctg aggtgtcagt ggcagacagg gacactgtgt agagcctttg ccaagcccca 28080
gtaggtgact catagctcag gcccttacag ttttggagca aggccctgtc atcatccaca 28140
gataaccact ccgttttgag aaacaggttt tggactgtgt attagtctgt ttcacactgc 28200
tataaagata ttacctgaga ctgggtaatt tataaagaaa agggggttag ttgactcact 28260
gttctgcatg gctggggagg cctcaggaaa cttacaatca tggcggaagg gaaagcagac 28320
acattttaca tggcggccag tgggagaaga atgagcaaga caggaactac caaaacttat 28380
aaaaccatca gatctcgtga gaactcactc attgtcatga ggacagcatg gaggaaacag 28440
cccccacgat ccagtcacct ccggccaggt ctctccctta acacctgggg attacaattc 28500
aagatgagat ttgggtgggg acacaaagcc taatcatatc agcctgtgtc taggtcttca 28560
tagaaactaa acacttgacc aagggccacc aagttaccac atggcctgag ctgcccatca 28620
tgatctgggg attatctgac ccatgttgct ataaagttgg gcgtgcacag cagcgctcca 28680
tttgaatgaa agtgatgtat tgtgatcagg ctcaagcagg tcctgaaggc aaaagtaggt 28740
tacgtgaaga agtggcccaa atgcctgtgg cccccactcc tgctccaggt gccttctctc 28800
tccccacctg catctgttgc tgcacaggga ggtccctctc atcaattgac atgggaagag 28860
aagactcagg ccatacttac aggtggtctg ctcgatatgc aggtgctatc agaaaatgga 28920
cagctgcagc cctacagccc ctgcggcaga ggcaaaggat ggaaaattcc attccaaaca 28980

```
cgagaaatgg gaaggaaagg actaactgag catgaccaaa tccaaaaccc aacaggacaa  29040
aattaaatct taaagctgaa gaataatttt ctttgactct ttgtcctacc ttctggacac  29100
actgggacaa ggctcctggt ggccccactc ctacggcttt gtgtgcctgt ggctttccca  29160
ggctggtggt gcatgctggt ggctctacag gtcccgagtg tcctctgctc ccttgggcac  29220
cactacacat tgtcctgtgg ggactctcca tggcccaaac ctgtagcagt tctcggcctg  29280
ggccccaggg tctccatgac acccagtgga atccaggagc aggaactttt cctccacagc  29340
acgtgcactc cgtgcatctg cagagctggc accgtgctga caccatcgag gtttaccgcc  29400
tgcgccttct gggctggcag cccaaggaac acctgtaccc acgtgagcct ccatgggggt  29460
gggccaggag tgatgcacca gcttgcaggg aggaacagag attgaggcaa gtctgggcag  29520
cacgccccga ggtctcatgg aggccctggg cccttctttt gaagccattc tgccctcaag  29580
accccggcac cctgagcctg tgatgggcat gacagtctgg aaggtctcgg aaatgccttg  29640
ggggtcattc tcccattgtc ttgatgagca gcttctgacc tccttctacc cgtactaatc  29700
tccttatcca aatttgcttg actacaccct tgctattctc tcctgaacat gctttcttat  29760
tctttttttt tttttatta tactttaagt tttagggtac atgtgcacaa tgcgcaggtt  29820
tgttacatat gtatacatgt gccatgctgg tgtgctgcac ccattaactc gtcatttagc  29880
attaggtata tctcctaatg ctatccctcc ccgctccccc caccccaaaa cgggccccag  29940
agggtgatgt tccccttgac gtgggcaggc taagagtttt ccaagtcttt aagttttgtt  30000
tcctttctat tatcaattct ttaactcatt tctcttttct cgccttttgc tataagcggt  30060
caacagaagt catgcagtac ccggagtgct ttgcttagag atttcttcca acaaatattc  30120
tagttcatcg cttttaaatt ctgcctccca caaagcccca gggcatggac acaattcagc  30180
caagttcttt gccact                                                  30196
```

<210> SEQ ID NO 10
<211> LENGTH: 21630
<212> TYPE: DNA
<213> ORGANISM: Homo sapiens

<400> SEQUENCE: 10

```
tgttgttggg ttgggggtgg gaggagggag agcatcagga agaatagcta atggatgctg     60
ggctgaatac ctgggcgatg gaatgatctg tgcagcaaac cgccatggca catgtttacc    120
tatgtaacaa acctgcacat cctgcacatg taccccctgaa cttgaaagct ggaatttttt    180
tttttttttt ttttactttt taagctcttt tgttaaaaac taagacacaa acacacatag    240
cctcggcctg cacagggtca gaatcatcag tttcactgtc tttcactgtc acatcttgac    300
cagttttgtg accggaaggt cttatgggca gtgacatgca tgcaactgtc atcttacgtt    360
atagcaatgc cttcttctgg atacctcctg aagaaactgc ctgaggttgt tttacattta    420
acttgtttta tatataagta gaaggagtac actctaaata aaaagtatag taaatacata    480
aacgagtaac gtagttgttt gttatcattg tcaagtactg tgtgctgtgc ataaatatat    540
gtgccagatt tttatatgac tggtagcacg gcaggtttac ttacaccagc attgcacaaa    600
acacaggagt aattgatacg gtttggctgt ttccccaccg acatctcatc ttgaatcgta    660
attcccataa tccccatgtg ttctgaaagg gacccggtgg gaggtaattg aatcatggag    720
gtggttaccc ccatgctgtt ctcgtgatag tgagtgagtt ctcacaagat ctgatggttt    780
tataaggagt tttccccct ttcatttggc acttctcctt gctgctgcca tgcgaagaaa    840
gacctgtttg ctccccccttc caccatgatt gtaagtttcc tgaggcctcc ccagccatgc    900
```

-continued

```
ttaactgtga gtcaattaaa cctctttcct ttataaatta cccaagttcg ggtatgtctt    960
tattagcaat gtgaggatgg actaatacaa aatgcattgt gctacaacat cattaggtga   1020
taggaatttt tcagctccac tataatctta tgggaccact atcacacatg tacccgttct   1080
tgaccaaagc atcctcatgc tgtgcacaac tgtactcagc caccggctga gtccccacat   1140
tggtttcctg acgtgtgggg tgagggccac tattgtgggc caactggaag ccattagagg   1200
tgcctctacc tagaaaaata gtcaaaagcg atacaataat agtcagtcaa aagctgcatt   1260
tccagaggaa tttcagaggt tagtgccacc atcaaatacc tgaaagatgc aggggcagtg   1320
atccccacca cagccccatt ccactcacct atttggccag tatggaagac aggcgggtcc   1380
tggagaatga caagggattg tcctaagctt gactccaact gcagctgctg ggccagattt   1440
ggttccattg cttgagcaaa ttagctcatc tcttgctacc tggtgtgcag ttattgatct   1500
ggcgaatgtg tccttctcca cccctgtcca caaggcccag cagaagccag gccagcaatg   1560
caccctcact gtcccacctc aggggcctct cgcctctcca gcctgtgtca gaggtaatcc   1620
tcaggggtct ggatcaccct tcccttcccc ggcatgtcac actggcccat tacactgatg   1680
acattatgct aactggacat aaggcacaag aagcagcaat tattctatac ttgttggtgt   1740
cagagggtgg gaaataaatc caactaaaat tcagaacctt ctacctcggt gaaattttta   1800
ggagtctagt gctgtggggc ctgctctaag gtgatacata gattgttgca actgaaccct   1860
cccacgatca aaagagaacg acaccaggtg agcccgtttg atgtgaggaa gacaggttct   1920
tcctcattta ggtgtctgac tctggcccat ttactgagtg atttgaaaag ctgctagttt   1980
tgaatgtggc ccagcagcag gtccaggctc tgtgcaagct gttctgccac ctgggccaat   2040
gacccagcag atccagtctg aggtgtcagt ggcagacagg gacactgtgt agagcctttg   2100
ccaagcccca gtaggtgact catagctcag gcccttacag ttttggagca aggccctgtc   2160
atcatccaca gataaccact ccgttttgag aaacaggttt tggactgtgt attagtctgt   2220
ttcacactgc tataaagata ttacctgaga ctgggtaatt tataaagaaa agggggttag   2280
ttgactcact gttctgcatg gctggggagg cctcaggaaa cttacaatca tggcggaagg   2340
gaaagcagac acattttaca tggcggccag tgggagaaga atgagcaaga caggaactac   2400
caaaacttat aaaaccatca gatctcgtga gaactcactc attgtcatga ggacagcatg   2460
gaggaaacag cccccacgat ccagtcacct ccggccaggt ctctccctta acacctgggg   2520
attacaattc aagatgagat ttgggtgggg acacaaagcc taatcatatc agcctgtgtc   2580
taggtcttca tagaaactaa acacttgacc aagggccacc aagttaccac atggcctgag   2640
ctgcccatca tgatctgggg attatctgac ccatgttgct ataaagttgg gcgtgcacag   2700
cagcgctcca tttgaatgaa agtgatgtat tgtgatcagg ctcaagcagg tcctgaaggc   2760
aaaagtaggt tacgtgaaga agtggcccaa atgcctgtgg cccccactcc tgctccaggt   2820
gccttctctc tccccacctg catctgttgc tgcacaggga ggtccctctc atcaattgac   2880
atgggaagag aagactcagg ccatacttac aggtggtctg ctcgatatgc aggtgctatc   2940
agaaaatgga cagctgcagc cctacagccc ctgcggcaga ggcaaaggat ggaaaattcc   3000
attccaaaca cgagaaatgg gaaggaaagg actaactgag catgaccaaa tccaaaaccc   3060
aacaggacaa aattaaatct taaagctgaa gaataatttt ctttgactct ttgtcctacc   3120
ttctggacac actgggacaa ggctcctggt ggccccactc ctacggcttt gtgtgcctgt   3180
ggctttccca ggctggtggt gcatgctggt ggctctacag gtcccgagtg tcctctgctc   3240
```

-continued ccttgggcac cactacacat tgtcctgtgg ggactctcca tggcccaaac ctgtagcagt 3300
tctcggcctg ggccccaggg tctccatgac acccagtgga atccaggagc aggaactttt 3360
cctccacagc acgtgcactc cgtgcatctg cagagctggc accgtgctga caccatcgag 3420
gtttaccgcc tgcgccttct gggctggcag cccaaggaac acctgtaccc acgtgagcct 3480
ccatgggggt gggccaggag tgatgcacca gcttgcaggg aggaacagag attgaggcaa 3540
gtctgggcag cacgccccga ggtctcatgg aggccctggg cccttctttt gaagccattc 3600
tgccctcaag accccggcac cctgagcctg tgatgggcat gacagtctgg aaggtctcgg 3660
aaatgccttg gggtcattc tcccattgtc ttgatgagca gcttctgacc tccttctacc 3720
cgtactaatc tccttatcca aatttgcttg actacaccct tgctattctc tcctgaacat 3780
gctttcttat tcttttttt ttttttatta tactttaagt tttagggtac atgtgcacaa 3840
tgcgcaggtt tgttacatat gtatacatgt gccatgctgg tgtgctgcac ccattaactc 3900
gtcatttagc attaggtata tctcctaatg ctatccctcc ccgctccccc caccccaaaa 3960
cgggccccag agggtgatgt tccccttgac gtgggcaggc taagagtttt ccaagtcttt 4020
aagttttgtt tcctttctat tatcaattct ttaactcatt tctcttttct cgccttttgc 4080
tataagcggt caacagaagt catgcagtac ccggagtgct ttgcttagag atttcttcca 4140
acaaatattc tagttcatcg cttttaaatt ctgcctccca caaagcccca gggcatggac 4200
acaattcagc caagttcttt gccactttgt aagagggaca gccctccccc agtttctaat 4260
aagatagttc tcatgtctgt ctaagacctc acgagaatgg ctttgactgt gtggatctcc 4320
accagcattc tgatcacgac cactgagatc attgctacca gcccagaggc tctctctaca 4380
gccctgccct cctcggcctg cactggagtc accttagcac caactccgtt cgcaggagtg 4440
tgtgcttttc cagcgtgcac ttcaaaacgt ttccagcctc tcccgtgacc cggttccggc 4500
tctgctgcca cattttcagg tgtttgttac agcaacagcc ccgcttcctg gtagcaatgt 4560
ctgtcttagc ctgtttgtgc tgctgtaaca aagcaccata gaataggtca tttatacgtc 4620
atagaaattg attgctcaca gttccagagg ctgggaatcc tgcactgcag gtgatgtctc 4680
gagaggacct tcttgccgcg tcctcacatg gcagaaaggg aaagggcaca caggcaccga 4740
gctcattcct cgccctttc taaagcactg atcccaccca ggagggcgga gcccccacgg 4800
cctcatcgcc ttccaaaggc cccacctctc actaccgttg cgttggggac ttttcaacat 4860
gaattttgga gggacacaaa tattcagacc acagtaagcc atgactaatg cacacagaaa 4920
actgaagttt caggatgtat ttgctctcat tcctctccat caactcaatg gcagctgtca 4980
gaaggctctc agacttgaat gggccttaat cccatctttg tcttctgttg atcggtccaa 5040
gtcaggcatt ttattgggcc tttgtctccc aaagcttgtt aaaatcctaa ctcttggagc 5100
agttggtttt tctgcccttg cggtgctctg aatttctgga tccatctctc tgttcacttt 5160
catctctgct tgtaagctgg gccttctttc tcaagctggt ctccgtctcg tgttgcggga 5220
cctaacacaa aactcgcaat gtggtgtttt cccacttcgc cccttatgct cctggctgag 5280
ccttcttgta ttcagcctgc caggtcacca ggagtgattt tagcaagttt gctgctccag 5340
ctccaccaag tccccatcac tcgggccccc ggtgcctgct ctcttggcag cagctgggtt 5400
tgggggttcc gactgctacc acaatacagc ctggcctgtc ctgactaata cagaagcagg 5460
ctctgtgaag gagggtgctg ccataagaag aaacgcaaat taacacgtat ctacacagtc 5520
tccgtggtgc acaacagtca gcttttcctg cttatgtgtc tgggctctgc ttgactgatc 5580
ttggctgggt gcattcccaa gacagcaagt cgtggctggc ctcgggcaca ggaaagggcg 5640

-continued

```
agagactggg gtcacagata caatctagca taggggggaca gataactcaa tgtttaaatt   5700
catagggtgc tggaccaaga gagggcatat ccaaacctga tgtgctcatc catcggagat   5760
gctgggtctg gagaaggtgt agtgactggg tggactttgg caggtcaaca gaggggtgga   5820
tggcggaaca gacgatacca tgtgttcacc acactgtttc ttcctcctag gcaaatggaa   5880
agactgcatt tcccagtcac ctctatggtt agtgtggttg catgagggtc atgtgaccga   5940
gttctgacct gtgggatatg ggaggaagca acgtaagcta cttcccaatc gcccttccct   6000
ttccaaggtg accttacagg acacacgttc ccaaagtcag ctcaaagatg aagagtcact   6060
tgaccaccat atgcaagtga aaaataaccc cgagacctca gggggtattt gttaactgca   6120
acgtagccta ctttcaaagc atggttcctg gaccagctgc atcacccggg aatgcggtag   6180
aaatgcagat tctcaggccc tgcccaggcc tcccaaatta aggatgctgg ggtggagcct   6240
agcaatctgc gtctaaaaag ctctccaggg caatctgaag gctgttcctg gccaggaaca   6300
gtggctcatg tctgtaatcc cagcactttg ggattacttg agaggacctt cttgccgtgt   6360
cctcacatgg cagaaaatga aagggcacac agggggatcg aggcgggtgg atcacttgaa   6420
gtcaggagtt ggagacaagc ctggccaaca tgatgaaacc ccatctctat taaaaataca   6480
aaaattagcc aggtgtggtg gtgcatgcct atagtcctag ctactcagga ggccgaggca   6540
ggagaattgc ttgaacccag gaggtggagg ttgcagtgag ccgagatcgt accactacgc   6600
tcccgcctgg gcgacagagc cagattccat ctcaaaataa ataaataaat aaaggctgtt   6660
ccaactatat aggagttcag gatactggca agggtgtgat taaagtgaag gaccaggtgt   6720
tcccagctgt gcaggcaaag aagtgcagtg aggaaagcat gcagtacggc tgcgtagagc   6780
actcccagca aagcaggtgg gcaaagcaaa cacacagggc ctggaggtgt ggaaggggtg   6840
caaggtttgg actttaaatc tcagagagga agcaacccaa aattaaagag accccaggga   6900
tggtgatggg cacagtgggg cagatgaagt tcactggaca ggggaggtca ggggcctagg   6960
ggccgtggtg tggggttgct tgtcccagct gggatggaca caggaattgg gctggagaag   7020
atgtacatga ggtggtcttg tctaaaccct gcacatccag ctccaagcat gcaggtaaat   7080
tcccccggaa ccaactccca tgccaacgtc agactcgaac aagtccaagg atgctgagta   7140
acagtcaggg ttctccagag aaaccgagtc agtaagatgt gtacatacac acagagagag   7200
attattgtaa ggacttggct cacacaatta cagaggctga gcagtcccaa gatccgtagt   7260
tgggaacctt ggagacccag gaggactgat ggtgtaagct cccgtctgaa aggcagcagg   7320
ctcaagaccc aaggagagcc aatgtttcag tttgagtttg aagacaggaa aaaaccaatg   7380
tcccagctca cccaggtaag aggacttccc tcttatttgt cacgcgcctc tgtgtgaaga   7440
gaccaccaaa taggttttgt gtgagcaatg aagcttttta atcacctggg tgcaggcaga   7500
ctgggtccaa aaaaggagtc agcaaaggga gataggggtg gggcagtttt ataggatttg   7560
ggtaggtagt ggaaaattac agttaaaggg ggtttttctt ttgtgggcag gggcgggggg   7620
gttacaaagt gctcggtggg gaccttctga tactcattga ccaggagaag gaatttcaca   7680
aggtcaattg attagttagg gtggggcagg aacaaatcac catggtggaa tgtcatcagt   7740
taaggcagca actgtctact ttcacttctt ttgtggttct tcagttgctt caggccatct   7800
ggatgtatac atgcaggctt gggctcagaa ccctgacacc actcagccat tttgttctat   7860
gcaggccttc agtgggtggg atgaggccct ctagaaaata aaaggtttcg ctctccctct   7920
ccctctcctt ctccctctcc gtctccctct ccctctcccc acggtctccc tctcatgcgg   7980
```

-continued

```
agccgaagct ggactgtact gctgccatct cggctcactg caacctccct gcctgattct   8040
cctgcctcag cctgccgagt gcctgcgatt gcaggcacgc gccaccacgc ctgactggtt   8100
ttggtggaga cgggattttg ctgtgatggc cgggccggtc tccagcccct aaccgcgagt   8160
gatccgccag ccttggcctc ccgaggtgcc gggattgcag acggactctc gttcactcag   8220
tgctcaatgg tgcccaggct ggagtgcagt ggtgtgatct cggctcacta caacctacac   8280
ctcccagccg cctgccttgg cctcccaaag tgctgagatt gcagcctctg cccggccgcc   8340
accccgtctg ggaagtgagg agtgtctctg cctggccgcc catcgtctgg gatgtgagga   8400
gcccctctgc ctggctgccc agtctggaaa gtgaggagcg tctccgcccg gccgccatcc   8460
catctaggaa gtgaggagcg cctcttccca gccgccatca catctaggaa gtgaggagtg   8520
tctctgcccg gccgcccatc gtctgagatg tggggagcgc ctctgacccg ccgccccatc   8580
tgggatgtga ggagcgcctc tgcccggccg agaccccgtc tgggaggtga ggagcgtctc   8640
tgcccggccg ccctgtctga gaagtgagga gaccctctgc ctggcaacca ccccgtctga   8700
gaagtgagga gcctctccgc ccggcagcca ccccatctgg gaagtgagga gcgtctccac   8760
ccggcagcca ccccgtccgg gagggaggtg gggggggtca gccccccgcc cggccagtcg   8820
ccccatccgg gagggaggtg gggggggtca gccccctgcc cggccagtcg ccccatccgg   8880
gagggaggtg ggggggtcag cccccagccc ggccagccgc cccgtctggg aggtgagggg   8940
cgcctctgcc cggccgtccc tactgggaag tgaggagccc ctctgcctgg ccagccgccc   9000
cgtccgggag ggaggtcagg gggtcagccc cccgcccggc cagccgcccc gtccgggagg   9060
tgaggggcgc ctctgcccgg ccgcccctac tgggaagtga ggagcccctc tgccctctgg   9120
gcccgtctgg gaggtgtgcc caacagctca ttgagaacgg gccaggatga caatggcggc   9180
tttgtggaat agaaaggtgg gaaaggtggg gaaaagattg agaaatcgga tggttgccgt   9240
gtctgtgtag aaagaagtag acatgggaga cttttcattt tgttctgcac taagaaaaat   9300
tcttctgcct tgggatcctg ttgatctgtg ccttaccccc aaacctgtgc tctctgaaac   9360
atgtgctgtg tccactcagg gttaaatgga ttaagggtgg tgcaagatgt gctttgttaa   9420
acagatgctt gaaggcagca tgctcgttaa gagtcatcac caatccctaa tctcaagtaa   9480
tcagggacac aaacactgcg gaaggccgga aggccgcagg gtcctctgcc taggaaaacc   9540
agagaccttt gttcacttgt ttatctgctg accttccctc cactattgtc ccatgaccct   9600
gccaaatccc cctctgtgag aaacacccaa gaattatcaa taaaaaaata aattaaaaaa   9660
aaaaaaaaag ttactcagga gaccctttta gaaatactta gggaaagata agctgtctcc   9720
ttgggatgac tgggctggtg tctgtgcata tgccttctct ggatccaagt gactttacca   9780
caccaagcct taagactgcc agactgttct ctccattgaa agccattctg caccactggc   9840
catacagaag gaatctcata ttccaggaga ctggcccaaa caggactgtt gagtggcctc   9900
taaggctttt agacgtcaaa agggtttata agaataatca tcataatata gttatgaatc   9960
agaaacatgc atacattttc ttaaatgacc ctgtggggac tggagttaaa aagggaggag  10020
tacccagatg caggcgtcta gcagaatgga cttgcttgag aatatcaagc aagacagcca  10080
aagaggactc ctaggattgt ctcaccagga cttctgaggc gactctaatg aaatgactta  10140
aaagtgtggt ggagtggctt ctgtggctcc cacaccggcc taatcctggt tgatattgca  10200
caaccagggt gcactgacaa tctctgggaa aaaagcaagg tctaatattc aaagcttggc  10260
aaacatgacc aagacttttt ctctttcctt tgaattattt tagttcccta attttttgtc  10320
ccatatgcca cttaattctt tttattttgt attaaaagtt gtgctcttgt ctcaaccttc  10380
```

-continued tttctagatt ggatcctgca tgttttttt atcattatac ttttggcagc cctaccacta 10440
ggcttcctga aatatagcac ctttgttttt gtttgtttgt ttgtttgttt tgagaccgag 10500
tttcgctctg tcacccaggc tggagtgcaa tggcacaatc tcagctcact gcaacctctg 10560
cctcctgggt tcaagcgatt ctcctacctc agcttcctga gtagctggga ttacaggtgc 10620
gtgccaccac ccccggctaa tttttgtgtt tttattgaga tggggtttca ccatgttggc 10680
cagactggtc tcaaactcct gatcccatga tctgcctgcc taggccttcc aaagtgctgg 10740
gattataggt gtgagccacc gcgccctgcc tgcacctttg ttatatagaa aattcttatc 10800
aacattattg tctactttta gactttattt tgttctattg aactattctg gttctagtac 10860
catacattaa aattatagct ttataatact ttttaacatc tgacaggatg tgctcccctt 10920
atcatccttc tttttcaata ttttatcatt ctcacagttt ttctcagatc aacttcacat 10980
gtaatttaca aaagaaatta aaattacatt ggtatttagg tggaaattat gttaaattta 11040
tgtactaatc tggagaagtc ttgttttgta ataataattc ttaccatgaa ggaaaatagc 11100
ttctctctcc gctgattcat gtttttctc atgtctctca gtagagttta tagcttttt 11160 tgtataagtt ctcataattg cttgaatata ttcctaatta tttaaaaaaa aaaaaaagaa 11220
aataaaaggt ttccactttc aaagttcccc ttcttgttaa agaatgaatc ataagtgtta 11280
gaaataacag tttcttttt ttttttttg gaagcatttc ccatttttat tcataaaatt 11340
attacttaaa attgcaaaag tagatttaca gagccacagg taacaaaaca ggaaatgaaa 11400
tgttccagac attccgaaaa gttcgaaaga aacacaccct agcctcaaaa tctccggtta 11460
aaccgtggtt gcacaacagg ttctatttat tcctgcattt tctcaataag ttcttcttta 11520
tatttgcctt tctcttttcc aacttgttga gacttggctt tgcgttcaag aattttttc 11580 cgatccttgt ccagttttag cctggtgata accaccttgc ttgggtgaat gcccacgtgg 11640
acagtcgtgc cgttggcctt ctcacgctgc acccgctcga tgtagatgac atatttcttt 11700
ctgtacacct ggattacctt gccaatttgc tgacctttgt agtgtcctcg aactacctgg 11760
acctcgtcgt ccttgcggat gggcatggag cggacattgt acttctgccg cagctccttg 11820
gagagcgggg atgacatgat cttcctgcgc acgtgtgagg gggcattgaa gtaacgtttg 11880
cggtttttac tgcggtccga ggtaacgaag ggattgaact tcatggtgac cctccggcta 11940
ctagctgcct cagaccctca acagtttctt ttaaagacta actttcttca agcctccttg 12000
ctttgtgcta ataactcttt gttaagctct atcctatgta actgttggac atcctcacca 12060
acatattcca gctcacagcc tatgcccctt ccttatttgg tgatgttatt gcctcctgag 12120
acttttcata agcaacttat ttgttcttcc ctgcacttac ctatttagga aagtttcagg 12180
ttattagcaa atcgggtatc actttaagat tgtgaggtcc cactccagcc aatggatgca 12240
ggacatagca gtaaggacaa cccaaatgcg taagggataa atacatctgc ttttcctttg 12300
ttcaggtgtg ctctcaccat tgttccatct gcgactgagc accatttctg caaaaagtaa 12360
agatggcctt gctgagagat cttttgtctc tgtgctgact tttcttcacg gcactgatta 12420
tctttttcta acaattttgg tggcaattgt atggggatat actttcctcc aggggcgtct 12480
ctagtcctct ctcacgaggg ggcactctgc tgcctcttgc agtggcctca ggggtaaggg 12540
accgagaccc atccggtgtg accaataaac ccggactctc agcaatgtgg aaagaaactg 12600
gccaacaacc tggggtaaag gatcctcaca taccgaggtg acgactctgt gcacagacca 12660
acgaaggaga agccacggga gccggtaaag tacttcttgg tggtcagatt ctggggggct 12720

-continued

```
gaatgtgtgt gtgcacgtga atgatcacag acaaccctgc ttgcggtgtt gtgtggatgg  12780
tgacaaatcc tactgctgga cggagtgttt gggtcctctc tgtgcttcca gagcaacctc  12840
agatggctta gggcagatcc tgccatggga tttatactgg cacgccaact ctaagagggg  12900
cctagctctc ccttggggga gtggccagag aggacaacac aagtgggaag tgtgcaaggg  12960
accttcagag gaggaaaggg aggaaacagg tcaacctctc acggcaggca aggcaagaca  13020
ccccctggtt tgagggggtc ttctgcaaat ttcagggagt tgaacctcat acaaacctcc  13080
ggtagtaaga aaaatattca gagttctcct ttcccttctt ctcgggggaa gaaagaggct  13140
aagctccact ccgcttgtcc cttccctagg ggaaggggaa ggagaaggga gaatagcagc  13200
ataagcgact ggcagaggca gggaaagacc ggcagaaagg aaagagaaac tgggagagga  13260
agtcagagag agagagagac aaagagggag tcaaagagag agaaagagag agacagagag  13320
tcagagagag agaaagagag agacagagac aaagagggag ttagagagag aaaaagagag  13380
acagagagta agagagagag agtcagagag agagaaagag aagtagtaaa gagaaaacag  13440
tgtaccctat tcctttaaaa gccagggtaa atttaaaacc tataattgat cattgaagat  13500
cttctctgtg accctagaac actccaatac tgcctgtaaa gaagcaagac gagtcacacc  13560
agtgactgca agaccctaga gctattaacc agttagtcca aactacccac cctgttgtta  13620
cagtaataga tgtaaaagat gccttctggg cttgtccatt tgcagaggac agccaggacc  13680
tatatgcctt tgagtgagaa gaccctcact ccggtggaaa atggtaatac caatagacgg  13740
tcttacccca agggtttacg gagtctccaa atttatttgg tcaaatattc aaataagtca  13800
tttaattagc aaaggtaaac agaaaattga gcttgaatgg attgaaggca tcacattctt  13860
gcctctgctg gagactaaat aagagcttag aaaattttgg gattagttgt atggataccg  13920
tcgtctatgg gtagactcat gccctaaaaa caaaactctt acacaaaaag ctcacacgag  13980
acagaccaaa ccccctcatg tggcaattac cagaaatcca acaggtggga aggttaaaac  14040
atctattagt aactgcccct gtcctagctt tactctcctt aagcagccat tccaccttgt  14100
tggtggtgta aacaacggcg tagcccaaaa acactgaggc cactgacaac ccatagcctt  14160
cctaatcaaa aatccttaac ccagtaaccc gcggatggtc caaatgcatt caatctgtag  14220
cagcaacttc tttgctgaca gaagaaagta gaaaaataac tttgagaaga aacctcattg  14280
tgagcacacc tcaccaggtc agaactatcc taagtcaaaa aaaaaaaaaa aaaaagaaaa  14340
gcaaaaaggt agcttactaa ctcaaaaaat ttaaaatatg aagcgattct gtcagaaaaa  14400
gatgatttaa cattaaccac tgatcattcc cttaacccag caggtttgct aacaggggat  14460
ctaactctta atgaattacc atacaaaggt ccaaccagac ctagaaggaa ctcccttcaa  14520
gacaggacaa tagatggttc ctcccaggtg aatgagggaa aaagccacaa tgggtattca  14580
ttaagtaatg gggaaatagg agtagagtta ggaaaattgc ctaggagttg gggagttgtt  14640
tgcactgagc caagccttaa gatactgaca gaatcaggaa ggagtcattg tgaaaagtga  14700
agtagagttt acctcctcaa aagactttcc tcccccatct aatcaggaat aaatagtaac  14760
ttctcttagt agcaaaatgt attcaaagac cagcgctaac attcttaaat atctgctaga  14820
cgtaataaag aaatcaatgt actttatgtc cttagctccc acaatttagt ctaaatgttt  14880
gctctggcat gcttatactg gtccaggcaa gcattaggtc ctatcctgtt cctcttcctt  14940
gtttgtgtct cacatgtccg tgtgaaaaga ccaccaaaca ggctttgtgt gagcaacaag  15000
gctgtgtatt tcacctgggt gcaggcgggc tgagtccgaa aagagagtca gcaaagggtg  15060
gtggattatc attagttcct acaggttttg gggtaggcgg ttgggttagg agcaatgttt  15120
```

tgccagcagg gggtggatct cgcagagtac attctcaagg gtggggagaa ttacaacgaa 15180
ccttcttaag ggttggggag attacagagt acattgatca gttagggtgg ggcagaaaca 15240
gatcacaatg gtggaatgtc atcagttaag gctattttca cttcttttgt ggatctttgg 15300
ttgcttcggg ccatctggat gtatacgtgc aggtcacagg ggatatgatg gtttagcttg 15360
ggcccagagg cctgacagtt tgaaggtgtt tttacctttc tcagcattcc acgagttact 15420
tcttcctttg ttctcctctg cctttgcctc ttttaaaaag ttctaagttg ctagccagtc 15480
gggacaaatg cagaatgtca ggcctctgag cccaagctaa gccatcgcat cccctgtgac 15540
ttgcacgtat atacgcccag atggcctgaa gtaactgaag aatcacaaaa gaagtgaata 15600
tgccctgccc caccttacct gatgacattc caccacaaaa gaagtgtaaa tggccggtcc 15660
ttgccttaag tgatgacatt accttgtgaa atcccttctc ctggctcatc ctggctcaaa 15720
aatctccccc actgagcacc ttgcgacccc ccactctgct cgccagagaa caactccact 15780
ttgactgtaa ttttccttta tctacccaaa tcctataaaa cggcccccacc cttatctccc 15840 ttcgctgact gtcttttcgg actcagcccg cctgcaccca ggtgaaataa acagccgcgt 15900
tgctcacaca aagcctgttt ggtggtctct tcacacggac gcgcgtgaaa cagaatgtga 15960
ggtcccgttc cagccaatgg aaaccagaca cagcagtagg gtggacgcgt caggttataa 16020
atgaccctgt ctcctttgct cagtgtactc tcgtggcaaa actgctgccg agtgtaccct 16080
ttctacagaa agtataaaaa tgaccttgcg taggaaatta aatttatgtt caagtgccat 16140
ttctttatgg caccggggag caagcatttc aaacatcatt tgtaccaatt ctaagttaaa 16200
tttggactaa acaaggtctt attaatagca aaggataatt gaaatcccaa acttacaagg 16260
ttttcaacaa aagtaaagtt tgctaaaagt taacagtata acatgtatta tcctaacttc 16320
taatgttgtg accttaggct gtctagtcca cagacataaa ggaagttcgc tttggaaaag 16380
aatggttatc atctttgaga gaaaaaaaat tgtttcgaag gtttaagcaa gttttgaaat 16440
attcattgta aaggaaacat attggctaaa gttaaagggg tatcttccag tttttctgtg 16500
aactggacat taaaataaaa gcccagtggg tttttcttaa agcgctaacc tgctctttaa 16560
caaaaattac gaaaggttaa aaattataaa agtttaaaaa aagagtctgg aaatctcacc 16620
ttgtggtcag accttaaaat tggatacata tgtctacaag gttttattaa aatgaagttt 16680
aacacgaata acacactaat gtaaaggtga aatttagctg atctggtata aaatcacaca 16740
ggaagcactg tcaaatataa aatggtgttt ggctttcttt ggtctaaaaa ctaataaaaa 16800
taggtactaa aggaaatttc tcagcaagaa ggcactaagg actataaaat ccactgctga 16860
tgtccccacc tttaaaacaa aagatcaatt tttagaaatg atatacttgg tttatcctcc 16920
acccttaaaa caaaaggtct tctagcacag gccctgccct gagagtttcc agtacatcag 16980
caccagcctg gggatcccgt tctcatcaaa gggtggaaag aagggaaact ggagccagcc 17040
tgggaaggac cctgccttgt gctgctgact accgagattg ctattcgtac aacggaaagg 17100
gggtggacac gtcccaccag agtcaagcaa gcaccattat caacagaatc atgggccatt 17160
gtttctggat caagccctac caaattaaag ctaaggaaag ctgagtctat ctctttcctt 17220
tcctttccta acccagtgcc tatatccatg actattccta ccactagcaa ctctaacccc 17280
actttagaga gtttctgtgg tttgggagca gaggtcactg gaagggatcc tataggcttc 17340
aaggtgcgct ttgttctccc tcctccacct cctacgactg ccccttttccc aaacctacaa 17400 catcaaacta tgcctcgcct catgccaaat gacacaagca agttcttaga agtagaaata 17460
ggagacccaa ggcaaaccct agccattgaa agagggtata aagacataaa tgccggttaa 17520
aacggattaa atatcccgtt cgcactttaa gcaaaagtga ccattaagct tgtgggcgcg 17580
gtaggccaga ggctcaggat gcctcctttc cactgggacg gtcctcaaat caagcggaca 17640
tggagtgcgt ggtagctctt ttcgaagatt ccaccacctg gaataacgaa ttgtgccaag 17700
ctctttctct gctatttcct gaagttcagt gccctgtggg tcagcccccg agggccatcc 17760
agccttcatc ttccaaaacc aattttacct cgtgtctcca acaacgaggg gaaaaaactt 17820
ggcattcctt ggagacttaa aaggttgcag taaagtcagg cacctccaaa agctgaccca 17880
tcggtctgcc cttattcatc cctgagcgga tgtatggtgg tattatggag gacctttact 17940
ggacactctg ccaaataatg agagcagtac tgatgctgta gttcagttgg ctatcccttt 18000
tactctggca tttcatcaac cagaaaaaga aaaaaaaatg tagcctcaat tcttacctct 18060
ttaacaacgc taataagtat actctttctt cgtaggtgtt atgtcgtacc atacatccag 18120
gagttcatca aaacaactaa gccaagacat gctaagaaag tttgaagagg aaaactatac 18180
agtaaaagag gagggaattg taggaagtaa aaagtttctg cttcaaagtt ccccttcttg 18240
ttaaagaata aatcataagt cttagaaata atagattctt ttaaagacta attttcttca 18300
agcctccttg ctttgtgcta atagctcttt gttaagccct atcctatgta actgttggac 18360
atgctcacag acacattcca gctcacagcc tatgcccctt ccttaattgg aaatgttatt 18420
gcttcctgaa accttttgta agcaacttct ttgttcttcc ttgcacttac ctatttagga 18480
aagtttcaaa tcgggtatca gtttaagata gtgaggtccc actccagcca atggatgcag 18540
gacacagcag taaggacaac ccaaatgcgt aagggataaa tacatctgct tttcctttgt 18600
tcaggtgtgc tctcaccatt gttccatctg cagttgagca ccctttctgc agaaagtaaa 18660
gatggccttg ctgagagatc ttttgtctct gtgctgactc ttcttcgcag caccgattat 18720
ctatttctaa caattttggt atttctaaca ggcccacaca cactgtgtgg gccaagctgc 18780
ttcactcagt ccactgatca aatgctcatc tcatcctcac agacacaccc aggatactgc 18840
ttgaccaaat atctggacaa cccatggccc agtcaagtcg acagaccaaa tgaactgtca 18900
cagacagctt ctgtccttgg aacggggtgg gattccacgg actctctccc ttcacagtgg 18960
agatgctcag tcagcaagct gccagaagtt cagagctggg gaagatataa agaggactgg 19020
gcatggaagc tgcaggaact agtcaggaac tgggagtacc taggagtcag ctcctgagtg 19080
tgcaggatca tggtgaaata gaaagttaga gaaggaagag tgtgtcaata tcagagcatt 19140
gtcttatagc acaggactta accctctcct aaggttccag ggagacagtg ccaaatcatc 19200
acttgagtgg tgcttagaag cttcagggca aaagagccaa ccctaagtac atttgtctac 19260
tggggctgcc atcacaaagc accgcagaca gggtggctta tacaacagac tcattgtctc 19320
acaatcctgg cggctggagt ccaagatcaa ggttttgcaa ggctagctcc tcctgaggcc 19380
tctcttggct tgtagatgac cggggccttc tctctgtgtc ctcacagggt cttccctcag 19440
tgcgtgtccg tgtcctcacc tcctcttgta agactccagt cctatgagat taggacccac 19500
tgtcatgaac tcatttactg ttgattacct ttgttttatg ttttttgttt ttttgagaca 19560
gggtcagtct ctgtcaccca ggctggagtg cagtggtgca atcatggctc actgcagcct 19620
caaactcctg ggctcaagga atcctcccac ctcaatctcc caagtagctg ggactacaga 19680
tgcataccac tgtgcctggg tgtattagtc tgttattgca cagctataaa gaaatacctg 19740
agagtgggta acttataaag aaaggaggtt taattggctc acggttcata gctgcttctg 19800
gggaggcctc aggaaagttt cagtcatggt ggaaggtgaa ggggaagcag acacgtctta 19860
cacggccaga cagttcctcc tacactggct gacactctct cctgccacct tgtgaagaag 19920
gtgcctgctt ccttttctgc catgactgta agtttcctga ggcctcccca gccatgtggg 19980
actgtgagtc aattaaacct cctttgttta taaattgccc agtctccggt agtatcttta 20040
taacagtgtg aggatgagct aatacacaca ggaagcagca atgccatcaa agagccaggg 20100
gccttgactg gcagaactag tgagaccatc accaaaacat ggcattcctt gggcaaggca 20160
ggtgcgcagc cagcaaggta ttgcttaatc tacatgatca aaagacatca ggatggttgt 20220
tcaggaggct gagaacagcc atcctattat ggctgagttg tgtcccctca aaatttatat 20280
actgaagtct taaccccccca ggacctcagt gtgtaagtat ttggagaaag ggcctttaaa 20340
gatgtagtta aattaaaatg aagacattag ggtgggccct aatccaatct gactggtgtc 20400
cttgtaagaa gaggagatga ggacacatgc agaggcatga ccacatgagg acacagggag 20460
aaggtggcca tctgcaaatc aaggagtgag gcctcgggag gaaccagcac taccaacacc 20520
ttgatctcgg acttccagtc tccagaacca tgagatgatg aaagtctgtg tttaagctgc 20580
ccagtctgtg atattgtttt gcaaccctaa tagatgaata cataccccaa tgaaaaagca 20640
tgatctcttg cccagtttct gcacctgaga cagttttcaa acccaaaccc cactgattga 20700
aggagggatt aggtcccagg aggacggacc ctgcagtacc atagcaggct cccccagtcc 20760
ttccccaccc caccactaaa ggtgtatttc agtaactgtg cactaggaaa agggcaatgc 20820
ccagggctgg gggactccgg gaccaagttg acactgagag ctggagtcaa ggtaccatca 20880
tgggcccact agagtagggc gtatggaggc cagcaaagtg caatcctggt ccacctctag 20940
ctcacactga gtcatccctt tgcattccca gaatgctgca tattccccca gaccctaaaa 21000
gtacactcag acaatcttgg tagttggcag aatcctcacg taggctcatt gtcctgtagg 21060
gtaaaaacta tcatagtgtt accaagtaga aacttctgaa actgcccacc accttagcca 21120
aggcaataca ccaaaaagaa aatctcattg gtggggaatg gcagagatgt gggcccccttt 21180 ggaagacttg aaggttgcag gtgaggcgat tcccatcatc tcccccattt tccagagaat 21240
gctaacagac tactgtcaac ttgtgatggg aaattttatg cgtccacttc actgggccat 21300
ggtgcccaga tgtttggtta aacattattc tgggtgtgtc tgcaaggtgt ttctggatat 21360
gcttagcatt tgaatctgtg gactgagaaa agcaggtcac tctctctggt aaaggtgggc 21420
ctcatccaat cagttgaagg tctgactaaa acaaaaagat taagcaagag aaaattcgct 21480
ctccctgcct gtcttagtct gtttatgttg ctataaagga atattggagc ctgggtaatt 21540
gataaagaaa agaggtttat ttggctcatg gttctgcagg ctgtacaaga aacatgacat 21600
ctgcatctgc tgctggtgag ggcctcaggc 21630

<210> SEQ ID NO 11
<211> LENGTH: 37113
<212> TYPE: DNA
<213> ORGANISM: Homo sapiens

<400> SEQUENCE: 11
tgtgggctcc cctctgctga tgggttcccc tctccagctg tggcttccct ctgctgatgg 60
ggtcccctct ccagctgggg ctccctccac tgatggggtt ccctctacag ctgtggctct 120
ctccactgat ggggtcccct ctccagctgg ggctccctcc actgatgtgg tcccctcttc 180
agcttgggct ccctccactg atggggtccc ctcttcagct ggggctcctc tccactgaca 240
gggtctcctt tccatctggg gctcccttgg ctgatgaagt cccttctcca ggtgaggctg 300

-continued

```
ctctctgctg acagggtccc ctctccagct aggtctcctc tctgttgata gggtcccctc    360
tccgggtggg ctcccctctg ctgacggggt cctctgatgg ggtccctact ccaggggggc    420
tcccctccat agatgagctc cccttcctgg gttgggtgac ccctccgccc tatctgtgtc    480
tgcaggttgg ggctaggcag tgctggccag catctgacaa cctccccttt ctgttcttgg    540
gcactgctca cttattcagg tctcagccag gcagcccctc caatggtaat cttcagagtc    600
cccttcagca acacagcttc ccctctgtgg cccagctcat gctgaagtaa acaaggcaat    660
gtcattaacg gctggtatca gcttgtacgg ggaaccagtg gccccagaag cctctgggga    720
ggcccaggct gtgaggatca ggggtccgga agagcctcta gagcgggaga aagaggcctc    780
aggggtccct cctcacaggg gatggtgaca acacggtagg gaatggaggg gtcagggctg    840
ggtccaggac acggtgaccc tggccagaaa aggccgggcc tggctggcac ccgcacgaag    900
ggaacggagc cagtgtggaa aagcaggccc gcgtcctctt ctgcactccc agcccccttta    960
aactacacac agcttgtagg aaggggatca gaggcccctg ggcgtcccat ggctatgctg   1020
cacctgggga catgaagcct agggtagctc agccagctct ggtcacggct gacagacagc   1080
ctcaccccaa cagcctcacc catccctcct cagggaacag ggtcctaaca agctgctttc   1140
cccatcccag tgttgaacaa aaactcatgg gtttagacaa gagtgaaggt gactcctcca   1200
ccacccatcc cacctccagc aggcagccac ccccaaaatt attgatttat taataaatca   1260
atgacaggtg ccagccagcc ccacctgtcc ccaacctgca aatgcagaca ggggtcactt   1320
ggtccaggga gaggagaccc tcagtggagg ggagacaccc tggagagggg accccatcag   1380
caaaggggag ccccagctgg agacagtaaa taggcagact attcactgtc ttcccccctca   1440
agccaggccc acagagtcac agagtatagc caccagcctc ctgggcccac ccgggaggcc   1500
ccaaccacac tccccctgct cagctcagcc cggatttctg gattctgctg cctgccaggg   1560
atcctgagga ggagatggta tcagagcctc accagccctt ctcataccca ggagtcctca   1620
tgatgataac agtgtgtgcg ccaggctgtg caggtgctgg ccgggatcct ctgaggggac   1680
gagatctcca tgggagggca ccactctgat gtccatcctg ggcttccgtg gccctgcctg   1740
gccactgccc gctgctcttg gtcaagatca tggaccctca gaggccaacc aggcctcagc   1800
ctgtgcctac agcatcctct ctactgccgg gcttctgaat tgctccttcc tcctgtctcc   1860
cacccagagc aagaacgaag gggaggcccc cagagccctg cagcgccggg agagactccc   1920
atccccaccc cgcatgccat caacacaaac tgccggagag tttaggggat cccacgactt   1980
ggggtctcca aagagacccc cgggacatct catcgagacc cccctgggca ctgcatgctc   2040
aggcttccca cccctggccc accccatggg gtgtgcccag tcccgcatct caccccatat   2100
ccatgcatgc atgcatgaac ctgaaagcac cccacaccct ctggtgctca gtcctcccct   2160
cctccctggg gtcccctccc ctccctgccc ccccaagcctt gcatccccct gcaaacctca   2220
caagggggaa ctatttctgt cctgaaagca gagagggccc ttttcttggg acctctccgc   2280
catctctgcc tccactccca gctgctgtca gctctggcct ggcccctgca ggaagcaatc   2340
actggtctcc ctgtttccca tctggcccca aggtctgttc ttgcccttcg accagagagg   2400
tttgaaagca caactcgggc cctgcgtgcc ctgctcccca gggctccaca cctctgagca   2460
cccgcgcagt aacggaggct cccagccccg cctcgcccca gggtcccctc caacactctc   2520
tggccttggg cctttgctat acccggggcc tggaagggcc ccctcatccc ccaagtgtca   2580
ggcaaaggtc tcagagcact gtccctgccc ggcgtgcttg gtcctgactg ctaggcccca   2640
aatcattcct tttcccatta cctcttggtt tctctgtagc tggggtcact accccaaatt   2700
```

cttgaattga ctgacgtgtc caactatttc atgttttccc cctctacact gggagcccta 2760
caagggcagg gccccctggg caagaatagt gccagccagg agcccctgga gaagatagct 2820
acacatgtgc cccaggcccc agatggcact cagccctgcc tgtcaatgct ggacataggg 2880
cagtttttat cctggctttc tacacaagga ggaaagacta accatgccag cgggcagcgg 2940
ccggatcacg tatgtcagta gaactctgac ccctgagaag cctggaagcc aaaccacacc 3000
tctgtagcaa tcacgccaca gactcaggcc acggctaacg gctgccagtt cacctatttt 3060
tgcccccaac tcaagaccaa ctggaggaag gcaaatatgt ccctgacgaa gggtggccgc 3120
ctccagcctc cccagcccag agcctcagcc tccccagccc actgcctcca gcaacacaca 3180
tctgaagcct tctctgttgg ttggttttat tggtattttg gaagattgtt tgtttttttgt 3240 tatgagatgg agcctcgctc tgtcccccag gctggagtgc agtggcgcga tctcggctca 3300
ctgcaagctc cgcctcctgg gttcaagcca ttctcctgtc tcagcctccc gagtagctgg 3360
gactacaggc acccgccacc gtgccaggct gatttttttg tatttttagt agagacgggg 3420
tttcaccatg ttagccatga tggtcttgat ctcctgacct catgatctgg ccatctcggc 3480
ctcccaaagt gctgggatta caggcgtgag ccactgcacc tggcctttgg aaggtctttt 3540
atacctttat tgagataaaa ttcttatgac ataaaactta gcataaactg tagacttagt 3600
tggtgtgact ttagagtagt ctcagaattg tgcaaccatc accactgcct acttttagaa 3660
cattttcaac atcccaaaga cagaaccccg taggcacctg ttagcagcca ctccccaccc 3720
agtccacgaa gccccaggca gccactcacc aatctacttt ccattaattt gcccattcta 3780
aacacttgaa aaaaatggta tcacaatggt cttttgggtt tggcttcttt ccctcagcat 3840
cataccctca aagttcatcc atgttgtagc tcgtatcggt acttcattca tttttatggc 3900
tgaataatat tccactgtat ggatagaccg atattttgtt tatttattta ttcattgatg 3960
aacatttgaa ttgttcccac tttttagcta ttaaaactag tgctggctgc gtgcagttgc 4020
tcatgcctgt aatcctagca ctttgggagg atgaggcagg cggatcactt gaggccaaga 4080
gtttgagacc agcctggcca acatggtgaa acccccatct ctaataaaaa tacaacaatt 4140
agccagacac ggtcatgcgt gcctgtaatc tcagctactc aggaggctga ggcaggggaa 4200
tctcttgaat ccgggggggca gaggttgcag tgagccaaga tcgcgccact gcactccagc 4260
ctgggcaaca gaccaagact ctgtctcaaa aaacaaaaca aaacaaaaca aaacaaacca 4320
gtactgctat gaacatgcat gtgcatattg ttatacagac atatgctttc atttctcttg 4380
gatacacaca cacacacaca cacacacaca cacacacaca cacacacacg tatatctagg 4440
actggaattg ctgattttta tggaaactct atatttagca ttttgagaaa cggccagtct 4500
gttttccgaa gtggctgcac tattttgcat tcccaccagc aatgaaggag ggttccaatt 4560
tctccatacc tctgccaaca cttgttattg tctgtctctt ttatttatag ccatcttgat 4620
gggtgcatcg tggtatctcg ctgtgttttg atttgcattt ccctgatgac taatgatggg 4680
gacatctttt catgagctta tcggtcatat gtacatcttc tttggagcaa gctctattct 4740
aatcctttgc ccatcattaa aggtaggtgg tttgtcttct tgttgataag ttagagttct 4800
ttacatgttt agatactagt cccttatcaa atagatgatt cacaaatgtt tgctgtcatt 4860
tcttgggttg tctttccact tccttgatgg tgtcttttca cgcacaaatg tttttagctt 4920
tggccaagtc caatttatct attttttctt ttgttgcctg tgcttttggt agtgtatatt 4980
aaaaaccatt gtttaacaca aggtcaccaa gatttattcc tatgttcttt cctaaggatt 5040

-continued

```
ttatttttc ttttcttttt ttttcttttt tttgagacaa agtctctctc tgtcgccaaa   5100
gctggagtgc aacggcacaa tctcagctca ctgcaacccc tgcctcctgg gttcaagcga   5160
ttcttctgcc tcagcctccc gagtagctgg gattacaggc gcccaccacc atgcccagct   5220
aatttttgtg tttttagcag agacggggtt tcaccatgtt ggccaggctg gactcaaact   5280
cctgatctca ggtgatccac tcgcctcggc ctcccaaact gctgggatta caggtgtgag   5340
ccactgcgcc tggccttcct aaggatatca taattttagt gcttacattt aggtctacga   5400
tccattttga gttaattttt gtgcacagca tgaggtaggg gtccaacttc attcttttgc   5460
acatggatat ctagttgtcc cagcaccatt ttctgaaaag actattcctt cccccattga   5520
attgtcttgg tacccttgtc aaaaatcaac tgatggccgg tctgaaggta gtgagttatc   5580
tcaattgatt gttcacagtc agttacagat ggaacacctc gttctactct ttcccgcctt   5640
ctcactgctg cacttgaaca gtctttaaaa aaatcaattg accataaatg caaggatttg   5700
ttcttggagt ctcaacttta ctgcattgat ctgtaggtct atccttatgc cagtaccaca   5760
ttgtcttgat tactgtagct ttgcagtaag tttgaatcag gaaatgtgag ccctccggtt   5820
ttgctcttct ctttctagat tgttttggct attctgaaac ccttgtattt ccttatgaat   5880
ttgaggatca gcttgtaaaa agacagatgg gattttgata gagattgtga agctatagat   5940
gaattcggga gtttggccat cttaacatta tgtctcctga tccatgactg caggatatct   6000
ttccatttaa ttcgatactc tttgattcct ttcaaaaata ttttgtattt ttcagtacac   6060
aagttttatg catcttttgt tgcatttatt tctaggtatg ttctttttgc caatattata   6120
aatgagattg tcttcttcac ttcatttttg gatggttcat tgctagtgta tagaaataaa   6180
atcgatgttt gtatattgat cttgtatcct gccacattgc tatgcatgtt tattagtttt   6240
aagggtttta gtggattttc tatatataat gtcatataat cagcaaatag aaagtttaat   6300
gtcttagtcc ttttgagctg ccacaacaga ctaccataaa ctgagtggct tataaacaac   6360
acaaatgtat ttcccacagt tctggagact gggatgtcca agatcaagac acccgtaggt   6420
ttggtgtctg gtcggggcct acttctgggt tcatagatga ctgtcttctc gctgtgtccc   6480
ccccatagtg aaaggaaggg gcccagggtc tttctaaggc ttcttttata aggacactaa   6540
tccaatatag gaaggctctg ccctcataac ctaatctccc aaaggcctca cttccaaatt   6600
ccatcacctg ggagtaaga atttcaacac tgggggggaca cagatattca gacatagcat   6660
ttttcttctt cctttctaat atgggtgccc ttgacatctt tttcttacct aattgccctg   6720
ccagagcctt ccagacagtg ttgaatggaa gtggggagca ttcaccccac cttactcctg   6780
atcatagggg aagaactatc cggctttcac cactgagcac cacgttagct ggggtatttt   6840
tgtcagcgct ctttatcagg tggaggcagg tcccttctat ttctagtgag ttcagtgctt   6900
ttttttttt ttaatcaggg aagagtgtga gcttgtgttt gggtgccttc cctgcgtctg   6960
ttgagatgat cttacggttt ctgtctctta ttctattgat atggcgtatt tattaccttg   7020
gttgcttttt ggatgttgat aacatccaaa ctcttctgcc acccctttta atagaaagct   7080
gtacaactcc ccaacctgcc tgggcgtgtc tgcccaagat gagtgctagt ggccgactcc   7140
ctgctagagt gagcactgca taaacagcct ctgcttgtcc tcatttgagt gatcttcatg   7200
tattccacga gaaatcaagg cacaggggtc tcatggtctc atgaatggct ccaccaactg   7260
aaggtgtgct ccatcggggc tgtgagtcac ctcacgccag gcagaaaggt ctctctgtca   7320
aacatggctt caaggaacca gggacctggt tcctcccaca ggccaggccc tgcccctaag   7380
tgcaatggga atatatgcac atgtcacctg tcccaaaatg ctgggagatg gcacttctgc   7440
```

-continued

```
agatggggaa actgagggac cagcccgaag tcacggggag gggaagactc ctacacacag   7500
ggaggagaag aacccagccg ggctgcaaac gcctgccctt cctcaacgtg cctccggctg   7560
tgcccacatc gctccagcag ctctgccttc ctcaggcata agccttctca gggcagggga   7620
ggcccaggga gcggcgctcc catcccaggc cgggctgctg agcaagcccc tcccctttct   7680
cccctcatcc tctgacagag tccacctgaa tatttgtcct ggagccagga tggaagctcc   7740
accaggccca gctaacaaca ggaacccttt cagacgcact tctgggtgcg tactgtgcca   7800
gtatcacaca gacacaagcc atgtccttgt cagccatggg atccccaagg tccccatgag   7860
gtcacaccag tgggccactg ggaagggcac ttcagatgtg gagctcccat gggccaggcc   7920
ctgcgaagtg gtcctcctac cccctcatag ccagtcttcc ctgtgagcct gcaagtgact   7980
gtgaatgtga gttccactct ggagctaaga cgggctgctg cccccgcaat cagatgtcag   8040
gcccatgaag ccctccatca tcccactgca gtcagaataa aatgcagcct ccctctggcc   8100
tccaggtccc aaggccagcc cccctgcctc ccaggctcac acctgcccct aacctgtgtc   8160
cagccccttt cccctggctc tgtctcctgc ttcccttgtg ttcctccaac ctcacctgtc   8220
tgtctggagt gctcctcccc ggctctgcct agctggctcc ttctcaggca tcagggcctg   8280
gatccactgt ggctcttcca agcctctgca cttggagtgc ctcagccccg tggttgagga   8340
gtgccccaac cctgtgaccc tctagcaagc atcctaggaa ttccgtccct ccccagcact   8400
gatatgacca tcgtgctgtg acacgtgtca tctccgccag agttgcagat cctccagggg   8460
aggggtctgc tgcctggctc ccacagccag ggcctggaac agtgcctgac acacagcagg   8520
cacccactaa atatttgatg catggctgaa gaggacaggc aggctggctg ctggctgggc   8580
atggcctgct tctgaggctg gtggtcaagg acacagtgtg catggatctg ccccctcctc   8640
ccacttcctg agagtggagc cagtgtctcc ctccacctac cacccccctgc tgaggacaca   8700
gctcacacct ttaacgggaa atgtccccat cactggggac agcagggagc tgatgggaga   8760
gcaggtgtcc aggacatcca gagaaatgtt tcctcacact ggaacccttt tctattccct   8820
tctaaacaaa aagaatcctc gaagactctc aagtgaccat atagtgtctt ttcttataat   8880
gtcacttcga caggcacaaa atgtaaaacc aggcataaac tactagtgct tgcagttctt   8940
acgcaggcat gaagccaaaa ccagtttaca aattaaccac caagaaaacc ggtagagcac   9000
agatgatgac gatagagctg ttttgtccaa tgtgagcgct actggccacc cagggccatg   9060
tgaatttaaa ttacgatgaa acacaatgaa aaatttggtt ccttgtggcc acatttccag   9120
tacccagtag tcatctgtgc caggggggtta tccaggtaca gaacattccc atcgttgcag   9180
aaggttctat cagctagcac tgggttggac gacacttgcc aagacgagct ggctagagga   9240
tggttctccg gacctggtcc cacgtggttc ccaggtaagc cccgcccag gatgcagccc   9300
cgttgtccat cagttttctt ggagagggca tgggaaacct tcgtcagtgt gtcatctcct   9360
gcaaaggcct tcgctccttc ctctggggag aaagcaccct tcactctctg aatcattagc   9420
ccaaagcagt aagtgcagca ggcctggccc cacaccttcc ggaagagcca cggtgtgagg   9480
ctggcatccc tggggcacga cacaaccagg atgtagacga aatagatgca atatctggag   9540
gttctcctat aggtgtctct ggcctcctgg acacttcaca ctgttctggg agctgccctc   9600
tcaggcccca gtgacctttt cagatgcaga ctcccacagc atgggtcagc aattctcccc   9660
ttccgtgaga cagggattgg ttacctgtac taggaccttg aggccaacac tgactagggg   9720
gcctcatgcc tgcccaggtt ccagccccgg agagcaatgt gagcaaagct tgctgtcttt   9780
```

-continued

```
gcaaagccaa ccactgtggc atcaactcct tcaggaagcc ctcccggatt gtccaaggtg   9840
ctcacctcct ttggggagcc ctcccagatt gtccaaggtg cttgagggag ggaggaatgg   9900
gttgttctcc cggcaccggg gctgcactcc tgggcagacg ctgcatgcct gtcctcaggc   9960
gcggccctgc tgccaccccc ttgggggctc ggagcgcgac agcagcttgg ggacgcctcc  10020
cgcgcccagc acggtgcacc tgggccctga ggtcctggcc gaaacgcgcc aagttggggg  10080
taggtgcagc gaccccatac ccctcggctg cgcgccctgg cggcaggagg cggggccggg  10140
ggcggggcgt gagctggccg gggcggggc ctatggaggg gcgggaccgc ggcgccctat  10200
aagtactgcg gagcgcaggc gcgcgcccgg ccagagagcg agcgcgcaac ggcggcgacg  10260
gcggcgaccc caccgcacat cctgccaggc ctccggcgcc cagggcgcac ggcgcgcccc  10320
cgtgccggcg gcccctgcgc ccatttcttg gcgcccccgc ccggtcggcc cgccaggccc  10380
ctttgccggc caccagccag gccccgcgcc ggcccgcccg ccgcccagga ccggcccgcg  10440
ccccgcaggc cgcccgccgc ccgcgccgcc atgggagtgg agggctgcac caagtgcatc  10500
aagtacctgc tcttcgtctt caatttcgtc ttctgggtaa gggctgcgcc gggggccggg  10560
gcgggagggg gcaggcacac actccacgtt gggcaggtcc cgcggcagcg tgctaggccc  10620
cgcgggcgca gcgcgggccg cgaagttgtg gggccacctg tgggctccag gagcggggtg  10680
gggggtcgcc cggggccacc gcgccccccg acattggggc tgagggctgc gagccgagtt  10740
tcggggcctc tgtgctcggg ggcccacctc tgcggccggg ccggggcttc tgggggccgc  10800
cgggcagttc ccgctgtggt ggtgatgggt gcggtggtcg cgggtcggga cccgagtacc  10860
cggccgcccc tcagctaagg aggggcctgc gcgggtccct ggccgcggat tccggactgc  10920
tgcttcgcgg ggacgagggg ggggctcgcg ggcgggactc ctggcgcccc gcccccatga  10980
gctcatcaag agccgccgcc cctggatggt ggggcggggg cgcacacttt gccggaggtt  11040
gggggcgatc cgcctcactc tttccccagc ccagctcact ctccaatctg cggtcaccac  11100
ccgagacctt cctgggggtc gcgcctaaaa ggagcgcaga ctcccgccgg gatggcccag  11160
aagctggggt gcgcgcaccc tggccgtccc tgcctgggag ccgatctccc tctcctcacc  11220
cagacacgtt ccagcggagg cctcctccca gaagggctct ggaggcctcg caggagtggg  11280
gatcccgcgg ttctgagttg gcacaaggaa gagagtggca ccaggggcct ggagtggatg  11340
gcagggtccg ggagtggggc cgctgctttg caagaggggc ccccacgctg ggcatctttg  11400
ggtgccagcg tgggtggagg agggtctttt gctgagaatg gctttctcct gaccgcagtc  11460
tttgctgctg ggaagtgact gatgggcttt cgccttttgt ttccatttcc tgtcggtgtt  11520
agaattgggg agggggtgga aatcccttct tggcctggaa ggactggagt gggtgtccat  11580
ggccgcggcc tccccgtggc cacgcccctg ggcatagact gcaagcccct ccccgtgccc  11640
cccaggctgt cacccccttc tcgtggaaga ctcggctgat gtcccagtgg accgagtgtt  11700
tctcaagttg aggcagggag ggcaaacttt ttaaatggcc cctggagcca gtgtgtggga  11760
ccagagacat ctgtttccca tctggacggc tgaggatccc agtgcggatg attatttgga  11820
gggggaagga cggaggctga actgaactct cagctgggag atgagtgggg cagtcacatc  11880
ccaccttccc caagccgggc tgttctgcac agcctgcttg ggacgctggt gggagtcact  11940
gtggctttcg gcactgccct ggcagtgggg gcagctaggc catttgggag gggctcgctt  12000
tccccaggcc gggccctggg acctcagccg ttgcttagtg gtggcctgct tcagcccagg  12060
catgtgggag aggcaccaga cacaggatgt ccctctgcca gcccctgaag ccccgtcccc  12120
tgacgaggcg agtgtggacc tgggggtggg ggctgaggga gactgtggac ctgggggtgg  12180
```

-continued gggctgaagg aaggtgtgga cctgggggca ggggccgagg gaaggtgtag gcctgggggt 12240
agtaggggct gagggagagt gtggacctgg gagtaggggc tgagggaggg tgtaggcctg 12300
ggggtggggg ctgagggaga gtgtggacct gggggtaggg gctgagggag agtgtggacc 12360
tgggggtggg ggttgaggga gggtgtggac ctgggggcag gggctgaggg agagtgtgga 12420
cctaggggca gaggctgaag gggagtcacg ggaggggact tctccggagg tggatttttg 12480
ctctctggac ggtgtgtcag cactgggtga gcccctcctg cctgcccagg ctgagaggtc 12540
tccctggcag ccccctggga gtgtcgccag ggcgggcctg gaagtttccc aggcagctgg 12600
ggtggagacc tgacacatcc caagggtgct tgttattaag gctcaaggaa atgtctctga 12660
ggcctcaccg ctcctctccc cagggcctgc tccctgcaaa gcattgagaa ctgagtccgt 12720
ccacagtcac tgtggaccca cccatccact ggggctcagt ggtagccagc aatgccaggc 12780
tgggtgaggt ggggttggtg ggcaccaccc tggtggaccc ccctccaccc tggtgtcgca 12840
gggtgtgtgg ctgagagcac agtgccatgg gcttgggcct ccttggtgga gtccccaaca 12900
cactgctctg gtcctgggcc tcggccttcc ccgtctgcag tgggggccca cagtgagcct 12960
acctcctggt ggtgttggtg gatttgctga catgcctgag tgttgacagg gggcttggtg 13020
caggaagggc tcagggcgtg ggtgttggcc aggggtccaa agggacctct gcctcagaga 13080
gcccagccca gacaggcagg atgtgcagtg gggaaggggc tgcgggaacc ctgcagggtc 13140
cagaaggaca cagtgcagtc ctgtgggctc tggggaggct ggtggggagg aggttgacaa 13200
tggatatctg ggtggggcac ttgttagaag ttccatttta gagaggaaag aggccttgcc 13260
tgtgggagaa ggcagctggg gtagcctgac ctctttccca ggaaggagcc cacacacaca 13320
cgcacaggca ctcacacaca cgaatgtgca cacacacaca ctcccacctt cacacacact 13380
cacactcttg ctgtctccct tcccaagcca aggtgcgagg gggaaggtct gggcagcatg 13440
cacctgcgcc ctgaccgctt tgggggccag tgagaactgg gctccctggg tgcgcggcgg 13500
gcccaagcag ggaggacatt gcagatgccc tggccaagca gcgtggaaat cctgtccctt 13560
gggtgggtct cggagcctcc atcagaggcg gctggcacct gagacccacc tgctgccagg 13620
agcagggcag gagagtttgt gtcccgggac agggaactgg cctgtgggag ccttgccttc 13680
ctcatctgtg taatggatat aagagtcttc tcctcggggg ctggccaggg agtccagaag 13740
aggtgtcacc agtccccgca gggagaagag cggtgtcccc cgcctgggac tggctgctcc 13800
cccaagctaa tgcagctggt agccacctcc cagtggcagg gcagccaaac ccggccggga 13860
aagagactga ttagaagcct cgctcacggg tatttctcgc ttccagacag cacatgactg 13920
tcatttggca cgtctttcgc cgtccttccg ggagaggggc tgcaaccctg gcaggcgctg 13980
tgggggaggg ggctaggaca tcctgtgcct ggtttcacca agtgggtgtg tggactttcc 14040
ctggctcccc caggctgtct ggctgcacag ctttggggaa acggccactg ggtcaagcgg 14100
gccgagaaga ggaagtctgt ggtttgtctc tgctacagac tggccccagt gaggctgtcc 14160
agcagtgcag ggcacagagc aaaagcaggg aggtatgggc ctacttcccc ggtcgcccct 14220
gtggctggct gtggctctgc cgggtgctga caagtcactc gccctccctg cggtcaccag 14280
ggtgcatgcc cgaaagccct ccattctttc ctgggtttga gggtccttct cctgcaccca 14340
ccccagcgcc cagttcagct caactttcag aaatctggtt cacccccaat ccctttctca 14400
taactgcttc caagcccaga caaggagaca gaccccaaaa gatccctacc cctatttccg 14460
cacctgaaat cgcaccacgg gaagagcttt gctcatagag tcaataaggc ttagagtcca 14520

-continued

```
ggcgcctgtg cgagggagca ggtcatcacc cttgtaccca ccgtggtttt agacaggacc  14580
ctgaggttgg ggtggggctg gggctggaga ggagccaggt gccctgcccc ttgcttgggc  14640
cccgtgtccc tgtgatccag gctgggcgtg ctatgggtgc tgggtgatat tccagccctg  14700
caggtgtccg ccttgttccc agcacccctc tgggcaagaa gaaccaggct ctcccagaaa  14760
tgggcttcag tgatctccac ttccaagtcg tccccacctg ccttgtagga cacagtggta  14820
cctggtatgc tgggcagcct tccaggaacc tctggactta ctcagtgtcc cccagcccta  14880
cacaccattc tttgtgtttc tgggcccaaa ctaagccccc caacctgggc tgcagagcaa  14940
gtgctgaatc atgagagacc cttgagggtc ctccaggtag gcccccagtg ctggaggagt  15000
cccctcaggc agggggccac gcccaagggt gtggaaggtc agctggcagc cggatctcac  15060
ttttggggct gtaggcttcc tgcactggcc gccaatgcca tggccgtggg atggccagga  15120
taaggcatct gccccccacc cccacccccc gcacaaggtc tttgagggct gcgggctcaa  15180
ggagttggcg gtagggctgg gggaccaggg gcacagagct tgtaagcgcc tctctccagg  15240
atgtgggtgg cccagcaggg gagctttgag agtccaggtg tgagattcca aatgctaggg  15300
gcctgagagg agggagccac cagcttggcc agagcctggt ggatcacgcc cccaccacgc  15360
cttgcccttc tctctggtca tgtgctctcc caccacgttt ggaaagttac tgcttccctc  15420
ttcctcagcc cctcgggctc ccagttatgg aagtggcgtg attcagagaa ggtaaaggat  15480
gggagggaga gggctgggtg atgggggacc ccgcagggcg ccctgtgctg ttacatggag  15540
ctccaggatc agggcaggtg ggcagcctgg ggtcctcact tctctcccca gccaggccag  15600
gtccctcaca gccctgccag gagcatgata tccgctgcgg tgcagaacta atctcaaagc  15660
tcaaacccag gtaacagtgt aggtaaaaca gatgacaggg catgagactc accccaggac  15720
aggcgaagga cccaggccga tgggggccca gaacagtcct gatcctggag ctccttcccg  15780
agtgggaccc caggggtttc cgaggggctt agagtagggc ttagaggctt agagtagggc  15840
tagggacttc ctggcttccc tgcctcggga acagctggtc ctggaagggg cttggtcctc  15900
ggggcactgg tgcccaccac ccctgatgcc tgggagacac cagcatcctc tgagcatgtg  15960
tgcgtcctcc tggtcccgag ggaagtgact cctcacatcc cccagctggc ggggccagag  16020
ggccagcatc ctcgcctgac acctattttt agatgctgag acaggcggct tcctcggggc  16080
caggggccct gtgagtggag cttccgcttc ctggcctagg agagaattcc tgctcctctt  16140
ccctccatgc tgccttttcg cccctggagg ccacaacggg gtcagagggg cagctgctca  16200
ccacctagga gggcctgaga gggccctacg tcacccaggg aggagtctgg ccccgtcccc  16260
aacctccaca cccaggcctg gcactgcccc ttcttggtgg gcagagagtg aggggttggc  16320
ctgcagggac ccaggctgga ggggccgttc acctccggcc cccagcgtcc cttcctggaa  16380
gcaccttggt gagcccctcc cctccttcac ccagtatctc caggggtact tcctcctttc  16440
cttcctgcct cagggcctca ctgtcctcct ggggagggtg tctcaggccc cagcacctcc  16500
cagtggctga gccgaatggg cacttcccgg tgtgtttccc atatgtgcag tccctaggtg  16560
tcggtgagca ggcacagagc ccgcagcgtg gccctgcctg gtggaccccc tccccaagag  16620
catcaaggga gggcctggac tagagacaca cagatgccca gcctgtacgt aaaggcgggt  16680
gagctgatgt accatcgtcc tcgtccccca ctggggtgcc tgggcaggac ttggggtgac  16740
cacttggccc gtctgggtgg gggtaaggta tgggtggggc gaccagatcc ctgccctttc  16800
ctgcagctgt gggggtgtgt gtgctggcct ggagagctcc cacccgaagt tctggctcct  16860
ggctgtccgg ggcctgcggg ggcagcgagc agctggcatg ggtaggggag ctgacctagg  16920
```

```
cctgcccggg cagcgcctgc tgccttttgc tccctttcag ctgcttcttg gaaacagcgg  16980
acaggctggg caggaaccca gtgtgcttgg cagcccccct tttaaagtcg attctgttat  17040
ttattaattc ccaggaagga gaaagaaaga aacaatcctt catagagtac aaacactgct  17100
tttagtagcc ttgcaaggag ccctccagga accccacagg ttacctgggc tccatcctga  17160
gagccaccct ccatccccaa tccccagcag agcatcttgt ggggtggggc ggcttgtggg  17220
gcggggcgcc ttgggaggcg gggtgtctcg ggaagcgggg cgtctcggga ggtggggtgg  17280
cttgtggggt ggggcatttc ctggggtggg gcgtctcgtg gggtgggaca gcttgggggg  17340
tggggcatct cgggaggcgg ggcgtcttgt ggggtagggc ggcttgtggg gtggggcatc  17400
ttgtggggta gggcggcttg tggggtgggg catcttgtgg ggtgggacgg cttgtggggt  17460
ggggcatctc gggaggtggg gcatctctgg ggcccggcca cttgggaggc ggggcatcct  17520
gggggcgggg catctcagag ggcgcctccg gaggctggag tatcttggga ggtgggagca  17580
ggtggcagag aggcttccca caggtgagct ttgagcaggg aggtgcctgt atggatggct  17640
ctgtggggag aggggtgaca ggagttccag attccggcac ttatgaaacc tcacagtgat  17700
ggagagccga gtgctgctgt gcaggctaag ttgtgtgcat gtcagcttct gcacttttat  17760
ttccttgttt gtagacaagg cagagagaag ctgagatggg cctgaggtcg ccttggtgaa  17820
aggcactcag cagccagggc cttgggctgc cctccctcat caccgtgaaa gcgggactct  17880
cttttaactg acatcgggct ccatagttac tccagtccta actttgatgg atcctaaaag  17940
tgcacttcta aggacgcggc ttcggtgttt cccatgccgc tgcttgcccc tgggaagcgt  18000
tggctctgcc tcggaagaag ttagcgccaa gatggcagcc tggggtcttt ggggcccaga  18060
agaaacactg gccccgggga gttcagtcat cagggactta ggatgtgggg gcttttcaaa  18120
cagctttatt tagacgtgat tgacacacag taaatacaga tgtttaaggg tacaacttgg  18180
taagttttga caaatttata cccccgtgaa accatcacca actccccagg tgcccctggg  18240
gcccttggga tctctgcttc ctgcccctcc tccccgtccc agggcaacca cgggccgtcg  18300
ctgtgggtgc acacagcatg catttcttca acaagcggac tcagaaggca cttgcacatc  18360
gttgctgttc tgcctctttg cttcagcatg attacccaga ggcgcacccg tgccgtggcc  18420
tgcccgtcgt ctatgcaccc gtgctgtggc gtgcccgtcg tctgtgtggc atgcctgtct  18480
gtgcacccgt gctgtggcgt gcccgtcgtc tgtgtggcat gcctgtctgt gcacccgtgc  18540
tgtggcgtgc ccgtcgtctg tgcacccgtg ctgtggtgtg cccgtcgtct gtgcacccgt  18600
gccgtggcgt gcccgtcgtc tgtgcacccg tgctgtggtg tgcccttcgt ctgttccttt  18660
tattgccggg cagggttgca cccacatgtg caagccagcg acggacccca ggttcacccg  18720
ttcaccggtc agtgggcata tgggttgttt cagtttgggg catttacaag aaacgtgcta  18780
gaacatttgt gtacaagtct tgtgtgaacc taagttcatt tctcttgggt aaatacctgt  18840
gcgtggagca gctgggtcat gtggtgaatg tgggtttcac tgcttaagca gcagttttac  18900
ataactgcca aactgttatt caaggtggct ggaccgtttt acagcccccg ttgtatgcgt  18960
cccagttgcc tcccccagca gcatgtggtg tggttggtct ttttcgtggc agccagtcca  19020
ctgggtgcgc tcggcatgtg gctgcagctt gacctgggtt tcctggtccc tggcaaggtg  19080
gagcatctct tcatgtgctt ttttgctgtg tgtggatctt gcggggaagg gtctgttcct  19140
gttttttgcc catctttcaa agattgggtt gccagttttc ttgctgttga gtttggaaag  19200
ctctgcatac gttcagggca caggtccttt accaggctct gccccaggtc tttcggagag  19260
```

-continued

```
caggtgtctt tcgcattcct gactctgggg aacctctagc cctgccacat ggggtttgtt  19320
atggggcagg ggcacctgtg cctttcccac cacggggctt ggggatttgg tgctgccatt  19380
gccctccctc gtaggtggcc ctagggggt ccctccgcct ccgtttcctc atccagaaac  19440
cggcagtgac catcaccacc attgttgtca cctagctcca gctcaaggtc cctgctgaag  19500
gtcggagagc ttggcatggc cccgtttgtc catgctaggg ctgggaagac caaggctcag  19560
gtgaggcctc tgcccagtgc ctggcactcc ttcttgcccc atttttccac ccagggtggc  19620
tcccgactac ttctggtagc ctcggggaca gttgaggtgg acaggctggc gtcaccccca  19680
tttccggctg tccctcccac cccctcctgg cccagctgtt ctgccctatt aaaagtcaca  19740
tgggccctcg ggtccttcct ggtgttggcc caggctcttt caggccctgc aggccaggac  19800
cagccttccc tgcaaccctc ggcagaggcc tggggccggg gcttgtctag gggcagcctc  19860
cccatacggc cctggagtct gaacagaagc cccttcccag agcacagcaa gaagctgcaa  19920
cgtggcctga agtcccacca ttagcaggtt tggggtttag gctgagcttt gccatcacta  19980
cctttctgtt aggacggtat gcccattaga tgggatcatc ccctcagcgc ccaggctaga  20040
ggaggggtgg tccctgccca gccagggagg gctgggggtg gatgggcctc tacagagcag  20100
cttccgagcc aggcacggtt ccatgatcag ctctgtttta tagaggggga cactgaggaa  20160
ccgggagcct ggggaccttc cagtggcccc acagctcctg tggctgagtc agggtttgtc  20220
accaggcctc tgtggggatg aggctccccc atccacctgc ccactctgt cctggaacag  20280
ctctcaaaac ggtctctgga ccacagtttc aaaagaaaat aagcaatgtt ttcaaaggcc  20340
ctggaggaag ccagagttac cacggcaact ctcggcctcg ccacctcctc ccgccaggct  20400
gcatctggag ccagctcagg agggcagcag ggtgaggaca gccaggctct ctggggccac  20460
cccccagccc ccacccttcc tgcctctcct gcactgtcca cggccctccc tgtgctccca  20520
cgggtataat gggcacagaa gaaccaggag ctgtctgccc ctgcaggatt ctggaagcca  20580
ggggcccctg gcctccctgg ggccttgtca tgtgaggggc acacgtgggg tcccagctgc  20640
cacatggctt ccagcgctgc ccgcaggtgt atgttgggcc cttggtgact ctaatgcacc  20700
ttccactcgg cacagaagag cttcagtctg gggcctgggc gggggaagta ggctgccatc  20760
ctcgctaaac caaagtgtga aaattgagtt gaaactccca taggagggca ggaggcacag  20820
ctcctcagaa gaaggtctga gaaaccacag cccaggttgt tgtttcgggt gtgtggagaa  20880
ggtgctctgg cagtcctgct acagggggac catcaacagc ccctttgggg tgagagcccc  20940
gtggctgctg gcaccagcag cccctatgag gcttatttta tttttgagac agggtcttgc  21000
tctgtcaccg aggctggagt gcagtggcac aatcataact cactgtagcc tcaacctcct  21060
gagctcaagc gatcctcctg cctcagcctc caaaggtgct gggattacag gcgcttgcta  21120
ccacgcccag ccccctctgg ccttattgtt tgccaggccc agctcaggtc ccggaggagg  21180
ggagacagga gtgtgaggga aagggggaag aggtatagag cccccagctc ctccacccac  21240
ccgaaccctc accgaggccc tagaccctag accggcctga ccggggggtc ctcaggccgg  21300
ggacttgggt gcaggccatg gtgctggggc ctgaagctca cgctctgctg agcacagccc  21360
cctgcccaac cccaccctgg ggccctgctt ccctggccag ggccattgga acaggagtgg  21420
ggctgtccag gtggtgttct tgggtccagc cctcagtttc tcttctgcag ttgaccggca  21480
gccctgcatc tgtggtgggg tcggcgcctg gtgctggtga ggcaaggcct cagctgctgg  21540
gacaggacct gcctggcacc cagctggtgg cagagccaag cattccgact cagctctggg  21600
agcagctgcc ttctgggctg gcattctccg ccagggggt tgtgccctcg tggccccccc  21660
```

-continued

```
cgggtgcctc ctcacctggc tgatttcatc tcctgtcccc ctgcctcctc ctccaggaag  21720
cccccagggc ctggccctcc ttgagagtgg catggaggag gaagaagact cgcccaggcc  21780
catgggagtc ggatggtggc cgcacttgtg gggccctgac cccataggct tcttcagcac  21840
gccctggcct gggtgatccc tgcctgaggg ctgtgcacgg ctcatctgcc agaccagatt  21900
ttaggggatt cttgtactgt cctcctggag cagcaggggg taaagcctga cccacccaga  21960
ctgtccagca acaagggcct cctgctgtgg gccagggacc ctggaactga ccaattgtgt  22020
cctagggacg cagagtcccc aggctgctag agggctgtgg ggccctgttt catgcctgaa  22080
gcaggaagaa accccaggag aggtctgaag gggacccagc ccccaccctg tctagcaggg  22140
aggagcctct gcaagaggcc gaggggtgct gaagtggagg aggatagagg cagcaggact  22200
cagggtcact ggtcatttat ggggatcaca cggctgcagt gtgccctgca tggtgctagg  22260
caccagggac agcagaggac aagcctgtgt cctctcccac caccagaggg ctgggcactg  22320
cccctaggga gagagggggc cttggtgtgt gcagaggggg gcctggggca cgtgcctggc  22380
ctggtcagat gatcagagtg ggctgggctg ggcctggtct ggggcccagt ctcaagggca  22440
gaccccacct ggctagagtt gattgtgtgc acaccggatg acccggcgtt gaaggcctct  22500
cctctctgtg agcctcatcc ccacctgcca gactcccagc acagcctgct tcctgcccca  22560
gctgctgagc gacagcgctg ggccggcttc tgcgcgcccc ttcccccagc ccatcttgga  22620
aaccacagca gcgtccttcc tcccaagtcc cttcccaggg ctgacatccc acagcaggga  22680
tgtatcccac aaaccccgca ggccctggtg cctacagctt ggcctggtaa catcaaatcc  22740
taccctctcc tcctggcagc aaagatgggg tgccccccacc ccagagttct cagcaccccc  22800
agacagaagc agtcccccag cgacctcaga actcttgggg cgctgccaca cccttgcagg  22860
agggggcagt gttcctggga tgctcaggtc ctggtatcac ctctggccag atacggaagg  22920
tgaaactaca gggcatccaa ttcaccttga acttcagata aacaccagat tatttttttg  22980
tatgtcccgt gcaatatttg ggacacactt accctaaaga agtattctgt tttcatctga  23040
gaggcagatt taaccggcgt cccgtgtctt cctggcagtc ctgccctgga gtcacactcc  23100
acaggtgcag ggcagggcca ggctccaagt agatggcggc caaagcaccc gccccatgct  23160
cctgactccc ggggctcttc agggcattgc gaaaaccagc agcagagctg acacctggtc  23220
cctgctcggg agccagcaag gcaggaggct gcttaggcct tgcgtgtggg gtgggcgcac  23280
tccctgctgc agtgctcttc gtacatgtga cactgttccc gctctttccc agctggctgg  23340
aggcgtgatc ctgggtgtgg ccctgtggct ccgccatgac ccgcagacca ccaacctcct  23400
gtatctggag ctgggagaca agcccgcgcc caacaccttc tatgtaggtg agtgcacatg  23460
tggccgcaga cgcattcagg gagggcttct aggaggaggc aggtcctagc cttttggatg  23520
gggacatgga gggtgaaaga cagtcgggca tggcgtgtcc gggcagggag gcggccctgg  23580
aaagggctct gggcacaagg gttgagatgg aggtgggcct gtggcctgct ggcccttctg  23640
gtctgagcca gggcaggggg tggcagctag gcctgggcag ggactgtgtg gagaccttgc  23700
ttattttaag tgtggggtta tttcgggggga ggctccctga gaagggtggg gctggatgcc  23760
tgggccacac agagcagccg aggcagctgg cgctgtggag cccgggaggg agggagggat  23820
ggagctcaag ggatggaacc cagtgagggg tggagacggg gcaggggagg ggtggagagg  23880
ggtggagacg ccccagaggc ggtgtgactc agctgcccct gcaggcagct gcaccttgct  23940
gccttattag gctgcgtgtg ggggactggg ctgccctccc tgcccccagg agcaggagca  24000
```

-continued

```
ggagtgatgg aggaggagga ggggaggggc aaggccagga ggaggaggag ggccatctca  24060
ctgtgcagag agcagcaccc ttcctcctgg tgcccctggc agggctggtg ctggtggggc  24120
tctgggagca tttgttgaga tgcttctggc cttgaaagga ggcccctggg atggctctgt  24180
tgccctcaca ggctgagggg tgggtgaggt gggcagcctg tgtgtcccca gtcctcaggg  24240
cttccctcag ccggcaggtg cccccaggcc tggagctgca gggccaggcc ccctgccagt  24300
tacggaggct gcttggcttg gttgctgaac cagggcccca ggaggccgaa atagccccac  24360
acctgcgccg tcccacctct ttgtccagtc accccagggc caggtgaggg ccctggccac  24420
acagcgtgcc cgttccttct tccccatgcc ccgctcatgg gtcagagggc cggtgctggg  24480
gtccagatgg tgtcaacagg gatggtccct gtcctcccca gagacagaag cctgtggccc  24540
acggagggtt tctgggccca gccgatccta gggagggtcc catggccctg cccataggtt  24600
cctggcctct ctcggggccg tggtgccctc acaggtggtg tcaggaagga cgggaaaggc  24660
tgcttgtccc aggggctcat gtggagacca ccccctgcac gcagctgggg cgctcctgcc  24720
tgtgtcctca gaagcactcg gcttagcttt gcccatgtgc ctgggctgtg ggtggcagag  24780
cccggccagc atcctccgat ctccaagggt gcatctctac tggaggcccc tcctgggcct  24840
cttgctcccc gcttcccaga tcattaggat atttggggtc cagaagggcc tcccagccat  24900
cctgggcctt gtcctccggg gccaccagtc cagccagtga caaccacagc atccccggcc  24960
tggaacgagg ctgcccccag cacgttcctc gtactcctgt ccagggacag gaggggctgc  25020
ccctgccacc gagtcccctt ctccaggacc tggggcctgt gggtgtgagg caggtgttct  25080
tggaaggggt cactctccag gcacccggcg gccaaggctt gtggctggag cagctcccgc  25140
tgtggggtcg gcgtcgggcc ccgtgtggcc ggagaggagc tgaagggtca cttagcttcg  25200
ggctggggcg aggacagggg acaccccaga gaggtatgcc aggcctcctt cctgcgcccc  25260
actctcggca gaagcagagg tcacaggctg tgctgaggcc ccatggtgct gccccccatga  25320
tgccagggtg aggctggcgt tggaagcagg tgtctgacct gcatggtgtc accgtggcca  25380
catcagagct ccagccccag agccgcccac cctcggtcct tggctgtggt ttccctgggc  25440
tggaggagcc tgccgttgtg ttggccacac gaccacagga cctgccaccc ccgacgtggg  25500
ctctgcctgg gcccccactg gacagggacc ccttggagct cctctggcca ccaagtcctc  25560
gcccattcca gaatcggcct tctggagcct cttgctgtcc ctgatgcggg ctgggccttg  25620
ccaagggctt tttttcctgc gccgggaaca gggtggattt gctgggctca ctcccctcag  25680
agacgctgcg ggtgcggtgg gttaggccca agggcgttaa gagaggaggc tggggtgggg  25740
ctggggcctg gcagggggtc tggcagccct gggcctccca cctcctgtca ggaccaaaaa  25800
aggcaacgcg cctctcctga cctgtacccc ggagtgaacc caaccttgca acccaggagt  25860
gtcagggcct gaggggaggg agacctggct cctgggtgcc gtgcccgtaa ggaggtggcc  25920
acctgcaggg cattcctggc agaggcttca tctggccagg taggaggctg ggtggccgag  25980
ccccaaatct gggtgtgttc tctgcctggc ggtgggtcct gccccaggca ccttctcctc  26040
tgggctggct gggcagggac aatgggcctg gctgcgagga gggggcctgg gctgccttct  26100
gcattgcctc ggtgacggga gatggcccct gcctgctgag ggatagggga gtgggcaggc  26160
agtgagagac actgacagct gtcccgcggg tacagggccc tgtctgggtg gccaggccca  26220
tgtctcgggc ccacagtgcg ccccccaccc ttggacggcg ccttctccct ccccaggtgc  26280
atgctgccca gccagggagc gtgggggagt tcgggagggc tggcctacac gccctggtcc  26340
agctgtccca ggtggggtgc tgggcttcag ccctcagccc agggcctagg aatccaactt  26400
```

-continued gatcctcccc acacagcagc caggttcaaa tgcaggtccc gtaacggaag tgctgctgtg 26460
cagcccagat tggggggcag gagccagcag ggccccccca ccctcttctc gcaccacact 26520
ggggaggcag cattggttcc agttccggtt cctgggctgc cctctcaacc ccggcctaca 26580
gtggggccca ccctgtgcct tctgatgcca ctcccacccc acgccaagtc ccagaggctt 26640
tgggagcggg tgaaggcggt gggtggcggg tggcaggtgc aggcggtggg tggtgggtgt 26700
ggcaggtggc gggccccacc gcaggtgtca tccctgcgaa gcacctgtcg ccagcactca 26760
gagcgctcat gaggtgccca gtccccatgt ggcctcctta gtctccgtcc tgtgtcatgg 26820
aagaggtaac tgaggcacag aaaactcacc aggccaggct gggatgtgag gtcccttgct 26880
gctcatccct ggcagtcagc aaccctacat cttcccagct gggcggcccg tggtgggttc 26940
ggcacccagg accctccggg gtcttgggct gtggcgagtg tgtaggcacc cacctggtgt 27000
ctctctcccc gcaaggcatc tacatcctca tcgctgtggg cgctgtcatg atgttcgttg 27060
gcttcctggg ctgctacggg gccatccagg aatcccagtg cctgctgggg acggtaaggc 27120
agggaggcgg gcctgtgcct gggccgggga ggggctgggg gctgcgtctg gccctgagga 27180
gggggcagag ctggtgctca gggcggagcc tagaattctg gggGaggtgg ctcctgtgcc 27240
ctgcttttcc cgtttggttt ttaaattaaa tcccaccgtg cttggtctcc atcgtggcca 27300
gttcctacgt gaccgctttt ctttgtcaaa aaatagccac aaatataaca gggagcaagc 27360
ctcagctctg aggccagcct cggcgtcccg ggcacaccgc cccctgtggg aagcccaggc 27420
ctggctgtgc catccagggc ctggccagtc caggaagagg gagcctatgc ccgtgtctcc 27480
agtgggggaa actgaggcag atcccatggc tccccccttcc gtggggagca ggaacaaggg 27540
ggtggggaag atcagtcagg ggtcatgctg ctgcacacgc ctccctgggg gctgcagaca 27600
tcctggactc accagcctgt gaccccaaac cacacgcccc gccccatcca ccccgtcctg 27660
tggagcctgg tgccgcgtgg ggacatcctg ggctttgacg gctcctccct gcgctgagtt 27720
ttagcctctg tgccccaggg ctccacacaa gccgctcact cctggtcagg tcgtgggctg 27780
gtggctccca ctagcccctc acagacacgc ctgctgggca cctgggtgtg tgtccttggg 27840
ccccgcctac agcctgccct ctttcctccc tctggccact gcccggctcc agttcttcac 27900
ctgcctggtc atcctgtttg cctgtgaggt ggccgccggc atctggggct ttgtcaacaa 27960
ggaccaggtg agcctgggtg tgcagggaca gggtggggtg ggtgacgggg gcaccctcct 28020
ctcctgtcgc gggtgggggt tgggctgact catggcttgt gggagctctt tgggctcttc 28080
ctgggtccca cttgccagga ggatctccag gggctttatg gaggaggcag cattggggct 28140
gagcaccagg ccagcctccc gtgtcccagc actcccgggg cagctgagag tgcagagtcc 28200
ttgtcctctg gggtctagcc tcgaagccac cctgcccagg gagagcctgg gaaaagtgcg 28260
tccgcctggg gcggggcggg gtgggggcaa ggagggggag gttcccccctg tgcatgtgac 28320 cgcacccctc ccccagatcg ccaaggatgt gaagcagttc tatgaccagg ccctacagca 28380
ggccgtggtg gatgatgacg ccaacaacgc caaggctgtg gtgaagacct tccacgagac 28440
ggtgcggccc cggggggcga gggcggggag cagggccccg ggaacccggc ggggtgtgtc 28500
tcgtcctgga tgaatcctgc ctacgcccag acctcaggag caggaggtgc ccttgggacc 28560
tccaggaccc ctggtctcaa ctggtcctcg ggtgggaacc tagtgggcca gggtggccca 28620
gggtgcggaa agctctgagc agcgcagctg aggaggaaga aggctggccc ctggatgcat 28680
tctgcagtgg ggagcgctgc gtacccctgg ccacctcccc atgggttccc tagagccacc 28740

-continued

```
gtccccctgg gcacatccag ggctgacctt gcacccctgc tctctgcagc ttgactgctg  28800
tggctccagc acactgactg ctttgaccac ctcagtgctc aagaacaatt tgtgtccctc  28860
gggcagcaac atcatcagca acctcttcaa ggtgcgcgag gccggtgggg ccgcgcctga  28920
ccccccgcat gtcccgcccc tgggtggggt cctaggggtg ggcaggtcac acggcagccc  28980
cacagggagc gaccacactg ggtggcatgg cccctgtcag ggctgctctg ctgggagggt  29040
tggggtggga ccgcatctgg cccacgagga aggcaggcgc cctgtgctgc gcattccggg  29100
tgaagaaggt ggaggctctg gggggtggga actcacctgc acccccagct ccacgtgtgc  29160
actcgtgggt gtggacgccc ctgacagcct gtagctggca gggcctgcag gccatatagt  29220
gccctgtgga agtttcctgc tgaggcctca gtggaagtcg tcatcagtga tgctttaggg  29280
gtctagtgac accaatgacc gtgatctcag tggaaaaggg cacagtgtgt cccaggcatt  29340
tcgcgtttat gttaaaacgg gtggaagata gcaagccggc agaggccggg ccgctgcacc  29400
cgcctgttcc gaggtgggta gggggtgggg ggctgttccc aggattcccc tctacgcttt  29460
ctgtggtgac cacggattac tgcgtgacaa cgggaagccg ggagccgagg cccggtccct  29520
gaccacgcgt gcctggccac ccctgcagga ggactgccac cagaagatcg atgacctctt  29580
ctccgggaag ctgtacctca tcggcattgc tgccatcgtg gtcgctgtga tcatggtgag  29640
cgggcggggg cggagggcct gctctctggg ctgccccttc cgcggggcct tgtgctgact  29700
gcgcccccca ccaccctcct gcagatcttc gagatgatcc tgagcatggt gctgtgctgt  29760
ggcatccgga acagctccgt gtactgaggc cccgcagctc tggccacagg gacctctgca  29820
gtgcccccta agtgacccgg acacttccga gggggccatc accgcctgtg tatataacgt  29880
ttccggtatt actctgctac acgtagcctt tttacttttg gggttttgtt tttgttctga  29940
actttcctgt tacctttca gggctgacgt cacatgtagg tggcgtgtat gagtggagac  30000
gggcctgggt cttggggact ggagggcagg ggtccttctg ccctggggtc ccagggtgct  30060
ctgcctgctc agccaggcct ctcctgggag ccactcgccc agagactcag cttggccaac  30120
ttggggggct gtgtccaccc agcccgcccg tcctgtgggc tgcacagctc accttgttcc  30180
ctcctgcccc ggttcgagag ccgagtctgt gggcactctc tgccttcatg cacctgtcct  30240
ttctaacacg tcgccttcaa ctgtaatcac aacatcctga ctccgtcatt taataaagaa  30300
ggaacatcag gcatgctacc aggcctgtgc agtccctcag tgccagtggt gtctgagacc  30360
taggggttgg ccggagggca ggggaatctg acatcggtgg ggcttggctc tgtggactct  30420
gtggggtcca gggtgagggt gggtgggtcg ggatccctgg tgttcaccaa aggagtcact  30480
ctgtaaaatt tggggagtta tttattctga gccaaatatg agcaccggtg gcctgtgaca  30540
cagccccagg tcctgagaac ttgtgcccaa ggcggtctgg ctacttaatt gtatacattt  30600
tagggacata ggacattgat cattacatct aagatgtacg ttggtttagt cggaaaggtg  30660
ggacgatttg aaggggaggg actttcaggt cataggcgga ttaaaagatg ttctgattaa  30720
taattggttg attttatcta aagacctgaa atcaatagaa tggactatct gggttaagag  30780
gagttgtgga gaccaagatt attatgcaga tgaagccgcc agattgtaaa tgtttcttat  30840
cagacttaaa aaggtaccag aatcttagtt aattctctcc tggatcagga aatagacctg  30900
gaaagggagg gggattctct atagaatgta gattttccca agagacagct ttgcagggcc  30960
atttcaaaat acatcagaga aatatatttt ggggtaaaat acttcggttt ctttcagggc  31020
ctgctgtcac gttggtatct tattactaca gagtctgttt tgtgagtctt aaggtctttt  31080
tatttttaga cagagttttg ctcttgtcac ccaggttgga gtgcaatggc gtgatctcag  31140
```

-continued

```
ctcactgcag cctcccctcc acctcccagg ttcaagcgat tctcctgcct cagcctcctg  31200
agtagctggg acaacaggca tgcaccaccc cacccagcta attttgtatt tttagtagag  31260
acggtgtttc gccacggtgg ccaggctagt ctcgaactcc tgacctcacg tgacacacca  31320
ggttttggga ttacaggtgt gagccaccac accggactaa ggtctctgtt ttaatgtgaa  31380
tgctggtcag ctgtgcctat gaggcatgtt cggccaccca cagtcatcat ggcctcaacg  31440
agcttttcag gtttacttta gaatgcattt ggccaagagg tgcccattca gttggttggg  31500
gttgcttaga attttacttt gggtttaaac cagggagcaa ctccaggtag caagggccct  31560
ttttgggagc gttctctcta ttctcttttg ggagaggccc tgtgttgcct gcagccactt  31620
ccaccctgcc ccttgggcac acaaggggca cacagtgtaa gcaggtgggc aggaggggtc  31680
gggcagccag ggaatgcagt gagatgggct tggggtaggg gctgggtgcg ctgcaggact  31740
cctcttcctc ctgagggatg gtaaaggatg gacacactgc cccctcccga gcatttgagg  31800
gtctctgccc tgcccatctg ttacctgtaa atgttccttt gaggagctga tggctcaggc  31860
ctgagccaca tctcagaggg tctggagggg aagaaagacc tcatcctact agggagcccc  31920
cccagcccac cagcgagcgg tggttggggg cagacaggct gtggggctaa ggagcccctg  31980
cactcccccg tccttttccc tttgtctgag cacctccagc cagtgggctt ggtctagact  32040
ctcctatctt tccccacatc gtggggtggg gcttgctctg ggttaggcta cttttcccta  32100
gttgtgggga ggggggtgct ggcacatttc actgttccct ggaggaaatg agtgcctggg  32160
aattcatatc tagggctccc agcagcctct ttgcaggcca atttggaaac tgtccccagc  32220
cctgcatttt aggggggttac agagtctctc agcaggccct cctcccctgc tgctcccaac  32280
ttgcaagcct gcactggttg ggagaacata atggtccaag gagccccctc tctactttcc  32340
gctgtgttcc ctgtggggag ggaagagcag tttaagaaat aaggaatccc aaaggcgcac  32400
agcagaccgg gggccgagga gtgggtcctg cttcccctcc ttttttctag gctgagccac  32460
agcaggtcct tgaatcctat ttcccagcgg atgccaggac agcaggccct gggggagttc  32520
tctctcgagc ctttcagagg gaccagaggt ctagcagcca aggagaactc agaatccttg  32580
agtgtgtggg gcaggaactc tcccagctga gaaggggcac aaggtgccaa ccatctaggg  32640
cccagtggcc aaggaagacg cggcttgtcg cagggagaat ctgggccctg gtcctccctt  32700
tcagggcggg cagctgacct gccccctgct gcggacaggc gaggccaggc tgctggctcg  32760
caagcatggc ggagcccaaa ccttccctgc tgccgcccgc ccagccacgg ctgacttgga  32820
agcttgagga gcgttcagca gcctccatcc tgcccgggag gaccggggac ctggaagggc  32880
ctggccctcg cttccctgca gcgccctagg gggacgtctc agtgcctccc ggagcccgga  32940
ccaatgcacc agagctgagg gcccaagggt gtgagggtgg ccgggcagtg gccccgagga  33000
cggcgcccca caagtttgcg gccagggccc agcaaacccc taggggtggg aaagcgtcgg  33060
cccagctagc gggtccagca gggctgcccc cttcaccgtg gcccagcggt cacgacccca  33120
cgtcctcatc gcgggctggg actgcctctg cgtctggcct gagcgggacc gtgggatcct  33180
ggggagcccc gcctcggtgc actgacagag cccagaagga gtgacggtta ccgcttccgg  33240
tcaggaccgg aagtgccggg aacggcattc gtcctccgtg cgagatgacg cacttcctgc  33300
ctgaggcggc cgctgttctc gcggcttccg gcaggtggcg ctgagaccac gggaagccag  33360
cctggctgtc ggttagccct cgagcattct gggaattgca ggcctggccc ctcctcttcc  33420
tgttcttggt caattccggt cttgtttccc caacaaatgc cgtcgtttcc ggggctgctt  33480
```

-continued

```
ccgagccgga cccaagggcc ggggcgtgga ggagtagagg ggcgagcgca tgcgcacagg  33540
actacacgtc ccgacaggcg tcgggagcgg cggcccagtt ccttgtggga gctgtagttc  33600
tgcaggcgcg gaagccgtgg tgctcggccg gcagagcact cggtttccca gagggctgag  33660
cgcgccgcac ggaggtgcgg cgccgaccaa gatggagact gccgagcagc cttgagccgg  33720
taggtttgtg gtgagggagg acgggccgcg cgggccggcc gagcctccgg gaggtcaccg  33780
agcgcagctt taatacctga gctcgaaggc cccgctgtgc tcgccgaccc ccgtacctcg  33840
cggccgggcc cttgggaccc acagcatcct tgtgaggccc ggaggcctgt ccagcccgac  33900
tggacagtgc cgaggggcac cgagagccag cttggcaccg agagttcgtt tgttctctgg  33960
cggggaggtc ttgctggcac atatagtgga gaaaggccgg gctctgcgtt catgtggaga  34020
aagagacggc ttccttcagc ctacggacat gaaggagtca actctacctt ccactcgttg  34080
ccggctttcg ccgagaaccc cgagaaacgg actaccggag tccctatctt gcagcccgat  34140
ccccgctacc cgtcggagtg ccccgctgac caggctgctt ctggccgcgg cggcgttccg  34200
ctgcagagga cgggagtgcg aatctgggaa gcagggttct ggttgaactc cagcttcgtc  34260
tgcaacatac tgtgtgactt gggcaaatta tttccccgc cccgttcctg ccagctttaa  34320
aacggtcatc agtgggggt gctgcgtatc ccctttcact ggggtggctt cttcactgag  34380
gagagtcgcg cctcagagga actgaggtcc tgcctgtgtt cgacctggtg gggggcacta  34440
agagcccctg atagtacccc tgaccccatc cttattgggt gcacaagaca caggtcactc  34500
tgggcgggca aggagttttg gtagcaggag aggagtcggt ggatggatgg ctgaggacag  34560
tgcagaaggg tgtggctggg ccgtcttttt ttgcctggaa attcaagttc tgaggcaccc  34620
agtcactcca gcactaaatg ggtgcaggag gcagcacttg tctgcccagc tggaaaggca  34680
gggtatgtgc tgagtgttac aggtggaagg ccactggagg tcgctccagg agccgcgggg  34740
atttacctct gcctaacagg gctgctcaag gtgatggtcg acaccccact ttcctgagag  34800
cttgaccctc agatgccagg gccttggctg cagattcctt gggagctccc ggggatcttc  34860
cagcaaatag gagcaaatct tttccccgtg gatcaggaag gtgcacgctc tttgtggaat  34920
acgactgctc accccgcaca gcaagcagct tataagtggc cctcctgcct gatttcagcc  34980
ctgggttcaa gccctgggtg gctgcttact accaaaatcg ctcagtagct ccaagcctgc  35040
ctgcagaggg ttggcaccat taaatgaggt aacgagtcaa aagtccctac cctgggtcct  35100
agcctgtcag gggctccgaa aacccaggct caggtcggtc ctgcccggca cctgtttcac  35160
acatgtacac tccggtctga ggttggtcct ctcccccacc ccacccacct gcagttgagc  35220
agctgaacag aggccatgcc ggggcactcc gaggcctgag acgaccacgc ctgtgccgct  35280
gaggaccttc atcagggctc cgtccacttg gcccgcttgg ctgtccaatc acactccagt  35340
gtcaaccact ggcacccagc agccaagaga ggtgagagga gggcttggag ggggaggcgg  35400
gactccaccc tgtgtgggac agttctgtca gttgaccctc cacttgtcca ggggcagtgg  35460
atctgcaggg ggaactcatt ctcaatactg ttcctcctga gaaacaaatt ttctgggctg  35520
ttttggttta ggtgtggcgt ggccctgggg acgcatggct gaggcaggaa caggtgagcc  35580
gtcccccagc gtggagggcg aacacgggac ggagtatgac acgctgcctt ccgacacagt  35640
ctccctcagt gactcggact ctgacctcag cttgcccggt ggtgctgaag tggaagcact  35700
gtccccgatg gggctgcctg gggaggagga ttcaggtcct gatgagccgc cctcaccccc  35760
gtcaggcctc ctcccagcca cggtgcagcc attccatctg agaggcatga gctccacctt  35820
ctcccagcgc agccgtgaca tctttgactg cctggagggg gcggccagac gggctccatc  35880
```

ctctgtggcc cacaccagca tgagtgacaa cggaggcttc aagcggcccc tagcgccctc 35940
aggccggtct ccagtggaag gcctgggcag ggcccatcgg agccctgcct caccaagggt 36000
gcctccggtc cccgactacg tggcacaccc cgagcgctgg accaagtaca gcctggaaga 36060
tgtgaccgag gtcagcgagc agagcaatca ggccaccgcc ctggccttcc tgggctccca 36120
gagcctggct gcccccactg actgcgtgtc ctccttcaac caggatccct ccagctgtgg 36180
ggaggggagg gtcatcttca ccaaaccagt ccgaggggtc gaagccagac acgagaggaa 36240
gagggtcctg gggaaggtgg gagagccagg caggggcggc cttgggaatc ctgccacaga 36300
caggggcgag ggccctgtgg agctggccca tctggccggg cccgggagcc cagaggctga 36360
ggagtggggc agccaccatg gaggcctgca ggaggtggag gcactgtcag ggtctgtcca 36420
cagtgggtct gtgccaggtc tcccgccggt ggaaactgtt ggcttccatg gcagcaggaa 36480
gcggagtcga gaccacttcc ggaacaagag cagcagcccc gaggacccag gtgctgaggt 36540
ctgagaggga gatggcccag cctgacccca ctggccactg ccatcctgct gccttcccag 36600
tggggctggt caggggcag cctggccact gcctagctgg aatgggagga agcctgcagg 36660
tggcaccggt ggccctggct gcagttctgg gcagcatcct cccaagcaga gaccttgctg 36720
aagctcctgg ggtgtggggt gtgggctgga agcactggct ccctggtagg gacaataaag 36780
gttttgggtc tttctgagac tttgtgtcta tctgggccct gcttacccaa agggctcagt 36840
tggcagcaag agctccccac acctgaccct cggtgccgga ccactcgagg gtggctgaca 36900
cctgcatccc tcaccagcac atcacccagg tgacagtgag aattggaaac cccaggcctc 36960
ctctagggct tgtggctcag tggcaggtgt ccagtgagtg ccctcaatgg gcctgagtgg 37020
gtacagaatc tgccctcccc caaccaaagc ccacatgatg ccatcagccc caggcctagt 37080
gcagaccaca gcttgggaag cgaaagggag atg 37113

<210> SEQ ID NO 12
<211> LENGTH: 15540
<212> TYPE: DNA
<213> ORGANISM: Homo sapiens

<400> SEQUENCE: 12
agccaagcat tccgactcag ctctgggagc agctgccttc tgggctggca ttctccgcca 60
ggggggttgt gccctcgtgg ccccccccgg gtgcctcctc acctggctga tttcatctcc 120
tgtccccctg cctcctcctc caggaagccc ccagggcctg gccctccttg agagtggcat 180
ggaggaggaa gaagactcgc ccaggcccat gggagtcgga tggtggccgc acttgtgggg 240
ccctgacccc ataggcttct tcagcacgcc ctggcctggg tgatccctgc ctgagggctg 300
tgcacggctc atctgccaga ccagatttta ggggattctt gtactgtcct cctggagcag 360
cagggggtaa agcctgaccc acccagactg tccagcaaca agggcctcct gctgtgggcc 420
agggaccctg gaactgacca attgtgtcct agggacgcag agtccccagg ctgctagagg 480
gctgtggggc cctgtttcat gcctgaagca ggaagaaacc ccaggagagg tctgaagggg 540
acccagcccc caccctgtct agcagggagg agcctctgca agaggccgag ggtgctgaa 600 gtggaggagg atagaggcag caggactcag ggtcactggt catttatggg gatcacacgg 660
ctgcagtgtg ccctgcatgg tgctaggcac cagggacagc agaggacaag cctgtgtcct 720
ctcccaccac cagagggctg ggcactgccc ctagggagag agggggcctt ggtgtgtgca 780
gaggggggcc tggggcacgt gcctggcctg gtcagatgat cagagtgggc tgggctgggc 840

```
ctggtctggg gcccagtctc aagggcagac cccacctggc tagagttgat tgtgtgcaca    900
ccggatgacc cggcgttgaa ggcctctcct ctctgtgagc ctcatcccca cctgccagac    960
tcccagcaca gcctgcttcc tgccccagct gctgagcgac agcgctgggc cggcttctgc   1020
gcgccccttc ccccagccca tcttggaaac cacagcagcg tccttcctcc caagtccctt   1080
cccagggctg acatcccaca gcagggatgt atcccacaaa ccccgcaggc cctggtgcct   1140
acagcttggc ctggtaacat caaatcctac cctctcctcc tggcagcaaa gatggggtgc   1200
ccccacccca gagttctcag cacccccaga cagaagcagt cccccagcga cctcagaact   1260
cttggggcgc tgccacaccc ttgcaggagg gggcagtgtt cctgggatgc tcaggtcctg   1320
gtatcacctc tggccagata cggaaggtga aactacaggg catccaattc accttgaact   1380
tcagataaac accagattat ttttttgtat gtcccgtgca atatttggga cacacttacc   1440
ctaaagaagt attctgtttt catctgagag gcagatttaa ccggcgtccc gtgtcttcct   1500
ggcagtcctg ccctggagtc acactccaca ggtgcagggc agggccaggc tccaagtaga   1560
tggcggccaa agcacccgcc ccatgctcct gactcccggg gctcttcagg gcattgcgaa   1620
aaccagcagc agagctgaca cctggtccct gctcgggagc cagcaaggca ggaggctgct   1680
taggccttgc gtgtggggtg ggcgcactcc ctgctgcagt gctcttcgta catgtgacac   1740
tgttcccgct ctttcccagc tggctggagg cgtgatcctg ggtgtggccc tgtggctccg   1800
ccatgacccg cagaccacca acctcctgta tctggagctg ggagacaagc ccgcgcccaa   1860
caccttctat gtaggtgagt gcacatgtgg ccgcagacgc attcagggag ggcttctagg   1920
aggaggcagg tcctagcctt ttggatgggg acatggaggg tgaaagacag tcgggcatgg   1980
cgtgtccggg cagggaggcg gccctggaaa gggctctggg cacaagggtt gagatggagg   2040
tgggcctgtg gcctgctggc ccttctggtc tgagccaggg caggggtgg cagctaggcc   2100
tgggcaggga ctgtgtggag accttgctta ttttaagtgt ggggttattt cggggggaggc   2160
tccctgagaa gggtggggct ggatgcctgg gccacacaga gcagccgagg cagctggcgc   2220
tgtggagccc gggagggagg gagggatgga gctcaaggga tggaacccag tgaggggtgg   2280
agacggggca ggggaggggt ggagaggggt ggagacgccc cagaggcggt gtgactcagc   2340
tgcccctgca ggcagctgca ccttgctgcc ttattaggct gcgtgtgggg gactgggctg   2400
ccctccctgc ccccaggagc aggagcagga gtgatggagg aggaggaggg gaggggcaag   2460
gccaggagga ggaggagggc catctcactg tgcagagagc agcacccttc ctcctggtgc   2520
ccctggcagg gctggtgctg gtggggctct gggagcattt gttgagatgc ttctggcctt   2580
gaaaggaggc ccctgggatg gctctgttgc cctcacaggc tgaggggtgg gtgaggtggg   2640
cagcctgtgt gtccccagtc ctcagggctt ccctcagccg gcaggtgccc ccaggcctgg   2700
agctgcaggg ccaggccccc tgccagttac ggaggctgct tggcttggtt gctgaaccag   2760
ggccccagga ggccgaaata gccccacacc tgcgccgtcc cacctctttg tccagtcacc   2820
ccagggccag gtgagggccc tggccacaca gcgtgcccgt tccttcttcc ccatgccccg   2880
ctcatgggtc agagggccgg tgctggggtc cagatggtgt caacagggat ggtccctgtc   2940
ctccccagag acagaagcct gtggcccacg gagggtttct gggcccagcc gatcctaggg   3000
agggtcccat ggccctgccc ataggttcct ggcctctctc ggggccgtgg tgccctcaca   3060
ggtggtgtca ggaaggacgg gaaaggctgc ttgtcccagg ggctcatgtg gagaccaccc   3120
cctgcacgca gctggggcgc tcctgcctgt gtcctcagaa gcactcggct tagctttgcc   3180
catgtgcctg ggctgtgggt ggcagagccc ggccagcatc ctccgatctc caagggtgca   3240
```

-continued

```
tctctactgg aggcccctcc tgggcctctt gctccccgct tcccagatca ttaggatatt   3300
tggggtccag aagggcctcc cagccatcct gggccttgtc ctccggggcc accagtccag   3360
ccagtgacaa ccacagcatc cccggcctgg aacgaggctg cccccagcac gttcctcgta   3420
ctcctgtcca gggacaggag gggctgcccc tgccaccgag tccccttctc caggacctgg   3480
ggcctgtggg tgtgaggcag gtgttcttgg aaggggtcac tctccaggca cccggcggcc   3540
aaggcttgtg gctggagcag ctcccgctgt ggggtcggcg tcgggccccg tgtggccgga   3600
gaggagctga agggtcactt agcttcgggc tggggcgagg acaggggaca ccccagagag   3660
gtatgccagg cctccttcct gcgccccact ctcggcagaa gcagaggtca caggctgtgc   3720
tgaggcccca tggtgctgcc cccatgatgc cagggtgagg ctggcgttgg aagcaggtgt   3780
ctgacctgca tggtgtcacc gtggccacat cagagctcca gccccagagc cgcccaccct   3840
cggtccttgg ctgtggtttc cctgggctgg aggagcctgc cgttgtgttg gccacacgac   3900
cacaggacct gccacccccg acgtgggctc tgcctgggcc cccactggac agggacccct   3960
tggagctcct ctggccacca agtcctcgcc cattccagaa tcggccttct ggagcctctt   4020
gctgtccctg atgcgggctg ggccttgcca agggcttttt ttcctgcgcc gggaacaggg   4080
tggatttgct gggctcactc ccctcagaga cgctgcgggt gcggtgggtt aggcccaagg   4140
gcgttaagag aggaggctgg ggtggggctg gggcctggca gggggtctgg cagccctggg   4200
cctcccacct cctgtcagga ccaaaaaagg caacgcgcct ctcctgacct gtaccccgga   4260
gtgaacccaa ccttgcaacc caggagtgtc agggcctgag gggagggaga cctggctcct   4320
gggtgccgtg cccgtaagga ggtggccacc tgcagggcat tcctggcaga ggcttcatct   4380
ggccaggtag gaggctgggt ggccgagccc caaatctggg tgtgttctct gcctggcggt   4440
gggtcctgcc ccaggcacct tctcctctgg gctggctggg cagggacaat gggcctggct   4500
gcgaggaggg ggcctgggct gccttctgca ttgcctcggt gacgggagat ggcccctgcc   4560
tgctgaggga taggggagtg ggcaggcagt gagagacact gacagctgtc ccgcgggtac   4620
agggccctgt ctgggtggcc aggcccatgt ctcgggccca cagtgcgccc cccacccttg   4680
gacggcgcct tctccctccc caggtgcatg ctgcccagcc agggagcgtg gggggagttcg  4740
ggagggctgg cctacacgcc ctggtccagc tgtcccaggt ggggtgctgg gcttcagccc   4800
tcagcccagg gcctaggaat ccaacttgat cctccccaca cagcagccag gttcaaatgc   4860
aggtcccgta acggaagtgc tgctgtgcag cccagattgg ggggcaggag ccagcagggc   4920
ccccccaccc tcttctcgca ccacactggg gaggcagcat tggttccagt tccggttcct   4980
gggctgccct ctcaaccccg gcctacagtg gggcccaccc tgtgccttct gatgccactc   5040
ccaccccacg ccaagtccca gaggctttgg gagcgggtga aggcggtggg tggcgggtgg   5100
caggtgcagg cggtgggtgg tgggtgtggc aggtggcggg ccccaccgca ggtgtcatcc   5160
ctgcgaagca cctgtcgcca gcactcagag cgctcatgag gtgcccagtc cccatgtggc   5220
ctccttagtc tccgtcctgt gtcatggaag aggtaactga ggcacagaaa actcaccagg   5280
ccaggctggg atgtgaggtc ccttgctgct catccctggc agtcagcaac cctacatctt   5340
cccagctggg cggcccgtgg tgggttcggc acccaggacc ctccggggtc ttgggctgtg   5400
gcgagtgtgt aggcacccac ctggtgtctc tctccccgca aggcatctac atcctcatcg   5460
ctgtgggcgc tgtcatgatg ttcgttggct tcctgggctg ctacggggcc atccaggaat   5520
cccagtgcct gctggggacg gtaaggcagg gaggcgggcc tgtgcctggg ccggggaggg   5580
```

-continued

```
gctgggggct gcgtctggcc ctgaggaggg ggcagagctg gtgctcaggg cggagcctag   5640
aattctgggg gaggtggctc ctgtgccctg cttttcccgt ttggttttta aattaaatcc   5700
caccgtgctt ggtctccatc gtggccagtt cctacgtgac cgcttttctt tgtcaaaaaa   5760
tagccacaaa tataacaggg agcaagcctc agctctgagg ccagcctcgg cgtcccgggc   5820
acaccgcccc ctgtgggaag cccaggcctg gctgtgccat ccagggcctg gccagtccag   5880
gaagagggag cctatgcccg tgtctccagt gggggaaact gaggcagatc ccatggctcc   5940
cccttccgtg gggagcagga acaagggggt ggggaagatc agtcaggggt catgctgctg   6000
cacacgcctc cctgggggct gcagacatcc tggactcacc agcctgtgac cccaaaccac   6060
acgccccgcc ccatccaccc cgtcctgtgg agcctggtgc cgcgtgggga catcctgggc   6120
tttgacggct cctccctgcg ctgagtttta gcctctgtgc cccagggctc cacacaagcc   6180
gctcactcct ggtcaggtcg tgggctggtg gctcccacta gcccctcaca gacacgcctg   6240
ctgggcacct gggtgtgtgt ccttgggccc cgcctacagc ctgccctctt tcctccctct   6300
ggccactgcc cggctccagt tcttcacctg cctggtcatc ctgtttgcct gtgaggtggc   6360
cgccggcatc tggggctttg tcaacaagga ccaggtgagc ctgggtgtgc agggacaggg   6420
tggggtgggt gacgggggca ccctcctctc ctgtcgcggg tgggggttgg gctgactcat   6480
ggcttgtggg agctctttgg gctcttcctg ggtcccactt gccaggagga tctccagggg   6540
ctttatggag gaggcagcat tggggctgag caccaggcca gcctcccgtg tcccagcact   6600
cccggggcag ctgagagtgc agagtccttg tcctctgggg tctagcctcg aagccaccct   6660
gcccagggag agcctgggaa aagtgcgtcc gcctggggcg gggcggggtg ggggcaagga   6720
gggggaggtt ccccctgtgc atgtgaccgc acccctcccc cagatcgcca aggatgtgaa   6780
gcagttctat gaccaggccc tacagcaggc cgtggtggat gatgacgcca acaacgccaa   6840
ggctgtggtg aagaccttcc acgagacggt gcggccccgg ggggcgaggg cggggagcag   6900
ggccccggga acccggcggg gtgtgtctcg tcctggatga atcctgccta cgcccagacc   6960
tcaggagcag gaggtgccct tggacctcc aggacccctg gtctcaactg gtcctcgggt   7020
gggaacctag tgggccaggg tggcccaggg tgcggaaagc tctgagcagc gcagctgagg   7080
aggaagaagg ctggcccctg gatgcattct gcagtgggga gcgctgcgta cccctggcca   7140
cctccccatg ggttccctag agccaccgtc cccctgggca catccagggc tgaccttgca   7200
cccctgctct ctgcagcttg actgctgtgg ctccagcaca ctgactgctt tgaccacctc   7260
agtgctcaag aacaatttgt gtccctcggg cagcaacatc atcagcaacc tcttcaaggt   7320
gcgcgaggcc ggtggggccg cgcctgaccc cccgcatgtc ccgcccctgg gtggggtcct   7380
aggggtgggc aggtcacacg gcagccccac agggagcgac cacactgggt ggcatggccc   7440
ctgtcagggc tgctctgctg ggagggttgg ggtgggaccg catctggccc acgaggaagg   7500
caggcgccct gtgctgcgca ttccgggtga agaaggtgga ggctctgggg ggtgggaact   7560
cacctgcacc cccagctcca cgtgtgcact cgtgggtgtg gacgcccctg acagcctgta   7620
gctggcaggg cctgcaggcc atatagtgcc ctgtggaagt ttcctgctga ggcctcagtg   7680
gaagtcgtca tcagtgatgc tttaggggtc tagtgacacc aatgaccgtg atctcagtgg   7740
aaaagggcac agtgtgtccc aggcatttcg cgtttatgtt aaaacgggtg gaagatagca   7800
agccggcaga ggccgggccg ctgcacccgc ctgttccgag gtgggtaggg ggtggggggc   7860
tgttcccagg attcccctct acgctttctg tggtgaccac ggattactgc gtgacaacgg   7920
gaagccggga gccgaggccc ggtccctgac cacgcgtgcc tggccacccc tgcaggagga   7980
```

-continued

```
ctgccaccag aagatcgatg acctcttctc cgggaagctg tacctcatcg gcattgctgc   8040
catcgtggtc gctgtgatca tggtgagcgg gcgggggcgg agggcctgct ctctgggctg   8100
ccccttccgc ggggccttgt gctgactgcg ccccccacca ccctcctgca gatcttcgag   8160
atgatcctga gcatggtgct gtgctgtggc atccggaaca gctccgtgta ctgaggcccc   8220
gcagctctgg ccacagggac ctctgcagtg ccccctaagt gacccggaca cttccgaggg   8280
ggccatcacc gcctgtgtat ataacgtttc cggtattact ctgctacacg tagccttttt   8340
acttttgggg ttttgttttt gttctgaact ttcctgttac cttttcaggg ctgacgtcac   8400
atgtaggtgg cgtgtatgag tggagacggg cctgggtctt ggggactgga gggcaggggt   8460
ccttctgccc tggggtccca gggtgctctg cctgctcagc caggcctctc ctgggagcca   8520
ctcgcccaga gactcagctt ggccaacttg gggggctgtg tccacccagc ccgcccgtcc   8580
tgtgggctgc acagctcacc ttgttccctc ctgccccggt tcgagagccg agtctgtggg   8640
cactctctgc cttcatgcac ctgtcctttc taacacgtcg ccttcaactg taatcacaac   8700
atcctgactc cgtcatttaa taaagaagga acatcaggca tgctaccagg cctgtgcagt   8760
ccctcagtgc cagtggtgtc tgagacctag ggttggccg gagggcaggg gaatctgaca   8820
tcggtggggc ttggctctgt ggactctgtg gggtccaggg tgagggtggg tgggtcggga   8880
tccctggtgt tcaccaaagg agtcactctg taaaatttgg ggagttattt attctgagcc   8940
aaatatgagc accggtggcc tgtgacacag ccccaggtcc tgagaacttg tgcccaaggc   9000
ggtctggcta cttaattgta tacattttag ggacatagga cattgatcat tacatctaag   9060
atgtacgttg gtttagtcgg aaaggtggga cgatttgaag gggagggact ttcaggtcat   9120
aggcggatta aaagatgttc tgattaataa ttggttgatt ttatctaaag acctgaaatc   9180
aatagaatgg actatctggg ttaagaggag ttgtggagac caagattatt atgcagatga   9240
agccgccaga ttgtaaatgt ttcttatcag acttaaaaag gtaccagaat cttagttaat   9300
tctctcctgg atcaggaaat agacctggaa agggaggggg attctctata gaatgtagat   9360
tttcccaaga gacagctttg cagggccatt tcaaaataca tcagagaaat atattttggg   9420
gtaaaatact tcggtttctt tcagggcctg ctgtcacgtt ggtatcttat tactacagag   9480
tctgttttgt gagtcttaag gtctttttat ttttagacag agttttgctc ttgtcaccca   9540
ggttggagtg caatggcgtg atctcagctc actgcagcct cccctccacc tcccaggttc   9600
aagcgattct cctgcctcag cctcctgagt agctgggaca acaggcatgc accaccccac   9660
ccagctaatt ttgtattttt agtagagacg gtgtttcgcc acggtggcca ggctagtctc   9720
gaactcctga cctcacgtga cacaccaggt tttgggatta caggtgtgag ccaccacacc   9780
ggactaaggt ctctgtttta atgtgaatgc tggtcagctg tgcctatgag gcatgttcgg   9840
ccacccacag tcatcatggc ctcaacgagc ttttcaggtt tactttagaa tgcatttggc   9900
caagaggtgc ccattcagtt ggttggggtt gcttagaatt ttactttggg tttaaaccag   9960
ggagcaactc caggtagcaa gggccctttt tgggagcgtt ctctctattc tcttttggga  10020
gaggccctgt gttgcctgca gccacttcca ccctgcccct tgggcacaca aggggcacac  10080
agtgtaagca ggtgggcagg aggggtcggg cagccaggga atgcagtgag atgggcttgg  10140
ggtaggggct gggtgcgctg caggactcct cttcctcctg agggatggta aaggatggac  10200
acactgcccc ctcccgagca tttgagggtc tctgccctgc ccatctgtta cctgtaaatg  10260
ttcctttgag gagctgatgg ctcaggcctg agccacatct cagagggtct ggaggggaag  10320
```

-continued

```
aaagacctca tcctactagg gagccccccc agcccaccag cgagcggtgg ttgggggcag  10380
acaggctgtg gggctaagga gcccctgcac tcccccgtcc ttttcccttt gtctgagcac  10440
ctccagccag tgggcttggt ctagactctc ctatctttcc ccacatcgtg gggtggggct  10500
tgctctgggt taggctactt ttccctagtt gtggggaggg gggtgctggc acatttcact  10560
gttccctgga ggaaatgagt gcctgggaat tcatatctag ggctcccagc agcctctttg  10620
caggccaatt tggaaactgt ccccagccct gcattttagg gggttacaga gtctctcagc  10680
aggccctcct cccctgctgc tcccaacttg caagcctgca ctggttggga gaacataatg  10740
gtccaaggag ccccctctct actttccgct gtgttccctg tggggaggga agagcagttt  10800
aagaaataag gaatcccaaa ggcgcacagc agaccggggg ccgaggagtg ggtcctgctt  10860
cccctccttt tttctaggct gagccacagc aggtccttga atcctatttc ccagcggatg  10920
ccaggacagc aggccctggg ggagttctct ctcgagcctt tcagagggac cagaggtcta  10980
gcagccaagg agaactcaga atccttgagt gtgtggggca ggaactctcc cagctgagaa  11040
ggggcacaag gtgccaacca tctagggccc agtggccaag gaagacgcgg cttgtcgcag  11100
ggagaatctg ggccctggtc ctccctttca gggcgggcag ctgacctgcc ccctgctgcg  11160
gacaggcgag gccaggctgc tggctcgcaa gcatggcgga gcccaaacct tccctgctgc  11220
cgcccgccca gccacggctg acttggaagc ttgaggagcg ttcagcagcc tccatcctgc  11280
ccgggaggac cggggacctg gaagggcctg gccctcgctt ccctgcagcg ccctaggggg  11340
acgtctcagt gcctcccgga gcccggacca atgcaccaga gctgagggcc caagggtgtg  11400
agggtggccg ggcagtggcc ccgaggacgg cgccccacaa gtttgcggcc agggcccagc  11460
aaacccctag ggtgggaaa gcgtcggccc agctagcggg tccagcaggg ctgcccccctt  11520
caccgtggcc cagcggtcac gaccccacgt cctcatcgcg ggctgggact gcctctgcgt  11580
ctggcctgag cgggaccgtg ggatcctggg gagccccgcc tcggtgcact gacagagccc  11640
agaaggagtg acggttaccg cttccggtca ggaccggaag tgccgggaac ggcattcgtc  11700
ctccgtgcga gatgacgcac ttcctgcctg aggcggccgc tgttctcgcg gcttccggca  11760
ggtggcgctg agaccacggg aagccagcct ggctgtcggt tagccctcga gcattctggg  11820
aattgcaggc ctggcccctc ctcttcctgt tcttggtcaa ttccggtctt gtttccccaa  11880
caaatgccgt cgtttccggg gctgcttccg agccggaccc aagggccggg gcgtggagga  11940
gtagaggggc gagcgcatgc gcacaggact acacgtcccg acaggcgtcg ggagcggcgg  12000
cccagttcct tgtgggagct gtagttctgc aggcgcggaa gccgtggtgc tcggccggca  12060
gagcactcgg tttcccagag ggctgagcgc gccgcacgga ggtgcggcgc cgaccaagat  12120
ggagactgcc gagcagcctt gagccggtag gtttgtggtg agggaggacg ggccgcgcgg  12180
gccggccgag cctccgggag gtcaccgagc gcagctttaa tacctgagct cgaaggcccc  12240
gctgtgctcg ccgacccccg tacctcgcgg ccgggccctt gggacccaca gcatccttgt  12300
gaggcccgga ggcctgtcca gcccgactgg acagtgccga ggggcaccga gagccagctt  12360
ggcaccgaga gttcgtttgt tctctggcgg ggaggtcttg ctggcacata tagtggagaa  12420
aggccgggct ctgcgttcat gtggagaaag agacggcttc cttcagccta cggacatgaa  12480
ggagtcaact ctaccttcca ctcgttgccg gctttcgccg agaaccccga gaaacggact  12540
accggagtcc ctatcttgca gcccgatccc cgctacccgt cggagtgccc cgctgaccag  12600
gctgcttctg gccgcggcgg cgttccgctg cagaggacgg gagtgcgaat ctgggaagca  12660
gggttctggt tgaactccag cttcgtctgc aacatactgt gtgacttggg caaattattt  12720
```

-continued

```
cccccgcccc gttcctgcca gctttaaaac ggtcatcagt ggggggtgct gcgtatcccc  12780
tttcactggg gtggcttctt cactgaggag agtcgcgcct cagaggaact gaggtcctgc  12840
ctgtgttcga cctggtgggg ggcactaaga gcccctgata gtacccctga ccccatcctt  12900
attgggtgca caagacacag gtcactctgg gcgggcaagg agttttggta gcaggagagg  12960
agtcggtgga tggatggctg aggacagtgc agaagggtgt ggctgggccg tcttttttttg  13020
cctggaaatt caagttctga ggcacccagt cactccagca ctaaatgggt gcaggaggca  13080
gcacttgtct gcccagctgg aaaggcaggg tatgtgctga gtgttacagg tggaaggcca  13140
ctggaggtcg ctccaggagc cgcggggatt tacctctgcc taacagggct gctcaaggtg  13200
atggtcgaca ccccactttc ctgagagctt gaccctcaga tgccagggcc ttggctgcag  13260
attccttggg agctcccggg gatcttccag caaataggag caaatctttt ccccgtggat  13320
caggaaggtg cacgctcttt gtggaatacg actgctcacc ccgcacagca agcagcttat  13380
aagtggccct cctgcctgat ttcagccctg ggttcaagcc ctgggtggct gcttactacc  13440
aaaatcgctc agtagctcca agcctgcctg cagagggttg gcaccattaa atgaggtaac  13500
gagtcaaaag tccctaccct gggtcctagc ctgtcagggg ctccgaaaac ccaggctcag  13560
gtcggtcctg cccggcacct gtttcacaca tgtacactcc ggtctgaggt tggtcctctc  13620
ccccacccca cccacctgca gttgagcagc tgaacagagg ccatgccggg gcactccgag  13680
gcctgagacg accacgcctg tgccgctgag gaccttcatc agggctccgt ccacttggcc  13740
cgcttggctg tccaatcaca ctccagtgtc aaccactggc acccagcagc caagagaggt  13800
gagaggaggg cttggagggg gaggcgggac tccaccctgt gtgggacagt tctgtcagtt  13860
gaccctccac ttgtccaggg gcagtggatc tgcagggggga actcattctc aatactgttc  13920
ctcctgagaa acaaattttc tgggctgttt tggtttaggt gtggcgtggc cctggggacg  13980
catggctgag gcaggaacag gtgagccgtc ccccagcgtg gagggcgaac acgggacgga  14040
gtatgacacg ctgccttccg acacagtctc cctcagtgac tcggactctg acctcagctt  14100
gcccggtggt gctgaagtgg aagcactgtc cccgatgggg ctgcctgggg aggaggattc  14160
aggtcctgat gagccgccct cacccccgtc aggcctcctc ccagccacgg tgcagccatt  14220
ccatctgaga ggcatgagct ccaccttctc ccagcgcagc cgtgacatct ttgactgcct  14280
ggagggggcg gccagacggg ctccatcctc tgtggcccac accagcatga gtgacaacgg  14340
aggcttcaag cggcccctag cgccctcagg ccggtctcca gtggaaggcc tgggcagggc  14400
ccatcggagc cctgcctcac caagggtgcc tccggtcccc gactacgtgg cacaccccga  14460
gcgctggacc aagtacagcc tggaagatgt gaccgaggtc agcgagcaga gcaatcaggc  14520
caccgccctg gccttcctgg gctcccagag cctggctgcc cccactgact gcgtgtcctc  14580
cttcaaccag gatccctcca gctgtgggga ggggagggtc atcttcacca aaccagtccg  14640
aggggtcgaa gccagacacg agaggaagag ggtcctgggg aaggtgggag agccaggcag  14700
gggcggcctt gggaatcctg ccacagacag gggcgagggc cctgtggagc tggcccatct  14760
ggccgggccc gggagcccag aggctgagga gtggggcagc caccatggag gcctgcagga  14820
ggtggaggca ctgtcagggt ctgtccacag tgggtctgtg ccaggtctcc cgccggtgga  14880
aactgttggc ttccatggca gcaggaagcg gagtcgagac cacttccgga acaagagcag  14940
cagccccgag gacccaggtg ctgaggtctg agagggagat ggcccagcct gaccccactg  15000
gccactgcca tcctgctgcc ttcccagtgg ggctggtcag gggcagcct ggccactgcc  15060
```

-continued

```
tagctggaat gggaggaagc ctgcaggtgg caccggtggc cctggctgca gttctgggca  15120

gcatcctccc aagcagagac cttgctgaag ctcctggggt gtggggtgtg ggctggaagc  15180

actggctccc tggtagggac aataaaggtt ttgggtcttt ctgagacttt gtgtctatct  15240

gggccctgct tacccaaagg gctcagttgg cagcaagagc tccccacacc tgaccctcgg  15300

tgccggacca ctcgagggtg gctgacacct gcatccctca ccagcacatc acccaggtga  15360

cagtgagaat tggaaacccc aggcctcctc tagggcttgt ggctcagtgg caggtgtcca  15420

gtgagtgccc tcaatgggcc tgagtgggta cagaatctgc cctcccccaa ccaaagccca  15480

catgatgcca tcagccccag gcctagtgca gaccacagct tgggaagcga aagggagatg  15540


<210> SEQ ID NO 13
<211> LENGTH: 25760
<212> TYPE: DNA
<213> ORGANISM: Homo sapiens

<400> SEQUENCE: 13

gatcacgata gccaagaaat agactcacac atgaggacag ctagtttgac aaaggtgcaa     60

agtcagttta atagagaaat tgtatctttt caaccaatga tgctggaaca attggatatc    120

cacctgcaaa aagacaaaat aactttgacc aattcctcaa gctgtattca aattcattaa    180

tgtaaaatga attagtaacc taatataaat gtaaaactgt gaaactgtta gatgaaaaca    240

tggtggaaaa tctttgtgac cttagattag tcacagaaag gatatgacgg caaaggcaca    300

attcataaaa gaaaggtggc taaatggaat gtcatcaaaa tttaaaaatt ccactctttt    360

gaaaggcagt cataagagaa taaagaaagc aagccatcag ctgataggaa atattcacaa    420

atcatattac gatgaaggac ttatatccag aatattcatt gcatattctc tgtgtatttt    480

caaaaatgaa tagtaagaaa acaaccctat aaaaatgagc aaaaaagata tacagatatc    540

tcctacacac ttgaccaaag aagatatatg gataataaat aaggtcatga aaacatgctc    600

aacatcatta atcattagga aaatgaaaat taaaaatcgt aatgagatat cgctacacac    660

ctattagaat ggttaaattt tcttgcttta aaactgatca taccaacttt tggcaaaggt    720

aggagaaact gtaattctca tgcactgtga gtgggaagat taatggtaca acccctttaa    780

aaaatgattt ggtagattct taaaaggtga aacacacacc ggccggccat atgatccatc    840

cattccactc ctaggtattt attcaagaaa aatgaaagca tttgtctcca caaagacttg    900

ttcatgaatg tttatagcat tggatcatag atagcccaaa ccagaaacaa tccaagtgac    960

gcctaacaag tgaaggtata agcaaatata cccattcatg ttatttatca ataaaaataa   1020

atgaacgatt gatacctgca acaatatcaa tgaatctcaa aataagtata tggcatgaga   1080

taagccagac aaaagaatac atcctgtatg tgtccattga cataacaccg tagaatgcaa   1140

agaatacctg atagaaggcg gatcagtggt tacctaaggc tggggaggag gggtgggagg   1200

aagggattac acagttgtaa tttaattacg aatttaaaac ttacaagaaa ttgttgacgg   1260

tgatgatggt ctcactgttg tacacatatg tcaaaattca taaaactctg cattttggcc   1320

cagtgtggta gctcacgcct gtaatcccag cactttggga ggctgaggca ggtggatcac   1380

ctgaggtcag gggttccaga cctgcctggc caacgtggtg aaacctcatc tctattaaaa   1440

atacaaaaaa cttagccggg cgtggtggca cgcacctata gtcccagcta ctcaggaggc   1500

tgaggcagga taattgcttg aaccctagat gcagaggttg cattgagccg agattgcacc   1560

actgcactct agcctgggca acagagagag acctatctaa aaaaaaaaaa aaaaaaaaaa   1620

aaaaaaaaaa acaaaaaaaa acctctatat tttaaatatg tgtagtttat tgtatgtcag   1680
```

```
ttagcccccca ataaacctat aacttcccag gggaaatggc tgagattgat gccaccttca   1740
aagagttaaa gaaggcctag gtagtaaccc ccaccatctc tctcgtgatt tcccctctct   1800
ggcctctctg cagactggct gaatcagaat agatgattgc agacctcaaa ctcaaccaag   1860
tagcaacacc aaatgggctg ccaggccaga tgtggtatct tcgtttaatc ttagattaaa   1920
ttagattcat ttaatctaag attaaattaa cactgcccct ggtacccggt atcagtagct   1980
acggattctg tgaatgaatt ctcttccatc tcatcaggag agagtgtgag aagcaatttg   2040
cattcgcaca ggagggacaa cagtacacag tcacagtttt gccccaggga tatgttaatt   2100
cttctgctct ttgtcacagt atagtccaaa gggaaaaggc cctctggaca ttccacagat   2160
tatcacgtta gttcactata ctgatggcag tctgttaact ggatctgacg agcaagcagg   2220
ggaaagtact ctggacgccc caagtaaggc acacgagcca ggctgggaga taaattccac   2280
gaagctttag aggcctgcta catcatgatc ttattaccat gaagttattg ccataaaatc   2340
tggcaaatcc catggtacaa gaggtatttg caatggagaa agacaccaca cacacagagc   2400
ccctggagaa cttcaaagaa gagtcatggc ccagactcct tgggctctgg aagaaggccg   2460
tgcagagaac gataccattc agaaagaggt tcctgctctc ctgtgggaac ctctagagaa   2520
agagtttctg gtcatggacg ttaagtgacc atgtggtcag agatgcccat cttgagctag   2580
gatctgttaa acccaccaaa tcagaaggtc aggcaagccc agcagcatcc agtatacatg   2640
ggaaaagaca cctcctggga ctgcgaacaa gcagagggca aaagaaagcg acataatccg   2700
gggatcggaa cccccacgtc atctaccagt gttgcactga cacctcttct tcagtccaca   2760
cctgtggcct cctgcagagg tccctctgac cagccgatgg agaaggaagg ggcctgagct   2820
tcactcattg gcaggttagc tagaaacgtt agtgagcccc caaaggactg ctcctgcact   2880
gcagcccact caggtggtgg tgatggtggc gatggggtaa ccctcccagg gggccgagct   2940
ttgagtgcag gacctggtcg tgcacttgta gggagagaag cgaaccaaat cagtggttct   3000
atttctagca gttttaggct ctacagggcc attcccagag cgggacgctt ccaccggaag   3060
acgctattaa gacagcttcc acctggtcac ttcgggctcc tggtatcaac aatctggcag   3120
agagaatgaa gttcccatac tggcaggggt aactggctgg gagcatcatg agaaggtatg   3180
aatacagtca tcaatggggg cgggcaggtg acccaccagg ggcatctctt ggtgctgcca   3240
tgcacagatc ttcccgcaag tagcaagcgc cacagtgtga gcatgataag gccatggtga   3300
ccacaggctg ctcaaggtcc cggctatctg acacggatgg aggaggaagg ggcggtggct   3360
atcagtcagg gccccaggca atgaaaatgg caatggcaat ggcaggagta ggcactggcg   3420
ttcatcccac tcagcctgtt agtgtcaatt tcccctggtg ttgggaccaa tttgatcctg   3480
gagaagctct cctcagggga gcaaacctcc tacacaggtg ggctgtgcgg ggggtggggg   3540
tggagtaagg cgtgttgggt catgggtgct actggtgtcc tccccaactc cttttatctg   3600
gaccgtgtgc ctatccccca gctgttaagt gttgacaact aatggctcaa tgaagagctg   3660
tttagctaaa gggaagcccc acatccggga cgtgtgtgcc ctgggggaca cacagcaaat   3720
gactgacaag gaggaacaga aggcagcctc ttgcttccag tcctgggaga ccatgctgaa   3780
gccctgcctc ctggcttatc tgtatctcct gcacaagaat tccagcccag gctctgtttc   3840
tagggagtgt gccctgagat gccagcgctt gagcttcgag agcacgaggg ggtaggttct   3900
ggtggacagg gaccccggtg tgacgacaac tgcaaggttc accttggacc ctggcactat   3960
cctcccacca ggctggaaaa ggagaccagg acatggcccc agcacagccc ccaggtgggc   4020
```

-continued

```
aaaccggcag gctgggctgg ctaagctctt ggtgttcttt gtgtgggggt aggtggggct   4080
ggtgagggcg ggactggctg caggtccttc agcgggtccc tgctggacct ccgtggcggg   4140
gacagggatg aaattaaaac agacccgact ccattcaatc tcagcgatcc atgactcagt   4200
gatgcccgga gctgcctccc tttctcctcc ctgggctccc accccgccgc gccccacccc   4260
attatgatcc cccccaaaat gcagagagcc cactagaggg aggaggctga gggctccagg   4320
ctgccctggt cagacaacac atcatgttcc ttcacctgca gatagaccct gagcccatca   4380
gtgaaacaag gggcccccag gagaatcaga atcctgaccc catcccaccc tccacaccag   4440
ctcaacggac tcccaggctg ccagaaaggc ctcatacgtc aaagtcagcc tcccagtcgg   4500
cctccgtttc caggtgtggg cctggagtgc cgtggcccag gtggtatcag aagctcgcag   4560
ggataggcct aagaggtgac cccaggggag ggccaggcca aggagctgca gagagggctg   4620
gggaagctcc agatccccca cctccttcaa aacacacctg aaacaccagc cagcaccagc   4680
accaccaaga tgagaaaggg ccctggaccg tctccaccag tgtcatgcag cagctgggct   4740
ggtcccctcc cttgggtccc catctgcccc acttgtacag gagctaacga cgcctgctgc   4800
ccacccagga ggacctagca ggagcccagt gtgaaggtgt ttgcaaaact ctggggaaag   4860
tgaaggtcag aggtgactcc cagcttccac ttaggacata gagagctgga aagagcccgg   4920
ctcccatcct taaactgcag cagcaacaaa aggcaccaag caacctgaaa agtcaggact   4980
tttctcaaaa ctctctgaga gctgaggtca cagggcaacc aactaaccca aaacaaaggg   5040
aaggcaggcg cctgcaggag gagacgggat gcaggctgtc accgagacag acgaggccag   5100
acaccaggaa gaagaacaca gccaaaatgt ttaatgagtt ggcaagggtc ggtgtggggt   5160
aatgggagag cacagaagcc ccaggggctg cggagtgaag ggaaatccac atccactgga   5220
aggtccccgt ggatttcacg ggatgctctc tttgtggtgt aggcccagca gaggggaaca   5280
gcagccactg tcccaaaggt acaaaaccta cataggttat tctcctcaat ggaacaaaac   5340
ccttagattg ctggaggaaa ggcaaaaaag gcaaaaaaca ctgtcacact tagggcacga   5400
gtagaaacca tcgaaactgg gggaatccta aaagccctgt gccctgggga gggataagct   5460
acatggtggg cccagagcta cagctgagcg tagggcagga gtcccaagaa tgcttcaccc   5520
acaagaccca aaggacatag ggttaatcag aaaaaaccga acagcccccc acctccagca   5580
cctgctgaca agcaccatgt aacaagtgac cctggagtgg gagaggccgc agagtgtggc   5640
ctgggagagt ctgcggagtg tggaaaccct ctccaaggta agcttatagc cgaaggctgg   5700
ttggacactg ggaaaagcct ctctatggta aacacaaagt agtgctggag ggatttgatg   5760
actgtggtgc tccagagata accatgacaa caccaaactg aaacccagct caactctgga   5820
cgagattagc cccaagcccc gcagtaaagg aacagcaaaa agaagggtat gcccatttcc   5880
aaaagcacaa aacgaatttc ttcagtctct actgtcctct gcacgatgtc tggatttcaa   5940
aaaattgatg aggcctatta aaaaaataaa taaataggcc agggtctgtg gctcacgcct   6000
gtaatcccag cactttggga ggccgaggca ggtggatcac gagttcaaga gatcgagacc   6060
atcctggcca atatggtgaa accccatctc tactaaaaat acaaaaatta gccgggtgtg   6120
gtggcacacg cctgtagtcc cagctacttg ggaggctgag gcaggagaat cgcttgaacc   6180
cgggagacag aggttgcagt gagccgagat cgcgccactg cgctccagcc tgggcaacaa   6240
gtgagactcc gtctcgaaaa ataaataaat aaataaataa taaataatag atgaatagat   6300
aacgtgctat caagacaaag caagcaaaat aatcagactg aaaggctggt ctcagtggct   6360
cacacctgga atcccagcac tttgggagac tgaggtggga ggatcgcttg agcccaagag   6420
```

-continued

```
tttgagacca gcctgggcaa cacagagaga cctacctcta caaaaaataa aaataaaaaa   6480
atcaactgtg catggtggtg cccacctgtg gttccagcta ctcgggaggc tgaagcagga   6540
gaatcacttg agcccaggag gtcaagcctg cagtgagtta agattgtact tctctactcc   6600
ggcccggggc agcagagtga ggccttgtct caaaataata atgataaaaa aagaaacaga   6660
ctcagatatg acacagccgt cggaactgtc agacaggaca ttttaaatac aataaatatg   6720
ctaaagactc taaggaccct aatggagaag ggggaaaata tgcaagctca gataggtcac   6780
ttcagcaaag agatggaaac tagaagaaga aatcaaatgg aaaagctaaa ataaaaaaca   6840
gtaacagcca tgagaagaag cctctggtgg gctcatgaat gtactagaca cagcaggaca   6900
gggtccgtga acttgaacac agttcagtaa aaaataccta aaatgcagag gaaaaaatat   6960
tgaaaagggg gaaaaagatg cccaaatctt tccaagaagt gtgggacata ttaagtgatc   7020
taacatatgt gtgaatggaa atctcagaaa gaaaagatag aaaacacagt gaaaaagaca   7080
gagttgaaga aataatgggt aagaatttta taaaatcatt gacaaacaat aagccacatg   7140
gccaagttca gagaatacca agcaagataa gtaccacatt ttttttttt ttttgagaca   7200
tagtttcgct cttgtcgccc aggctggagt gcaatggtgt gatctcggct cactgcaacc   7260
tctgcctcct gggtccaagt gattctcctg cctcagcctc ccaagtagct gggattacag   7320
gtgcctgcta ccaggcccgg agtagagaca gagtttcacc atgttggcca ggctggtctg   7380
gaacccctga cctcaggtga tccacccacc tcagcctccc aaaggctggg attacaggtg   7440
tgagccactg tgcccggccg gtaagtacca tttttaaaa actgaaggca tatcacattt   7500
aaactgctga aaacccaaga caaaagcgaa aatcttgaaa gcaaccagag aatacaggta   7560
cattccatag agacacaaga aaaacagaaa tatggtagca gacttctaaa cttctcgtca   7620
gaaacaaagt cagccaggga tgaaagaaaa acaacaacaa aaaaactgtt gattcagaat   7680
tctatatccg gtacaaatat ctttcagaaa aaaaggagaa ataaagtctt tctcagacaa   7740
acaaaaactg tagaatttgt tactgaaaga ccttcactat aagaaatgtt aaaggaagtt   7800
cttcaggcaa aaacatgata ccagacagag acttggatct acacaaagaa gcaaagtgca   7860
ctagaaatgg aataaatgaa agtacaaata gaatttcttt ctttctcatt tttaattgct   7920
ctaaaagata actgactaaa gaaaaaattg tggtcacgta ttatatgtct atagtataat   7980
gtaaaataga atgtatgaca ataatagcac aaacagtggg aggaaggaat tgagaatatg   8040
cagttgtaaa tttattatat aacacacaga gcaaggtaat atcatttggt agacaatgat   8100
tatttaaaga tgtatattat aaaacctaag acaactatta atttaaaaaa taagatataa   8160
atgataagcc aatagtggaa actaaatgga atcataaaaa gtactcagtt aatccaaaag   8220
aaggcagaaa agggagtggg gggacaacag acggaataaa tagaaaagag ttagcaagat   8280
ggtaaattaa atccaagcat atggccagaa gcagtggctc gggcatgtaa tcccaacatt   8340
ttaggaggct aaggtgggag gattccttaa gcccaggagt tcagaggcta taatgagcta   8400
tgatcatacc accgcactcc agcctgggca acagaatgag atcccatctc taaaaaaaga   8460
aaaacactcc aaatacataa ataaataatt atattaatct caacacacca atgaaaagag   8520
atgatcaatt tgaataaaca aaagacccaa ctatatgcta tctatatgaa acccacttta   8580
aatataaaga cataaataag gttaaagtaa aaggatggaa aatatgtgac acagaagcat   8640
gcgtcaaaat aaagatgcag cagctacatt catctcagac aaagtaggct tcagaacaag   8700
gactattaca agggataagt gagacctcac ataacaataa aggagttgca ttttctgaga   8760
```

-continued

```
aaacaatcct cagtgtgtag gcacctacca acaaaggctg aaaacacaga aagcaaaaaa   8820
tgataaaata aaatgtaaca ctcattcatg atttttaaaa aactgtcaac aaacaaggaa   8880
tgtaagagaa ctgaacctaa taaaaggcga agctgaaata caaaaaaaaa aaaaaaaaaa   8940
gctaacatac taaatggtga aaggctgagt accccctaaga ttgtaaagaa ggtatgatat  9000
cccctctcac acttcttttt tttttttttt gagagtctcg ctctgtcgcc caggctggag   9060
tgcagtggcg cgatctcggc tcactgcaag ctccgcctcc tgggttcacg ccattctcct   9120
gcctcagcct cccaagtagc tgggactaca ggcgcccacc accacgcctg gctaattttt   9180
tttgtatttt tttagtagag acggggtttc accatgttag ccaggatggt cttgatctcc   9240
tgacctcatg atctgcccgc ctcggccttc caaagtgccg ggattacagg cgtgagccac   9300
tgcacccggg cccctctcac acttctattc catattttac aggaaggcct agccaagata   9360
ttaaggcaag aaaaagaaag aaatggtata caaatttgaa aggcagaaat aaaactaagt   9420
caattcacaa tgacatgaat gttgcataga aaattcccca aacaactaga gaaaactcct   9480
caaatgaaca ggagagttga gcaagatctc agtataaagt caatatacaa aagtgagttg   9540
tattaatatt tctgtttgct agcaacaaac aattagaatt ttacattttc aaaatagatc   9600
cacttataat aatgctcccc atatgaaaaa cttgggcaca gatgtaacaa aaaaagtatt   9660
ctgatctaaa cgaacagaaa aatatactat gttcatggat tagatgagtc aatattatta   9720
agatgtcagt tctccccacg ttgatctaga tattcataca tcccaataat tttcccagca   9780
gaatgttttg tagatgttga caagttgatt caaaaattca tatggaaatt aaaatgctct   9840
aggatagtca aaataattta ggaaaattat tttctggtca ctatctgatt tcactgatat   9900
gttactatat atttactatt tactacctga tttgactata aagctatagc aatcaagaca   9960
ctgaggtatt ggtgaaggcg tagactcagc tcagtgggat tgaatagaga gcccagaagt  10020
ggatccatat aaatatagtc aagtcaattt tggcaaagat gcaaagggaa atcagtagag  10080
aaagggcagc cttatcaaca aacggaactg gatctattgg atgtccatat gcaaaaaatg  10140
aacctggaca cacatatatc acaccttaca caaaaattaa ctctaaatga atcatagacc  10200
ttaacgtaaa atatacaact ataaaacttc tagaagaaaa cagagaaaat ctttgtgcct  10260
ataggaaagc cagggtcttc agcctcggta ctgttgccat ttggggatgt agctcctgtg  10320
tgggggctgg tctgtgcacc agggaggttt agcagcggtg tgctccagtt gtgacaacta  10380
acaatgtccc cagacactgc ccaatgtcct ctgggggcaa aacaggcctg aattgagaag  10440
agaaagttct cagctgtgac gtggaagcat aacccataac aggaaaaaaa aaagttaata  10500
cacgggactt tgttaaatgt aaaacttttc ttctgtaaat ggccatgtta agatattgaa  10560
aagacaaacc acaggctggg aaaaaatatt tgcaattaca ttatcagatg cagaatttgt  10620
attcagaata cacaaagaac tcgaaactca acaatcagaa aacaaacagc ccaattaaaa  10680
aaatcggcaa agggcttgac agacatgtca ccaaagaagg gaggcagatg gcaaagaagc  10740
cccaaaagat gtgccacagg gttcgtttca gggaaatgca aaccgcaaga gacctgtgtg  10800
ctcctgcgtg ctcccgtgtg ctcctgctta ctcctgtgtg ctcccgtgtg ctcctgtgta  10860
ctcctgctgc gaagggtaaa atgaagcaaa acagcgaaaa ctcacagcac acaacctagt  10920
gccagcgagg atggggagca agtgggcctc acgccctgct gcagagtgca ctatggcaca  10980
gcccctgtgt gtgcctgggg ggcctgtggg tgacaggggg acaaagaaga ggttggcaga  11040
gatggcagag cagcctcctg gtgctggact tcctcaccca gccaggatgg cctgggcctg  11100
caccagtgct gcctgagaca gcgagtctca acctgctcca ggggcgtgtg cgtttctgcg  11160
```

-continued

```
tgtgtgtgtg tgtgtgtgtc catgcatgtg tctctatgaa tatatgtgct gtatttgcat  11220
gtgtgtgtgt gtctatgtgt gcatatgtct gtgtctgtgt gtctttctgt gtgtgcggtc  11280
tgtgtctgtg ggtctacacg tgtatatgtg catgtgtctg tgtgtgtcgc agtgtgttac  11340
tgtgtctgcg cgtgtgtgca tgcatatgtg caggagggag ggagggctca ggccttagca  11400
gagtccctgg ggctctggga gtggagggca gtgaggctga ggctggtgca aaggtggttt  11460
caggcgctca ggtgaagtgg agcagaaaca gaagttggaa tccagcccca gcgggcgggc  11520
ggcagcagca gtgccggccc tgcccagaac aggttcgacc tgagccggca ctgcccggct  11580
gccctggggc tagggaggct gagacagaga agggaagcca gagggtgggg gtgggggccc  11640
ggcactggca gagctgcctg ccctcaacga ccgcccctgc cggagacccc cgccccaccc  11700
gctgtggttc tgctggccca ggtttcgctg ggcccactcc cagggtttgg catcactgga  11760
gcccagggtc ccccccgcac cctccccaca gccttggccc tgctgctgcc tgcctcctcc  11820
agggtacccc gaggcccacg tcaggagacc cgcctcaggc agcagtggcc cggtggctgc  11880
ttctgcctag cccgcagcac gtgccaccct gggcgcactg ccttcccgaa ggctctcctc  11940
cctccccggg gcgctccctc ccactctgga atgcctccct gcctgcacag caggagtgtt  12000
tggctgaggt ctgcagcccc gacacaggtc acctcccacg cctatggggg cttcagaaag  12060
tcccggaatc ggccgggcgc cctggctcat gcctgtaatc ccagcacttt gggaggccga  12120
ggcgggcgga tgatgaggtg aggagatcga gaccatcctg gctaacacag tgaaaccccg  12180
tctctactaa aaatacaaaa aattagccgg gcgcggtggc gggcgcctgt agtcccagct  12240
actcgggagg ctgaggcagg agaatggcgt gaacccggga ggcggagctt gcagtgagcc  12300
gagatcgcgc cactgcactc cagcctggga gacagagtga gactccgtct caaaaaaaaa  12360
aaaaaaaaaa aaaagaaagt cccagaatcc cagacatcta acaggatggg gtcccagaga  12420
ccctccaccc acccatctcc ctgacttcca cacaggcagg gatgaaggac tgagggagag  12480
tgggagaggg taactgtggc ggtcacgaag ggtcctcagg tccccgtcct tatcccaagc  12540
cccatccagg ccagaaccgc ggagtgggtg tgcagagcac tcaggcagcc tgtgaatccc  12600
cacagccact tccctaccct gagacctcag agaatgacct ggcctctgtc tttctgtttc  12660
attttattta tttttatctc cagcttgttt gtgaagttca ggggtaccag tgcaggatgt  12720
gcaggatcct tgtcacaagc atccttctca cgaccctgcc tcactccaaa aggggtatca  12780
ggtaggtgag cagaaacgcc ccttcctgaa tgcctgtcct tgtcccacca caaggatgag  12840
gatgcctgct cagagggcac agggagaagc caatggcata gggtgcacag cagcgagggc  12900
caagggacaa ggagtggggg gcccccacct gcccagcgtg acctgctgac cacagctcct  12960
cagcggcggg acaaagcctg cccatggggc cctcagtggc caccctggat gcaaacacgg  13020
ttaatggtca ggcccagcct gtcccctcct gcgcacaaac tcagggcaga gcagagagct  13080
tacatccacc aagacccaga caaaagaaag ccccaagaac acccttaaag gcagccaaac  13140
cctggagctg cctcgggccc atcgatggga gcacaagagg tgaatcctgc tacgggcacc  13200
gtggccgtct acgcgaccgc agcaaagagg aacatggacg actcacagac gcagagacgg  13260
ggggtccatg ctgtgtggtg atgttcacct gcagctcagg gacaaaccct acctacggtg  13320
acagatgtca ggaggggtga agggtgaggg agggagggcc tgttagctgg agcgggtctc  13380
agggatgcct gctgctgctg ctggaaacat tctgcacagg ggttcgggtg gaggttctgg  13440
gagtgtcacc cgtgcacact tgtcagcatg ctctccaggt cctgcatttg aggtgcctgt  13500
```

-continued

```
accccagtgg aaagatgacg gacagagctg ctcaaccact gccctggacc gcattctgca  13560
gggtgcctta gaaggcccag gaggaaaggg gactccaggc tgggcaccgg tggtccacag  13620
gcttccagag cagcccagct tggccgttgt gtcccagtca ctgggagcta acgaggacgc  13680
accctcatgg gggtatgtgc ccacccagtc ccctccgtag agagcctggg agcctctgtg  13740
atagggcgtc ctggcccagg gctcccaagg ccaagtatga agtctcattc ccccagacaa  13800
ccttcacctc caggctgcat aacctctact gacccctctc aatcccacct cttctttttg  13860
tccatgaagg cagtcgggaa atgcagcctg tgcttcggag aggcgggcag ggctggggtc  13920
acccccgccc caggcagtgg gataggagat gcgccagggt caggtccctt gctgcaagcc  13980
tgcaacccgt gcctgtatgt gccagccggg cctgccaatc catccttcac cctgcaggac  14040
cctcccgtct acaggtccca gctctgtgtg ggcctggcca gccctggggc catggctgag  14100
acctgagtcc tcaaaggact gccccttctg agagcagaat cctgctgccc ccagaagacc  14160
aggtgttcaa cctgagccct gatcctaaaa cccatggtcc tctctctcct ccagaatccc  14220
tctgccagcc tccaagagcc gcctgctgct ctcctggtgc ttctcacacc cctgggggat  14280
ggcagggggg cggggagccc agcagaaatt ggagcagaga ggacatggag ggctgagggg  14340
tgagggggca gaccgaatgt atcctctctg cccatgcgtc ttcccccagg atgctacctg  14400
aggtctcggg agaggggcat ctgggaaggc ttcctggagg aagatgagtg cctctctctc  14460
atgagggagg ggctccaggg aggtcagtgt gaacttgtgt tggcacaaag gcagccctgg  14520
ccgagggggc gaaggcagtg tgaagtggga ctcacttccc ccaaagatgc agagggatgt  14580
cgggagacct ggcaggcggc cctgggcagt tcagttgacc ccaccttacc ctaccaggct  14640
gcaggaagcc cctgccccca cctggagccg ctacgggttt tcctagctca gccctaaagg  14700
ctcagcccga ctagatacag gccaactaga gaggtcatgt cagggctgag ggggtggctg  14760
ccaggggtgg ctgctgtggg gaagagcatc ccagcccgca ggccctgcta ccccaggcag  14820
agctgcccgt tgtgtcccgc acgaagagct ttccctgcct gggaatcccg ctctgccccc  14880
caccagccag tggctttgga agttcgtcca gcaaccctgg agtctcagtt tccatgcctg  14940
taatatgggc acagcactca ctccaggatg aacagaagcc gggccaggaa agcagtccct  15000
ggcctggcac cacagcaggg gctgtgaggg ggatggttcc acagttgctg gaggtcgaca  15060
gggaccgaag cacacatgag tgccagatgg gccccacgat gggattccgg cgagggtggt  15120
gcagggagcc acctatacag aggacaattg actgcagaag tgccaggctc atgccctcca  15180
cggatggaga ggccgtcacc tccgggggat gccccagggc cgcatacccg tgcagtggcg  15240
ctggagtggc agtgggcgcc tgccccacac taatgcacac acacatcagt gcacacccac  15300
agccacgcca gagaaagcca caggccctga ggggctgccc catgccagcc tgccagctgc  15360
cacacccctc ccacaaagcc tggctctggc ccgggacaca gggagcccag acccatccag  15420
ctttcccctc aatgccccgg gtcctcccac aaattcatcc tgcctcaagc ctcagtctcc  15480
acttccgaca aatgggtctc aagctctctg ctctgtccac cctgcatggc ggtgtgggca  15540
gcacagagcc agcctggtgg gggctgggga ctctggaagg ggtgctcagg gaggggccgg  15600
gctctggggc ccagaaggcc ttggaaggta gtccaggcgg gtcccggaac aagtgttgca  15660
tgagcaccaa atggctcaga gctcccgaaa cctggcgtgc ctgtgagagc cgttgagacc  15720
ccttttcaag gccctgcctg acagcccaca aaagacattc aaatgagaga caaatatttg  15780
gggccccaag gttgagccca gcccagcctc tcaggcccag cccaagctgc tcccaggctc  15840
tcatttgggt attaattgca tttcgtttag agatttgcat gcttatcacg cgggtggtgg  15900
```

-continued

```
ccagccgtgg gggcctggcc agcctggaca gaatcccaag gctcgtaggc aaatgccagg  15960
aggaggggt gggcagagga cccaggagcc tcccgaatgg tatcaggaga gcaagcctgg  16020
gctaggctgc gggccatcag cgtgggccct gggccacgac ctggcatcca tgtggacctg  16080
agcacgacaa caggacaagc agagaaaaaa gtggatccca aaaacagggc tcccaggcca  16140
acttctccct aacaccagct cccagcaccc caccggggac tgcagcccct ccatggtcaa  16200
tcagggtagc cctggggtcc ctgtcacatg acgtatgccc accctccgac agccctgcag  16260
cctgtgggac ggcccgtgtg ctcgccgagg cgcttggaac cttggagggc aggctctcag  16320
aagattggct cagggaccct ctggtccacc ctctcggcat cccagggtgt cctggtccca  16380
ggagatgcct catcccaggc cacacggggc cctaggcctt tccgtcctca gccctgtcta  16440
ctctaccctc tacaagagag gtccagaagg ggcagtgctt gacccaagaa gaagaggctg  16500
taactatgga gaggttggga gggggaagtg gccctaaggg ctggagtttt agaaagccct  16560
cttgttcctg cccattatgg gttggatttt atgccctcca gactcacatg tggctgtttt  16620
tggagccagg gcctttaaag aggtaattaa gttaaagtga ggtcattggg gggaccctaa  16680
tcccatgtga ccgatatcct tagtaagagg aggtgaagac acagacacgc acagagggat  16740
ggccacgtga agacacaggg agaaggcagc gtctacaagc caaggagaga ggccttcgga  16800
ggtgggggc ctgcggaatg gtgagagact aatttctgct gtgtaggccc cctagtgtgc  16860
ggggcttttt cacgcagcac aggccaaccc attgcagcct ctcctgctgt taggacccca  16920
agtccatcct cagggacatt aattaacata ggaacttttt atcctgatgg tgtcacctcc  16980
taggcagaac agggacccgg aggcaggcct agctgcgaac ccccagccct ccctgtcctt  17040
ctcgcaggac agcgggtctg gggctgaagg ctgtgacgct gcccctgcct ggatcacaac  17100
aggcaggacg gctgagcagg cacacatctg tctctccctc tgctgatctg tggccttgga  17160
caggggctac tctgggggag ctgacaggtg accccccag gaggcccctc cctgcctctg  17220
ggctgggaat ccacctctgt ggagcccctg ggaatggcct gtttcaaata cgtaagtggg  17280
agcaaggtct catcctcagc gggggacatc gctgggggca aggccagtgg gtgggtggga  17340
aggtttctgt ggcactgggg cctcctgttg attgattcac ccaattaatc acagccagca  17400
gctggggagg gggtaggaag gcggtgaagg gaaaaggagc ccacagccgg gaggccctgg  17460
gaggttggca gaggcctgca cctgcctgca gccagccctc cggcccagcc ctcttccctc  17520
ctttcggagg ggccagagca tggggtgcta agggctcagt ctttaacccc tccccagctc  17580
tcagggagcc cctcccatgc tccccaggcc tctgccccac ttgcacctcc ccgggcccca  17640
gggcacagga cgctttcccc accctttggg aggctgaggg tgtcaggagg cctgggctga  17700
gtgctggctt ccgtctcact ggcttgcaga caagaccctc catttcggtg gaaaaacagc  17760
aagaacagca cccccctcca ggcagaccca agggaggcat cggtgtgagg gcttcaagct  17820
ctgtactgtg ggtttaagcc ttgcacctct ggatacctgt gggcctcggg cagatcactg  17880
agcctccctg catctggaag tcggggtgag accccctcaga gggggctggg aggaggaagg  17940
gcccctcttg atgggcagcc cccaccctcc acctactgcc ctgccctccc agccttcagg  18000
gtcctcccca gcttctgtgg gctcccaggt ggacctgggc caccccctgag accccgaaga  18060
gctcaaggcc agctaatagc ccacaggctc aggacagcac tggacaggcc tctgggccca  18120
cctggcccca ctcccgattt ttatgggaac aaagactgaa ggtgtggccc caaaggaacc  18180
acccctcccc cagtgccccg ctgctgggaa aagggtcagc agagtttggg tctcccccca  18240
```

-continued

```
caagccctct gggctgtgcg tgctacagct gaggacatgg cgttgagggg caggccgcct  18300
ccaaccccgt ccaccttgcc ctgtctagct ctgtccaagg ctctctccgg ctggctaatc  18360
acctctgggc acagctgtgc tgctgaggtc tctgggatga ctgaaggtct ttgaaggcca  18420
ctttgggaga agcgaaggtg catggacacc agggaccctg ctcacagcga gtgtccctgc  18480
cccatccctt tctgcattga gtgggacaag cttgcttcca tttgggggat cgccatctga  18540
ctattccact tgtcttaggg tggggcagag attaggtgat gtggaggggc ttctctacat  18600
ggccccccctg ccccagctct gaggggtagc accagagtgg gtttcaccag cgtagggcac  18660
gtaggccccg ccatgaacag ggccccaacc ttggtttaat gctttgctac tgccatctta  18720
aagttctttt tttattttt attttgcttt attttttatt agagatgggg tctcccagtg  18780
ttgcccaggc tggtcttgaa ctcctggctc aagcaatcct ccggcctcag cctcccaaag  18840
cactgggatg acacgtgtga gccaccttgc ctggcctttg gaatctgact acttttatct  18900
tctaacttgt tttgcaggtg caggccaacg gcatacagca gcactcacat aagcaaagga  18960
gagcgtgcac aaggcgccaa atgtatatcc accctcactc gtccccccac ttgagtagcg  19020
catccacgat gcccacagac accaggccac acagaaaagg tgccagggac ccacagcagt  19080
gcaaggcagc gtgtcacacc tacgcatgag caagccgggc gctgatggcc accgagcagc  19140
cacgttttcc attcaaatcc gcacttgcta aggatgcagc aggaagccag tggtgttcta  19200
acaaacgtgc aggacccggg aacctgtcat gtcctttctt acttgtgcga cttctctgtg  19260
ttagccgagg tctcttgctg atggatctac ccacagtgcc ttttgtcttt gaacttgtcc  19320
cttccctcct tcctcgccca tcagcgagca ggaggtggag ggtgctggtg gaacaagcct  19380
gcgtcaagga gtgaaatcag ctgatttcat ttttgtgcag tttccactgt tctagtagca  19440
aatgaaatag agacgcctgt gccaggacaa aacacacact gtgtcattcc agtgattccg  19500
catagaagtt aaatgctctt atgcttgcat tttaaactgg catcacataa tataaagatg  19560
gataactaca ttcacgctag tcacttaaat tcctaatctt tcttactcag aatggcatta  19620
aatagtgagt ataaaataag aagtataaaa tagtaagtca agaggttgac tatagaagaa  19680
agaaaaatgc tttatatttt agcaccttga acatgacatc acgatcacct tctccctgga  19740
atcagtttct aacttccagg tggggactag gcctggacca tgagctccta gcagagccct  19800
gctgccccca cagcagagcc caggacaggc tggcacctgg gccaggtgag gctctgtcca  19860
ggctcactga tctcaaatgc tgaactgcta aggatgtcat gtccccaaag gagccgccag  19920
gctcagcctc acttcctgga aggcgtgaac attgcaagaa tgtggaagtg aaagagtcca  19980
gggcttaaat ctcaattctc atcattttca agctgagtcc aagggagaga agacagtcat  20040
ggattcttag tttctgtttc tggttgagcc agcagggtcc cttcctcatc cctcttttct  20100
gcttatcact agagacagaa actaaaacca tgactttagg ctgctgagag cctaaaacaa  20160
aacgacagca agagaaggtg ggttggacca gcttgcctgt gacttcaggc acttcatctt  20220
tactgggcac tgggtgaatg acagtgtggg gaggggtctt cataacacgg caatcagcag  20280
cccactgtgc ccaggagact cgcctgtggt cctggttatc aaccacagcc ctttccagtc  20340
tcaaaaatgt ccccgctggg acagcaagtt acatcgtcgc tacaagtcct gtctcctggg  20400
agatgcagtc cagcagcact acatcctctg agcagcaggt gccaagtggg atgaactgga  20460
taaggactgc attcggggaa acgcccgtgt gaaaggaaat acacaggaag gaggtggcaa  20520
cgggtgggaa gccactagac cacgacgcga ttctgcccca gtgaaggcga ggggatagcc  20580
tgggcctaga tcgctgtgag gtctatggaa gtttccacaa gcttgctggg tagttctcga  20640
```

-continued

```
ggcaaactcg gaaagggagt cccttgtctc cctggaacgg atctttcttg gcatctctgt  20700
cacactcatt aggtgggcct ggtgtcaacc ccatttgcag gccaccccaa acttgatcaa  20760
aggtccgctt ctggcacccc ataccctgtc ctacaggaaa tacagggaca ggctcccaat  20820
aacaacaccc agcacggtgc catcaacacc accacgcaca cgggggctca acggaacaga  20880
catctccgct tcttcaatga agacactgga gggaaattgc ttacaaggcg cttaagagac  20940
ctattaagca aacttgatgt gtggacctgc ggcggatccc gattctataa ggccaactgc  21000
acaaaaccac gagacccccct gaggactgcg ccattggctg ggtccccgat gatatgaaag  21060
aacggtggtt catttgagcg ggtgatgttt ttgcggtttc ctttagaggc acacgtgaaa  21120
catgacgggt gaaaggattc aaagtctggg atttgcttca aagcaacgca gggatggcgt  21180
gggggatgga tggggcagga agggccttga aactggtgct ggaggcttcc cagggctgcc  21240
ctggagccca gtgcgtcctc caccggccag actgtacaac ggttggatcc tgtgtccact  21300
gctaggaccc aggctccacg agcacgggct tgtgtggcac acggatgcac cctaagtcct  21360
ggcacagaga ctgctcaaca aaggcctcgg tgcttttgtg tatgtttgaa attttccata  21420
ataaaatgaa aaatgggaaa atgggaaaac aaaaatggca gcactactta ccctctgcag  21480
agttttgtcc gcttcacgcc agtgggtggc agtcgtttcc tctgccctgg ccttccatcg  21540
tttccccccct accctcttca cccacccaac agccccctgt ggtcctggca gctgtgggcc  21600
tttccttgag gtcaaggtgt ggagtcctgg ggagggctca gggaggccac cgacccgggt  21660
gtggattctg ggagaagcct gtgggatgtc cctccctggg tgaccacggc aatgtgcccc  21720
ctcctgtccc ttggccaagg ccagttccct gagccctgca gccccaagcc acagctggtc  21780
cactgacccc agttgagcct ggtcctcatc agaccagctg accccctttga cccccgctac  21840
agactcggct ttgaccttgg ctgctgagga gcccccacct ggactgaggc tgcagctggc  21900
gagagaggag ccctgagctc ctctgataag aagggacctg gccagcctga cgtttgagac  21960
ccaggcatcc cggtagcctg ggtgtcctgt tgccgtggtt attcaggagc cacccactct  22020
gggacaacac cagctgctcc cacctcgcag ggctcccacg gctctgtccc aaccactcct  22080
ttctgaagga aggggtgcct ctgcgcccta aagaaaccgg gggagcccca caacccctcc  22140
cccaccagga cactaaaagg cagctttcgg tacagtgaga catcaaagcc tcctaggccc  22200
tgagtcaaag gtatagccgt gtaatatccc agtgccagct ctccggctgc ggggagcctg  22260
gcgcaaagct tccaagcctt ccttgttcct ttcaagagcc gctcttagaa ttcaggtgag  22320
cggagacctg cagggcctcc ccagtgcggg caaaacccaa agctagcgag agggcagcct  22380
ccaggcacct ctcactaact cctcccagag gccgttgagg tgggtctggt caaacccatt  22440
tgcaagttaa cccacttgcc ctgggctgcc cagctgccac gttagtggag atctgagcgt  22500
ggtggcctgc gcaggagccc atgccctcag ccccacagcc ggtgctctct ggtcagacca  22560
cctcagccta gccccacacc cagcacttac cccagccctc gggatgggtc agcagcctcc  22620
agcctgcagc ttccaagcca gcgagtagcc ctgtctggac aacccaccag cccaccacct  22680
cctggaggat gcccccagcc tcacaaggtg tcccaatggc tccgctatca acggcctggc  22740
tgcactccag atctcaccca gacccaccct acggaggagg cagcagggtt tgaggagtag  22800
tgaccacgga agtctggccg tcacctggga agtgtaggtg ataggagcca ctggtaaaca  22860
gaactgattt atttataaag ttcacgctcc cttgaagagg tgtgccccac acaggcttct  22920
ccctagcaga gcagcagtgc ccacaaaccc accccagggt gggctgtcac gggggcctca  22980
```

-continued

```
cgccagggac cccgcccctc agggactgct cgtgtccaga tcttggccag catggaaaac  23040
tccagatagt gggggcaggg gtccaggtca tctttattac gccccaggtc aagggttctt  23100
tgtacaaaaa taggtctccg tttgccagca gtgtccctcc agcagctcaa gttaatgtgt  23160
agaaaatgga ttctctgtgc ccttagaaaa tcctctcccc tccggaaaaa tctccaagtg  23220
ttggtgcccc ccgccccact gcagtcgaga agctgtgggg aggggcggcg tcggaggaag  23280
ccgccagccc ttatggggcc agctccaagc ccgtttccac cgcggcattg gtcaggctgg  23340
gccggacgaa cgaggcggcg tcggcggtgc ggggggtggt gggtgggtcc ccggctcgct  23400
gggggcggag cgcgggccgg tccacctggc gggctccccg gcgatgagcg cgccggccgc  23460
tcgctcggct tccggggctg aggctgcggg gggaaggtgg ggaaccaaac gcgcgtcaac  23520
gcgggcgcgg gcccggggca gaccccgccc gggccggccc tgcccgcacc tcccccaagc  23580
gaactcggca gtttcgtttg ctcggttggt tttggagtct tgagtccgtg ggtgccgcga  23640
ctcggtctga gacacggcgg gggcggggcg ggcgctcgga gccgcggtga gtcagggctc  23700
cgcgcccgcc gactcatttc tgccgccccg gcccgggagc gcgatttgca atgcaaagtc  23760
accccgcctc cagcacccca atctgcccca ggatccgcca gcactagaga cctcaacggc  23820
ccgacggccg ctcccctccc ctcgtctacc cctccctcgt cggcggctga gccgcgaggg  23880
gaagttttgc aatcccggac aaacaaacgc cggtcttgca cgggcttgaa aaactttggg  23940
ggaaatgaag agtgagcgaa atcgaagcca tcgctcgggc ctggcgctcg gctccgcggg  24000
ctcctggggg cgcgacccgc cgggcctgcc caccccgtcc ctccaccccg gcccccggcc  24060
ctccctcctc cctgcctccc ggctgttacc tcataggtcg agggcgctca gtagccccct  24120
aaccagctgg agaagtcgag tagctcgcgc tccgcaggac tcagcgcgcc ttcgcagccg  24180
ctgtcgtccg acgagtaggc ggaacgcggg gagccgggct ccgagctgcc cccgcggccc  24240
ggggacgaag aagcgcggga gggcgaggcg gcgaccgggg tggtccctgg cggcccgcgg  24300
ggcgcagacg gccgcacggc ctgcggcctc agccctcccg ccagcgcgtt gcgcacggcg  24360
tcgtgctcgg ccagcaggcg ctgcagcgcg cggatgtact ccacggctga gcgcagcgtc  24420
tccaccttgc tcagcttctt gctggcgccg ccgtgcggca cgtgctgccg cagcgcctgg  24480
aagcccaagt tcaccagctt cacgcggttg cgctcgcgct cattgcgccg cgctacggcc  24540
gctgcgccgc ctccggtctc tgcggtggcc ggtcgccgcc gccggctgca gcgcaacagt  24600
tccggggacg cgggtctccg ccgggcagcg cagccgacag ggacgggggg cgcagggggc  24660
gcggacctgg gcagtgtgcc gccgtccatc gcgcctgcat ccacccgccc gctccaggtc  24720
ccggcgcgcc gcaggaaggt gcaggcagag gaaccggagg cgacggggaa aactgtggcg  24780
ccccaagggg gcttctggca cggcgccgcc aggcaactcc ccagggcacg cgtcctaggt  24840
cgtctggagc ccggggatag gaggcctagt ggtggcaggc cgtacgcgcc agggagcgtg  24900
ggacgctcgt gtcccgcgcg tgcggccgga ctctcccagg tctccgcagg cgcggcgcag  24960
gcggctggtt tttaaatgta tagataaccc tcctccgcgc cgccgccgtc gcctttctca  25020
cgccctcctt ccttcgcctc gccctcccgc cacgcttcgc cctccccctc gcgcgatcac  25080
attctgtaag gcccaaagcg tgcgcatgtc cccctagccc atcccccgga cgcagtccac  25140
agatccccag tgcgcccaac tggcgaaatc tgcgagttcc cggtgcgccc cctgctcccg  25200
gcaggtgctt agtgcgcccc caaagcaagg tacgcaggtc ctgggttgag ccttcccgta  25260
cccccaccct aaccccgcgc gcagccccgc cagtcccaag agccgccaga ccttcgcacg  25320
cgcagcgcgc gctgtgggag ggaaggcgcg gccctggcga caacacggct gttcgggagg  25380
```

```
cgcgcaagat ccccgggggc agcacgcgcc gcgcagccca cacccacgcc ccaccctcct  25440
ggggccgagg aggcgggggc cagggtctca gccaatcgtg ggccacccgt ttggccaatc  25500
gcgcagggcg cggctccacg cccggcccca ttgaggaagc gcgtacgcgt ggcgcgtggc  25560
tcacggggag catcgctaac aaagctgggt tcctgctggg ccccgccctg ctcctcgccc  25620
ccgcgactgg gctgggcgcg ctgtccccta gcgcagctat gtcccgagcg cgcccccacc  25680
tgtgcgttaa tctactggga atgggggtgg actgcgcctt acctggggcg gggtggggct  25740
taaggagtgg tcgagactga                                              25760
```

<210> SEQ ID NO 14
<211> LENGTH: 38360
<212> TYPE: DNA
<213> ORGANISM: Homo sapiens

<400> SEQUENCE: 14

```
tgtgcaaggg accttcagag gaggaaaggg aggaaacagg tcaacctctc acggcaggca     60
aggcaagaca ccccctggtt tgagggggtc ttctgcaaat ttcagggagt tgaacctcat    120
acaaacctcc ggtagtaaga aaaatattca gagttctcct ttcccttctt ctcgggggaa    180
gaaagaggct aagctccact ccgcttgtcc cttccctagg ggaaggggaa ggagaaggga    240
gaatagcagc ataagcgact ggcagaggca gggaaagacc ggcagaaagg aaagagaaac    300
tgggagagga agtcagagag agagagagac aaagagggag tcaaagagag agaaagagag    360
agacagagag tcagagagag agaaagagag agacagagac aaagagggag ttagagagag    420
aaaaagagag acagagagta agagagagag agtcagagag agagaaagag aagtagtaaa    480
gagaaaacag tgtaccctat tcctttaaaa gccagggtaa atttaaaacc tataattgat    540
cattgaagat cttctctgtg accctagaac actccaatac tgcctgtaaa gaagcaagac    600
gagtcacacc agtgactgca agaccctaga gctattaacc agttagtcca aactacccac    660
cctgttgtta cagtaataga tgtaaaagat gccttctggg cttgtccatt tgcagaggac    720
agccaggacc tatatgcctt tgagtgagaa gaccctcact ccggtggaaa atggtaatac    780
caatagacgg tcttacccca agggtttacg gagtctccaa atttatttgg tcaaatattc    840
aaataagtca tttaattagc aaaggtaaac agaaaattga gcttgaatgg attgaaggca    900
tcacattctt gcctctgctg gagactaaat aagagcttag aaaattttgg gattagttgt    960
atggataccg tcgtctatgg gtagactcat gccctaaaaa caaaactctt acacaaaaag   1020
ctcacacgag acagaccaaa ccccctcatg tggcaattac cagaaatcca acaggtggga   1080
aggttaaaac atctattagt aactgcccct gtcctagctt tactctcctt aagcagccat   1140
tccaccttgt tggtggtgta aacaacggcg tagcccaaaa acactgaggc cactgacaac   1200
ccatagcctt cctaatcaaa aatccttaac ccagtaaccc gcggatggtc caaatgcatt   1260
caatctgtag cagcaacttc tttgctgaca gaagaaagta gaaaaataac tttgagaaga   1320
aacctcattg tgagcacacc tcaccaggtc agaactatcc taagtcaaaa aaaaaaaaaa   1380
aaaaagaaaa gcaaaaaggt agcttactaa ctcaaaaaat ttaaaatatg aagcgattct   1440
gtcagaaaaa gatgatttaa cattaaccac tgatcattcc cttaacccag caggtttgct   1500
aacaggggat ctaactctta atgaattacc atacaaaggt ccaaccagac ctagaaggaa   1560
ctcccttcaa gacaggacaa tagatggttc ctcccaggtg aatgagggaa aaagccacaa   1620
tgggtattca ttaagtaatg gggaaatagg agtagagtta ggaaaattgc ctaggagttg   1680
```

-continued

```
gggagttgtt tgcactgagc caagccttaa gatactgaca gaatcaggaa ggagtcattg   1740
tgaaaagtga agtagagttt acctcctcaa aagactttcc tcccccatct aatcaggaat   1800
aaatagtaac ttctcttagt agcaaaatgt attcaaagac cagcgctaac attcttaaat   1860
atctgctaga cgtaataaag aaatcaatgt actttatgtc cttagctccc acaatttagt   1920
ctaaatgttt gctctggcat gcttatactg gtccaggcaa gcattaggtc ctatcctgtt   1980
cctcttcctt gtttgtgtct cacatgtccg tgtgaaaaga ccaccaaaca ggctttgtgt   2040
gagcaacaag gctgtgtatt tcacctgggt gcaggcgggc tgagtccgaa aagagagtca   2100
gcaaagggtg gtggattatc attagttcct acaggttttg ggtaggcgg ttgggttagg   2160
agcaatgttt tgccagcagg gggtggatct cgcagagtac attctcaagg gtggggagaa   2220
ttacaacgaa ccttcttaag ggttggggag attacagagt acattgatca gttagggtgg   2280
ggcagaaaca gatcacaatg gtggaatgtc atcagttaag gctattttca cttcttttgt   2340
ggatctttgg ttgcttcggg ccatctggat gtatacgtgc aggtcacagg ggatatgatg   2400
gtttagcttg ggcccagagg cctgacagtt tgaaggtgtt tttacctttc tcagcattcc   2460
acgagttact tcttcctttg ttctcctctg cctttgcctc ttttaaaaag ttctaagttg   2520
ctagccagtc gggacaaatg cagaatgtca ggcctctgag cccaagctaa gccatcgcat   2580
cccctgtgac ttgcacgtat atacgcccag atggcctgaa gtaactgaag aatcacaaaa   2640
gaagtgaata tgccctgccc caccttacct gatgacattc caccacaaaa gaagtgtaaa   2700
tggccggtcc ttgccttaag tgatgacatt accttgtgaa atcccttctc ctggctcatc   2760
ctggctcaaa aatctccccc actgagcacc ttgcgacccc ccactctgct cgccagagaa   2820
caactccact ttgactgtaa ttttccttta tctacccaaa tcctataaaa cggccccacc   2880
cttatctccc ttcgctgact gtcttttcgg actcagcccg cctgcaccca ggtgaaataa   2940
acagccgcgt tgctcacaca aagcctgttt ggtggtctct tcacacggac gcgcgtgaaa   3000
cagaatgtga ggtcccgttc cagccaatgg aaaccagaca cagcagtagg gtggacgcgt   3060
caggttataa atgaccctgt ctcctttgct cagtgtactc tcgtggcaaa actgctgccg   3120
agtgtaccct ttctacagaa agtataaaaa tgaccttgcg taggaaatta aatttatgtt   3180
caagtgccat ttctttatgg caccggggag caagcatttc aaacatcatt tgtaccaatt   3240
ctaagttaaa tttggactaa acaaggtctt attaatagca aaggataatt gaaatcccaa   3300
acttacaagg ttttcaacaa aagtaaagtt tgctaaaagt taacagtata acatgtatta   3360
tcctaacttc taatgttgtg accttaggct gtctagtcca cagacataaa ggaagttcgc   3420
tttggaaaag aatggttatc atctttgaga gaaaaaaaat tgtttcgaag gtttaagcaa   3480
gttttgaaat attcattgta aaggaaacat attggctaaa gttaaagggg tatcttccag   3540
tttttctgtg aactggacat taaaataaaa gcccagtggg tttttcttaa agcgctaacc   3600
tgctctttaa caaaaattac gaaaggttaa aaattataaa agtttaaaaa aagagtctgg   3660
aaatctcacc ttgtggtcag accttaaaat tggatacata tgtctacaag gttttattaa   3720
aatgaagttt aacacgaata acacactaat gtaaaggtga aatttagctg atctggtata   3780
aaatcacaca ggaagcactg tcaaatataa aatggtgttt ggctttcttt ggtctaaaaa   3840
ctaataaaaa taggtactaa aggaaatttc tcagcaagaa ggcactaagg actataaaat   3900
ccactgctga tgtccccacc tttaaaacaa aagatcaatt tttagaaatg atatacttgg   3960
tttatcctcc acccttaaaa caaaaggtct tctagcacag gccctgccct gagagtttcc   4020
agtacatcag caccagcctg ggatcccgt tctcatcaaa gggtggaaag aagggaaact   4080
```

ggagccagcc tgggaaggac cctgccttgt gctgctgact accgagattg ctattcgtac 4140
aacggaaagg gggtggacac gtcccaccag agtcaagcaa gcaccattat caacagaatc 4200
atgggccatt gtttctggat caagccctac caaattaaag ctaaggaaag ctgagtctat 4260
ctctttcctt tcctttccta acccagtgcc tatatccatg actattccta ccactagcaa 4320
ctctaacccc actttagaga gtttctgtgg tttgggagca gaggtcactg gaagggatcc 4380
tataggcttc aaggtgcgct ttgttctccc tcctccacct cctacgactg cccctttccc 4440
aaacctacaa catcaaacta tgcctcgcct catgccaaat gacacaagca agttcttaga 4500
agtagaaata ggagacccaa ggcaaaccct agccattgaa agagggtata aagacataaa 4560
tgccggttaa aacggattaa atatcccgtt cgcactttaa gcaaaagtga ccattaagct 4620
tgtgggcgcg gtaggccaga ggctcaggat gcctcctttc cactgggacg gtcctcaaat 4680
caagcggaca tggagtgcgt ggtagctctt ttcgaagatt ccaccacctg gaataacgaa 4740
ttgtgccaag ctctttctct gctatttcct gaagttcagt gccctgtggg tcagcccccg 4800
agggccatcc agccttcatc ttccaaaacc aattttacct cgtgtctcca acaacgaggg 4860
gaaaaaactt ggcattcctt ggagacttaa aaggttgcag taaagtcagg cacctccaaa 4920
agctgaccca tcggtctgcc cttattcatc cctgagcgga tgtatggtgg tattatggag 4980
gacctttact ggacactctg ccaaataatg agagcagtac tgatgctgta gttcagttgg 5040
ctatcccttt tactctggca tttcatcaac cagaaaaaga aaaaaaaatg tagcctcaat 5100
tcttacctct ttaacaacgc taataagtat actctttctt cgtaggtgtt atgtcgtacc 5160
atacatccag gagttcatca aaacaactaa gccaagacat gctaagaaag tttgaagagg 5220
aaaactatac agtaaaagag gagggaattg taggaagtaa aaagtttctg cttcaaagtt 5280
ccccttcttg ttaaagaata aatcataagt cttagaaata atagattctt ttaaagacta 5340
attttcttca agcctccttg ctttgtgcta atagctcttt gttaagccct atcctatgta 5400
actgttggac atgctcacag acacattcca gctcacagcc tatgcccctt ccttaattgg 5460
aaatgttatt gcttcctgaa accttttgta agcaacttct ttgttcttcc ttgcacttac 5520
ctatttagga aagtttcaaa tcgggtatca gtttaagata gtgaggtccc actccagcca 5580
atggatgcag gacacagcag taaggacaac ccaaatgcgt aagggataaa tacatctgct 5640
tttcctttgt tcaggtgtgc tctcaccatt gttccatctg cagttgagca ccctttctgc 5700
agaaagtaaa gatggccttg ctgagagatc ttttgtctct gtgctgactc ttcttcgcag 5760
caccgattat ctatttctaa caattttggt atttctaaca ggcccacaca cactgtgtgg 5820
gccaagctgc ttcactcagt ccactgatca aatgctcatc tcatcctcac agacacaccc 5880
aggatactgc ttgaccaaat atctggacaa cccatggccc agtcaagtcg acagaccaaa 5940
tgaactgtca cagacagctt ctgtccttgg aacggggtgg gattccacgg actctctccc 6000
ttcacagtgg agatgctcag tcagcaagct gccagaagtt cagagctggg gaagatataa 6060
agaggactgg gcatggaagc tgcaggaact agtcaggaac tgggagtacc taggagtcag 6120
ctcctgagtg tgcaggatca tggtgaaata gaaagttaga gaaggaagag tgtgtcaata 6180
tcagagcatt gtcttatagc acaggactta accctctcct aaggttccag ggagacagtg 6240
ccaaatcatc acttgagtgg tgcttagaag cttcagggca aaagagccaa ccctaagtac 6300
atttgtctac tggggctgcc atcacaaagc accgcagaca gggtggctta tacaacagac 6360
tcattgtctc acaatcctgg cggctggagt ccaagatcaa ggttttgcaa ggctagctcc 6420

-continued

```
tcctgaggcc tctcttggct tgtagatgac cggggccttc tctctgtgtc ctcacagggt   6480
cttccctcag tgcgtgtccg tgtcctcacc tcctcttgta agactccagt cctatgagat   6540
taggacccac tgtcatgaac tcatttactg ttgattacct ttgttttatg tttttgttt    6600
ttttgagaca gggtcagtct ctgtcaccca ggctggagtg cagtggtgca atcatggctc   6660
actgcagcct caaactcctg ggctcaagga atcctcccac ctcaatctcc caagtagctg   6720
ggactacaga tgcataccac tgtgcctggg tgtattagtc tgttattgca cagctataaa   6780
gaaatacctg agagtgggta acttataaag aaaggaggtt taattggctc acggttcata   6840
gctgcttctg ggaggcctc aggaaagttt cagtcatggt ggaaggtgaa ggggaagcag   6900
acacgtctta cacggccaga cagttcctcc tacactggct gacactctct cctgccacct   6960
tgtgaagaag gtgcctgctt ccttttctgc catgactgta agtttcctga ggcctcccca   7020
gccatgtggg actgtgagtc aattaaacct cctttgttta taaattgccc agtctccggt   7080
agtatcttta taacagtgtg aggatgagct aatacacaca ggaagcagca atgccatcaa   7140
agagccaggg gccttgactg gcagaactag tgagaccatc accaaaacat ggcattcctt   7200
gggcaaggca ggtgcgcagc cagcaaggta ttgcttaatc tacatgatca aaagacatca   7260
ggatggttgt tcaggaggct gagaacagcc atcctattat ggctgagttg tgtcccctca   7320
aaatttatat actgaagtct taaccccca ggacctcagt gtgtaagtat ttggagaaag    7380
ggcctttaaa gatgtagtta aattaaaatg aagacattag ggtgggccct aatccaatct   7440
gactggtgtc cttgtaagaa gaggagatga ggacacatgc agaggcatga ccacatgagg   7500
acacagggag aaggtggcca tctgcaaatc aaggagtgag gcctcgggag gaaccagcac   7560
taccaacacc ttgatctcgg acttccagtc tccagaacca tgagatgatg aaagtctgtg   7620
tttaagctgc ccagtctgtg atattgtttt gcaaccctaa tagatgaata cataccccaa   7680
tgaaaaagca tgatctcttg cccagtttct gcacctgaga cagttttcaa acccaaaccc   7740
cactgattga aggagggatt aggtcccagg aggacggacc ctgcagtacc atagcaggct   7800
cccccagtcc ttccccaccc caccactaaa ggtgtatttc agtaactgtg cactaggaaa   7860
agggcaatgc ccagggctgg gggactccgg gaccaagttg acactgagag ctggagtcaa   7920
ggtaccatca tgggcccact agagtagggc gtatggaggc cagcaaagtg caatcctggt   7980
ccacctctag ctcacactga gtcatccctt tgcattccca gaatgctgca tattccccca   8040
gaccctaaaa gtacactcag acaatcttgg tagttggcag aatcctcacg taggctcatt   8100
gtcctgtagg gtaaaaacta tcatagtgtt accaagtaga aacttctgaa actgcccacc   8160
accttagcca aggcaataca ccaaaaagaa aatctcattg gtggggaatg gcagagatgt   8220
gggcccctt ggaagacttg aaggttgcag gtgaggcgat tcccatcatc tcccccattt    8280
tccagagaat gctaacagac tactgtcaac ttgtgatggg aaattttatg cgtccacttc   8340
actgggccat ggtgcccaga tgtttggtta aacattattc tgggtgtgtc tgcaaggtgt   8400
ttctggatat gcttagcatt tgaatctgtg gactgagaaa agcaggtcac tctctctggt   8460
aaaggtgggc ctcatccaat cagttgaagg tctgactaaa acaaaaagat taagcaagag   8520
aaaattcgct ctccctgcct gtcttagtct gtttatgttg ctataaagga atattggagc   8580
ctgggtaatt gataaagaaa agaggtttat ttggctcatg gttctgcagg ctgtacaaga   8640
aacatgacat ctgcatctgc tgctggtgag ggcctcaggc tgcttccact cctgacagaa   8700
gatgaagggg agccagtgtg tgcagaggtc acatggtgag agaaacaagt gaacatggga   8760
ctgccaggtt gttttcaaca accagctgtc aggggaactc agagtgagaa ctcactcact   8820
```

```
accatgagga tggcaccaag ccatccatga gggatctgcc ctcacaaccc aaacaccccc   8880
attagacacc acctccagca ctgaggacca aatttcaaca tgattgatag cccagctcaa   8940
agagccgctt gtctttgagc tgggatatca gtgttctgcc ttcacactca gattggaact   9000
tacaccatca gctctcctgg gtctccagct tgcagatggc agatggggat actttccaac   9060
ctccataatc acaggagcca attcccccta aaaagcccct gtgtatatgt acagctaatc   9120
ccaagctcca ctgagcagta gcccagtgga ttgttgctgt gccagctgtg ctatatttgc   9180
tggagcagag ggctgtggaa tggggtacat gttaagcacc cattagtggg tggatttgtt   9240
ctatgccatc cctatttaaa aagagccctg gacacctttt gggggacatc atcattctgc   9300
ccaccacccc gggacaggag gcacatgaat gaactcacag gtgtggccat gagaggtgaa   9360
gagcttggta tcacgtgttc attcccaaca gagagcatcc accagggagc cactaagcaa   9420
ccagttagac agaatggccg cagtccttga cttcagccag cctctgtccc cgaccacctg   9480
agtgctggcc ccctgggtgc atgcatggag cagctttggt ggtagaaagg gatgctgacc   9540
atgaaatcaa cagcacagct ccacccacca aggctggtct agccactgct gccacaaatg   9600
cccaacctgt ctgcaacatg ggctgctgag aagcccccac taggcactat ccatagagaa   9660
agttgacaag gcaacagaag catccatccc attgggggca gcaattcaac tccactagaa   9720
ttgacacata acccaggctg atccccaggc cttattaagt gttgatccac caaacagggc   9780
atgcgtagca gtgccttgga ccaagggacc cactttacaa cacagggagg aggtgcagcc   9840
atggcacatg gcacatggca catggccatg gcatctgctg gtcctatcac agcccacacc   9900
actcagacgc agccagcacc acagagcagg ggagcagcct tttcagagct ccatgaaggc   9960
cccagcgtgg gggtgatact gttcaaggat ggggtgtcac attgtggaac tcagtagtca  10020
ctccaactca acagccacca tggggtgcta tgtccccaac aggcctcgga accaaggggc  10080
agaagcagca gcggcccctg taccaccact gccagtgacc tgctgtgggt tttgtgcatg  10140
ctgttccctc cactctaggc tgccagtccg gggtcgtggt ttccacaggg gacaacgcca  10200
ccagtggaca gataggagac ccactgaaat ttaggctaca gccgatgcct tgtcactttg  10260
gattatttgt ccctggagac caacagtcat gacaacgagc ccccaaactg ggagggaggt  10320
gggccgtggc catcaggagg cagtagaact gctactccat gaggggacag gaaagaatac  10380
atttggtgcc tggtgatcca agtggtggga cttgggggac ttggtgttcc ctcaactgct  10440
ttattcatga gtggacaagt acaacagcca tggcctgagc agggatggtg accagggccc  10500
cagacccctc actgaggagg gtcccagttg gcccactggg taggccacag agactagaag  10560
aggtgcccac tgacagggaa ggaaccaaac atgagtcagg gaagaacaag ggtcatgaca  10620
gccatggcca agacgctatg gggcacaggc tgtagttggc tgtttctcta aacttgtaaa  10680
cccaggtatt agtcagcgtt ctccagagaa tcagaacccc aggatatata catacagaca  10740
tatgagagga tttatgaggg gaatcggctc acatgattat gcaggctgag aagtctcatg  10800
acaggctgtc tgcaagctgg aaacctagag aagctggtgc ggggctcatt ccaagtccaa  10860
aggcctcaga accaggggag cggattgtgt aactctgagt ccgaggccaa aggcctgaaa  10920
actggtggtg gtggagtggc tactggtgtg agtcccagag cacaatggct ggagaacccg  10980
gagttccgat gtccacagtc aggagaagat gggttgccta gccctggaga gaaggagaat  11040
tcgtcattcc ctgccttttt tctctctcta ggccctcaac ctattggatg gtgccaacca  11100
catcaagtga gggtagatct tccttattca gtccatggat tcaaataaca atctctttca  11160
```

-continued

```
aatctaccct cacagatacc cagaaataat gctttgcaag atgtgatggt taattttggg  11220
tgtcaacttt actagattaa gtgataccca ggtatctgga aaagcattat ttctgggtgt  11280
gtctgtaata taggttggat gtcaccctct accccctacc caaatctcat gttgaattgt  11340
aatccttcat gctggaggtg gggcctggtg ggaggtgatt ggatcacgag gtggatcctt  11400
catagcttga tgatgtcctc atggcagtca taagatcagg ctgtttgaaa gtgtgtggca  11460
cctcccccac ctctctcttg ctcctgcttt tgccatgtga tgtgcctatt ccccctttgc  11520
cttccaccat gattggaagt ttcctgaggc gtccccagaa gcagatgctt ctatgcttcc  11580
tgtacagcct gcagaactgt gagccaatta aacctctttt cttataaatt atccagtctc  11640
ttttatctca ggtctttctt ttcttttctt ttcttttctt ttctttcttt tctttctctt  11700
ctctttctct ttctttcttt ttctttcttt ctgtctttct ttctttcaga cagatttccc  11760
tcagtctcct acagtgcagt ggcgcaatct cagctcactg caacctccac atcccaggtt  11820
caagccattt ttgtgcctca gcctctcgag tagctgggat tacagtcatg caccactgtg  11880
cccagctaat tttgtgtttt tggtagacac agggtttctc catgctggcc aggcttgtct  11940
caaactcctg acctcaggtg atccacctgc cttggcccct caaagtgctg ggattatagc  12000
caccatgcct ggccccaggt attttttttac aggagtgcaa gaatggccta atacagaaac  12060
ttggtaccag ggagaaagat atttctataa agatatctga aaatgtggaa gcaactttgc  12120
aactgggtta caggcagaag ttggaagatc ttgaaaggct cacaagaaga gaggaagatg  12180
aaggaaagtt tggaacctct tagagactgg ttaaatggct gtgaccaaaa tgctaatagt  12240
gatatggaca gtgaaggaca ggctgatgaa gtctcagatg gaaatgagaa acttatttgg  12300
aactacagca aaagtcacat gtgttatgcc ttagcaaaca cttgactgca tcctgttcat  12360
gccttaggga tctgtggaag tttgagcttg agagtgatga ctcaaggtat ctggcagaag  12420
atatttctag gcagcaaagc attcaagatg tggcctggct gcttctaaca acctacacac  12480
agatgcggga gcaaagaaat gacctaaagt tggaatttac atttaaaagg aaagcagagt  12540
gtaaacattt aaaaaaattt gcagcctggt caagtggtag agaaagaaac agctttttca  12600
ggaaataaat tcaagcacac tctggagcta ccgcttacta gagaaatttg cacaactgaa  12660
acagagccaa gtgctaatat ccaaagacaa tggggaaaag gcctcaaagg catttcagaa  12720
acttccaaag aagcccctcc catcacaagc tcagaggcct aggaggaaag aatggtttca  12780
tggaccaaac ccagggccca gtgccctgca cagccttggg acactgttcc ccacatctcg  12840
gccactctgg gttcagcctc agctaaaacg ggtccaggta caacttgggc tgccattaca  12900
gctccagaga gtgcaagcca taagccttgg cagcttccgt gtagtgttaa acctgcagcc  12960
acacagaatg taaaagtgaa ggaggcttag gagcctccac ctagatttca gaggatgtat  13020
ggaaaagcct gggtgcccag gaggaagcct gccacagggg cagttacctc acagagaacc  13080
tctactaagg cagtgcaggg ggggaatgtg gggctggagg ccccacacag agtctccagt  13140
ggggcacttc ctagtggacc catgggaagg aagggggcca ctgtcctcca ggccccagga  13200
tggtagatcc actggaagct tgcactctgc acatagaaaa gcagcaggca ctcaacaacc  13260
tgtgacagca gccacaagag ctgcaccctg cagagataca ggggcagagt ggcccaaggc  13320
ctggggtggc acacccctcg caccagcatg ccctggaaat gggacatgga gtcaaaggag  13380
actaccctag agctttaaga tttaatgact gccctgctgg gttttggact tgtatgcagc  13440
ctgtagtccc tttcttttgg ccaatttctc ccttttggaa catgaatgtt tacccaatgc  13500
ccatatcccc aatgtatctc agaagtaaat aactttttta attttacagg cttgtagatg  13560
```

gaagggactt gccttgactc agttgagaca ttgaactttt gagttaatgc tgaaatgagt 13620
gaagactttg gaggactatt aggaaggtat gattgtattc ggcaacagga gaaggatatg 13680
agatttggag gcccaggggc taaatgatat agtttggatg tcctttccaa acttcatgtt 13740
gaacagtaat ctccaatgtt ggaagtggag ccttggtggg aggtgattgg atcacagggg 13800
cagatcccac atggcttggt gatgtccttg atctggacac aagatctggc tgtttaaaag 13860
tgtgtggcac ctccccccac ctctctcttg ctcatgcttt tgccatgtga catgcctgct 13920
ccccctttgc cttttgccat gattggaagc ttcctgaggc ctccccagaa gcagatgctg 13980
ctgtgcttcc tatacagcct gcagaaacat gagccaatta catctgtttt cttataaatt 14040
acccagttgc aggtctttcc taatagcagt gcaatgacag cctaatacag tctgtgaagg 14100
tgttctcaga agacatcggc acttgaatca gtggactgag tgtcttagtc catttgtgct 14160
gctataagaa aatgcctgaa actgggtact ttatagagaa gataaactta ttttctcaca 14220
gttctggagg ccgggaagtt caagatcaag gtgccagcaa gtatattgtc tggtgaggga 14280
ccctatctct gcgtccaaga tggtgtgttg tggcagcctt ctccagaggg aacgaatgct 14340
ggggtcctcg catggaggat agtggaagag caatacaggg tgaactgtcc ttgaagcctt 14400
tttgacaggg tagtaattca gttatgagga cagagcctgc ataacttaat cacttcccaa 14460
aagccctact tcttaatacc accacaatgg gattacattt caacatgaat ttctaggggg 14520
tatgttcaaa tcatagcatt ctactcctag tcccccaaaa tgtatgacct tatcacatta 14580
aaaatacata cattccatcc cagtaactcc aaaagtctta actcattcca gcatcaactt 14640
taaaatcaaa gtccaaagtc ttatttaaac atcgtctaca tcagatatga ttgacactct 14700
aggtaacatt catcttgagg caaattgctc tccagctgta aacctatgaa atcaaacaag 14760
ttacatgctt ccaaaatatc atggtaggac agacagggga tagatatttc cattgcaaaa 14820
gggaacacta ggaaagaaaa aagcgataat agatcccaag taaatccaaa atccaacaag 14880
gcaagcaaaa tcagatcttg aaacttgaca atgatctcct ttgactccct gtcatgcctt 14940
ccagataccc tagggtggga gttgggcccc caagtctcca ggtggtcctg cccccatggc 15000
tttgccggct gtggctccca agcatgacag tcccctgctt ttggctgtcc caggctggag 15060
ttgcacagca gtgtttctac tggcttgtgg ttgagggggc cctgacccca tggctctatt 15120
aggccatgcc tccatagcac gtgctctgtg tgtgcctgca gaagatgctg ccaaggcgta 15180
ttgcctgtgc ctctggaggg gcagcctgag ccacacctgg gcccatgtga gccatagctg 15240
aggcagctga ggagtgctac actggaatgc agggagcaga gacttgaggc agtactgggc 15300
atgaaggccc aaggtcccat aggtactcag ggaccctcca gagccctggg ttcctccctt 15360
gactccattc tgccctcaaa gcaaatgcag ggagcagaga cttgaggcag tactgggcat 15420
gaaggcctaa ggtcctgtag gtacccaggg accgtccaga gccctgggtt cctcccttga 15480
ctcccttctg ccctcaaagc cctagaactc taagcctgtg atggccatgg cagcctggaa 15540
gagctttgag atgccgtcag ggcctttctt ccattgtctt aacggacagc acctgacttc 15600
cctctatcgc caggaatctt atcaaatggt ccctgggcca caccctttgt tttctctcct 15660
acacgcgtgg ccaagctgag actcttccaa acctttaagt tctgcttctc ttttgattat 15720
agattctgtc tttaactcat ttctctcttt cttgcatttt accatacaca gttgagagaa 15780
gccatgcagc tcccttagcg ttttgcttag agatttcttc ctctgaatat tctagttcat 15840
cactgttaaa ttctgcctcc cacaaagccc tcaggcacag acacaattca gcctagttcc 15900

-continued

```
ttaccacttt gtaacaggaa cggtctttcc tccagattcc aataagatat tccttgctgt  15960
gatctaacac ttcatcttta ctattcatat ttctaccagc attgggatca tgattactta  16020
aacatttctc tttttttttt agatggagcc ttgctctgtc gcccaggctg gagtgcagtg  16080
gtgggatctc ggctcactgc aagctccacc tcccgggttc acgccattct cctgcctcag  16140
cctcccgagt agctgggact accggcgccc gccaccacgc ccagctaatt ttttgtattt  16200
ttagtagaga cggggtttca ccgtgttagc caggataatc tctatctcct gaccttgtga  16260
tccgcccacg tcggcctccc aaagtgctgg gattacaggc gtgagccacc gcgcccggcc  16320
cacttaaaca ttcctaagaa gactgaggct ctgtctacag atctcctctt cttctaaacc  16380
tgcaccagaa ttgcctttaa tactctgttc atagccattt aggctttttc tgccatgcac  16440
tctgaaacac ttccagactc taccagcagt ttgaaatctg cttccacatt ttcaggtatt  16500
tataacatca acaccccact tatgtttagc aaattatgtc tccgtccctt tgtgcggcca  16560
taataaaata cctgtaactt ggtcatttct acaacagatt tattatgtca cagtacggga  16620
ggctggaaaa agtgcaagat caggacactg gctgttttgg tgtctggtga gggtcccagt  16680
ctcttcttca agatgaagac ttgttgctgc ctctcctgaa ggggacaaat gctgtgtcac  16740
cacactgtgg atagtggaag agcaatacaa ggtgaactgt ctctgaagcc tttttttataa  16800
gagcgttggt ccattcatga ggactgagcc ctcatgactt aatcacttct caaaaaaacgc  16860
taccgcttaa taccaccaca gcggggatta agtttaaata taatgtttgg aggccaggtg  16920
cagtggctca tgcctgtaat cccagcactt tgggagggtg aggcgggcag atcgcttgag  16980
gtcatcagtt caagaccagc ctggccaaca tggagaaact ctatctctac aaaatacaaa  17040
aattaactgg gcgtggtggt gcgtgcacac ctatggtccc agctactcgg gaggttgagg  17100
catggcttaa agccaggagg ttgcagtgag ctgagatcgc gccactgcac tccagcctgg  17160
gcaacagact gagactctgt ctcaaaaaaa aaaaaaaaaa acttggagaa ggcaaattca  17220
aagcacgaca gtagagaagg tccatcctcg cccaacgtga gtgggcactg tccaatcagc  17280
agtgggccca gataaggaaa aaaggtagaa gaaaggcgaa ctctccctct ctgcctctcc  17340
ccactctccc ttctgcagct gggacaccca tcttctcttg cctttggata tcagaactcc  17400
agattcttca gccttcgcac tctgagactt gtaccagtgg cctccgggtc tcaggccttc  17460
agctgcagac tgagagttac ccaactggct ttcctgattg acgcttagac tgtaccacat  17520
aaatggcttc cctggtcccc agcttgcaga tggcctattg tgggaatttt cagcctctgt  17580
aatcattgta atcatatgag cccattccca taataaatcc cttctcatgt atctatgtat  17640
ctatacctgt atcaatccta tttctttctt tttttttttt ttgagacaga gtcttgctct  17700
gtcacccagg ctggagtgca gtggcgtgtt ctcagctcaa tgcaacctcc gcctcccagg  17760
ttcaggcgat tctcctgcct cagcctcccg agtagctggg actacaggca cccgccacca  17820
cgcccagcta atttttgtat ttttagtaga gacggggttt catcatgttg gccaggatag  17880
tctccatctc ttggcctcgt gattcacccg cctcggcctc ccagagtgct gggattacag  17940
gcgtaagcca gcacacctgg cctcgatgct atttctatcc tatcggttct gtttacctga  18000
agaaccctaa cataggtttt ggtatcagga tgattctaga gaaacagaat cataagaatg  18060
agttttctga atgtgtattg tgtttttcgg aattggtttt ctaatatgac ttgacttaaa  18120
agtgagaaga actctacttc caacagtaca caggacactg atggtccatg gtgtgaatag  18180
tttatgaaaa tatgcaaatt tctgcattgt atactcctag taaaccactt acaagaggca  18240
aggagcttag tgactctgta tatgatattt tcgaacattt gtggaaaacc agggaatata  18300
```

-continued gtgacgtggg ctggttacca gttggttgct ggacaaagtg atgaaatcac aggatgtgct 18360
cagtgattca aattcccagt tccagctctg tataaataac ctgtgagtgg ctgagtgaac 18420
cctgaaggag aacctccttt cctgtagccc tggggccaag actgctgaaa agcaaccaca 18480
agtcctcgtc ctgaaactgg atgaattaca acgcaagttg aactctcagc cttgcggggt 18540
gtccactgtt ccagtgaggg cattggctgg gaaacagagg atcctgtaag ttgggatgaa 18600
gacatatgga aggaccctga tgaagctggg gacggtcagc ctctaagtta ggatgagtca 18660
ttttgtcagc agaagcagcc tccctgcacc cagtggcagt gctacaccca cccccagtgc 18720
tacacccctc ccccagtggt actggccttt ccaccttctc tgaggcatta atctgtgttg 18780
cctgaggaaa gggtaaggac ttcccctaag gcagttgctg attctcctcg ggtccctccc 18840
ccaacccttc cctttgcttt aagacctata acaagactca cagcccagca ggcccctgaa 18900
ggtgaggccc acagtgtgac acaggaggag gcgagccaca ccccagaaga gccactcgac 18960
ctctctgatt tatacagaca gacacctggg agcatgagtg ggaacggacg ttgggtgtag 19020
ggcactgggg gaggaacatg gaggtggagg gaccaggtgt gcaggcatgt ccaccaagta 19080
gagcctgaat tccaggctgc aactcaggga cttggaaaag ctctaactgg ctggtcggtt 19140
gaaacatgga tcaaaggatg cctgcagtga gcgagctgga gatgcctaaa ctcccttggc 19200
ttaacataga ggaaggggtt caaaggctca ttcccaaagg agatcagaat gtgacaatga 19260
aaacctcctc acctaccctg ggagggccca aaacgcagac ctttcacaac agggatcccc 19320
aaccccccgg gccatggact ggtactggtc catggcctgt taggaactgg gccacacagc 19380
aggaggtgag cggtgggtga gtgagtgaaa tccgtattta tagccactcc ccatcacttg 19440
catgaccacc tgagcttggc ctcctgtcag atcagcagca gcatcagatt ctcataggag 19500
tgcaaaccct actgtgaact gcacatacga aggatctagg ctgcaacgct ccttatgaga 19560
atctaatgcc tgatgatgtg tggctgtctc ccatcctccc cagatgggac tgtctagttg 19620
caggaaatcg agcgcaggcc tcccactgat tctacatgat ggcgagttgt ataattattt 19680
ccttacatat tacaatgtaa taataataca gataaagtga acaataaatg taatgtgttt 19740
gaatcatccc aaaaccatcc tccaactccg ggtctgtgga aaaatattct gccatgaaac 19800
tagtccctca tgccaaaaag gttgaggact gctgtctcac aacactgaaa tatagacttg 19860
tgagggagcc cagtctcctt gaagagctct gagattgttc ttctctgtag gccagactca 19920
ctgtgggaac tgcagtcaat caactgagaa acttacatgt gatgggaata attggatcct 19980
ggggtagcag tggccaagtg ggggcattca agcaccaaag gcaaagttgg catggttacc 20040
atgatagaca gcagaggcaa agtagcagtc agacctgagt tacaggtcca acccatgtag 20100
acctatggca ctggctggtt accatgtttt tcctagcagt gaaacagatg ggaagcctgc 20160
tcaattccta ctggatacaa gcagaaaact tacagatcaa gtggacaaaa ctctaagtcc 20220
aatcataaaa acagagaatc atggcctcag tctttcacag acttgagcca gtctatgaac 20280
ccagaaagag tgaaagaaag gctgggtacc cttgaggaag gaccccagga tggccaaaaa 20340
tgtatatata ctgttaattc tttccctggt cttctccaaa ggggtctatg gccttctatc 20400
tgtgtaactg tgtattggaa aaaagaaaat aatgtggcat ttcaggacga ttggacactg 20460
gctctgtcct gacattgatt ttaggagatg ctggaacgac actgtggccc tccagttagg 20520
gaggggctta gggagccagg tgatcaatgg agttttagct caggtctgac tctgtgggtc 20580
cagcgggtac ccagcccatc ctgtggtcat cttcccagct ccagatgtgt aagtggaaca 20640
gacacactca gcagccagca gagtccccac atgcgtcccg tgacctggtg tgtgaaggct 20700
actgtggtgg gaaaggccaa gtggaagcca ttagagaggt ctctacctag aaccgtcagt 20760
caaaagccat cccacatccc tggagggact gcagacatca gtgccaccac caaggacttg 20820
agaggtgcag gggcggcgat ccccaccaca gcccattctc cccacctatt cggcccacag 20880
gggagacagg tgggtcctgg agaatgacag gggactgtcc taagtttgac tccagctgca 20940
gctgctgggc cagacgaggt tccatcgctt gagcaaatta gcacatctcc tgctccctgg 21000
tgcgaagctc ttgatccagc aaatgcgttc tcctccaccc ccgtccacag ggcccagcag 21060
aagccaggcc agcgatgcac cctcgccgcc ccacctgagg ggcctctcgc ctctccagcc 21120
cgtgtcagag gtaattctca ggagtctcga tcacctctcc cttccccagg atgtcacact 21180
ggcccattac actggtgaca tcatgttgat gggacgtaag gcacaagaag tagcctccat 21240
cctagacttg ttggtgtcgg agggtgggga ataaacccaa ctggaattca gagccttcta 21300
cctcagggaa atttccagtg gtgtgaggcc tgttctaagg tgaaggacag gttgttgcag 21360
ctgaaccctc ctacaaccaa aagagaagaa cggcactaag tgggcctgtc tgatgtgggg 21420
ttgacacgtt ctttctcttt gaggtgtcca actctgtcca tttactgagt gatttgaaaa 21480
gctgctagtt agttttaagc atggcccaga gcaagagaag tctctgcagt aggtccaggc 21540
tctgtgcatg ccgctctgcc acgtgggcca catgacccgg cagatccact ggtgcctggg 21600
gtgtcagtgg cagacagaga ccctgtgtgg agtctttgcc aggcccctgt aggtgaatca 21660
cggctcaggc ctttaggatt ttggaggaag gtcctgtcat cattcacaga taacccactc 21720
tccttcagag aaacagctct tgccctgctt ctgggccttt gtagaaatta aacacttggc 21780
agtgtgaatc tataatccca gcactttggg aggctgaggt gggcaggtca cctgaggtca 21840
ggagttcaag accagcctgg ccaacatggc gaaaccctgt ctctactaaa aatacaaaat 21900
tagccaggtg tggtggcgag tgcctgtaat accagctact tgggaggtgg aggcacgaga 21960
atcagttgaa cccgggaggc ggaggttgca gtgagccaaa atggtgccgc tgcactccag 22020
cctgggtgac agagggagac tctgtctcat aaaaaaagaa aagaaaagaa agaaaaaaag 22080
aaaaggaaac taaactagac aagggccacc aagttaccac gtgacttgaa tggctcatca 22140
tgatctgggg actttctgac ccacgtagcc ataaagtcgt gtgcacagca gtgctgcatc 22200
agccagtgga agcaggggat aggtgatcag gcccaagcag gtcctgaagg cacaaggaag 22260
ttacgtgaag tagtggccca aagcctgtgg ccccactgct gctcccctgc cttctccctc 22320
cctgtctgca cctgtggctg catggggagt tcctctgatt agttgacgga ggaagagaag 22380
actcaggccg gacttacaaa tggttctgct cagtatgcag acactaccgg aaagtggaca 22440
gctgcagccc tgtagcccct gggggatatc cctcagacag tggtgaagag gaatcttccc 22500
cgtgggtaga acttccggca tgcacctgtg tgtgctccgc ttagaaggag cagatgtgtg 22560
atgatatttc attcatggct gttgccagta atttaagtgg atggaggtgc ttgaaaggaa 22620
catgattgga aaattggtga tgaagaaatg tgtggaagag atgtatagat agccctttct 22680
gaacatgcta atgacatcca gatatttgtg tcccatgtga atgctcacca aagggtgacc 22740
tcagcagagg acttcagtaa tcaggtggac agcatgagct actctatgga caccagtgag 22800
ccttttccca gccacccctc tcatcaccca gtgagctcct gagcgaagtg gctgtggtgg 22860
cagggatgga ggttgtgcgt gggctcagca acatggactt ccactgacca aggccaagct 22920
gagtaccacc agcactgtat gcccagtgtg ccagcagcag agaccaacac tcagcctgat 22980
aagctccatt cctgagtgat cagcccagtg cctgggggca ggtgggtgac actggacagc 23040

-continued

```
tcccatcatg gaaggggcgc tgaggctcca ttccccagcg tgttgagccc ggtgcctggg  23100
ggcgggtggg tgacactgga cggttcccat catgggaggg gcgctggttt gttctcactg  23160
ggataggcgc ctgccatgga tatggatttg tcttccctgc acacagtgct tctgtcgtca  23220
ctaccatctg tgggctcaga actcctcatc taatgccgtg ctgtccacac agcattgctt  23280
tgacgaagga actcactttg cagccaaaga agcgtggcag tgggctcatg ctcgtggtat  23340
tcacgggtct taccgtgttc tccatcatcc tgaagcagct ggcgtgatag aacggtggaa  23400
tgggcttttg cagacacagc tccagcacaa gctgggtggc agtcccttgc agggctgggg  23460
caaggtgctg ctccaggagg ctgtccgtgc tctgaatcag tgtccaatat gtggagctgt  23520
ctctcccaca gtcaggattc acccgtccgg gaaccaaggg gcagaagtgg gagtggcacc  23580
acccaccatc agccccagtg acccactagc agtgtttttg tttcctgttc ccatgacttt  23640
acgctctgct ggcctagggg ccttggttcc aaggtgagga atgctgccac caggagacac  23700
aacaatgact ccattgaact ggaagttaag gtggcacctg ggcagttggg gctcctcaag  23760
cctcagaatc aacaggccga taagagagtt tggatgctgg ctggggattg atccagagga  23820
cccaggggac atcgaactgc actccacacc agaggtgcgg aagagcacgg ggaatgcagg  23880
aggcccctta gggcttcttt aagtgtaacc acaccctgtg gttaagatcc ctggggccag  23940
gctcggtggc tcacgcctgt aatcccagca ctttgggagg ccgaggcggg cggatcacga  24000
ggtcaggaga ttcagaccat cctggctaac acggtgaaac cccatctcta ctaaaaatac  24060
caaaaaatta gccgggcatg gtggcaggca cctgtagtcc cagctacttg tgaggctgaa  24120
gcaggagaat ggcgtgaacc cgggaggcgg agcttgcagt gagccgagat cgcgccactg  24180
caccccagcc tgggcgacag agcaagactc cgtctcaaaa ataaaaaata ataataaaaa  24240
aataatccct gggaaagcac agcaatgcaa gtttccttag gaaactacag caaggccgag  24300
acccttaagc actgaggcct tgggtcacct ggccaggtac agaaccacta ccggctgagg  24360
tgcttgctga gggcaaaggg actacagaat gggcagtggt tataaacacc aggtactcct  24420
gtagcttggc cagtagcaga aatgaggatt gcaactttca cgagtgtttc ctctccattt  24480
tgttaagaaa gcatttgtgc atatgtgtac ataagttaag caaatatctg ttttctttcc  24540
tctcttactc ctttatcatg taacataaga tctattgatt ttgtctcagt atcaaggtat  24600
cgtgaatttt acatgacagt attgaggtcg tgcgatatcg ggagagtcga catcactcga  24660
ggacttcacc tcctcttcca gggaaggagt cagtgcgtgt ctggttgtat gcgggacagt  24720
catcacatgt tagttggaac catgaccttg ctgctgtcta tttggagatg aagtacggtt  24780
taaggaggtg tgtatgggtt ccaagctgac aaggagtgaa cttgtgacgg ttcgtttcag  24840
ctgtcaactt gactggatga agggatatcc agagagcatg aaagcattat ctctgggtgt  24900
gcctgtgagg gcatttccgg agagactggc gattgaatcc gtgggctgaa taaggaagat  24960
ctgtcttcac ccaaagtggg agggcaccat ccaatccact gagggcccag gcagaacggg  25020
aagatgaatt cgtgctctct tgctctctct tcccccacca gagctgggac acccacctcc  25080
tactgccctt agacatcaga actcctggtt ctctgggctt tggaccctgg aacttatacc  25140
agtggcccct ctgactgcga gttacactgt cggcctccct ggttctcaga tcttcaggct  25200
tgaactgagc cacactacca gcctccctgg gtctccagct tgcacagaca gggcaaatca  25260
tgggacttct cagtctccat actcatgtga gccgattccc atcataaacc ccctttcttc  25320
catccatcca tccatccatc catccatcca tccatccatc catccagcta tctatctagc  25380
```

-continued

```
taccgagcta gctacctgta tctttactta tctctatcta tgtctaccta tatctatatc  25440
tctgtctaca tctctatatc tatctgatct atctctatct ctatggtaat ctcaatctgt  25500
ctgtctgtct gtccgtctct ctgtctatct gtctccctcc ctgtctgtct atctgcctgt  25560
ctgcctgcct gtctatctgt ctgtctgcct gtctgcctgt ctgtctgcct gtctgcctgt  25620
ctatctgact gtctgcctgc ctatctgtct gtctgtctgt ctttatctct atggatctgt  25680
acttatttat ctatctcatt ccgtgtatct gtctctatat ctatacatct acatcatgga  25740
ggactatggt agatgctcac tgctgtgcac tgcaccgtcc ctcccagcgg gaccacagca  25800
ctggtccagc cagctgccca cagctctcag cttgctcctc ccgaggaaat gccctcagcc  25860
aaaggcagct gcctcaccca tggcttctcc ctgccctgga agccacctct acccaatgaa  25920
tggtcgatgg aggaagcaac aggtcaggtc cttcacctga attcatggcc tctctaaagg  25980
gccccttcag ctccaaaagc acccgaggca tcatcagaaa ccttctttgc gagtggagca  26040
cagctcagct gcccccacct gctccttccc tctctcacag cctttgtccc caagagcact  26100
tgccacttta cccttgacct acatgtctct atctggcagt gtctcttggg gaaccgaacc  26160
tcagacagtt tgcaagcaac aaattccaaa ggtcgtgcct gggcctggag ctctgctgac  26220
atggaagcca tgcccacctg ggacctgagg gtgtttcttg tctcacaggc ctgatattga  26280
gtggtgtgca tctgcatacc caggtggttg ttaaaacaca gaacggcttc catgctggtt  26340
gaacgacccc taccttgagc ctccaggtgt cccccagagg ccaccccggt tccttccccc  26400
agggtccaag cagggcacga cagacagctt ctggaacatc actcaatgcc gtggccagcc  26460
ccattctgat gggtctgcac caatcggggc tgcttgttaa gcatgactaa agtctcctgc  26520
agtcgtctgc taggactgcc acagcaaagc gccacagtct ggcagccttc acagagacat  26580
ttatctcccc agccctgggg gcctcaagtc caagctcaag ttgttgttgg ggctggttcc  26640
ttcgggggct acgaggtggc ctctgcccag tccctccagc ctctgcccag tccctccagc  26700
ctctggggct cccaggcagc ctcgtgtttc ttggctcgtg gagcatcact ctaatctctg  26760
ccttcacctt cacatggcgt ccttcctgtg tgtgcgtctg catccaactt cccctgttcc  26820
taaggtcacc ggtcagatct gagcaggata ctaatggcca tatcttagtt acatctgcag  26880
tgaccctatt tccaaataag gtcacatatg aggcactgaa ggtcgggact gcaacatgct  26940
tgttctccta tcatggaatc agaccagcag gtgggtcaca ttccgccaga gggagagtgg  27000
gcagacgccc aaagggctgg atgtatacag ctccaggaag aaccgcagtt gcagctgctt  27060
ggacaggtgt gggcactcac agcctcccat gacagccctg gctgggggct ccatccacag  27120
cccctggtgg ggtggggcaa ggcccttcct tctgacccac aggaccttgg accccctgggg  27180
cactgcagag ggactcaggg tcagaccagc agcctttgac atggccaaga gtgaaagtga  27240
tggggaccca cgagccatca gagctctgtc tccagagcct gcacagggag tgttgggaca  27300
aggagcaaag gaatcgggag cacatcaagg caggcaccag atttggaaga acgccccggg  27360
ggaggtgctc ccaggcgagt ggggcagagg gcagtctcct cctgggcttc cctgggtccc  27420
agcccggccc ggctgggcgt cccactgtct ttggtgtggt gtgctccctg cctgtggccc  27480
tgtgatggga gtcctgcttc tctaaacagt gagaccctca cagaacccgt cagcatgtcc  27540
aaagcacctg gaggagaaaa gatttgtctc ctcattcgtc actaggttca tggttgaggc  27600
tctcacagca aaagacagat taacaagaga aaagcagaca catttattca atataagttt  27660
catctcgtat aggagccttc ggaaatgagg acccagcact tcgggaggcc gaggtggaca  27720
gaccatttga agtcaggagt tccgagacca gcctggccaa catggtgaaa ccccatctct  27780
```

actaaaaata caaaattagc cgggcatggt ggcatgtgcc tgcagtccca gctaccgggg 27840
tggctgaggc aggagacttg cttgaacccg ggaggtggag gttgcagtga gccgagatca 27900
cgccattaca cttcagccag ggtgacagag tgaaactccg tctcaaaaaa aaaaaaaaaa 27960
agaaaaagaa aaggaaaaag aaatgaggac ccaagggaag agggaaaccc gtgtattttt 28020
atgtggagtt tgatggagag tcatgcagag tgtgattgga ttagacaaag tgggtgtact 28080
cgtccgttct tgcactgtat aaagaatact tgagactgcg taattcataa agaaaggagg 28140
tttacttggc ttacagttcc ccaggctgta cagaaagcat ggtgctggca tccacatggc 28200
ttctgggggc gggctcagga aacttacaat catggcggaa ggcaaaggag gagctggcac 28260
ttcacgtggc cggagcagga ggaagcccag agggagagag gggaggtgcc atatgccttt 28320
aaacaagcag gtctcatgag aactcactat cacgagaaca gcactggggg gaaatccacc 28380
cccatgagcc aatcacctcc agcaggcccc acctccagca ttggggatta caattcaaca 28440
tgagatttag gcaggtacac agatccaaac cgtatcaggg tgtggcctaa tggtgataca 28500
ctggggagac ttggcctgtg gtcttagtcc atcgtgtgct gttagaacag aaaaccacag 28560
actggctaac ttattggccc ctggtcctag aggctgggag gtccgagatc gacaggccac 28620
ctctggcaag ggtctttgtg ctgccttatc ccatgacaga agggcaaaga gagggagaga 28680
gagacagcca gagagaaggg gaccaaactc atccttctgt cagagcccgc tcccacgaca 28740
atgatgttag tccatcatga ttacagagat gggggacaca ttcagaccac agcagccccc 28800
tcaacccgca cacactgcac attgagggga gggccgggag actggaagga aacatcagag 28860
tctggagaag accaccagga tcaccagggc tatgctctca cccggcaccc agcaccgagg 28920
ggctcatggg aaacaagacg ggtctctcgg tgcacgagtg ctgggcacac atagtccacc 28980
gtgcatcctg ggctgatgat ctggaccctg gtcctgtgca gccctggggt ggggctccag 29040
gctgagatca gccacgtctg ggggaggaga cagtgttccc agtctcacct tgccccacgg 29100
actctgacag gggttgaaga agcaaggagg ctccaaggac tggggagggg gagtctggcc 29160
gacgatctag gagcatcaag gcgcctgctc cctctcggcg tggcccggtc ctgtaggtgg 29220
tcagttatgc aatgccactg ccttcctacc tcacaaggag ggtgggtgga ctcagaagcc 29280
aggcccaggc ttccttcttg gctcaggcaa ggaacatagg gggctttgag ctttgcttat 29340
tcatttaaca actgaacccc tagtctgtgc caggccccca tttaaatggt ccctgggata 29400
cagcagggtc cagaatgggc ccagaccctg cccccatagc tgaccttctg gagagcctga 29460
ggagtgaggg gtgccctcca ggcacggcag acggggcagg ctctgcattc gggggctcca 29520
gctgctttcc caccacccac ccactccacc cgagcccttc tgggtcagct gggctcctgg 29580
ctctgcccgc ctggggtgca agacgccaag ttccttcctg gacagtgaga gaaccatgcc 29640
aaaaagaaat gaaaggaagg cagacggcga gatgagggag agggtgggca cccagccagg 29700
gaccgcagag acgaggagga ggcacagaga cccactgtcc ccagccactg ccagtgaggc 29760
tggcccaggg ccaggggctg ggcgtccctg gcatgcatgt ggctcccagt gcccccacgt 29820
ccaacaggag tggggcggcc ccctcttctg ccacatcccc atcccacctc ccattccatt 29880
cactggtctc atttttaagt ttttctctcc cagttattca ggattgattt ggagagcaga 29940
gcgatggctg caggtggctc ttcattttcc ttcacctaag aagcaaacca tcatccaccc 30000
caagcttgtc tctccagcct gccccctaca tgaggacaac ctccctcctc ttccacggtg 30060
gcgctgttcc cactggaggc ccaggcttgg ccatccgttc attcttggag tcctcaagag 30120

-continued

```
attgtcagct ctgcagtggg gagcagccgc tgtcaaagac cctggaactt cctccctgct  30180
gcgtccacca acccccactg cccgctgggc actcccaacc tgaaacaagc ttgctcgctg  30240
caaaagcctc acctctgacc caacttccca ctcccaggat acccaacctg gccttccctc  30300
tggataccc tgtgggctcc cctctgctga tgggttcccc tctccagctg tggcttccct  30360
ctgctgatgg ggtcccctct ccagctgggg ctccctccac tgatggggtt ccctctacag  30420
ctgtggctct ctccactgat ggggtcccct ctccagctgg ggctccctcc actgatgtgg  30480
tcccctcttc agcttgggct ccctccactg atggggtccc ctcttcagct ggggctcctc  30540
tccactgaca gggtctcctt tccatctggg gctcccttgg ctgatgaagt cccttctcca  30600
ggtgaggctg ctctctgctg acagggtccc ctctccagct aggtctcctc tctgttgata  30660
gggtcccctc tccgggtggg ctcccctctg ctgacggggt cctctgatgg ggtccctact  30720
ccaggggggc tcccctccat agatgagctc cccttcctgg gttgggtgac ccctccgccc  30780
tatctgtgtc tgcaggttgg ggctaggcag tgctggccag catctgacaa cctcccettt  30840
ctgttcttgg gcactgctca cttattcagg tctcagccag gcagcccctc caatggtaat  30900
cttcagagtc cccttcagca acacagcttc ccctctgtgg cccagctcat gctgaagtaa  30960
acaaggcaat gtcattaacg gctggtatca gcttgtacgg ggaaccagtg gccccagaag  31020
cctctgggga ggcccaggct gtgaggatca ggggtccgga agagcctcta gagcgggaga  31080
aagaggcctc aggggtccct cctcacaggg gatggtgaca acacggtagg gaatggaggg  31140
gtcagggctg ggtccaggac acggtgaccc tggccagaaa aggccgggcc tggctggcac  31200
ccgcacgaag ggaacggagc cagtgtggaa aagcaggccc gcgtcctctt ctgcactccc  31260
agccccttta aactacacac agcttgtagg aaggggatca gaggcccctg ggcgtcccat  31320
ggctatgctg cacctgggga catgaagcct agggtagctc agccagctct ggtcacggct  31380
gacagacagc ctcaccccaa cagcctcacc catccctcct cagggaacag ggtcctaaca  31440
agctgctttc cccatcccag tgttgaacaa aaactcatgg gtttagacaa gagtgaaggt  31500
gactcctcca ccacccatcc cacctccagc aggcagccac ccccaaaatt attgatttat  31560
taataaatca atgacaggtg ccagccagcc ccacctgtcc ccaacctgca aatgcagaca  31620
ggggtcactt ggtccaggga gaggagaccc tcagtggagg ggagacaccc tggagagggg  31680
accccatcag caaaggggag ccccagctgg agacagtaaa taggcagact attcactgtc  31740
ttccccctca agccaggccc acagagtcac agagtatagc caccagcctc ctgggcccac  31800
ccgggaggcc ccaaccacac tccccctgct cagctcagcc cggatttctg gattctgctg  31860
cctgccaggg atcctgagga ggagatggta tcagagcctc accagccctt ctcataccca  31920
ggagtcctca tgatgataac agtgtgtgcg ccaggctgtg caggtgctgg ccgggatcct  31980
ctgaggggac gagatctcca tgggagggca ccactctgat gtccatcctg ggcttccgtg  32040
gccctgcctg gccactgccc gctgctcttg gtcaagatca tggaccctca gaggccaacc  32100
aggcctcagc ctgtgcctac agcatcctct ctactgccgg gcttctgaat tgctccttcc  32160
tcctgtctcc cacccagagc aagaacgaag gggaggcccc cagagccctg cagcgccggg  32220
agagactccc atccccaccc cgcatgccat caacacaaac tgccggagag tttaggggat  32280
cccacgactt ggggtctcca aagagacccc cgggacatct catcgagacc cccctgggca  32340
ctgcatgctc aggcttccca cccctggccc accccatggg gtgtgcccag tcccgcatct  32400
caccccatat ccatgcatgc atgcatgaac ctgaaagcac cccacaccct ctggtgctca  32460
gtcctcccct cctccctggg gtcccctccc ctccctgccc cccaagcctt gcatccccct  32520
```

gcaaacctca caagggggaa ctatttctgt cctgaaagca gagagggccc ttttcttggg 32580
acctctccgc catctctgcc tccactccca gctgctgtca gctctggcct ggcccctgca 32640
ggaagcaatc actggtctcc ctgtttccca tctggcccca aggtctgttc ttgcccttcg 32700
accagagagg tttgaaagca caactcgggc cctgcgtgcc ctgctcccca gggctccaca 32760
cctctgagca cccgcgcagt aacggaggct cccagccccg cctcgcccca gggtcccctc 32820
caacactctc tggccttggg cctttgctat acccggggcc tggaagggcc ccctcatccc 32880
ccaagtgtca ggcaaaggtc tcagagcact gtccctgccc ggcgtgcttg gtcctgactg 32940
ctaggcccca aatcattcct tttcccatta cctcttggtt tctctgtagc tggggtcact 33000
accccaaatt cttgaattga ctgacgtgtc caactatttc atgttttccc cctctacact 33060
gggagcccta caagggcagg gccccctggg caagaatagt gccagccagg agcccctgga 33120
gaagatagct acacatgtgc cccaggcccc agatggcact cagccctgcc tgtcaatgct 33180
ggacataggg cagtttttat cctggctttc tacacaagga ggaaagacta accatgccag 33240
cgggcagcgg ccggatcacg tatgtcagta gaactctgac ccctgagaag cctggaagcc 33300
aaaccacacc tctgtagcaa tcacgccaca gactcaggcc acggctaacg gctgccagtt 33360
cacctatttt tgcccccaac tcaagaccaa ctggaggaag gcaaatatgt ccctgacgaa 33420
gggtggccgc ctccagcctc cccagcccag agcctcagcc tccccagccc actgcctcca 33480
gcaacacaca tctgaagcct tctctgttgg ttggttttat tggtattttg gaagattgtt 33540
tgttttttgt tatgagatgg agcctcgctc tgtcccccag gctggagtgc agtggcgcga 33600
tctcggctca ctgcaagctc cgcctcctgg gttcaagcca ttctcctgtc tcagcctccc 33660
gagtagctgg gactacaggc acccgccacc gtgccaggct gatttttttg tatttttagt 33720
agagacgggg tttcaccatg ttagccatga tggtcttgat ctcctgacct catgatctgg 33780
ccatctcggc ctcccaaagt gctgggatta caggcgtgag ccactgcacc tggcctttgg 33840
aaggtctttt ataccttttat tgagataaaa ttcttatgac ataaaactta gcataaactg 33900
tagacttagt tggtgtgact ttagagtagt ctcagaattg tgcaaccatc accactgcct 33960
acttttagaa cattttcaac atcccaaaga cagaaccccg taggcacctg ttagcagcca 34020
ctccccaccc agtccacgaa gccccaggca gccactcacc aatctacttt ccattaattt 34080
gcccattcta aacacttgaa aaaaatggta tcacaatggt cttttgggtt tggcttcttt 34140
ccctcagcat catacctca aagttcatcc atgttgtagc tcgtatcggt acttcattca 34200
tttttatggc tgaataatat tccactgtat ggatagaccg atattttgtt tatttattta 34260
ttcattgatg aacatttgaa ttgttcccac tttttagcta ttaaaactag tgctggctgc 34320
gtgcagttgc tcatgcctgt aatcctagca ctttgggagg atgaggcagg cggatcactt 34380
gaggccaaga gtttgagacc agcctggcca acatggtgaa acccccatct ctaataaaaa 34440
tacaacaatt agccagacac ggtcatgcgt gcctgtaatc tcagctactc aggaggctga 34500
ggcaggggaa tctcttgaat ccggggggca gaggttgcag tgagccaaga tcgcgccact 34560
gcactccagc ctgggcaaca gaccaagact ctgtctcaaa aaacaaaaca aaacaaaaca 34620
aaacaaacca gtactgctat gaacatgcat gtgcatattg ttatacagac atatgctttc 34680
atttctcttg gatacacaca cacacacaca cacacacaca cacacacaca cacacacacg 34740
tatatctagg actggaattg ctgattttta tggaaactct atatttagca ttttgagaaa 34800
cggccagtct gttttccgaa gtggctgcac tattttgcat tcccaccagc aatgaaggag 34860

-continued

```
ggttccaatt tctccatacc tctgccaaca cttgttattg tctgtctctt ttatttatag  34920
ccatcttgat gggtgcatcg tggtatctcg ctgtgttttg atttgcattt ccctgatgac  34980
taatgatggg gacatctttt catgagctta tcggtcatat gtacatcttc tttggagcaa  35040
gctctattct aatcctttgc ccatcattaa aggtaggtgg tttgtcttct tgttgataag  35100
ttagagttct ttacatgttt agatactagt cccttatcaa atagatgatt cacaaatgtt  35160
tgctgtcatt tcttgggttg tctttccact tccttgatgg tgtcttttca cgcacaaatg  35220
tttttagctt tggccaagtc caatttatct attttttctt ttgttgcctg tgcttttggt  35280
agtgtatatt aaaaaccatt gtttaacaca aggtcaccaa gatttattcc tatgttcttt  35340
cctaaggatt ttatttttc ttttcttttt ttttcttttt tttgagacaa agtctctctc  35400
tgtcgccaaa gctggagtgc aacggcacaa tctcagctca ctgcaacccc tgcctcctgg  35460
gttcaagcga ttcttctgcc tcagcctccc gagtagctgg gattacaggc gcccaccacc  35520
atgcccagct aatttttgtg tttttagcag agacggggtt tcaccatgtt ggccaggctg  35580
gactcaaact cctgatctca ggtgatccac tcgcctcggc ctcccaaact gctgggatta  35640
caggtgtgag ccactgcgcc tggccttcct aaggatatca taattttagt gcttacattt  35700
aggtctacga tccattttga gttaattttt gtgcacagca tgaggtaggg gtccaacttc  35760
attcttttgc acatggatat ctagttgtcc cagcaccatt ttctgaaaag actattcctt  35820
cccccattga attgtcttgg taccettgtc aaaaatcaac tgatggccgg tctgaaggta  35880
gtgagttatc tcaattgatt gttcacagtc agttacagat ggaacacctc gttctactct  35940
ttcccgcctt ctcactgctg cacttgaaca gtctttaaaa aaatcaattg accataaatg  36000
caaggatttg ttcttggagt ctcaacttta ctgcattgat ctgtaggtct atccttatgc  36060
cagtaccaca ttgtcttgat tactgtagct ttgcagtaag tttgaatcag gaaatgtgag  36120
ccctccggtt ttgctcttct ctttctagat tgttttggct attctgaaac ccttgtattt  36180
ccttatgaat ttgaggatca gcttgtaaaa agacagatgg gattttgata gagattgtga  36240
agctatagat gaattcggga gtttggccat cttaacatta tgtctcctga tccatgactg  36300
caggatatct ttccatttaa ttcgatactc tttgattcct ttcaaaaata ttttgtattt  36360
ttcagtacac aagttttatg catcttttgt tgcatttatt tctaggtatg ttctttttgc  36420
caatattata aatgagattg tcttcttcac ttcattttg gatggttcat tgctagtgta  36480
tagaaataaa atcgatgttt gtatattgat cttgtatcct gccacattgc tatgcatgtt  36540
tattagtttt aagggtttta gtggattttc tatatataat gtcatataat cagcaaatag  36600
aaagtttaat gtcttagtcc ttttgagctg ccacaacaga ctaccataaa ctgagtggct  36660
tataaacaac acaaatgtat ttcccacagt tctggagact gggatgtcca agatcaagac  36720
acccgtaggt ttggtgtctg gtcggggcct acttctgggt tcatagatga ctgtcttctc  36780
gctgtgtccc ccccatagtg aaaggaaggg gcccagggtc tttctaaggc ttcttttata  36840
aggacactaa tccaatatag gaaggctctg ccctcataac ctaatctccc aaaggcctca  36900
cttccaaatt ccatcacctg gggagtaaga atttcaacac tggggggaca cagatattca  36960
gacatagcat ttttcttctt cctttctaat atgggtgccc ttgacatctt tttcttacct  37020
aattgccctg ccagagcctt ccagacagtg ttgaatggaa gtggggagca ttcaccccac  37080
cttactcctg atcatagggg aagaactatc cggctttcac cactgagcac cacgttagct  37140
ggggtatttt tgtcagcgct ctttatcagg tggaggcagg tcccttctat ttctagtgag  37200
ttcagtgctt tttttttttt ttaatcaggg aagagtgtga gcttgtgttt gggtgccttc  37260
```

-continued

```
cctgcgtctg ttgagatgat cttacggttt ctgtctctta ttctattgat atggcgtatt  37320

tattaccttg gttgcttttt ggatgttgat aacatccaaa ctcttctgcc accccttttta  37380

atagaaagct gtacaactcc ccaacctgcc tgggcgtgtc tgcccaagat gagtgctagt  37440

ggccgactcc ctgctagagt gagcactgca taaacagcct ctgcttgtcc tcatttgagt  37500

gatcttcatg tattccacga gaaatcaagg cacaggggtc tcatggtctc atgaatggct  37560

ccaccaactg aaggtgtgct ccatcggggc tgtgagtcac ctcacgccag gcagaaaggt  37620

ctctctgtca aacatggctt caaggaacca gggacctggt tcctcccaca ggccaggccc  37680

tgcccctaag tgcaatggga atatatgcac atgtcacctg tcccaaaatg ctgggagatg  37740

gcacttctgc agatggggaa actgagggac cagcccgaag tcacggggag gggaagactc  37800

ctacacacag ggaggagaag aacccagccg ggctgcaaac gcctgccctt cctcaacgtg  37860

cctccggctg tgcccacatc gctccagcag ctctgccttc ctcaggcata agccttctca  37920

gggcagggga ggcccaggga gcggcgctcc catcccaggc cgggctgctg agcaagcccc  37980

tccccttttct cccctcatcc tctgacagag tccacctgaa tatttgtcct ggagccagga  38040

tggaagctcc accaggccca gctaacaaca ggaacccttt cagacgcact tctgggtgcg  38100

tactgtgcca gtatcacaca gacacaagcc atgtccttgt cagccatggg atccccaagg  38160

tccccatgag gtcacaccag tgggccactg ggaagggcac ttcagatgtg gagctcccat  38220

gggccaggcc ctgcgaagtg gtcctcctac cccctcatag ccagtcttcc ctgtgagcct  38280

gcaagtgact gtgaatgtga gttccactct ggagctaaga cgggctgctg cccccgcaat  38340

cagatgtcag gcccatgaag                                             38360
```